US008476253B2

(12) United States Patent
Ikeda et al.

(10) Patent No.: US 8,476,253 B2
(45) Date of Patent: Jul. 2, 2013

(54) AMIDE DERIVATIVE

(75) Inventors: Takuya Ikeda, Tokyo (JP); Takanori Yamazaki, Tokyo (JP); Hiroshi Tsuchida, Tokyo (JP)

(73) Assignee: Daiichi Sankyo Company, Limited, Tokyo (JP)

(*) Notice: Subject to any disclaimer, the term of this patent is extended or adjusted under 35 U.S.C. 154(b) by 0 days.

(21) Appl. No.: 13/234,514

(22) Filed: Sep. 16, 2011

(65) Prior Publication Data

US 2012/0071467 A1  Mar. 22, 2012

Related U.S. Application Data

(63) Continuation of application No. PCT/JP2010/054291, filed on Mar. 15, 2010.

(30) Foreign Application Priority Data

Mar. 17, 2009  (JP) ................. 2009-065029

(51) Int. Cl.
*C07D 401/04* (2006.01)
*A61K 31/438* (2006.01)

(52) U.S. Cl.
USPC ........................... 514/178; 546/17

(58) Field of Classification Search
USPC ........................... 546/17; 514/178
See application file for complete search history.

(56) References Cited

U.S. PATENT DOCUMENTS

| 3,472,861 | A  | 10/1969 | Zeile et al. |
| 5,512,570 | A  | 4/1996 | Dorn et al. |
| 5,576,317 | A  | 11/1996 | Gonsalves |
| 6,511,975 | B1 | 1/2003 | Nishi et al. |
| 7,070,800 | B2 | 7/2006 | Bechtold-Peters et al. |
| 7,365,067 | B2 | 4/2008 | Nishi et al. |
| 7,728,144 | B2 | 6/2010 | Ji et al. |
| 2003/0004157 | A1 | 1/2003 | Buser et al. |
| 2004/0167167 | A1 | 8/2004 | Mammen et al. |
| 2005/0203131 | A1 | 9/2005 | Mammen et al. |
| 2005/0203167 | A1 | 9/2005 | Mammen et al. |
| 2006/0205775 | A1 | 9/2006 | Ji et al. |
| 2006/0205777 | A1 | 9/2006 | Mu et al. |
| 2006/0281740 | A1 | 12/2006 | Ji et al. |
| 2007/0197570 | A1 | 8/2007 | Nishi et al. |

FOREIGN PATENT DOCUMENTS

| EP | 0 443 132 A1 | 8/1991 |
| EP | 1 213 281 A1 | 6/2002 |
| JP | 2006-160639 | 6/2006 |
| JP | 2007-084530 A | 4/2007 |
| NZ | 330198 | 6/2000 |
| WO | WO 97/26968 | 7/1997 |
| WO | WO 2008/079346 | 7/2008 |
| WO | 2010-007561 A1 | 1/2010 |

OTHER PUBLICATIONS

Santicioli, Paulo et al. "Antimuscarinic, calcium channel blocker and tachykinin NK2 receptor antagonistic actions of otilonium bromide in the circular muscle of guinea-pig colon," Naunym-Schmiedeberg's Arch Pharmacology, 359: 420-427 (1999).
Barnes, Peter J. et al. "Neuropeptides in the Respiratory Tract (Part I)," American Review of Respiratory Disease, 144: 1187-1198 (1991).
Barnes, Peter J. et al. "Neuropeptides in the Respiratory Tract (Part II)," American Review of Respiratory Disease, 144: 1391-1399 (1991).
Barnes, Peter J. "Muscarinic Receptor Subtypes in Airways," Life Sciences, 52(5-6): 521-527 (1993).
Gross, Nicholas J. "Anticholinergic agents in asthma and COPD," European Journal of Pharmacology, 533: 36-39 (2006).
Quartara, Laura, et al., "Tachykinin receptor antagonists in clinical trials," *Expert Opinion Investig. Drugs* (2009), 18(12): 1843-1864.
Norman, Peter, "Long-acting muscarinic $M_3$ receptor antagonists," *Expert Opinion Ther. Patents* (2006), 16(9): 1315-1320.
Norman, Peter, "Long-acting muscarinic $M_3$ receptor antagonists," *Expert Opinion Ther. Patents* (2006), 16(9): 1321-1326.
International Search Report (English translation), PCT Application No. PCT/JP2010/054291, Filed Mar. 15, 2010, (5 pages), Dated Apr. 20, 2010.
International Preliminary Report on Patentability (English translation), PCT Application No. PCT/JP2010/054291, Filed Mar. 15, 2010, (8 pages), Dated Oct. 18, 2011.

*Primary Examiner* — Rita Desai
(74) *Attorney, Agent, or Firm* — Dorsey and Whitney LLP

(57) ABSTRACT

Compounds or pharmacologically acceptable salts thereof are provided. In various embodiments the compounds have an antagonistic effect on a neurokinin $NK_1$ receptor, a neurokinin $NK_2$ receptor, and a muscarine $M_3$ receptor. The compounds are useful as therapeutic agents for bronchial asthma, chronic obstructive pulmonary disease, or the like.

29 Claims, No Drawings

AMIDE DERIVATIVE

CROSS-REFERENCE TO RELATED APPLICATIONS

This application is a Continuation of PCT Patent Application No. PCT/JP2010/054291, filed on Mar. 15, 2010, entitled "AMIDE DERIVATIVE," which claims priority to Japanese Application No. 2009-065029, filed Mar. 17, 2009, the contents of all of which are hereby incorporated in their entirety by reference.

TECHNICAL FIELD

The present invention relates to a compound or a pharmacologically acceptable salt thereof that has an excellent antagonistic effect on a neurokinin $NK_1$ receptor, a neurokinin $NK_2$ receptor, and a muscarine $M_3$ receptor and is useful as a therapeutic agent for bronchial asthma, chronic obstructive pulmonary disease, or the like.

BACKGROUND ART

In bronchial asthma or chronic obstructive pulmonary disease (COPD), bronchoconstriction, airway inflammation, mucus secretion, coughing, and the like increase. Substance P or neurokinin A is associated with an airway contracting effect, an inflammatory effect, coughing, and mucus secretion. A compound that antagonizes receptors of both substance P and neurokinin A (a neurokinin $NK_1$ receptor and a neurokinin $NK_2$ receptor) may suppress the above-mentioned physiological effects (Non-Patent Documents 1 and 2). Although nonpeptidic low-molecular weight compounds that antagonize both the neurokinin $NK_1$ receptor and the neurokinin $NK_2$ receptor have been disclosed (Patent Documents 1 and 2), the use of the compounds as pharmaceuticals has not been approved. Meanwhile, acetylcholine exhibits a potent airway contracting effect by acting on a muscarinic $M_3$ receptor (Non-Patent Document 3). Compounds that antagonize the muscarinic $M_3$ receptor have a bronchodilating effect (Patent Documents 3, 4, and 5) and are used as bronchodilating agents (Non-Patent Document 4). It has been described that a bronchodilating effect which is more potent than the bronchodilating effect exhibited by antagonizing each of the receptors individually is exhibited by antagonizing both the muscarinic $M_3$ receptor and the neurokinin receptors (Patent Document 6). However, since no compound that antagonizes the neurokinin $NK_1$ receptor and the neurokinin $NK_2$ receptor has been marketed as a therapeutic agent for bronchial asthma or COPD, single agents cannot be used in combination. There has been demand for a single compound which has potent bronchodilating, anti-inflammatory, antiussive, and expectorant effects by antagonizing all of the neurokinin $NK_1$ receptor, the neurokinin $NK_2$ receptor, and the muscarinic $M_3$ receptor.

CITATION LIST

Patent Document

Patent Document 1: U.S. Pat. No. 6,511,975
Patent Document 2: U.S. Pat. No. 7,365,067
Patent Document 3: U.S. Patent No. 2004/167167
Patent Document 4: U.S. Patent No. 2005/203131
Patent Document 5: U.S. Patent No. 2006/281740
Patent Document 6: Japanese Patent Laid-Open No. 2006-160639

Non-Patent Document

Non-Patent Document 1: American Review of Respiratory Disease, 1991, vol. 144, 1187-1198
Non-Patent Document 2: American Review of Respiratory Disease, 1991, vol. 144, 1391-1399
Non-Patent Document 3: Life Sciences, 1993, vol. 52, 521-527
Non-Patent Document 4: European Journal of Pharmacology, 2006, vol. 533, 36-39

DISCLOSURE OF THE INVENTION

Problems to be Solved by the Invention

The inventors of the present invention assiduously studied the synthesis of a single compound that has an antagonistic effect on all of the neurokinin $NK_1$ receptor, the neurokinin $NK_2$ receptor, and the muscarine $M_3$ receptor as well as a pharmacological activity over a long period. As a result, they found compounds that solely exhibited an antagonistic effect on all the receptors and showed drug efficacy in a sustained manner. Thus, the present invention was accomplished.

Means for Solving the Problems

The present invention relates to:
A compound represented by general formula (I):

[Formula 1]

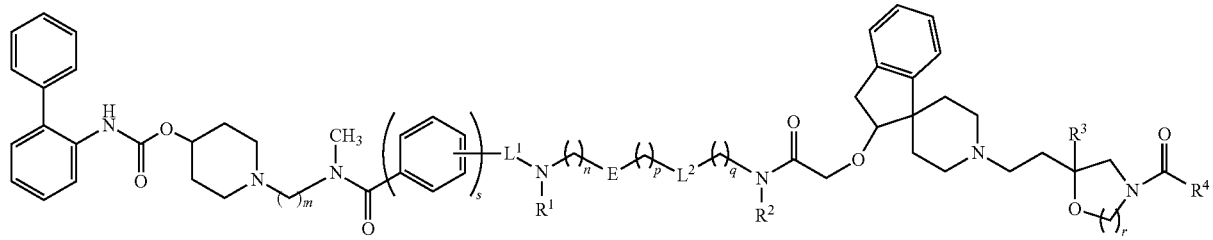

(I)

[wherein
$R^1$ represents a hydrogen atom, a $C_1$-$C_6$ alkyl group, a ($C_3$-$C_6$ cycloalkyl)methyl group, a $C_2$-$C_7$ alkoxycarbonyl group or a benzyl group, $R^2$ represents a hydrogen atom, a $C_1$-$C_6$ alkyl group or a $C_2$-$C_7$ alkoxycarbonyl group, $R^3$ represents a phenyl group that may be substituted with 1 to 5 group(s) independently selected from Substituent Group A, or a heterocyclic group that may be substituted with 1 to 3 group(s) independently selected from Substituent Group A, $R^4$ represents a phenyl group that may be substituted with 1 to 5 group(s) independently selected from Substituent Group A, or a heterocyclic group that may be substituted with 1 to 3 group(s) independently selected from Substituent Group A, $L^1$ represents a $C_1$-$C_{10}$ alkylene group or a $C_1$-$C_{10}$ alkylene group in which one of the methylene groups is replaced by an oxygen atom (when $R^1$ is a $C_1$-$C_6$ alkyl group, any carbon atom of $R^1$ may bind to any carbon atom of $L^1$), $L^2$ represents a carbonyl group, a hydroxymethylene group, an ester group, a group represented by the formula —N($R^5$)—, a group represented by the formula —N($R^5$)—C(=O)—, a group represented by the formula —C(=O)—N($R^5$)—, a group represented by the formula —N($R^5$)—C(=O)—O— or a group represented by the formula —O—C(=O)—N($R^5$)— ($R^5$ represents a hydrogen atom, a $C_1$-$C_6$ alkyl group, a $C_3$-$C_6$ cycloalkyl group or a $C_1$-$C_6$ alkoxy group [when $R^2$ and $R^5$ are both a $C_1$-$C_6$ alkyl group, they may bind to each other via any carbon atoms thereof]), E represents a phenylene group that may be substituted with 1 to 4 group(s) independently selected from Substituent Group A, or a heteroarylene group that may be substituted with 1 or 2 group(s) independently selected from Substituent Group A (provided that E binds to a methylene group on either side via a carbon atom thereof) (when $R^1$ or $R^5$ is a $C_1$-$C_6$ alkyl group, any carbon atom of $R^1$ or $R^5$ may bind to any carbon atom of E), m represents an integer of 1 to 4,
n represents an integer of 0 to 4,
p represents an integer of 0 to 2,
q represents an integer of 1 to 10,
r represents 1 or 2,
s represents 0 or 1, and Substituent Group A represents the group consisting of a halogen atom, a $C_1$-$C_6$ alkyl group, a $C_1$-$C_6$ halogenated alkyl group, a hydroxy group, a $C_1$-$C_6$ alkoxy group, a $C_1$-$C_6$ halogenated alkoxy group, a cyano group, a carboxyl group, a $C_2$-$C_7$ alkylcarbonyloxy group, a $C_2$-$C_7$ alkoxycarbonyloxy group, a carbamoyl group, a nitro group, and an amino group]

or a pharmacologically acceptable salt thereof.

Preferred embodiments of the present invention include:

The compound or pharmacologically acceptable salt thereof according to (1), wherein the general formula (I) is the general formula (II):

[Formula 2]

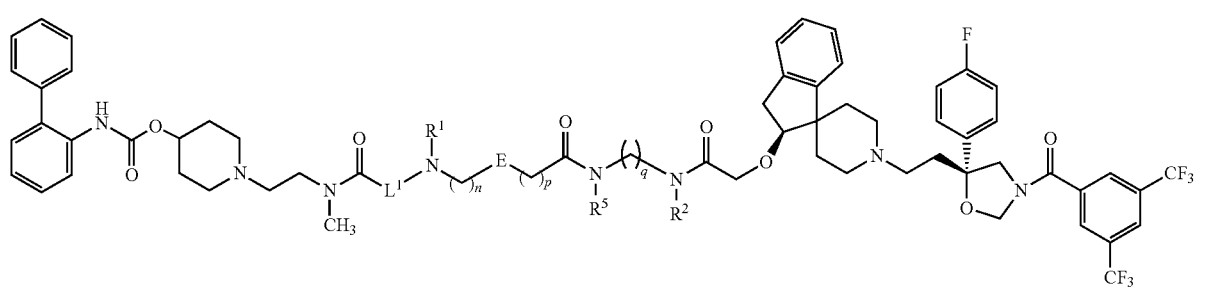

(II)

or the general formula (III):

[Formula 3]

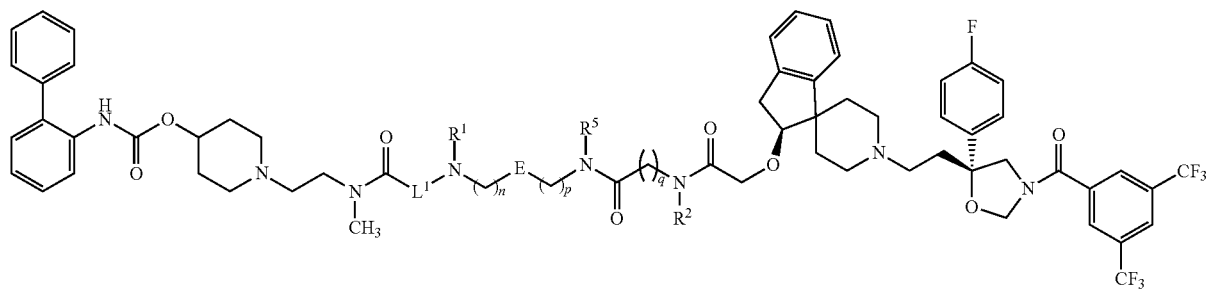

(III)

(3) The compound or pharmacologically acceptable salt thereof according to (1), wherein the general formula (I) is the general formula (II);

(4) The compound or pharmacologically acceptable salt thereof according to (1), wherein the general formula (I) is the general formula (III);

(5) The compound or pharmacologically acceptable salt thereof according to any one of (1) to (4), wherein $R^1$ is a hydrogen atom or a $C_1$-$C_6$ alkyl group;

(6) The compound or pharmacologically acceptable salt thereof according to any one of (1) to (4), wherein $R^1$ is a hydrogen atom, a methyl group or an ethyl group;

(7) The compound or pharmacologically acceptable salt thereof according to any one of (1) to (4), wherein $R^1$ is a hydrogen atom or a methyl group;

(8) The compound or pharmacologically acceptable salt thereof according to any one of (1) to (7), wherein $R^2$ is a $C_1$-$C_6$ alkyl group;

(9) The compound or pharmacologically acceptable salt thereof according to any one of (1) to (7), wherein $R^2$ is a methyl group;

(10) The compound or pharmacologically acceptable salt thereof according to any one of (1) to (9), wherein $R^5$ is a hydrogen atom, a $C_1$-$C_6$ alkyl group or a $C_3$-$C_6$ cycloalkyl group;

(11) The compound or pharmacologically acceptable salt thereof according to any one of (1) to (9), wherein $R^5$ is a hydrogen atom, a methyl group or a cyclopropyl group;

(12) The compound or pharmacologically acceptable salt thereof according to any one of (1) to (9), wherein $R^5$ is a methyl group;

(13) The compound or pharmacologically acceptable salt thereof according to any one of (1) to (12), wherein $L^1$ is a $C_1$-$C_8$ alkylene group or a $C_3$-$C_8$ alkylene group in which one of the methylene groups is replaced by an oxygen atom;

(14) The compound or pharmacologically acceptable salt thereof according to any one of (1) to (12), wherein $L^1$ is an ethylene group, a trimethylene group, a tetramethylene group, a pentamethylene group, a hexamethylene group, a methyleneoxytrimethylene group, an ethyleneoxyethylene group or a trimethyleneoxymethylene group;

(15) The compound or pharmacologically acceptable salt thereof according to any one of (1) to (12), wherein $L^1$ is an ethylene group, a trimethylene group, a tetramethylene group, a pentamethylene group, a methyleneoxytrimethylene group, an ethyleneoxyethylene group or a trimethyleneoxymethylene group;

(16) The compound or pharmacologically acceptable salt thereof according to any one of (1) to (15), wherein E is a phenylene group that may be substituted with 1 or 2 group(s) independently selected from a halogen atom and a $C_1$-$C_6$ alkyl group, a thienylene group, a thiazolylene group, a pyridinylene group, a pyrimidinylene group or a benzothiazolylene group that may be substituted with one group selected from a halogen atom and a $C_1$-$C_6$ alkyl group;

(17) The compound or pharmacologically acceptable salt thereof according to any one of (1) to (15), wherein E is a 1,3-phenylene group, a 1,4-phenylene group, a 2,5-thienylene group, a group represented by the formula (IV), a group represented by the formula (V), a group represented by the formula (VI), a group represented by the formula (VII), a group represented by the formula (VIII), a group represented by the formula (IX), a group represented by the formula (X), a group represented by the formula (XI) or a group represented by the formula (XII) (wherein $C_n$, and $C_p$ represent a single bond, $C_n$ binds to the group represented by the formula —(CH$_2$)$_n$—, and $C_p$ binds to the group represented by the formula —(CH$_2$)$_p$—);

[Formula 4]

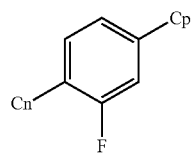

(IV)

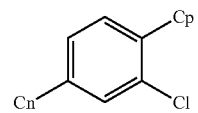

(V)

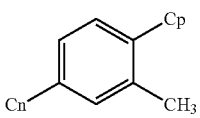

(VI)

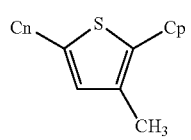

(VII)

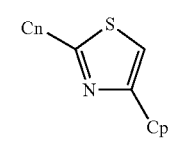

(VIII)

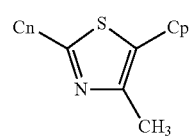

(IX)

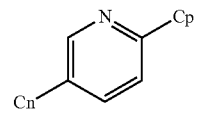

(X)

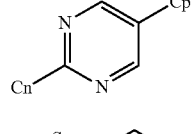

(XI)

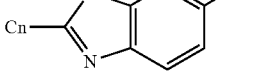

(XII)

(18) The compound or pharmacologically acceptable salt thereof according to any one of (1) to (15), wherein E is a 1,4-phenylene group, a 2,5-thienylene group, a group represented by the formula (IX), a group represented by the formula (X), a group represented by the formula (XI) or a group represented by the formula (XII);

(19) The compound or pharmacologically acceptable salt thereof according to any one of (1) to (18), wherein n is an integer of 0 to 2;

(20) The compound or pharmacologically acceptable salt thereof according to any one of (1) to (18), wherein n is 0 or 1;

(21) The compound or pharmacologically acceptable salt thereof according to any one of (1) to (20), wherein p is 0 or 1;

(22) The compound or pharmacologically acceptable salt thereof according to any one of (1) to (20), wherein p is 0;

(23) The compound or pharmacologically acceptable salt thereof according to any one of (1) to (22), wherein q is an integer of 1 to 6;

(24) The compound or pharmacologically acceptable salt thereof according to any one of (1) to (22), wherein q is 2 or 3;

(25) The compound or pharmacologically acceptable salt thereof according to (1), wherein the general formula (I) is the general formula (II) or the general formula (III), $R^1$ is a hydrogen atom or a $C_1$-$C_6$ alkyl group, $R^2$ is a $C_1$-$C_6$ alkyl group, $R^5$ is a hydrogen atom, a $C_1$-$C_6$ alkyl group or a $C_3$-$C_6$ cycloalkyl group, $L^1$ is a $C_1$-$C_8$ alkylene group or a $C_3$-$C_8$ alkylene group in which one of the methylene groups is replaced by an oxygen atom, E is a phenylene group that may be substituted with 1 or 2 group(s) independently selected from a halogen atom and a $C_1$-$C_6$ alkyl group, a thienylene group, a thiazolylene group, a pyridinylene group, a pyrimidinylene group or a benzothiazolylene group that may be substituted with one group selected from a halogen atom and a $C_1$-$C_6$ alkyl group, n is an integer of 0 to 2, p is 0 or 1, and q is an integer of 1 to 6;

(26) The compound or pharmacologically acceptable salt thereof according to (1), wherein the general formula (I) is the general formula (II) or the general formula (III), $R^1$ is a hydrogen atom, a methyl group or an ethyl group, $R^2$ is a methyl group, $R^5$ is a hydrogen atom, a methyl group or a cyclopropyl group, $L^1$ is an ethylene group, a trimethylene group, a tetramethylene group, a pentamethylene group, a hexamethylene group, a methyleneoxytrimethylene group, an ethyleneoxyethylene group or a trimethyleneoxymethylene group, E is a 1,3-phenylene group, a 1,4-phenylene group, a 2,5-thienylene group, a group represented by the formula (IV), a group represented by the formula (V), a group represented by the formula (VI), a group represented by the formula (VII), a group represented by the formula (VIII), a group represented by the formula (IX), a group represented by the formula (X), a group represented by the formula (XI) or a group represented by the formula (XII), n is 0 or 1, p is 0, and q is 2 or 3;

(27) The compound or pharmacologically acceptable salt thereof according to (1), wherein the general formula (I) is the general formula (II) or the general formula (III), $R^1$ is a hydrogen atom or a methyl group, $R^2$ is a methyl group, $R^5$ is a methyl group, $L^1$ is an ethylene group, a trimethylene group, a tetramethylene group, a pentamethylene group, a methyleneoxytrimethylene group, an ethyleneoxyethylene group or a trimethyleneoxymethylene group, E is a 1,4-phenylene group, a 2,5-thienylene group, a group represented by the formula (IX), a group represented by the formula (X), a group represented by the formula (XI) or a group represented by the formula (XII), n is 0 or 1, p is 0, and q is 2 or 3;

(28) The compound or pharmacologically acceptable salt thereof according to (1), wherein the general formula (I) is the general formula (II), $R^1$ is a hydrogen atom or a $C_1$-$C_6$ alkyl group, $R^2$ is a $C_1$-$C_6$ alkyl group, $R^5$ is a hydrogen atom, a $C_1$-$C_6$ alkyl group or a $C_3$-$C_6$ cycloalkyl group, $L^1$ is a $C_1$-$C_8$ alkylene group or a $C_3$-$C_8$ alkylene group in which one of the methylene groups is replaced by an oxygen atom, E is a phenylene group that may be substituted with 1 or 2 group(s) independently selected from a halogen atom and a $C_1$-$C_6$ alkyl group, a thienylene group, a thiazolylene group, a pyridinylene group, a pyrimidinylene group or a benzothiazolylene group that may be substituted with one group selected from a halogen atom and a $C_1$-$C_6$ alkyl group, n is an integer of 0 to 2, p is 0 or 1, and q is an integer of 1 to 6;

(29) The compound or pharmacologically acceptable salt thereof according to (1), wherein the general formula (I) is the general formula (II), $R^1$ is a hydrogen atom, a methyl group or an ethyl group, $R^2$ is a methyl group, $R^5$ is a hydrogen atom, a methyl group or a cyclopropyl group, $L^1$ is an ethylene group, a trimethylene group, a tetramethylene group, a pentamethylene group, a hexamethylene group, a methyleneoxytrimethylene group, an ethyleneoxyethylene group or a trimethyleneoxymethylene group, E is a 1,3-phenylene group, a 1,4-phenylene group, a 2,5-thienylene group, a group represented by the formula (IV), a group represented by the formula (V), a group represented by the formula (VI), a group represented by the formula (VII), a group represented by the formula (VIII), a group represented by the formula (IX), a group represented by the formula (X), a group represented by the formula (XI) or a group represented by the formula (XII), n is 0 or 1, p is 0, and q is 2 or 3;

(30) The compound or pharmacologically acceptable salt thereof according to (1), wherein the general formula (I) is the general formula (II), $R^1$ is a hydrogen atom or a methyl group, $R^2$ is a methyl group, $R^5$ is a methyl group, $L^1$ is an ethylene group, a trimethylene group, a tetramethylene group, a pentamethylene group, a methyleneoxytrimethylene group, an ethyleneoxyethylene group or a trimethyleneoxymethylene group, E is a 1,4-phenylene group, a 2,5-thienylene group, a group represented by the formula (IX), a group represented by the formula (X), a group represented by the formula (XI) or a group represented by the formula (XII), n is 0 or 1, p is 0, and q is 2 or 3;

(31) The compound or pharmacologically acceptable salt thereof according to (1), wherein the general formula (I) is the general formula (III), $R^1$ is a hydrogen atom or a $C_1$-$C_6$ alkyl group, $R^2$ is a $C_1$-$C_6$ alkyl group, $R^5$ is a hydrogen atom, a $C_1$-$C_6$ alkyl group or a $C_3$-$C_6$ cycloalkyl group, $L^1$ is a $C_1$-$C_8$ alkylene group or a $C_3$-$C_8$ alkylene group in which one of the methylene groups is replaced by an oxygen atom, E is a phenylene group that may be, substituted with 1 or 2 group(s) independently selected from a halogen atom and a $C_1$-$C_6$ alkyl group, a thienylene group, a thiazolylene group, a pyridinylene group, a pyrimidinylene group or a benzothiazolylene group that may be substituted with one group selected from a halogen atom and a $C_1$-$C_6$ alkyl group, n is an integer of 0 to 2, p is 0 or 1, and q is an integer of 1 to 6;

(32) The compound or pharmacologically acceptable salt thereof according to (1), wherein the general formula (I) is the general formula (III), $R^1$ is a hydrogen atom, a methyl group or an ethyl group, $R^2$ is a methyl group, $R^5$ is a hydrogen atom, a methyl group or a cyclopropyl group, $L^1$ is an ethylene group, a trimethylene group, a tetramethylene group, a pentamethylene group, a hexamethylene group, a methyleneoxytrimethylene group, an ethyleneoxyethylene group or a trimethyleneoxymethylene group, E is a 1,3-phenylene group, a 1,4-phenylene group, a 2,5-thienylene group, a group represented by the formula (IV), a group represented by the formula (V), a group represented by the formula (VI), a group represented by the formula (VII), a group represented by the formula (VIII), a group represented by the formula (IX), a group represented by the formula (X), a group represented by the formula (XI) or a group represented by the formula (XII), n is 0 or 1, p is 0, and q is 2 or 3;

(33) The compound or pharmacologically acceptable salt thereof according to (1), wherein the general formula (I) is the general formula (III), $R^1$ is a hydrogen atom or a methyl group, $R^2$ is a methyl group, $R^5$ is a methyl group, $L^1$ is an ethylene group, a trimethylene group, tetramethylene group, a pentamethylene group, a methyleneoxytrimethylene group, an ethyleneoxyethylene group or a trimethyleneoxymethylene group, E is a 1,4-phenylene group, a 2,5-thienylene group, a group represented by the formula (IX), a group represented by the formula (X), a group represented by the formula (XI) or a group represented by the formula (XII), n is 0 or 1, p is 0, and q is 2 or 3;

(34) A compound, which is 1-{2-[{6-[({5-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-2-thienyl}(methyl)amino]hexanoyl}(methyl)amino]ethyl}piperidin-4-yl biphenyl-2-ylcarbamate, 1-(2-{[6-({5-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-2-thienyl}amino)hexanoyl](methyl)amino}ethyl)piperidin-4-yl biphenyl-2-ylcarbamate, 1-{2-[{6-[({6-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]pyridin-3-yl}methyl)(methyl)amino]hexanoyl}(methyl)amino]ethyl}piperidin-4-yl biphenyl-2-ylcarbamate, 1-{2-[{6-[({6-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]pyridin-3-yl}methyl)amino]hexanoyl}(methyl)amino]ethyl}piperidin-4-yl biphenyl-2-ylcarbamate, 1-{2-[{6-[{5-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-2-thienyl}(methyl)amino]hexanoyl}(methyl)amino]ethyl}piperidin-4-yl biphenyl-2-ylcarbamate, 1-(2-{[6-({6-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]pyridin-3-yl}amino)hexanoyl](methyl)amino}ethyl)piperidin-4-yl biphenyl-2-ylcarbamate, 1-(2-{[6-({4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-2-fluorophenyl}amino)hexanoyl](methyl)amino}ethyl)piperidin-4-yl biphenyl-2-ylcarbamate, 1-(2-{[6-({5-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]pyrimidin-2-yl}amino)hexanoyl](methyl)amino}ethyl)piperidin-4-yl biphenyl-2-ylcarbamate, 1-(2-{[6-({4-[{2-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]ethyl}(methyl)carbamoyl]phenyl}amino)hexanoyl](methyl)amino}ethyl)piperidin-4-yl biphenyl-2-ylcarbamate, 1-(2-{[6-({4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-3-methylphenyl}amino)hexanoyl](methyl)amino}ethyl)piperidin-4-yl biphenyl-2-ylcarbamate, 1-(2-{[6-({4-[{3-[({[(2S)-t-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(cyclopropyl)carbamoyl]phenyl}amino)hexanoyl](methyl)amino}ethyl)piperidin-4-yl biphenyl-2-ylcarbamate, 1-{2-[{[3-({4-[{3-[({[(2S)-1-'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}amino)propoxy]acetyl}(methyl)amino]ethyl}piperidin-4-yl biphenyl-2-ylcarbamate, 1-{2-[{3-[2-({4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}amino)ethoxy]propanoyl}(methyl)amino]ethyl}piperidin-4-yl biphenyl-2-ylcarbamate, 1-(2-{[6-({5-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-4-methyl-2-thienyl}amino)hexanoyl](methyl)amino}ethyl)piperidin-4-yl biphenyl-2-ylcarbamate, 1-(2-{[5-({4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}amino)pentano yl](methyl)amino}ethyl)piperidin-4-yl biphenyl-2-ylcarbamate, 1-(2-{[4-({4-[{3-[({[(2S)-1-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}amino butanoyl](methyl)amino}ethyl)piperidin-4-yl biphenyl-2-ylcarbamate, 1-{2-[{4-[{4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}(methyl)amino]butanoyl}(methyl)amino]ethyl}piperidin-4-yl biphenyl-2-ylcarbamate, 1-{2-[{5-[{4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}(methyl)amino]pentanoyl}(methyl)amino]ethyl}piperidin-4-yl biphenyl-2-ylcarbamate, 1-(2-{[7-({4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}amino)heptanoyl](methyl)amino}ethyl)piperidin-4-yl biphenyl-2-ylcarbamate, 1-{2-[{7-[{4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}(methyl)amino]heptanoyl}(methyl)amino]ethyl}piperidin-4-yl biphenyl-2-ylcarbamate, 1-{2-[{6-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]benzyl}(methyl)amino]hexanoyl}(methyl)amino]ethyl}piperidin-4-yl biphenyl-2-ylcarbamate, 1-(2-{[6-({3-[{3-[({[(2S)-1-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}amino)hexanoyl](methyl)amino}ethyl)piperidin-4-yl biphenyl-2-ylcarbamate, 1-(2-{[4-(1-{4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methy)amino]propyl}(methyl)carbamoyl]phenyl}piperidin-4-yl)butanoyl](methyl)amino}ethyl)piperidin-4-yl biphenyl-2-ylcarbamate, 1-(2-{[6-({4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}amino)hexanoyl](methyl)amino}ethyl)piperidin-4-yl biphenyl-2-ylcarbamate, 1-{2-[{6-[{4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]benzyl}(methyl)amino]hexanoyl](methyl)amino]ethyl}piperidin-4-yl biphenyl-2-ylcarbamate, 1-(2-{[6-({4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]benzyl}amino)hexanoyl](methyl)amino}ethyl)piperidin-4-yl biphenyl-2-ylcarbamate, 1-{2-[{6-[{4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}(methyl)amino]hexanoyl}(methyl)amino]ethyl}piperidin-4-yl biphenyl-2-ylcarbamate, 1-{2-[(6-{[4-({4-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]butanoyl}amino)phenyl]amino}hexanoyl)(methyl)amino]ethyl}piperidin-4-yl biphenyl-2-ylcarbamate, 1-(2-{[6-({4-[{4-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]butanoyl}(methyl)amino]phenyl}amino)hexanoyl](methyl)amino}ethyl)piperidin-4-yl biphenyl-2-ylcarbamate, 1-(2-{[6-({4-[{3-[({[(2S)-1-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-3-chlorophenyl}amino)hexanoyl](methyl)amino}ethyl)piperidin-4-yl biphenyl-2-ylcarbamate, 1-{2-[{6-[(4-{2-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)amino]-2-oxoethyl}-1,3-thiazol-2-yl)amino]hexanoyl}(methyl)amino]ethyl}piperidin-4-yl biphenyl-2-ylcarbamate, 1-(2-{[6-({5-[{2-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]ethyl}(methyl)carbamoyl]-4-methyl-2-thienyl}amino)hexanoyl](methyl)amino}ethyl)piperidin-4-yl biphenyl-2-ylcarbamate, 1-(2-{[6-({6-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-1,3-benzothiazol-2-yl}amino)hexanoyl](methyl)amino}ethyl)piperidin-4-yl biphenyl-2-ylcarbamate, 1-{2-[(N-{4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}-β-alanyl)(methyl)amino]ethyl}piperidin-4-yl biphenyl-2-ylcarbamate, 1-{2-[(N-{4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}-N-methyl-β-alanyl)(methyl)amino]ethyl}piperidin-4-yl biphenyl-2-ylcarbamate, 1-(2-{[6-({5-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-4-methyl-1,3-thiazol-2-yl}amino)hexanoyl](methyl)amino}ethyl)piperidin-4-yl biphenyl-2-ylcarbamate, 1-{2-[{6-[{5-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-4-methyl-1,3-thiazol-2-yl}(methyl)amino]hexanoyl}(methyl)amino]ethyl}piperidin-4-yl biphenyl-2-ylcarbamate, 1-(2-{[6-({5-[{2-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]ethyl}(methyl)carbamoyl]-4-methyl-1,3-thiazol-2-yl}amino)hexanoyl](methyl)amino}ethyl)piperidin-4-yl biphenyl-2-ylcarbamate, 1-{2-[{6-[{5-[{2-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]ethyl}(methyl)carbamoyl]-4-methyl-1,3-thiazol-2-yl}(methyl)amino]hexanoyl}(methyl)amino]ethyl}piperidin-4-yl biphenyl-2-ylcarbamate or 1-{2-[{6-[(4-{[4-({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)-1,4-diazepan-1-yl]carbonyl}phenyl)amino]hexanoyl}(methyl)amino]ethyl}piperidin-4-yl biphenyl-2-ylcarbamate;

or a pharmacologically acceptable salt thereof;

(35) 1-{2-[{6-[({5-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-2-thienyl}methyl)amino]hexanoyl](methyl)amino]ethyl}piperidin-4-yl biphenyl-2-ylcarbamate, 1-(2-{[6-({5-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-2-thienyl}amino)hexanoyl](methyl)amino}ethyl)piperidin-4-yl biphenyl-2-ylcarbamate, 1-{2-[{6-[({6-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]

pyridin-3-yl}methyl)(methyl)amino]hexanoyl}(methy)
amino]ethyl}piperidin-4-yl biphenyl-2-ylcarbamate,
1-{2-[{6-[({6-[{3-[({[(2S)-1'-{2-[(5R)-3-[3,5-bis(trifluo-
romethyl)benzoyl]-5-(4-fluorophenyl)-1,3-oxazolidin-5-
yl]ethyl}-2,3-dihydrospiro[indene-1,4'-piperidin]-2-yl]
oxy}acetyl)(methy)amino]propyl}(methyl)carbamoyl]
pyridin-3-yl}methyl)amino]hexanoyl}(methyl)amino]
ethyl}piperidin-4-yl biphenyl-2-ylcarbamate,
1-{2-[{6-[{5-[({[(2S)-1'-{2-[(5R)-3-[3,5-bis(trifluo-
romethyl)benzoyl]-5-(4-fluorophenyl)-1,3-oxazolidin-5-
yl]ethyl}-2,3-dihydrospiro[indene-1,4'-piperidin]-2-yl]
oxy}acetyl)(methyl)amino]propyl}(methyl)carbamoyl]-
2-thienyl}(methyl)amino]hexanoyl}(methyl)amino]
ethyl}piperidin-4-yl biphenyl-2-ylcarbamate,
1-{2-[{6-({6-[{3-[({[(2S)-1'-{2-[(5R)-3-[3,5-bis(trifluorom-
ethyl)benzoyl]-5-(4-fluorophenyl)-1,3-oxazolidin-5-yl]
ethyl}-2,3-dihydrospiro[indene-1,4'-piperidin]-2-yl]
oxy}acetyl)(methyl)amino]propyl}(methyl)carbamoyl]
pyridin-3-yl}amino)hexanoyl](methyl)amino}ethyl)
piperidin-4-yl biphenyl-2-ylcarbamate,
1-(2-{[6-({4-[{3-[({[(2S)-1'-{2-[(5R)-3-[3,5-bis(trifluorom-
ethyl)benzoyl]-5-(4-fluorophenyl)-1,3-oxazolidin-5-yl]
ethyl}-2,3-dihydrospiro[indene-1,4'-piperidin]-2-yl]
oxy}acetyl)(methyl)amino]propyl}(methyl)carbamoyl]-
2-fluorophenyl}amino)hexanoyl](methyl)amino}ethyl)
piperidin-4-yl biphenyl-2-ylcarbamate,
1-(2-{[6-({5-[{3-[({[(2S)-1'-{2-[(5R)-3-[3,5-bis(trifluorom-
ethyl)benzoyl]-5-(4-fluorophenyl)-1,3-oxazolidin-5-yl]
ethyl}-2,3-dihydrospiro[indene-1,4'-piperidin]-2-yl]
oxy}acetyl)(methyl)amino]propyl}(methyl)carbamoyl]
pyrimidin-2-yl}amino)hexanoyl](methyl)amino}ethyl)
piperidin-4-yl biphenyl-2-ylcarbamate,
1-(2-{[6-({4-[{2-[({[(2S)-1'-{2-[(5R)-3-[3,5-bis(trifluorom-
ethyl)benzoyl]-5-(4-fluorophenyl)-1,3-oxazolidin-5-yl]
ethyl}-2,3-dihydrospiro[indene-1,4'-piperidin]-2-yl]
oxy}acetyl)(methyl)amino]ethyl}(methyl)carbamoyl]
phenyl}amino)hexanoyl](methyl)amino}ethyl)piperidin-
4-yl biphenyl-2-ylcarbamate,
1-(2-{[6-({4-[{3-[({[(2S)-1'-{2-[(5R)-3-[3,5-bis(trifluorom-
ethyl)benzoyl]-5-(4-fluorophenyl)-1,3-oxazolidin-5-yl]
ethyl}-2,3-dihydrospiro[indene-1,4'-piperidin]-2-yl]
oxy}acetyl)(methyl)amino]propyl}(methyl)carbamoyl]-
3-methylphenyl}amino)hexanoyl](methyl)amino}ethyl)
piperidin-4-yl biphenyl-2-ylcarbamate,
1-(2-{[6-({4-[{3-[({[(2S)-1'-{2-[(5R)-3-[3,5-bis(trifluorom-
ethyl)benzoyl]-5-(4-fluorophenyl)-1,3-oxazolidin-5-yl]
ethyl}-2,3-dihydrospiro[indene-1,4'-piperidin]-2-yl]
oxy}acetyl)(methyl)amino]propyl}(cyclopropyl)
carbamoyl]phenyl}amino)hexanoyl](methyl)
amino}ethyl)piperidin-4-yl biphenyl-2-ylcarbamate,
1-{2-[{[3-({4-[{3-[({[(2S)-1'-{2-[(5R)-3-[3,5-bis(trifluo-
romethyl)benzoyl]-5-(4-fluorophenyl)-1,3-oxazolidin-5-
yl]ethyl}-2,3-dihydrospiro[indene-1,4'-piperidin]-2-yl]
oxy}acetyl)(methy)amino]propyl}(methyl)carbamoyl]
phenyl}amino)propoxy]acetyl}(methyl)amino]
ethyl}piperidin-4-yl biphenyl-2-ylcarbamate,
1-{2-[{3-[2-({4-[{3-[({[(2S)-1'-{2-[(5R)-3-[3,5-bis(trifluo-
romethyl)benzoyl]-5-(4-fluorophenyl)-1,3-oxazolidin-5-
yl]ethyl}-2,3-dihydrospiro[indene-1,4'-piperidin]-2-yl]
oxy}acetyl)(methyl)amino]propyl}(methyl)carbamoyl]
phenyl}amino)ethoxy]propanoyl}(methyl)amino]
ethyl}piperidin-4-yl biphenyl-2-ylcarbamate,
1-(2-{[6-({5-[{3-[({[(2S)-1'-{2-[(5R)-3-[3,5-bis(trifluorom-
ethyl)benzoyl]-5-(4-fluorophenyl)-1,3-oxazolidin-5-yl]
ethyl}-2,3-dihydrospiro[indene-1,4'-piperidin]-2-yl]
oxy}acetyl)(methyl)amino]propyl}(methyl)carbamoyl]-
4-methyl-2-thienyl}amino)hexanoyl](methyl)
amino}ethyl)piperidin-4-yl biphenyl-2-ylcarbamate,
1-(2-{[5-({4-[{3-[({[(2S)-1'-{2-[(5R)-3-[3,5-bis(trifluorom-
ethyl)benzoyl]-5-(4-fluorophenyl)-1,3-oxazolidin-5-yl]
ethyl}-2,3-dihydrospiro[indene-1,4'-piperidin]-2-yl]
oxy}acetyl)(methyl)amino]propyl}(methyl)carbamoyl]
phenyl}amino)pentano yl](methyl)amino}ethyl)
piperidin-4-yl biphenyl-2-ylcarbamate,
1-(2-{[4-({4-[{3-[({[(2S)-1'-{2-[(5R)-3-[3,5-bis(trifluorom-
ethyl)benzoyl]-5-(4-fluorophenyl)-1,3-oxazolidin-5-yl]
ethyl}-2,3-dihydrospiro[indene-1,4'-piperidin]-2-yl]
oxy}acetyl)(methyl)amino]propyl}(methyl)carbamoyl]
phenyl}amino)butanoyl](methyl)amino}ethyl)piperidin-
4-yl biphenyl-2-ylcarbamate,
1-{2-[{4-[{4-[{3-[({[(2S)-1'-{2-[(5R)-3-[3,5-bis(trifluo-
romethyl)benzoyl]-5-(4-fluorophenyl)-1,3-oxazolidin-5-
yl]ethyl}-2,3-dihydrospiro[indene-1,4'-piperidin]-2-yl]
oxy}acetyl)(methyl)amino]propyl}(methyl)carbamoyl]
phenyl}(methyl)amino]butanoyl}(methy)amino]
ethyl}piperidin-4-yl biphenyl-2-ylcarbamate,
1-{2-[{5-[{4-[{3-[({[(2S)-1'-{2-[(5R)-3-[3,5-bis(trifluo-
romethyl)benzoyl]-5-(4-fluorophenyl)-1,3-oxazolidin-5-
yl]ethyl}-2,3-dihydrospiro[indene-1,4'-piperidin]-2-yl]
oxy}acetyl)(methyl)amino]propyl}(methyl)carbamoyl]
phenyl}(methyl)amino]pentanoyl}(methyl)amino]
ethyl}piperidin-4-yl biphenyl-2-ylcarbamate,
1-(2-{[7-({4-[{3-[({[(2S)-1'-{2-[(5R)-3-[3,5-bis(trifluorom-
ethyl)benzoyl]-5-(4-fluorophenyl)-1,3-oxazolidin-5-yl]
ethyl}-2,3-dihydrospiro[indene-1,4'-piperidin]-2-yl]
oxy}acetyl)(methyl)amino]propyl}(methyl)carbamoyl]
phenyl}amino)heptanoyl](methyl)amino}ethyl)piperidin-
4-yl biphenyl-2-ylcarbamate,
1-{2-[{7-[{4-[{3-[({[(2S)-1'-{2-[(5R)-3-[3,5-bis(trifluo-
romethyl)benzoyl]-5-(4-fluorophenyl)-1,3-oxazolidin-5-
yl]ethyl}-2,3-dihydrospiro[indene-1,4'-piperidin]-2-yl]
oxy}acetyl)(methyl)amino]propyl}(methyl)carbamoyl]
phenyl}(methyl)amino]heptanoyl}(methyl)amino]
ethyl}piperidin-4-yl biphenyl-2-ylcarbamate,
1-{2-[{6-[{3-[{3-[({[(2S)-1'-{2-[(5R)-3-[3,5-bis(trifluo-
romethyl)benzoyl]-5-(4-fluorophenyl)-1,3-oxazolidin-5-
yl]ethyl}-2,3-dihydrospiro[indene-1,4'-piperidin]-2-yl]
oxy}acetyl)(methyl)amino]propyl}(methyl)carbamoyl]
benzyl}(methyl)amino]hexanoyl}(methyl)amino]
ethyl}piperidin-4-yl biphenyl-2-ylcarbamate,
1-(2-{[6-({3-[{3-[({[(2S)-1'-{2-[(5R)-3-[3,5-bis(trifluorom-
ethyl)benzoyl]-5-(4-fluorophenyl)-1,3-oxazolidin-5-yl]
ethyl}-2,3-dihydrospiro[indene-1,4'-piperidin]-2-yl]
oxy}acetyl)(methyl)amino]propyl}(methyl)carbamoyl]
phenyl}amino)hexanoyl](methyl)amino}ethyl)piperidin-
4-yl biphenyl-2-ylcarbamate,
1-(2-{[4-(1-{4-[{3-[({[(2S)-1'-{2-[(5R)-3-[3,5-bis(trifluo-
romethyl)benzoyl]-5-(4-fluorophenyl)-1,3-oxazolidin-5-
yl]ethyl}-2,3-dihydrospiro[indene-1,4'-piperidin]-2-yl]
oxy}acetyl)(methy)amino]propyl}(methyl)
carbamoyl}phenyl]piperidin-4-yl)butanoyl](methyl)
amino}ethyl)piperidin-4-yl biphenyl-2-ylcarbamate,
1-(2-{[6-({4-[{3-[({[(2S)-1'-{2-[(5R)-3-[3,5-bis(trifluorom-
ethyl)benzoyl]-5-(4-fluorophenyl)-1,3-oxazolidin-5-yl]
ethyl}-2,3-dihydrospiro[indene-1,4'-piperidin]-2-yl]
oxy}acetyl)(methyl)amino]propyl}(methyl)carbamoyl]
phenyl}amino)hexanoyl](methyl)amino}ethyl)piperidin-
4-yl biphenyl-2-ylcarbamate,
1-{2-[{6-[{4-[{3-[({[(2S)-1'-{2-[(5R)-3-[3,5-bis(trifluo-
romethyl)benzoyl]-5-(4-fluorophenyl)-1,3-oxazolidin-5-
yl]ethyl}-2,3-dihydrospiro[indene-1,4'-piperidin]-2-yl]
oxy}acetyl)(methyl)amino]propyl}(methyl)carbamoyl]

benzyl}(methyl)amino]hexanoyl}(methyl)amino]
ethyl}piperidin-4-yl biphenyl-2-ylcarbamate, 1-(2-{[6-({4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]benzyl}amino)hexanoyl](methyl)amino}ethyl)piperidin-4-yl biphenyl-2-ylcarbamate, 1-{2-[{6-[{4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methy)amino]propyl}(methyl)carbamoyl]phenyl}(methyl)amino]hexanoyl}(methyl)amino]ethyl}piperidin-4-yl biphenyl-2-ylcarbamate, 1-(2-{[6-{[4-({4-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]butanoyl}amino)phenyl]amino}hexanoyl)(methyl)amino]ethyl}piperidin-4-yl biphenyl-2-ylcarbamate, 1-(2-{[6-({4-[{4-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]butanoyl}(methyl)amino]phenyl}amino)hexanoyl](methyl)amino}ethyl)piperidin-4-yl biphenyl-2-ylcarbamate, 1-(2-{[6-({4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-3-chlorophenyl}amino)hexanoyl](methyl)amino}ethyl)piperidin-4-yl biphenyl-2-ylcarbamate, 1-{2-[{6-[(4-{2-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)amino]-2-oxoethyl}-1,3-thiazol-2-yl)amino]hexanoyl}(methyl)amino]ethyl}piperidin-4-yl biphenyl-2-ylcarbamate, 1-(2-{[6-({5-[{2-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]ethyl}(methyl)carbamoyl]-4-methyl-2-thienyl}amino)hexanoyl](methyl)amino}ethyl)piperidin-4-yl biphenyl-2-ylcarbamate, 1-(2-{[6-({6-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4''-piperidin]-2-yl]oxy}acetyl)(methyl)amino]propyl}methyl)carbamoyl]-1,3-benzothiazol-2-yl}amino)hexanoyl](methyl)amino}ethyl)piperidin-4-yl biphenyl-2-ylcarbamate, 1-{2-[(N-{4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}-β-alanyl)(methyl)amino]ethyl}piperidin-4-yl biphenyl-2-ylcarbamate, 1-{2-[(N-{4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}-N-methyl-β-alanyl)(methyl)amino]ethyl}piperidin-4-yl biphenyl-2-ylcarbamate, 1-(2-{[6-({5-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-4-methyl-1,3-thiazol-2-yl}amino)hexanoyl](methyl)amino}ethyl)piperidin-4-yl biphenyl-2-ylcarbamate, 1-{2-[{6-[{5-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-4-methyl-1,3-thiazol-2-yl}(methyl)amino]hexanoyl}(methyl)amino]ethyl}piperidin-4-yl biphenyl-2-ylcarbamate, 1-(2-{[6-({5-[{2-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]ethyl}(methyl)carbamoyl]-4-methyl-1,3-thiazol-2-yl}amino)hexanoyl](methyl)amino}ethyl)piperidin-4-yl biphenyl-2-ylcarbamate, 1-{2-[{6-[{5-[{2-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]ethyl}(methyl)carbamoyl]-4-methyl-1,3-thiazol-2-yl}(methyl)amino]hexanoyl}(methyl)amino]ethyl}piperidin-4-yl biphenyl-2-ylcarbamate or 1-{2-[{6-[(4-{[4-({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)-1,4-diazepan-1-yl]carbonyl}phenyl)amino]hexanoyl}(methyl)amino]ethyl}piperidin-4-yl biphenyl-2-ylcarbamate;

(36) A compound, which is 1-{2-[{6-[({5-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-2-thienyl}methyl)amino]hexanoyl}(methyl)amino]ethyl}piperidin-4-yl biphenyl-2-ylcarbamate, 1-(2-{[6-({6-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]pyridin-3-yl}amino)hexanoyl](methyl)amino}ethyl)piperidin-4-yl biphenyl-2-ylcarbamate, 1-(2-{[6-({5-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methy)amino]propyl}(methyl)carbamoyl]pyrimidin-2-yl}amino)hexanoyl](methyl)amino}ethyl)piperidin-4-yl biphenyl-2-ylcarbamate, 1-(2-{[6-({4-[{2-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]ethyl}(methyl)carbamoyl]phenyl}amino)hexanoyl](methyl)amino}ethyl)piperidin-4-yl biphenyl-2-ylcarbamate, 1-{2-[{[3-({4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}amino)propoxy]acetyl}(methyl)amino]ethyl}piperidin-4-yl biphenyl-2-ylcarbamate, 1-{2-[{3-[2-({4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}amino)ethoxy]propanoyl}(methyl)amino]ethyl}piperidin-4-yl biphenyl-2-ylcarbamate, 1-(2-{[5-({4-[{3-[({[(2S)-1'-{2-[(5R)-3-[3,5-bis(trifluoromethyl)benzoyl]-5-(4-fluorophenyl)-1,3-oxazolidin-5-yl]

ethyl}-2,3-dihydrospiro[indene-1,4'-piperidin]-2-yl]
oxy}acetyl)(methyl)amino]propyl}(methyl)carbamoyl]
phenyl}amino)pentanoyl](methyl)amino}ethyl)piperidin-
4-yl biphenyl-2-ylcarbamate,
1-{2-[{4-[{4-[{3-[({[(2S)-1'-{2-[(5R)-3-[3,5-bis(trifluo-
romethyl)benzoyl]-5-(4-fluorophenyl)-1,3-oxazolidin-5-
yl]ethyl}-2,3-dihydrospiro[indene-1,4'-piperidin]-2-yl]
oxy}acetyl)(methyl)amino]propyl}(methyl)carbamoyl]
phenyl}(methyl)amino]butanoyl}(methyl)amino]
ethyl}piperidin-4-yl biphenyl-2-ylcarbamate,
1-{2-[{5-[{4-[{3-[({[(2S)-1'-{2-[(5R)-3-[3,5-bis(trifluo-
romethyl)benzoyl]-5-(4-fluorophenyl)-1,3-oxazolidin-5-
yl]ethyl}-2,3-dihydrospiro[indene-1,4'-piperidin]-2-yl]
oxy}acetyl)(methyl)amino]propyl}(methyl)carbamoyl]
phenyl}(methyl)amino]pentanoyl}(methyl)amino]
ethyl}piperidin-4-yl biphenyl-2-ylcarbamate,
1-(2-{[6-({4-[{3-[({[(2S)-1'-{2-[(5R)-3-[3,5-bis(trifluorom-
ethyl)benzoyl]-5-(4-fluorophenyl)-1,3-oxazolidin-5-yl]
ethyl}-2,3-dihydrospiro[indene-1,4'-piperidin]-2-yl]
oxy}acetyl)(methyl)amino]propyl}(methyl)carbamoyl]
phenyl}amino)hexanoyl](methyl)amino}ethyl)piperidin-
4-yl biphenyl-2-ylcarbamate,
1-{2-[{6-[{4-[{3-[({[(2S)-1'-{2-[(5R)-3-[3,5-bis(trifluo-
romethyl)benzoyl]-5-(4-fluorophenyl)-1,3-oxazolidin-5-
yl]ethyl}-2,3-dihydrospiro[indene-1,4'-piperidin]-2-yl]
oxy}acetyl)(methyl)amino]propyl}(methyl)carbamoyl]
benzyl}(methyl)amino]hexanoyl}(methyl)amino]
ethyl}piperidin-4-yl biphenyl-2-ylcarbamate,
1-(2-{[6-({4-[{3-[({[(2S)-1'-{2-[(5R)-3-[3,5-bis(trifluorom-
ethyl)benzoyl]-5-(4-fluorophenyl)-1,3-oxazolidin-5-yl]
ethyl}-2,3-dihydrospiro[indene-1,4'-piperidin]-2-yl]
oxy}acetyl)(methyl)amino]propyl}(methyl)carbamoyl]
benzyl}amino)hexanoyl](methyl)amino}ethyl)piperidin-
4-yl biphenyl-2-ylcarbamate,
1-{2-[{6-[{4-[{3-[({[(2S)-1'-{2-[(5R)-3-[3,5-bis(trifluo-
romethyl)benzoyl]-5-(4-fluorophenyl)-1,3-oxazolidin-5-
yl]ethyl}-2,3-dihydrospiro[indene-1,4'-piperidin]-2-yl]
oxy}acetyl)(methy)amino]propyl}(methyl)carbamoyl]
phenyl}(methyl)amino]hexanoyl}(methyl)amino]
ethyl}piperidin-4-yl biphenyl-2-ylcarbamate,
1-(2-{[6-({4-[{4-[({[(2S)-1'-{2-[(5R)-3-[3,5-bis(trifluorom-
ethyl)benzoyl]-5-(4-fluorophenyl)-1,3-oxazolidin-5-yl]
ethyl}-2,3-dihydrospiro[indene-1,4'-piperidin]-2-yl]
oxy}acetyl)(methyl)amino]butanoyl}(methyl)amino]
phenyl}amino)hexanoyl](methyl)amino}ethyl)piperidin-
4-yl biphenyl-2-ylcarbamate,
1-(2-{[6-({6-[{3-[({[(2S)-1'-{2-[(5R)-3-[3,5-bis(trifluorom-
ethyl)benzoyl]-5-(4-fluorophenyl)-1,3-oxazolidin-5-yl]
ethyl}-2,3-dihydrospiro[indene-1,4'-piperidin]-2-yl]
oxy}acetyl)(methyl)amino]propyl}(methyl)carbamoyl]-
1,3-benzothiazol-2-yl}amino)hexanoyl](methyl)
amino}ethyl)piperidin-4-yl biphenyl-2-ylcarbamate,
1-{2-[(N-{4-[{3-[({[(2S)-1'-{2-[(5R)-3-[3,5-bis(trifluorom-
ethyl)benzoyl]-5-(4-fluorophenyl)-1,3-oxazolidin-5-yl]
ethyl}-2,3-dihydrospiro[indene-1,4'-piperidin]-2-yl]
oxy}acetyl)(methyl)amino]propyl}(methyl)carbamoyl]
phenyl}-β-alanyl)(methyl)amino]ethyl}piperidin-4-yl
biphenyl-2-ylcarbamate,
1-(2-{[6-({5-[{3-[({[(2S)-1'-{2-[(5R)-3-[3,5-bis(trifluorom-
ethyl)benzoyl]-5-(4-fluorophenyl)-1,3-oxazolidin-5-yl]
ethyl}-2,3-dihydrospiro[indene-1,4'-piperidin]-2-yl]
oxy}acetyl)(methyl)amino]propyl}(methyl)carbamoyl]-
4-methyl-1,3-thiazol-2-yl}amino)hexanoyl](methyl)
amino}ethyl)piperidin-4-yl biphenyl-2-ylcarbamate or
1-{2-[{6-[(4-{[4-({[(2S)-1'-{2-[(5R)-3-[3,5-bis(trifluorom-
ethyl)benzoyl]-5-(4-fluorophenyl)-1,3-oxazolidin-5-yl]
ethyl}-2,3-dihydrospiro[indene-1,4'-piperidin]-2-yl]
oxy}acetyl)-1,4-diazepan-1-yl]carbonyl}phenyl)amino]
hexanoyl](methyl)amino]ethyl}piperidin-4-yl biphenyl-
2-ylcarbamate;
or a pharmacologically acceptable salt thereof;
(37) 1-{2-[{6-[({5-[{3-[({[(2S)-1'-{2-[(5R)-3-[3,5-bis
(trifluoromethyl)benzoyl]-5-(4-fluorophenyl)-1,3-oxazoli-
din-5-yl]ethyl}-2,3-dihydrospiro[indene-1,4'-piperidin]-2-
yl]oxy}acetyl)(methyl)amino]propyl}(methyl)carbamoyl]-
2-thienyl}methyl)amino]hexanoyl}(methyl)amino]
ethyl}piperidin-4-yl biphenyl-2-ylcarbamate,
1-(2-{[6-({6-[{3-[({[(2S)-1-{2-[(5R)-3-[3,5-bis(trifluorom-
ethyl)benzoyl]-5-(4-fluorophenyl)-1,3-oxazolidin-5-yl]
ethyl}-2,3-dihydrospiro[indene-1,4'-piperidin]-2-yl]
oxy}acetyl)(methyl)amino]propyl}(methyl)carbamoyl]
pyridin-3-yl}amino)hexanoyl](methyl)amino}ethyl)
piperidin-4-yl biphenyl-2-ylcarbamate,
1-(2-{[6-({5-[{3-[({[(2S)-1'-{2-[(5R)-3-[3,5-bis(trifluorom-
ethyl)benzoyl]-5-(4-fluorophenyl)-1,3-oxazolidin-5-yl]
ethyl}-2,3-dihydrospiro[indene-1,4'-piperidin]-2-yl]
oxy}acetyl)(methyl)amino]propyl}(methyl)carbamoyl]
pyrimidin-2-yl}amino)hexanoyl](methyl)amino}ethyl)
piperidin-4-yl biphenyl-2-ylcarbamate,
1-(2-{[6-({4-[{2-[({[(2S)-1'-{2-[(5R)-3-[3,5-bis(trifluorom-
ethyl)benzoyl]-5-(4-fluorophenyl)-1,3-oxazolidin-5-yl]
ethyl}-2,3-dihydrospiro[indene-1,4'-piperidin]-2-yl]
oxy}acetyl)(methyl)amino]ethyl}(methyl)carbamoyl]
phenyl}amino)hexanoyl](methyl)amino}ethyl)piperidin-
4-yl biphenyl-2-ylcarbamate,
1-{2-[{[3-({4-[{3-[({[(2S)-1'-{2-[(5R)-3-[3,5-bis(trifluo-
romethyl)benzoyl]-5-(4-fluorophenyl)-1,3-oxazolidin-5-
yl]ethyl}-2,3-dihydrospiro[indene-1,4'-piperidin]-2-yl]
oxy}acetyl)(methyl)amino]propyl}(methyl)carbamoyl]
phenyl}amino)propoxy]acetyl}(methyl)amino]
ethyl}piperidin-4-yl biphenyl-2-ylcarbamate,
1-{2-[{3-[2-({4-[{3-[({[(2S)-1'-{2-[(5R)-3-[3,5-bis(trifluo-
romethyl)benzoyl]-5-(4-fluorophenyl)-1,3-oxazolidin-5-
yl]ethyl}-2,3-dihydrospiro[indene-1,4'-piperidin]-2-yl]
oxy}acetyl)(methyl)amino]propyl}(methyl)carbamoyl]
phenyl}amino)ethoxy]propanoyl}(methyl)amino]
ethyl}piperidin-4-yl biphenyl-2-ylcarbamate,
1-(2-{[5-({4-[{3-[({[(2S)-1'-{2-[(5R)-3-[3,5-bis(trifluorom-
ethyl)benzoyl]-5-(4-fluorophenyl)-1,3-oxazolidin-5-yl]
ethyl}-2,3-dihydrospiro[indene-1,4'-piperidin]-2-yl]
oxy}acetyl)(methyl)amino]propyl}(methyl)carbamoyl]
phenyl}amino)pentanoyl](methyl)amino}ethyl)piperidin-
4-yl biphenyl-2-ylcarbamate,
1-{2-[{4-[{4-[{3-[({[(2S)-1'-{2-[(5R)-3-[3,5-bis(trifluo-
romethyl)benzoyl]-5-(4-fluorophenyl)-1,3-oxazolidin-5-
yl]ethyl}-2,3-dihydrospiro[indene-1,4'-piperidin]-2-yl]
oxy}acetyl)(methyl)amino]propyl}(methyl)carbamoyl]
phenyl}(methyl)amino]butanoyl}(methyl)amino]
ethyl}piperidin-4-yl biphenyl-2-ylcarbamate,
1-{2-[{5-[{4-[{3-[({[(2S)-1'-{2-[(5R)-3-[3,5-bis(trifluo-
romethyl)benzoyl]-5-(4-fluorophenyl)-1,3-oxazolidin-5-
yl]ethyl}-2,3-dihydrospiro[indene-1,4'-piperidin]-2-yl]
oxy}acetyl)(methyl)amino]propyl}(methyl)carbamoyl]
phenyl}(methyl)amino]pentanoyl}(methyl)amino]
ethyl}piperidin-4-yl biphenyl-2-ylcarbamate,
1-(2-{[6-({4-[{3-[({[(2S)-1'-{2-[(5R)-3-[3,5-bis(trifluorom-
ethyl)benzoyl]-5-(4-fluorophenyl)-1,3-oxazolidin-5-yl]
ethyl}-2,3-dihydrospiro[indene-1,4'-piperidin]-2-yl]
oxy}acetyl)(methyl)amino]propyl}(methyl)carbamoyl]
phenyl}amino)hexanoyl](methyl)amino}ethyl)piperidin-
4-yl biphenyl-2-ylcarbamate,
1-{2-[{6-[{4-[{3-[({[(2S)-1'-{2-[(5R)-3-[3,5-bis(trifluo-
romethyl)benzoyl]-5-(4-fluorophenyl)-1,3-oxazolidin-5-
yl]ethyl}-2,3-dihydrospiro[indene-1,4'-piperidin]-2-yl]

oxy}acetyl)(methyl)amino]propyl}(methyl)carbamoyl]
benzyl}(methyl)amino]hexanoyl}(methyl)amino]
ethyl}piperidin-4-yl biphenyl-2-ylcarbamate, 1-(2-{[6-({4-[{3-[({[(2S)-1'-{2-[(5R)-3-[3,5-bis(trifluorom-
ethyl)benzoyl]-5-(4-fluorophenyl)-1,3-oxazolidin-5-yl]
ethyl}-2,3-dihydrospiro[indene-1,4'-piperidin]-2-yl]
oxy}acetyl)(methy)amino]propyl}(methyl)carbamoyl]
benzyl}amino)hexanoyl](methyl)amino}ethyl)piperidin-
4-yl biphenyl-2-ylcarbamate, 1-{2-[{6-[{4-[{3-[({[(2S)-1'-{2-[(5R)-3-[3,5-bis(trifluo-
romethyl)benzoyl]-5-(4-fluorophenyl)-1,3-oxazolidin-5-
yl]ethyl}-2,3-dihydrospiro[indene-1,4'-piperidin]-2-yl]
oxy}acetyl)(methyl)amino]propyl}(methyl)carbamoyl]
phenyl}(methyl)amino]hexanoyl}(methyl)amino]
ethyl}piperidin-4-yl biphenyl-2-ylcarbamate, 1-(2-{[6-({4-[{-4-[({[(2S)-1'-{2-[(5R)-3-[3,5-bis(trifluo-
romethyl)benzoyl]-5-(4-fluorophenyl)-1,3-oxazolidin-5-
yl]ethyl}-2,3-dihydrospiro[indene-1,4'-piperidin]-2-yl]
oxy}acetyl)(methyl)amino]butanoyl}(methyl)amino]
phenyl}amino)hexanoyl](methyl)amino}ethyl)piperidin-
4-yl biphenyl-2-ylcarbamate, 1-(2-{[6-({6-[{3-[({[(2S)-1'-{2-[(5R)-3-[3,5-bis(trifluorom-
ethyl)benzoyl]-5-(4-fluorophenyl)-1,3-oxazolidin-5-yl]
ethyl}-2,3-dihydrospiro[indene-1,4'-piperidin]-2-yl]
oxy}acetyl)(methyl)amino]propyl}(methyl)carbamoyl]-
1,3-benzothiazol-2-yl}amino)hexanoyl](methyl)
amino}ethyl)piperidin-4-yl biphenyl-2-ylcarbamate, 1-{2-[(N-{4-[{3-[({[(2S)-1'-{2-[(5R)-3-[3,5-bis(trifluorom-
ethyl)benzoyl]-5-(4-fluorophenyl)-1,3-oxazolidin-5-yl]
ethyl}-2,3-dihydrospiro[indene-1,4'-piperidin]-2-yl]
oxy}acetyl)(methyl)amino]propyl}(methyl)carbamoyl]
phenyl}-β-alanyl)(methyl)amino]ethyl}piperidin-4-yl
biphenyl-2-ylcarbamate, 1-(2-{[6-({5-[{3-[({[(2S)-1'-{2-[(5R)-3-[3,5-bis(trifluorom-
ethyl)benzoyl]-5-(4-fluorophenyl)-1,3-oxazolidin-5-yl]
ethyl}-2,3-dihydrospiro[indene-1,4'-piperidin]-2-yl]
oxy}acetyl)(methyl)amino]propyl}(methyl)carbamoyl]-
4-methyl-1,3-thiazol-2-yl}amino)hexanoyl](methyl)
amino}ethyl)piperidin-4-yl biphenyl-2-ylcarbamate or 1-{2-[{6-[(4-{[4-({[(2S)-1'-{2-[(5R)-3-[3,5-bis(trifluorom-
ethyl)benzoyl]-5-(4-fluorophenyl)-1,3-oxazolidin-5-yl]
ethyl}-2,3-dihydrospiro[indene-1,4'-piperidin]-2-yl]
oxy}acetyl)-1,4-diazepan-1-yl]carbonyl}phenyl)amino]
hexanoyl}(methyl)amino]ethyl}piperidin-4-yl biphenyl-
2-ylcarbamate;

(38) A compound or a pharmacologically acceptable salt thereof having an antagonistic effect on a neurokinin $NK_1$ receptor, a neurokinin $NK_2$ receptor, and a muscarine $M_3$ receptor;

(39) A compound or a pharmacologically acceptable salt thereof having both a partial structure having an antagonistic effect on a neurokinin $NK_1$ receptor and a neurokinin $NK_2$ receptor and a partial structure having an antagonistic effect on a muscarine $M_3$ receptor;

(40) A pharmaceutical composition comprising a compound or a pharmacologically acceptable salt thereof according to any one of (1) to (39) as an active ingredient;

(41) The pharmaceutical composition according to (40), which has a bronchodilating effect and an anti-inflammatory effect;

(42) The pharmaceutical composition according to (40), for treatment and/or prevention of a disease mediated by a neurokinin $NK_1$ receptor, a neurokinin $NK_2$ receptor, and/or a muscarine $M_3$ receptor;

(43) The pharmaceutical composition according to (40), for treatment and/or prevention of a respiratory disease, an allergic disease, and/or a neurological disease;

(44) The pharmaceutical composition according to (40), for treatment and/or prevention of a respiratory disease and/or a neurological disease;

(45) The pharmaceutical composition according to (40), for treatment and/or prevention of bronchial asthma, bronchitis, chronic obstructive pulmonary disease, coughing, sputum oversecretion, rhinitis, pain, anxiety, depression, convulsion, Parkinson's disease, incontinence of urine, irritable bowel syndrome, prostate hypertrophy, vomiting, peptic ulcer, retina testing, acute iritis, keratitis, miosis, saliva oversecretion caused by an anesthetic, airway secretion, and/or ulcer;

(46) The pharmaceutical composition according to (40), for treatment and/or prevention of bronchial asthma, bronchitis, chronic obstructive pulmonary disease, coughing, sputum oversecretion, pain, anxiety, depression, convulsion, Parkinson's disease, irritable bowel syndrome, and/or prostate hypertrophy;

(47) The pharmaceutical composition according to (40), for treatment and/or prevention of bronchial asthma and/or chronic obstructive pulmonary disease;

(48) The pharmaceutical composition according to any one of (43) to (47), for via pulmonary administration and/or nasal administration;

(49) Use of a compound or a pharmacologically acceptable salt thereof according to any one of (1) to (39) for production of a pharmaceutical composition;

(50) The use according to (49), wherein the pharmaceutical composition has a bronchodilating effect and an anti-inflammatory effect;

(51) The use according to (49), wherein the pharmaceutical composition is for treatment and/or prevention of a disease mediated by a neurokinin $NK_1$ receptor, a neurokinin $NK_2$ receptor, and/or a muscarine $M_3$ receptor;

(52) The use according to (49), wherein the pharmaceutical composition is intended for treatment and/or prevention of a respiratory disease, an allergic disease, and/or a neurological disease;

(53) The use according to (49), wherein the pharmaceutical composition is intended for treatment and/or prevention of a respiratory disease and/or a neurological disease;

(54) The use according to (49), wherein the pharmaceutical composition is intended for treatment and/or prevention of bronchial asthma, bronchitis, chronic obstructive pulmonary disease, coughing, sputum oversecretion, rhinitis, pain, anxiety, depression, convulsion, Parkinson's disease, incontinence of urine, irritable bowel syndrome, prostate hypertrophy, vomiting, peptic ulcer, retina testing, acute iritis, keratitis, miosis, saliva oversecretion caused by an anesthetic, airway secretion, and/or ulcer;

(55) The use according to (49), wherein the pharmaceutical composition is intended for treatment and/or prevention of bronchial asthma, bronchitis, chronic obstructive pulmonary disease, coughing, sputum oversecretion, pain, anxiety, depression, convulsion, Parkinson's disease, irritable bowel syndrome, and/or prostate hypertrophy;

(56) The use according to (49), wherein the pharmaceutical composition is intended for treatment and/or prevention of bronchial asthma and/or chronic obstructive pulmonary disease;

(57) The use according to any one of (52) to (56), wherein the pharmaceutical composition is intended for via pulmonary administration and/or nasal administration;

(58) A method for treating and/or preventing a disease comprising administering a pharmacologically effective amount of a compound or a pharmacologically acceptable salt thereof according to any one of (1) to (39) to a homeotherm;

(59) The method according to (58), wherein the disease is a disease mediated by a neurokinin $NK_1$ receptor, a neurokinin $NK_2$ receptor, and/or a muscarine $M_3$ receptor;

(60) The method according to (58), wherein the disease is a respiratory disease, an allergic disease, and/or a neurological disease;

(61) The method according to (58), wherein the disease is a respiratory disease and/or a neurological disease;

(62) The method according to (58), wherein the disease is bronchial asthma, bronchitis, chronic obstructive pulmonary disease, coughing, sputum oversecretion, rhinitis, pain, anxiety, depression, convulsion, Parkinson's disease, incontinence of urine, irritable bowel syndrome, prostate hypertrophy, vomiting, peptic ulcer, retina testing, acute iritis, keratitis, miosis, saliva oversecretion caused by an anesthetic, airway secretion, and/or ulcer;

(63) The method according to (58), wherein the disease is bronchial asthma, bronchitis, chronic obstructive pulmonary disease, coughing, sputum oversecretion, pain, anxiety, depression, convulsion, Parkinson's disease, irritable bowel syndrome, and/or prostate hypertrophy;

(64) The method according to (58), wherein the disease is bronchial asthma and/or chronic obstructive pulmonary disease;

(65) The method according to any one of (60) to (64), wherein a compound or a pharmacologically acceptable salt thereof described in any one selected from (1) to (39) is administered by via pulmonary administration and/or by nasal administration; and

(66) The method according to any one of (58) to (65), wherein the homeotherm is a human.

In the present invention, a "halogen atom" is a fluorine atom, a chlorine atom, a bromine atom or an iodine atom, preferably a fluorine atom or a chlorine atom, and more preferably a fluorine atom.

In the present invention, a "$C_1$-$C_6$ alkyl group" is a straight or branched chain alkyl group having 1 to 6 carbon atom(s). For example, the $C_1$-$C_6$ alkyl group is a methyl group, an ethyl group, a propyl group, an isopropyl group, a butyl group, an isobutyl group, an s-butyl group, a t-butyl group, a pentyl group, an isopentyl group a 2-methylbutyl group, a neopentyl group, a 1-ethylpropyl group, a hexyl group, an isohexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group or a 1,2-dimethylbutyl group, preferably a straight or branched chain alkyl group having 1 to 4 carbon atom(s) ($C_1$-$C_4$ alkyl group), more preferably a methyl group or an ethyl group ($C_1$-$C_2$ alkyl group), and even more preferably a methyl group.

In the present invention, a "$C_1$-$C_6$ halogenated alkyl group" is a group in which 1 to 5 same or different "halogen atom"(s) described above bind to the above-described "$C_1$-$C_6$ alkyl group". For example, the $C_1$-$C_6$ halogenated alkyl group may be a trifluoromethyl group, a trichloromethyl group, a difluoromethyl group, a dichloromethyl group, a dibromomethyl group, a fluoromethyl group, a 2,2,2-trifluoroethyl group, a 2,2,2-trichloroethyl group, a 2-bromoethyl group, a 2-chloroethyl group or a 2-fluoroethyl group, preferably a group in which 1 to 5 same or different "halogen atom"(s) described above bind to the above-described "$C_1$-$C_4$ alkyl group" ($C_1$-$C_4$ halogenated alkyl group), more preferably a group in which 1 to 5 same or different "halogen atom"(s) described above bind to the above-described "$C_1$-$C_2$ alkyl group" ($C_1$-$C_2$ halogenated alkyl group), and even more preferably a trifluoromethyl group or a fluoromethyl group.

In the present invention, a "$C_1$-$C_6$ alkoxy group" is a straight or branched chain alkoxy group having 1 to 6 carbon atom(s) in which the above-described "$C_1$-$C_6$ alkyl group" binds to an oxygen atom. For example, the $C_1$-$C_6$ alkoxy group may be a methoxy group, an ethoxy group, a propoxy group, an isopropoxy group, a butoxy group, an isobutoxy group, an s-butoxy group, a t-butoxy group, a pentoxy group, a 2-methylbutoxy group, a 3-ethylpropoxy group, a neopentoxy group, a hexyloxy group or a 2,3-dimethylbutoxy group, preferably a straight or branched chain alkoxy group having 1 to 4 carbon atom(s) ($C_1$-$C_4$ alkoxy group), more preferably a methoxy group, an ethoxy group, a propoxy group or an isopropoxy group ($C_1$-$C_3$ alkoxy group), even more preferably a methoxy group or an ethoxy group ($C_1$-$C_2$ alkoxy group), and particularly preferably a methoxy group.

In the present invention, a "$C_1$-$C_6$ halogenated alkoxy group" is a group in which 1 to 5 same or different "halogen atom"(s) described above bind to the above-described "$C_1$-$C_6$ alkoxy group". For example, the $C_1$-$C_6$ halogenated alkoxy group may be a trifluoromethoxy group, a trichloromethoxy group, a difluoromethoxy group, a dichloromethoxy group, a dibromomethoxy group, a fluoromethoxy group, a 2,2,2-trifluoroethoxy group, a 2,2,2-trichloroethoxy group, a 2-chloroethoxy group, a 2-fluoroethoxy group or a pentafluoroethoxy group, preferably a group in which 1 to 5 same or different "halogen atom"(s) described above bind to the above-described "$C_1$-$C_4$ alkoxy group" ($C_1$-$C_4$ halogenated alkoxy group), more preferably a group in which 1 to 5 same or different "halogen atom"(s) described above bind to the above-described "$C_1$-$C_2$ alkoxy group" ($C_1$-$C_2$ halogenated alkoxy group), and even more preferably a trifluoromethoxy group.

In the present invention, a "$C_2$-$C_7$ alkylcarbonyloxy group" is a group in which a carbonyl group bonded to one of the above-described "$C_1$-$C_6$ alkyl group" binds to an oxygen atom. For example, the $C_2$-$C_7$ alkylcarbonyloxy group may be an acetoxy group, a propionyloxy group, a butyryloxy group, an isobutyryloxy group, a pentanoyloxy group, a pivaloyloxy group, a varelyloxy group or an isovarelyloxy group, preferably a group in which a carbonyl group bonded to one of the above-described "$C_1$-$C_4$ alkyl group" binds to an oxygen atom ($C_2$-$C_5$ alkylcarbonyloxy group), more preferably an acetoxy group or a propionyloxy group ($C_2$-$C_3$ alkylcarbonyloxy group), and even more preferably an acetoxy group.

In the present invention, a "$C_2$-$C_7$ alkoxycarbonyl group" is a group in which the above-described "$C_1$-$C_6$ alkoxy group" binds to a carbonyl group. For example, the $C_2$-$C_7$ alkoxycarbonyl group may be a methoxycarbonyl group, an ethoxycarbonyl group, a propoxycarbonyl group, an isopropoxycarbonyl group, a butoxycarbonyl group or a t-butoxycarbonyl group, preferably a group in which the above-described "$C_1$-$C_4$ alkoxy group" binds to a carbonyl group ($C_2$-$C_5$ alkoxycarbonyl group), and more preferably a methoxycarbonyl group or an ethoxycarbonyl group ($C_2$-$C_3$ alkoxycarbonyl group).

In the present invention, a "$C_2$-$C_7$ alkoxycarbonyloxy group" is a group in which a carbonyl group bonded to one of the above-described "$C_1$-$C_6$ alkoxy group" binds to an oxygen atom. For example, the $C_2$-$C_7$ alkoxycarbonyloxy group may be a methoxycarbonyloxy group, an ethoxycarbonyloxy group, a propoxycarbonyloxy group, an isopropoxycarbonyloxy group, a butoxycarbonyloxy group, an s-butoxycarbonyloxy group or a t-butoxycarbonyloxy group, preferably a group in which a carbonyl group bonded to one of the above-described "$C_1$-$C_4$ alkoxy group" binds to an oxygen atom ($C_2$-$C_5$ alkoxycarbonyloxy group), more preferably a methoxycarbonyloxy group or an ethoxycarbonyloxy group ($C_2$-$C_3$ alkoxycarbonyloxy group), and even more preferably a methoxycarbonyloxy group.

In the present invention, a "$C_3$-$C_6$ cycloalkyl group" is a cyclopropyl group, a cyclobutyl group, a cyclopentyl group or a cyclohexyl group, and preferably a cyclopropyl group.

In the present invention, a "($C_3$-$C_6$ cycloalkyl)methyl group" is a cyclopropylmethyl group, a cyclobutylmethyl group, a cyclopentylmethyl group or a cyclohexylmethyl group, and preferably a cyclopropylmethyl group.

In the present invention, a "heterocyclic group" is a 4- to 7-membered heterocyclic group which contains 1 to 3 sulfur atom(s), oxygen atom(s) or/and nitrogen atom(s) and may further contain 1 or 2 nitrogen atom(s) and in which the sulfur atom(s) may be bonded to 2 oxygen atoms. For example, the heterocyclic group may be an "aromatic heterocyclic group" such as a furyl group, a thienyl group, a pyrrolyl group, an azepinyl group, a pyrazolyl group, an imidazolyl group, an oxazolyl group, an isoxazolyl group, a thiazolyl group, an isothiazolyl group, a 1,3,4-oxadiazolyl group, a 1,3,4-thiadiazolyl group, a triazolyl group, a tetrazolyl group, a thiadiazolyl group, a pyranyl group, a pyridyl group, a pyridazinyl group, a pyrimidinyl group or a pyrazinyl group or a "saturated or partially unsaturated heterocyclic group" such as a tetrahydropyranyl group, a tetrahydrothienyl group, a morpholinyl group, a thiomorpholinyl group, a pyrrolidinyl group, a pyrrolinyl group, an imidazolidinyl group, a pyrazolidinyl group, a piperidinyl group, a piperazinyl group, an oxazolinyl group, an oxazolidinyl group, an isoxazolidinyl group, a thiazolinyl group, a thiazolidinyl group, a pyrazolidinyl group, a dioxolanyl group, a dioxanyl group, or a 5,6-dihydro-4H-1,3-oxazine group. The above-described heterocyclic group may be condensed with another cyclic group such as a benzene ring ("condensed bicyclic heterocyclic group"). For example, the condensed bicyclic heterocyclic group may be a benzothienyl group, a benzothiazolyl group, a benzooxazolyl group, an isobenzofuranyl group, a 1,3-dihydroisobenzofuranyl group, a quinolyl group, a 1,3-benzodioxolanyl group, a 1,4-benzodioxanyl group, an indolyl group, an isoindolyl group or an indolinyl group. The heterocyclic group is preferably a pyridyl group or a pyrimidinyl group.

In the present invention, a "phenyl group that may be substituted with 1 to 5 group(s) independently selected from Substituent Group A" is a phenyl group or a phenyl group that is substituted with 1 to 5 group(s) independently selected from Substituent Group A, preferably a phenyl group that may be substituted with 1 to 5 group(s) independently selected from Substituent Group A, more preferably a 4-fluorophenyl group, a 3,4-difluorophenyl group, a 3,4-dichlorophenyl group or a 3-bromo-4-fluorophenyl group, even more preferably a 4-fluorophenyl group in the case of $R^3$, and more preferably a 3,5-bis(trifluoromethyl)phenyl group or a 3,4,5-trimethoxyphenyl group, even more preferably a 3,5-bis(trifluoromethyl)phenyl group in the case of $R^4$.

In the present invention, a "heterocyclic group that may be substituted with 1 to 3 group(s) independently selected from Substituent Group A" is the above-described "heterocyclic group" or the above-described "heterocyclic group" that is substituted with 1 to 3 group(s) independently selected from Substituent Group A, preferably a pyridyl group or a pyrimidinyl group that may be substituted with 1 to 3 group(s) independently selected from Substituent Group A.

In the present invention, a "$C_1$-$C_{10}$ alkylene group" is a divalent group obtained by removing 2 hydrogen atoms from a straight or branched chain saturated hydrocarbon having 1 to 10 carbon atom(s). For example, the $C_1$-$C_{10}$ alkylene group may be a methylene group, a methylmethylene group, an ethylene group, a propylene group, a trimethylene group, a tetramethylene group, a 1-methyltrimethylene group, a 2-methyltrimethylene group, a 3-methyltrimethylene group, a pentamethylene group or a hexamethylene group, preferably a divalent group obtained by removing 2 hydrogen atoms from a straight or branched chain saturated hydrocarbon having 1 to 8 carbon atom(s) ($C_1$-$C_8$ alkylene group), and more preferably an ethylene group, a trimethylene group, a tetramethylene group, a pentamethylene group or a hexamethylene group.

In the present invention, a "$C_1$-$C_{10}$ alkylene group in which one of the methylene groups is replaced by an oxygen atom" is the above-described "$C_1$-$C_{10}$ alkylene group" in which one of the methylene groups is replaced by an oxygen atom. For example, the $C_1$-$C_{10}$ alkylene group in which one of the methylene groups is replaced by an oxygen atom may be a methyleneoxymethylene group, a methyleneoxyethylene group, an ethyleneoxymethylene group, an ethyleneoxyethylene group, a methyleneoxytrimethylene group, a methyleneoxytetramethylene group or a methyleneoxypentamethylene group, preferably a $C_3$-$C_8$ alkylene group in which one of the methylene groups is replaced by an oxygen atom, and more preferably a methyleneoxytrimethylene group, an ethyleneoxyethylene group or a trimethyleneoxymethylene group.

In the present invention, a "group represented by the formula —N($R^5$)—" is a divalent group obtained by removing 2 hydrogen atoms from a "compound represented by the formula $R^5NH_2$", preferably an amino group, a methylamino group or an ethylamino group.

In the present invention, a "group represented by the formula —N($R^5$)—C(=O)—" is a divalent group obtained by removing 2 hydrogen atoms from a "compound represented by the formula H—N($R^5$)—C(=O)—H", preferably, an aminocarbonyl group or a methylaminocarbonyl group, and more preferably a methylaminocarbonyl group.

In the present invention, a "group represented by the formula —C(=O)—N($R^5$)—" is a divalent group obtained by removing 2 hydrogen atoms from a "compound represented by the formula H—C(=O)—N($R^5$)—H", preferably a carbonylamino group or a carbonylmethylamino group, and more preferably a carbonylmethylamino group.

In the present invention, a "group represented by the formula —N($R^5$)—C(=O)—O—" is a divalent group obtained by removing 2 hydrogen atoms from a "compound represented by the formula H—N($R^5$)—C(=O)—O—H", and preferably an aminocarbonyloxy group.

In the present invention, a "group represented by the formula —O—C(=O)—N($R^5$)—" is a divalent group obtained by removing 2 hydrogen atoms from a "compound represented by the formula H—O—C(=O)—N($R^5$)—H", preferably an oxycarbonylamino group.

In the present invention, a "phenylene group" is a divalent group obtained by removing 2 hydrogen atoms from benzene, for example, a 1,2-phenylene group, a 1,3-phenylene group or a 1,4-phenylene group, preferably a 1,3-phenylene group or a 1,4-phenylene group, and more preferably a 1,4-phenylene group.

In the present invention, a "heteroarylene group" is a divalent group obtained by removing 1 hydrogen atom each on two different carbon atoms of a "heterocyclic ring" of the above-described "heterocyclic group" (provided that the heterocyclic ring contains 2 or more carbon atoms), preferably a thienylene group, a thiazolylene group, a pyridinylene group, a pyrimidinylene group, a pyridazinylene group or a benzothiazolylene group, and more preferably a thienylene group, a thiazolylene group, a pyridinylene group, a pyrimidinylene group or a benzothiazolylene group.

In the present invention, a "phenylene group that may be substituted with 1 to 4 group(s) independently selected from Substituent Group A" is a phenylene group or a phenylene group that is substituted with 1 to 4 group(s) independently selected from Substituent Group A, preferably a phenylene group or a phenylene group that is substituted with 1 or 2 group(s) independently selected from a halogen atom and a $C_1$-$C_6$ alkyl group, more preferably a 1,3-phenylene group, a 1,4-phenylene group, a group represented by the formula (IV), a group represented by the formula (V) or a group represented by the formula (VI), and even more preferably a 1,4-phenylene group.

In the present invention, a "heteroarylene group that may be substituted with 1 or 2 group(s) independently selected from Substituent Group A" is a heteroarylene group or a heteroarylene group that is substituted with 1 or 2 group(s) independently selected from Substituent Group A, preferably a thienylene group, a thiazolylene group, a pyridinylene group, a pyrimidinylene group, a benzothiazolylene group, or a thienylene group, a thiazolylene group, a pyridinylene group, a pyrimidinylene group or a benzothiazolylene group that is substituted with one group selected from a halogen atom and a $C_1$-$C_6$ alkyl group, more preferably a 2,5-thienylene group, a group represented by the formula (VII), a group represented by the formula (VIII), a group represented by the formula (IX), a group represented by the formula (X), a group represented by the formula (XI) or a group represented by the formula (XII), and even more preferably a 2,5-thienylene group, a group represented by the formula (IX), a group represented by the formula (X), a group represented by the formula (XI) or a group represented by the formula (XII).

In the present invention, when "s represents 1," $L^1$ binds to the 2-, 3-, or 4-position of a phenyl group, and preferably binds to the 3- or 4-position.

In the present invention, preferred $R^1$ is a hydrogen atom or a $C_1$-$C_6$ alkyl group, more preferred $R^1$ is a hydrogen atom, a methyl group, or an ethyl group, and even more preferred $R^1$ is a hydrogen atom or a methyl group.

In the present invention, preferred $R^2$ is a $C_1$-$C_6$ alkyl group, and more preferred $R^2$ is a methyl group.

In the present invention, preferred $R^3$ is a phenyl group that may be substituted with 1 to 5 group(s) independently selected from Substituent Group A, more preferred $R^3$ is a 4-fluorophenyl group, a 3,4-difluorophenyl group, a 3,4-dichlorophenyl group, or a 3-bromo-4-fluorophenyl group, and even more preferred $R^3$ is a 4-fluorophenyl group.

In the present invention, preferred $R^4$ is a phenyl group that may be substituted with 1 to 5 group(s) independently selected from Substituent Group A, more preferred $R^4$ is a 3,5-bis(trifluoromethyl)phenyl group or a 3,4,5-trimethoxyphenyl group, and even more preferred $R^4$ is a 3,5-bis(trifluoromethyl)phenyl group.

In the present invention, preferred $L^1$ is a $C_1$-$C_8$ alkylene group or a $C_3$-$C_8$ alkylene group in which one of methylene group(s) is replaced by an oxygen atom, more preferred $L^1$ is an ethylene group, a trimethylene group, a tetramethylene group, a pentamethylene group, a hexamethylene group, a methyleneoxytrimethylene group, an ethyleneoxyethylene group or a trimethyleneoxymethylene group, and even more preferred $L^1$ is an ethylene group, a trimethylene group, a tetramethylene group, a pentamethylene group, a methyleneoxytrimethylene group, an ethyleneoxyethylene group or a trimethyleneoxymethylene group.

In the present invention, preferred $L^2$ is a group represented by the formula —N($R^5$)—C(=O)— or a group represented by the formula —C(=O)—N($R^5$)—.

In the present invention, preferred $R^5$ is a hydrogen atom, a $C_1$-$C_6$ alkyl group or a $C_3$-$C_6$ cycloalkyl group, more preferred $R^5$ is a hydrogen atom, a methyl group or a cyclopropyl group, and even more preferred $R^5$ is a methyl group.

In the present invention, preferred E is a phenylene group that may be substituted with 1 or 2 group(s) independently selected from a halogen atom and a $C_1$-$C_6$ alkyl group or a thienylene group, a thiazolylene group, a pyridinylene group, a pyrimidinylene group or a benzothiazolylene group that may be substituted with one group selected from a halogen atom and a $C_1$-$C_6$ alkyl group, more preferred E is a 1,3-phenylene group, a 1,4-phenylene group, a 2,5-thienylene group, a group represented by the formula (IV), a group represented by the formula (V), a group represented by the formula (VI), a group represented by the formula (VII), a group represented by the formula (VIII), a group represented by the formula (IX), a group represented by the formula (X), a group represented by the formula (XI) or a group represented by the formula (XII), and even more preferred E is a 1,4-phenylene group, a 2,5-thienylene group, a group represented by the formula (IX), a group represented by the formula (X), a group represented by the formula (XI) or a group represented by the formula (XII).

In the present invention, preferred m is 2.

In the present invention, preferred n is an integer of 0 to 2, and more preferred n is 0 or 1.

In the present invention, preferred p is 0 or 1, and more preferred p is 0.

In the present invention, preferred q is an integer of 1 to 6, and more preferred q is 2 or 3.

In the present invention, preferred r is 1.

In the present invention, preferred s is 0.

In the present invention, a preferred general formula (I) is the general formula (II) or the general formula (III), and a more preferred general formula (I) is the general formula (II).

The compound or pharmacologically acceptable salt thereof represented by the general formula (I) of the present invention includes all isomers (such as a keto-enol isomer, a diastereomer, an optical isomer, a rotamer, etc.).

The compound or pharmacologically acceptable salt thereof represented by the general formula (I) of the present invention has various isomers because asymmetric carbon atom(s) exist in the molecule. These isomers and mixtures of these isomers of the present invention are all represented by a single formula, specifically, the general formula (I). Accordingly, the present invention includes all of these isomers and mixtures of these isomers in any ratio.

The aforementioned stereoisomers can be obtained by synthesizing the compound of the present invention using a stereospecific raw material compound or using an asymmetric synthesis or asymmetric induction technique or by isolating the synthesized compound of the present invention by a common optical resolution or separation method if desired.

The compound or pharmacologically acceptable salt thereof represented by the general formula (I) of the present invention may contain unnatural proportions of atomic isotopes at one or more of the atoms that constitute such compounds. Examples of atomic isotopes include deuterium ($^2$H), tritium ($^3$H), iodine-125 ($^{125}$I) and carbon-14 ($^{14}$C). The above-described compounds may be radiolabeled with radioisotopes such as tritium ($^3$H), iodine-125 ($^{125}$I) or carbon-14 ($^{14}$C). Radiolabeled compounds are useful as therapeutic or prophylactic agents, research reagents such as assay reagents, and diagnostic agents such as in vivo diagnostic imaging agents. All isotopic variants of the compounds of the present invention, whether radioactive or not, are included in the scope of the present invention.

A "pharmacologically acceptable salt thereof" refers to a salt that is free of prominent toxicity and which can be used as a pharmaceutical. The compound represented by the general formula (I) of the present invention can be converted to a salt by reacting with an acid in the case the compound has a basic group such as an amino group, or by reacting with a base in the case of having an acidic group such as a carboxyl group.

Examples of salts based on a basic group include salts of hydrohalic acids such as hydrofluorides, hydrochlorides, hydrobromides or hydroiodides, salts of inorganic acids such as nitrates, perchlorates, sulfates or phosphates; $C_1$-$C_6$ alkylsulfonates such as methanesulfonates, trifluoromethanesulfonates or ethanesulfonates, arylsulfonates such as benzenesulfonates or p-toluenesulfonates; salts of organic acids such as acetates, malates, fumarates, succinates, citrates, ascorbates, tartrates, oxalates or maleates; and, salts of amino acids such as salts of glycine, lysine, arginine, ornithine, glutamic acid and aspartic acid.

On the other hand, examples of salts based on acidic groups include metal salts such as alkali metal salts such as sodium salts, potassium salts or lithium salts, alkaline earth metal salts such as calcium salts or magnesium salts, metal salts such as aluminum salts or iron salts; amine salts such as inorganic salts such as ammonium salts, or organic salts such as salts of t-octylamine, dibenzylamine, morpholine, glucosamine, phenylglycine alkyl esters, ethylenediamine, N-methylglucamine, guanidine, diethylamine, triethylamine, dicyclohexylamine, N,N'-dibenzylethylenediamine, chloroprocaine, procaine, diethanolamine, N-benzylphenethylamine, piperazine, tetramethylammonium or tris(hydroxymethyl)aminomethane; and, salts of amino acids such as salts of glycine, lysine, arginine, ornithine, glutamic acid and aspartic acid.

The compound or pharmacologically acceptable salt thereof represented by the general formula (I) of the present invention may become a hydrate by incorporating water molecule(s) by being left in the atmosphere or by recrystallizing, and such hydrates are also included in the salts of the present invention.

The compound or pharmacologically acceptable salt thereof represented by the general formula (I) of the present invention may become a solvate by absorbing another type of solvent, and such solvates are also included in the salts of the present invention.

A "compound having an antagonistic effect on a neurokinin $NK_1$ receptor, a neurokinin $NK_2$ receptor, and a muscarine $M_3$ receptor" is a compound having all of a neurokinin $NK_1$ receptor antagonistic effect, a neurokinin $NK_2$ receptor antagonistic effect, and a muscarine $M_3$ receptor antagonistic effect.

The expression "having a neurokinin $NK_1$ receptor antagonistic effect" means to have an ability to bind specifically to a crude membrane sample of neurokinin $NK_1$ receptor-expressing cells and have a neurokinin $NK_1$ receptor antagonistic effect evaluated by inhibiting or suppressing an action of a neurokinin $NK_1$ receptor agonist, such as substance P-induced airway contraction. Whether a specific compound has such an antagonistic effect can be easily determined by those skilled in the art according to the following method, for example.

Examples of such a method include a method in which the ability to bind to a neurokinin $NK_1$ receptor is measured according to the measurement method (2.3 Receptor binding assay) described in the literature (European Journal of Pharmacology, 2008, vol. 586, 306-312) and airway contraction is measured according to the literature (a modified method of the methods described in British Journal of Pharmacology and Chemotherapy, 1962, vol. 19, 168-182 and European Journal of Pharmacology, 1992, vol. 231, 31-38). When the ability to bind to a neurokinin $NK_1$ receptor is a predetermined constant value (Ki=1 µM, preferably Ki=10 nM) or lower and the dose intratracheally administered for the suppression effect is a predetermined constant value ($ID_{50}$=1 mg/kg, preferably $ID_{50}$=50 µg/kg) or lower, an antagonistic effect is determined.

The receptor of substance P is a neurokinin $NK_1$ receptor.

The expression "having a neurokinin $NK_2$ receptor antagonistic effect" means to have an ability to bind specifically to a crude membrane sample of neurokinin $NK_1$ receptor-expressing cells and have a neurokinin $NK_2$ receptor antagonistic effect evaluated by inhibiting or suppressing an action of a neurokinin $NK_2$ receptor agonist, such as neurokinin A-induced airway contraction. Whether a specific compound has such an antagonistic effect can be easily determined by those skilled in the art according to the following method, for example.

Examples of such a method include a method in which the ability to bind to a neurokinin $NK_2$ receptor is measured according to the measurement method (2.3 Receptor binding assay) described in the literature (European Journal of Pharmacology, 2008, vol. 586, 306-312) and airway contraction is measured according to the measurement method (2.6 Bronchoconstriction in guinea pigs). When the ability to bind to a neurokinin $NK_2$ receptor is a predetermined constant value (Ki=1 µM, preferably Ki=10 nM) or lower and the dose intratracheally administered for the suppression effect is a predetermined constant value ($ID_{50}$=1 mg/kg, preferably $ID_{50}$=50 µg/kg) or lower, an antagonistic effect is determined.

The expression "having a muscarine $M_3$ receptor antagonistic effect" means to have an ability to bind specifically to a crude membrane sample of muscarine $M_3$ receptor-expressing cells and have a muscarine $M_3$ receptor antagonistic effect evaluated by inhibiting or suppressing an action of a muscarine $M_3$ receptor agonist, such as acetylcholine-induced airway contraction. Whether a specific compound has such an antagonistic effect can be easily determined by those skilled in the art according to the following method, for example.

Examples of such a method include a method in which the ability to bind to a muscarine $M_3$ receptor is measured according to the measurement method (Human muscarinic receptor studies) described in the literature (Life Sciences, 1993, vol. 52, 537-544) and airway contraction is measured according to the measurement method (a modified method of the method described in Bronchospasmolysis in anaesthetized dogs). When the ability to bind to a muscarine $M_3$ receptor is a predetermined constant value (Ki=1 µM, preferably Ki=10 nM) or lower and the dose intratracheally administered for the suppression effect is a predetermined constant value ($ID_{50}$=1 mg/kg, preferably $ID_{50}$=50 µg/kg) or lower, an antagonistic effect is determined.

Such a method for identifying a "compound having an antagonistic effect on a neurokinin $NK_1$ receptor, a neurokinin $NK_2$ receptor, and a muscarine $M_3$ receptor" also falls within the scope of the present invention. This method comprises (i) a step of determining whether a test compound has a neurokinin $NK_1$ receptor antagonistic effect; (ii) a step of determining whether the test compound has a neurokinin $NK_2$ receptor antagonistic effect; and (iii) a step of determining whether the test compound has a muscarine $M_3$ receptor antagonistic effect. In this method, the steps (i) to (iii) can be performed in any order, or two or more steps can be performed in parallel. A test compound that is determined to have a receptor antagonistic effect in all the steps (i) to (iii) is identified as a "compound having an antagonistic effect on a neurokinin $NK_1$ receptor, a neurokinin $NK_2$ receptor, and a muscarine $M_3$ receptor."

The step (i) comprises (a) a step of measuring an ability of a test compound to bind to a neurokinin $NK_1$ receptor and (b) a step of determining whether the test compound inhibits or suppresses an action of a neurokinin $NK_1$ receptor agonist. Examples of the neurokinin $NK_1$ receptor agonist include substance P. Examples of the action of a neurokinin $NK_1$ receptor agonist include substance P-induced airway contraction.

The step (ii) comprises (c) a step of measuring an ability of a test compound to bind to a neurokinin $NK_2$ receptor and (d) a step of determining whether the test compound inhibits or suppresses an action of a neurokinin $NK_2$ receptor agonist. Examples of the neurokinin $NK_2$ receptor agonist include neurokinin A. Examples of the action of a neurokinin $NK_2$ receptor agonist include neurokinin A-induced airway contraction.

The step (iii) comprises (e) a step of measuring an ability of a test compound to bind to a muscarine $M_3$ receptor and (f) a step of determining whether the test compound inhibits or suppresses an action of a muscarine $M_3$ receptor agonist. Examples of the muscarine $M_3$ receptor agonist include acetylcholine and methacholine. Examples of the action of a muscarine $M_3$ receptor agonist include acetylcholine-induced airway contraction.

For the above-described step of measuring an ability to bind to each receptor, tissues or cells of an animal in which the receptor polypeptide is endogenously expressed, a transgenic animal or a cell membrane fraction in which a recombinant receptor polypeptide is expressed, intact cells, or the like and a labeled substance bonded to each receptor can be used.

Furthermore, a compound identified as a "compound having an antagonistic effect on a neurokinin $NK_1$ receptor, a neurokinin $NK_2$ receptor, and a muscarine $M_3$ receptor" in the method of the present invention is useful as a medicament and particularly useful as an agent for preventing or treating bronchial asthma, bronchitis, chronic obstructive pulmonary disease, coughing, sputum oversecretion, rhinitis, pain, anxiety, depression, convulsion, Parkinson's disease, incontinence of urine, irritable bowel syndrome, prostate hypertrophy, vomiting, peptic ulcer, retina testing, acute iritis, keratitis, miosis, saliva oversecretion caused by an anesthetic, airway secretion, and/or ulcer. Therefore, a method of the present invention for identifying the "compound having an antagonistic effect on a neurokinin $NK_1$ receptor, a neurokinin $NK_2$ receptor, and a muscarine $M_3$ receptor" is also included in the present invention as a method for identifying an agent for preventing or treating such diseases.

As compounds having an antagonistic effect on a neurokinin $NK_1$ receptor and/or a neurokinin $NK_2$ receptor, compounds having various structures are known. Examples of these compounds include compounds described in U.S. Pat. Nos. 6,511,975, 7,365,067, 2003/4157, U.S. Pat. Nos. 5,512,570, and 5,576,317, European Patent Nos. 443132 and 5080893, and Expert Opin. Investig. Drugs (2009) 18 (12): 1843-1864.

As compounds having a muscarine $M_3$ receptor antagonistic effect, compounds having various structures are known. Examples of these compounds include compounds described in U.S. Patent Publication Nos. 2004/167167, 2005/203131, 2006/281740, and 2005/203167, European Patent No. 1213281, U.S. Pat. Nos. 3,472,861, and 7,070,800, Expert Opin. Ther. Patents (2006) 16 (9): 1315-1320, and Expert Opin. Ther. Patents (2006) 16 (9): 1321-1326.

Advantageous Effects of Invention

The compound of the present invention or a pharmacologically acceptable salt thereof represented by the general formula (I) is useful as a medicament because the compound exhibits an antagonistic effect on a neurokinin $NK_1$ receptor, a neurokinin $NK_2$ receptor, and a muscarine $M_3$ receptor and particularly useful as an agent for preventing or treating bronchial asthma, bronchitis, chronic obstructive pulmonary disease, coughing, sputum oversecretion, rhinitis, pain, anxiety, depression, convulsion, Parkinson's disease, incontinence of urine, irritable bowel syndrome, prostate hypertrophy, vomiting, peptic ulcer, retina testing, acute iritis, keratitis, miosis, saliva oversecretion caused by an anesthetic, airway secretion, and/or ulcer.

The three most common complaints of chronic obstructive pulmonary disease (COPD) are breathlessness, chronic coughing, and chronic sputum secretion. The underlying cause of the disease is inflammation of the airway. Neurokinin A and substance P are reported to be associated with coughing and sputum as well as inflammation in COPD. Acetylcholine is associated with breathlessness. The compound of the present invention or a pharmacologically acceptable salt thereof represented by the general formula (I) suppresses all the major symptoms of COPD by antagonizing a neurokinin $NK_1$ receptor, a neurokinin $NK_2$ receptor, and a muscarine $M_3$ receptor simultaneously, and can also contribute to suppression of progression of pathological conditions by resolving inflammation, which is an underlying cause.

The compound of the present invention or a pharmacologically acceptable salt thereof represented by the general formula (I) exhibits sustained drug efficacy.

Cytotoxicities noted in neurokinin $NK_1$ receptor antagonists, neurokinin $NK_2$ receptor antagonists, and neurokinin $NK_1$ receptor and neurokinin $NK_2$ receptor antagonists are reduced in the compound of the present invention or a pharmacologically acceptable salt thereof represented by the general formula (I).

When a combined drug of neurokinin $NK_1$ receptor antagonists, neurokinin $NK_2$ receptor antagonists (or neurokinin $NK_1$ receptor and neurokinin $NK_2$ receptor antagonists), and muscarine $M_3$ receptor antagonists is used or these antagonists are concomitantly used, distributions in the lungs need to be examined for the respective ingredients. However, the distributions are extremely complicated. Distributions in the lungs of a single compound such as the compound of the present invention or a pharmacologically acceptable salt thereof represented by the general formula (I) can be easily examined, and drug efficacy can be confirmed by determining that the compound reaches an affected area.

The compound of the present invention or a pharmacologically acceptable salt thereof represented by the general formula (I) is also excellent in terms of high safety.

MODE FOR CARRYING OUT THE INVENTION

The compound represented by the general formula (I) of the present invention can be produced by Methods A to I described below.

The compound represented by the general formula (I) of the present invention can be synthesized by successively binding two or more compounds selected from compounds represented by a general formula (XIII) through a general formula (XXIX), it being understood that the order of binding is arbitrary, and compounds can be bonded in any order. Furthermore, an amino group, a hydroxy group, and/or a carboxyl group may be protected by using a protective group if necessary. The step requiring protection and deprotection is performed according to a known method (for example, "Protective Groups in Organic Synthesis" [the method described in Theodora W. Greene, Peter G. M. Wuts, 1999, Wiley-Interscience Publication]).

Compounds represented by the general formula (XIII) through the general formula (XXIX) are known compounds or are produced easily according to a known method or a similar method using a known compound as a starting material. For example, a compound represented by the general formula (XIII) is produced according to U.S. Patent Publication No. 2005/203131.

[Formula 5]

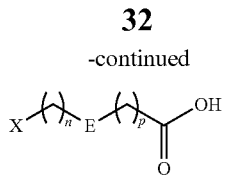
(XIII)

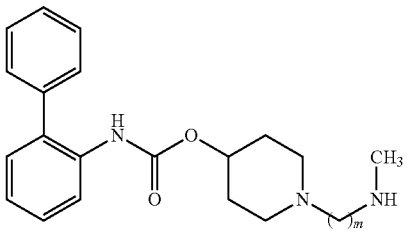
(XIV)

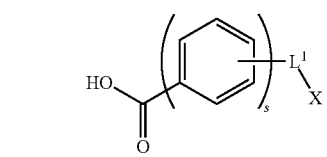
(XV)

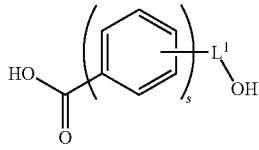
(XVI)

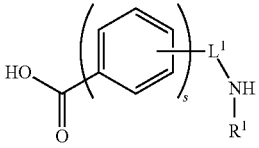
(XVII)

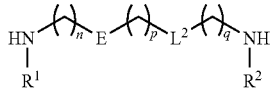
(XVIII)

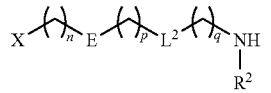
(XIX)

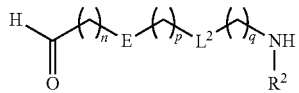
(XX)

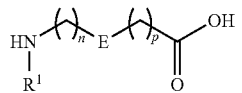
(XXI)

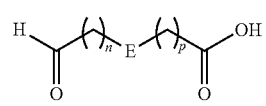
(XXII)

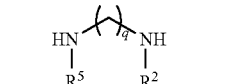
(XXIII)

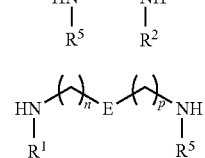
(XXIV)

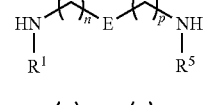
(XXV)

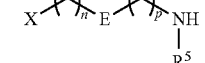
(XXVI)

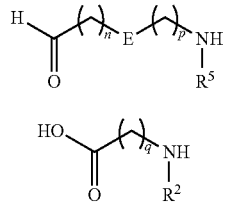
(XXVII)

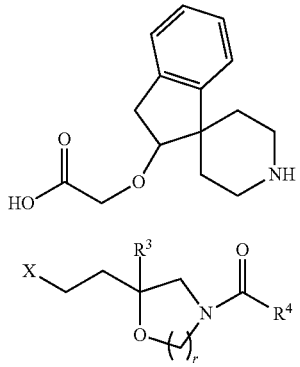
(XXVIII)

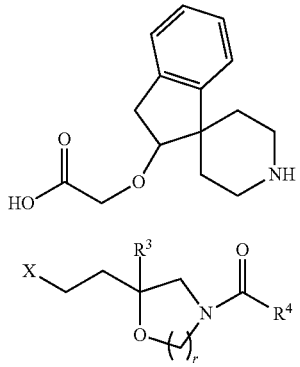
(XXIX)

$R^1, R^2, R^3, R^4, R^5, L^1, L^2, E, m, n, p, q, r$, and $s$ represent the same meanings as defined above, and X represents a leaving group.

The "leaving group" in the definition of X is usually a group that is eliminated as a nucleophilic residue. For example, the leaving group may be a halogen atom such as a fluorine atom, a chlorine atom, a bromine atom or an iodine atom; a lower alkanesulfonyloxy group such as a methanesulfonyloxy group or an ethanesulfonyloxy group; a lower halogenoalkanesulfonyloxy group such as a trifluoromethanesulfonyloxy group or a pentafluoroethanesulfonyloxy group; an arylsulfonyloxy group such as a benzenesulfonyloxy group, a p-toluenesulfonyloxy group or a p-nitrobenzenesulfonyloxy group, preferably a halogen atom, and more preferably a bromine atom or an iodine atom.

The following Methods A to I show methods of bonding at binding sites of compounds represented by the general formula (XIII) through the general formula (XXIX).

The solvent used in a reaction at each step of the following Methods A to I is not particularly limited so long as the solvent does not inhibit the reaction and dissolves the starting material to some extent, and, for example, is selected from the following solvent group. The solvent group consists of hydrocarbons such as pentane, hexane, heptane, octane, petroleum ether, ligroin and cyclohexane; amides such as formamide, N,N-dimethylformamide, N,N-dimethylacetamide, N-methyl-2-pyrrolidone, N-methyl-2-pyrrolidinone and hexamethylphosphoric triamide; ethers such as diethyl ether, diisopropyl ether, tetrahydrofuran, dioxane, dimethoxyethane, diethylene glycol dimethyl ether and cyclopentyl methyl ether; alcohols such as methanol, ethanol, n-propanol, i-propanol, n-butanol, 2-butanol, 2-methyl-1-propanol, t-butanol, isoamyl alcohol, diethylene glycol, glycerine, octanol, cyclohexanol and methyl cellosolve; sulfoxides such as dimethyl sulfoxide; sulfones such as sulfolane; nitriles such as acetonitrile, propionitrile, butyronitrile and isobutyronitrile; esters such as ethyl formate, ethyl acetate, propyl acetate, butyl acetate and diethyl carbonate; ketones such as acetone, methyl ethyl ketone, 4-methyl-2-pentanone, methyl isobutyl ketone, isophorone and cyclohexanone; nitro compounds such as nitroethane and nitrobenzene; halogenated hydrocarbons such as dichloromethane, 1,2-dichloroethane, chlorobenzene, dichlorobenzene, chloroform and carbon tetrachloride; aromatic hydrocarbons such as benzene, toluene and xylene; carboxylic acids such as acetic acid, formic acid, propionic acid, butyrylic acid and trifluoroacetic acid; amines such as N-methylmorpholine, triethylamine, tripropylamine, tributylamine, diisopropylethylamine, dicyclohexylamine, N-methylpiperidine, pyridine, 2,6-lutidine, 4-pyrrolidinopyridine, picoline, 4-dimethylaminopyridine, 2,6-di(t-butyl)-4-methylpyridine, quinoline, N,N-dimethylaniline, N,N-diethylaniline, 1,5-diazabicyclo[4.3.0]nona-5-ene (DBN), 1,4-diazabicyclo[2.2.2]octane (DABCO), 1,8-diazabicyclo[5.4.0]undeca-7-ene (DBU) and piperidine; water; and mixed solvents of these solvents.

Examples of a base used in a reaction at each step of the following Methods A to I include inorganic bases such as alkali metal carbonates such as sodium carbonate, potassium carbonate, lithium carbonate and cesium carbonate; alkali metal hydrogencarbonates such as sodium hydrogencarbonate, potassium hydrogencarbonate and lithium hydrogencarbonate; alkali metal acetates such as sodium acetate, potassium acetate, lithium acetate and cesium acetate; alkali metal hydrides such as lithium hydride, sodium hydride and potassium hydride; alkali metal hydroxides such as sodium hydroxide, potassium hydroxide, barium hydroxide and lithium hydroxide; and alkali metal fluorides such as sodium fluoride and potassium fluoride; alkali metal alkoxides such as sodium methoxide, sodium ethoxide, sodium t-butoxide, potassium methoxide, potassium ethoxide, potassium t-butoxide and lithium methoxide; alkali metal trialkylsiloxides such as sodium trimethylsiloxide, potassium trimethylsiloxide and lithium trimethylsiloxide; mercaptan alkali metals such as sodium thiomethoxide and sodium thiomethoxide; organic bases such as N-methylmorpholine, triethylamine, tripropylamine, tributylamine, N,N-diisopropylethylamine, dicyclohexylamine, N-methylpiperidine, pyridine, 2,6-lutidine, 4-pyrrolidinopyridine, picoline, 4-(N,N-dimethylamino)pyridine (DMAP), 2,6-di(t-butyl)-4-methylpyridine, quinoline, N,N-dimethylaniline, N,N-diethylaniline, 1,5-diazabicyclo[4.3.0]nona-5-ene (DBN), 1,4-diazabicyclo[2.2.2]octane (DABCO) and 1,8-diazabicyclo[5.4.0]undeca-7-ene (DBU); organic metal bases such as n-butyllithium, lithium diisopropylamide and lithium bis(trimethylsilyl)amide; or amino acids such as proline.

Examples of a condensing agent used in a reaction at each step of the following Methods A to I include lower dialkyl azodicarboxylate-triphenylphosphines such as diethyl azodicarboxylate-triphenylphosphine; carbodiimide derivatives such as N,N'-dicyclohexylcarbodiimide (DCC) and 1-ethyl-3-(3-dimethylaminopropyl)carbodiimide (EDCI); 2-halo-1-lower alkylpyridinium halides such as 2-chloro-1-methylpyridinium iodide; diarylphosphorylazides such as diphenylphosphorylazide (DPPA); phosphoryl chlorides such as diethylphosphoryl chloride; imidazole derivatives such as N,N'-carbodiimidazole (CDI); and benzotriazole derivatives such as O-(7-azabenzotriazol-1-yl)-N,N,N',N'-tetramethyluronium hexafluorophosphate (HATU) and (1H-benzotriazol-1-yloxy)tripyrrolidinophosphonium hexafluorophosphate (PyBOP).

When a condensing agent is used in a reaction at each step of the following Methods A to I, additives for promoting dehydration or suppressing side reactions may be added if necessary. Additives used are not particularly limited so long as the additives are generally known, and may be 1-hydroxybenzotriazole (HOBt), N-hydroxysuccinimide (HOSu), 1-hydroxy-7-azabenzotriazole (HOAt), hydroxy-3,4-dihydro-4-oxo-1,2,3-benzotriazine (HOOBt) and DMAP.

In a reaction at each step of the following Methods A to I, the reaction temperature varies depending on the solvent, the starting material, the reagent, and the like, and the reaction time varies depending on the solvent, the starting material, the reagent, the reaction temperature, and the like.

In a reaction at each step of the following Methods A to I, each target compound is collected from a reaction mixture according to a usual method after the reaction is completed. For example, after the reaction mixture is suitably neutralized, or insoluble matter that is present is removed by filtration, organic solvents that are not miscible, such as water and ethyl acetate, are added to separate an organic layer containing the target compound, the organic layer is washed with water or the like, dried with anhydrous magnesium sulfate, anhydrous sodium sulfate, or the like and filtered, and the solvent is evaporated to give a target compound. The resulting target compound can be separated and purified by a usual method, such as recrystallization, reprecipitation, distillation, or a method commonly used for separation and purification of an organic compound (for example, adsorption column chromatography using a carrier such as silica gel, alumina, magnesium-silica gel Florisil, or Sephadex LH-20 [Pharmacia], partition column chromatography using a carrier such as AMBERLITE XAD-11 [Rohm and Haas Company], or DIAION HP-20 [Mitsubishi Chemical Corporation], ion exchange chromatography, normal phase or reverse phase column chromatography using silica gel or alkylation silica gel, preferably, various high performance liquid chromatography [HPLC]). Furthermore, a target compound at each step can be used in the following reaction as it is without purification.

Method A is a method for bonding an amino group of a compound represented by the general formula (XIII) to a carboxyl group of a compound represented by the general formula (XIV), a compound represented by the general formula (XV) or a compound represented by the general formula (XVI) and comprises step (i) or (ii).

This step is performed by converting and activating a carboxyl group of a compound represented by the general formula (XIV), a compound represented by the general formula (XV) or a compound represented by the general formula (XVI) to an acid halide, a mixed acid anhydride, or the like in a solvent using a halogenating agent, an agent for forming an acid anhydride, or the like, and then reacting the acid halide, the mixed acid anhydride, or the like with a compound represented by the general formula (XIII) in the presence or absence of a base.

The solvent used in this step is preferably a halogenated hydrocarbon, and more preferably dichloromethane.

Examples of the halogenating agent, the agent for forming an acid anhydride, or the like used in this step include acid halogenating agents such as thionyl chloride and oxalyl chloride; phosphorus chlorides such as phosphorus trichloride and phosphorus pentachloride; chloroformic acid esters such as ethyl chloroformate and isobutyl chloroformate; acid halogenates such as acetyl chloride and pivaloyl chloride; acid anhydrides such as acetic anhydride and trifluoroacetic anhydride; and phosphoranes such as dichlorotriphenyl phosphorane and dibromotriphenyl phosphorane, preferably oxalyl chloride, isobutyl chloroformate, pivaloyl chloride or trifluoroacetic anhydride, and more preferably pivaloyl chloride.

The base used in this step is preferably an organic base, more preferably triethylamine, diisopropylethylamine, pyridine or DMAP, and even more preferably triethylamine or diisopropylethylamine.

The reaction temperature in this step is usually $-10°$ C. to $60°$ C., and preferably $0°$ C. to $30°$ C.

The reaction time in this step is usually 10 minutes to 24 hours, and preferably 1 hour to 12 hours.

(ii) This step is performed by reacting a compound represented by the general formula (XIII) with a compound represented by the general formula (XIV), a compound represented by the general formula (XV) or a compound represented by the general formula (XVI) in the presence of a condensing agent in the presence or absence of a base in a solvent.

The solvent used in this step is preferably a halogenated hydrocarbon, an ether, an amide or a mixed solvent thereof, and more preferably dichloromethane, tetrahydrofuran, N,N-dimethylformamide or a mixed solvent thereof.

The condensing agent used in this step is preferably DCC, EDCI, CDI, HATU or PyBOP, and more preferably EDCI.

The base used in this step is preferably an organic base, more preferably triethylamine, diisopropylethylamine or pyridine, and even more preferably triethylamine.

The additive used in this step is preferably DMAP.

The reaction temperature in this step is usually $-20°$ C. to $100°$ C., preferably $0°$ C. to $80°$ C., and more preferably $20°$ C. to $50°$ C.

The reaction time in this step is usually 10 minutes to 48 hours, and preferably 1 hour to 24 hours.

Method B is a step of bonding an amino group of a compound represented by the general formula (XVII), a compound represented by the general formula (XX) or a compound represented by the general formula (XXIV) to a carbon atom next to a leaving group by eliminating the leaving group of a compound represented by the general formula (XIV).

This step is performed by reacting a compound represented by the general formula (XIV) with a compound represented by the general formula (XVII), a compound represented by the general formula (XX) or a compound represented by the general formula (XXIV) in the presence or absence of a base in a solvent.

The solvent used in this step is preferably a nitrile or an amide, more preferably acetonitrile, isobutyl nitrile, N,N-dimethylformamide, N,N-dimethylacetamide or hexamethylphosphoric triamide, and even more preferably N,N-dimethylformamide or hexamethylphosphoric triamide.

The base used in this step is preferably an organic base, more preferably triethylamine or diisopropylethylamine, and even more preferably diisopropylethylamine.

The reaction temperature in this step is usually $0°$ C. to $150°$ C., and preferably $50°$ C. to $100°$ C.

The reaction time in this step is usually 10 minutes to 48 hours, and preferably 1 hour to 24 hours.

Method C is a step of oxidizing a hydroxyl group of a compound represented by the general formula (XV) to convert the group to an aldehyde group and bonding the aldehyde group to an amino group of a compound represented by the general formula (XVII), a compound represented by the general formula (XX) or a compound represented by the general formula (XXIV) and comprises steps (i) and (ii).

This step is performed by reacting a compound represented by the general formula (XV) with an oxidizing agent in a solvent.

The solvent used in this step is preferably a halogenated hydrocarbon, an ether or a mixed solvent thereof, more preferably dichloromethane, tetrahydrofuran or a mixed solvent thereof, and even more preferably dichloromethane.

The oxidizing agent used in this step is not particularly limited so long as the oxidizing agent is used for the usual oxidation reaction of an alcohol. Examples of the oxidizing agent include chromic acids such as pyridinium chlorochromate (PCC) and pyridinium dichromate (PDC); combinations of various electrophilic agents such as DCC, anhydrous trifluoroacetic acid, thionyl chloride, oxalyl chloride, chlorine, N-chlorosuccinimide (NCS) or a sulfur trioxide-pyridine complex, with dimethyl sulfoxide; oxoammoniums such as 2,2,6,6-tetramethylpiperidine 1-oxyl (TEMPO); metal and metal complexes such as tetrapropylammonium perruthenate (TPAP) and manganese dioxide; 1 oxidizing agents such as 1,1-triacetoxy-1,1-dihydro-1,2-benziodoxol-3(1H)-one (Dess-Martin Periodinane, Dess-Martin reagent), o-iodoxybenzoic acid (IBX) and Oxone™ (Oxone: $2 KHSO_5 KHSO_4 K_2SO_4$), preferably a combination of an electrophilic agent and dimethyl sulfoxide, Dess-Martin reagent or TEMPO, and more preferably a combination of a sulfur trioxide-pyridine complex and dimethyl sulfoxide.

The reaction temperature in this step is usually $-80°$ C. to $100°$ C., and preferably $-10°$ C. to $30°$ C.

The reaction time in this step is usually 10 minutes to 6 hours, and preferably 30 minutes to 3 hours.

(ii) This step is performed by reacting an aldehyde compound obtained in the above (i) with a compound represented by the general formula (XVII), a compound represented by the general formula (XX) or a compound represented by the general formula (XXIV) under reducing conditions in the presence or absence of a base in a solvent.

The solvent used in this step is preferably an alcohol, a carboxylic acid, a mixed solvent of an alcohol and an ether, a mixed solvent of an alcohol and water or a mixed solvent of a carboxylic acid and water, and more preferably methanol, ethanol, acetic acid, a mixed solvent of methanol or ethanol and diethyl ether, tetrahydrofuran or dioxane, a mixed solvent of methanol or ethanol and water or a mixed solvent of acetic acid and water.

The reducing conditions used in this step are not particularly limited so long as the conditions are reducing conditions commonly used for imine reduction. Examples of the conditions include reduction using an alkali metal borohydride such as sodium borohydride, sodium triacetoxyborohydride or cyanosodium borohydride; and catalytic reduction using hydrogen or ammonium formate and a metal catalyst such as palladium or platinum, and preferably reduction using an alkali metal borohydride.

The alkali metal borohydride used in this step is preferably sodium triacetoxyborohydride. If necessary, acetic acid, molecular sieves, Lewis acid or the like may be added.

The catalyst used in this step is not particularly limited so long as the catalyst is commonly used for a catalytic reduction reaction. Examples of the catalyst include palladium-carbon, palladium black, Raney nickel, platinum oxide, platinum black, rhodium-aluminium oxide, triphenylphosphine-rhodium chloride, palladium-barium sulfate, and preferably platinum oxide or palladium-carbon.

The pressure in the catalytic reduction in this step is not particularly limited and is usually 1 to 10 atm.

The reaction temperature in this step is usually 0° C. to 100° C., and preferably 20° C. to 70° C.

The reaction time in this step is usually 5 minutes to 48 hours, and preferably 1 hour to 24 hours.

Method D is a step of bonding an amino group of a compound represented by the general formula (XVI) to a carbon atom next to a leaving group by eliminating the leaving group of a compound represented by the general formula (XVIII), a compound represented by the general formula (XXI) or a compound represented by the general formula (XXV).

This step is performed in the same manner as in the step of the above Method B by reacting a compound represented by the general formula (XVI) with a compound represented by the general formula (XVIII), a compound represented by the general formula (XXI) or a compound represented by the general formula (XXV) in the presence or absence of a base in a solvent.

Method E is a step of bonding an amino group of a compound represented by the general formula (XVI) to an aldehyde group of a compound represented by the general formula (XIX), a compound represented by the general formula (XXII) or a compound represented by the general formula (XXVI).

This step is performed in the same manner as in the step (ii) of the above Method C by reacting a compound represented by the general formula (XVI) with a compound represented by the general formula (XIX), a compound represented by the general formula (XXII) or a compound represented by the general formula (XXVI) under reducing conditions in the presence or absence of a base in a solvent.

Method F is a step of bonding an amino group of a compound represented by the general formula (XVII), a compound represented by the general formula (XVIII), a compound represented by the general formula (XIX), a compound represented by the general formula (XXIII) or a compound represented by the general formula (XXVII) to a carboxyl group of a compound represented by the general formula (XXVIII).

This step is performed by reacting a compound represented by the general formula (XVII), a compound represented by the general formula (XVIII), a compound represented by the general formula (XIX), a compound represented by the general formula (XXIII) or a compound represented by the general formula (XXVII) with a compound represented by the general formula (XXVIII) in the presence of condensing agent in the presence or absence of a base in a solvent.

The solvent used in this step is preferably a halogenated hydrocarbon, and more preferably dichloromethane.

The condensing agent used in this step is preferably pivaloyl chloride, isobutyl chloroformate or EDCI, and more preferably pivaloyl chloride.

The base used in this step is preferably triethylamine or diisopropylethylamine, and more preferably triethylamine.

The reaction temperature in this step is usually −10° C. to 60° C., and preferably 0° C. to 30° C.

The reaction time in this step is usually 10 minutes to 24 hours, and preferably 1 hour to 6 hours.

Method G is a step of bonding an amino group of a compound (XXVIII) to a carbon atom next to a leaving group by eliminating the leaving group of a compound represented by the general formula (XXIX).

This step is performed by reacting a compound (XXVIII) with a compound represented by the general formula (XXIX) in the presence or absence of a base in a solvent.

The solvent used in this step is preferably a nitrile or an amide, more preferably acetonitrile, isobutyl nitrile, N,N-dimethylformamide, N,N-dimethylacetamide or hexamethylphosphoric acid triamide, and even more preferably acetonitrile.

The base used in this step is preferably an alkali metal carbonic acid salt, and more preferably sodium hydrogencarbonate.

The reaction temperature in this step is usually −80° C. to 150° C., and preferably 50° C. to 100° C.

The reaction time in this step is usually 10 minutes to 24 hours, and preferably 1 hour to 8 hours.

Method H is a step of bonding a carboxyl group of a compound represented by the general, formula (XX), a compound represented by the general formula (XXI) or a compound represented by the general formula (XXII) to an amino group of a compound represented by the general formula (XXIII).

This step is performed by reacting a compound represented by the general formula (XX), a compound represented by the general formula (XXI) or a compound represented by the general formula (XXII) with a compound represented by the general formula (XXIII) in the presence of condensing agent in the presence or absence of a base in a solvent.

The solvent used in this step is preferably a halogenated hydrocarbon, and more preferably dichloromethane.

The condensing agent used in this step is preferably pivaloyl chloride, isobutyl chloroformate or EDCI, and more preferably EDCI.

The base used in this step is preferably an organic base, more preferably triethylamine or diisopropylethylamine, and even more preferably triethylamine.

The reaction temperature in this step is usually −10° C. to 60° C., and preferably 0° C. to 30° C.

The reaction time in this step is usually 10 minutes to 24 hours, and preferably 1 hour to 6 hours.

Method I is a step of bonding an amino group of a compound represented by the general formula (XXIV), a compound represented by the general formula (XXV) or a compound represented by the general formula (XXVI) to a carboxyl group of a compound represented by the general formula (XXVII).

This step is performed in the same manner as in the step of the above Method H by reacting a compound represented by the general formula (XXIV), a compound represented by the general formula (XXV) or a compound represented by the general formula (XXVI) with a compound represented by the general formula (XXVII) in the presence of a condensing agent in the presence or absence of a base in a solvent.

Combinations of compounds represented by the general formula (XIII) through the general formula (XXIX) for producing the compound represented by the general formula (I) of the present invention by Methods A to I are described in (a) to (I) below.

(a): (XIII)-A-(XIV)-B-(XVII)-F-(XXVIII)-G-(XXIX)

The above combination means that a binding site of a compound represented by the general formula (XIII) and a binding site of a compound represented by the general formula (XIV) are bonded by Method A, a binding site of a compound represented by the general formula (XIV) and a binding site of a compound represented by the general formula (XVII) are bonded by Method B, a binding site of a compound represented by the general formula (XVII) and a binding site of a compound (XXVIII) are bonded by Method F, a binding site of a compound (XXVIII) and a binding site of a compound represented by the general formula (XXIX) are bonded by Method G to produce the compound represented by the general formula (I) of the present invention. The (b) to (I) shown below have similar meanings.

(b): (XIII)-A-(XIV)-B-(XX)-H-(XXIII)-F-(XXVIII)-G-(XXIX).

(c): (XIII)-A-(XIV)-B-(XXIV)-I-(XXVII)-F-(XXVIII)-G-(XXIX).

(d): (XIII)-A-(XV)-C-(XVII)-F-(XXVIII)-G-(XXIX).

(e): (XIII)-A-(XV)-C-(XX)-H-(XXIII)-F-(XXVIII)-G-(XXIX).

(f): (XIII)-A-(XV)-C-(XXIV)-I-(XXVII)-F-(XXVIII)-G-(XXIX).

(g): (XIII)-A-(XVI)-D-(XVIII)-F-(XXVIII)-G-(XXIX).

(h): (XIII)-A-(XVI)-E-(XIX)-F-(XXVIII)-G-(XXIX).

(i): (XIII)-A-(XVI)-D-(XXI)-H-(XXIII)-F-(XXVIII)-G-(XXIX).

(j): (XIII)-A-(XVI)-E-(XXII)-H-(XXIII)-F-(XXVIII)-G-(XXIX).

(k): (XIII)-A-(XVI)-D-(XXV)-I-(XXVII)-F-(XXVIII)-G-(XXIX).

(l): (XIII)-A-(XVI)-E-(XXVI)-I-(XXVII)-F-(XXVIII)-G-(XXIX).

In the above description, a protective group of an amino group, a hydroxy group or a carboxyl group means a protective group that can be cleaved by a chemical method such as hydrogenolysis, hydrolysis, electrolysis or photodegradation and refers to a protective group conventionally used in the field of organic synthetic chemistry (for example, refer to T. W. Greene et al., Protective Groups in Organic Synthesis, 3rd Edition, John Wiley & Sons, Inc. [1999]).

In the above description, a protective group of a hydroxy group is not particularly limited so long as the protective group is a protective group of a hydroxy group used in the field of organic synthetic chemistry. Examples of the protective group of a hydroxy group include a formyl group; "alkylcarbonyl groups" such as $C_2$-$C_7$ alkylcarbonyl groups such as an acetyl group, a propionyl group, a butyryl group and an isobutyryl group, $C_1$-$C_6$ halogenated alkylcarbonyl groups such as a chloroacetyl group, a dichloroacetyl group, a trichloroacetyl group and a trifluoroacetyl group, alkoxyalkylcarbonyl groups such as a methoxyacetyl group, and unsaturated alkylcarbonyl groups such as an acryloyl group, a propioloyl group, a methacryloyl group, a crotonoyl group, an isocrotonoyl group and a (E)-2-methyl-2-butenoyl group; "arylcarbonyl groups" such as arylcarbonyl groups such as a benzoyl group, an α-naphthoyl group, and a β-naphthoyl group, halogenated arylcarbonyl groups such as a 2-bromobenzoyl group and a 4-chlorobenzoyl group, $C_1$-$C_6$ alkylated arylcarbonyl groups such as a 2,4,6-trimethylbenzoyl group and a 4-toluoyl group, $C_1$-$C_6$ alkoxylated arylcarbonyl groups such as a 4-anisoyl group, nitro arylcarbonyl groups such as a 4-nitrobenzoyl group and a 2-nitrobenzoyl group, $C_2$-$C_7$ alkoxycarbonylated arylcarbonyl groups such as a 2-(methoxycarbonyl)benzoyl group, and arylated arylcarbonyl groups such as a 4-phenylbenzoyl group; "alkoxycarbonyl groups" such as the above-described "$C_2$-$C_7$ alkoxycarbonyl group" and $C_2$-$C_7$ alkoxycarbonyl groups that are substituted with a halogen atom or a tri-($C_1$-$C_6$ alkyl)silyl group such as a 2,2,2-trichloroethoxycarbonyl group and a 2-trimethylsilylethoxycarbonyl group; "tetrahydropyranyl groups or tetrahydrothiopyranyl groups" such as a tetrahydropyran-2-yl group, a 3-bromotetrahydropyran-2-yl group, a 4-methoxytetrahydropyran-4-yl group, a tetrahydrothiopyran-2-yl group and a 4-methoxytetrahydrothiopyran-4-yl group; "tetrahydrofuranyl groups or tetrahydrothiofuranyl groups" such as a tetrahydrofuran-2-yl group and a tetrahydrothiofuran-2-yl group; "silyl groups" such as tri-($C_1$-$C_6$ alkyl)silyl groups such as a trimethylsilyl group, a triethylsilyl group, an isopropyldimethylsilyl group, a t-butyldimethylsilyl group, a methyldiisopropylsilyl group, a methyldi-t-butylsilyl group and a triisopropylsilyl group and ($C_1$-$C_6$ alkyl)diarylsilyl groups or di-($C_1$-$C_6$ alkyl)arylsilyl groups such as a diphenylmethylsilyl group, a diphenylbutylsilyl group, a diphenylisopropylsilyl group, and a phenyldiisopropylsilyl group; "alkoxymethyl groups" such as ($C_1$-$C_6$ alkoxy)methyl groups such as a methoxymethyl group, a 1,1-dimethyl-1-methoxymethyl group, an ethoxymethyl group, a propoxymethyl group, an isopropoxymethyl group, a butoxymethyl group, and a t-butoxymethyl group, ($C_1$-$C_6$ alkoxy)-($C_1$-$C_6$ alkoxy)methyl groups such as a 2-methoxyethoxymethyl group, and ($C_1$-$C_6$ halogenated alkoxy)methyl groups such as a 2,2,2-trichloroethoxymethyl group and a bis(2-chloroethoxy)methyl group; "substituted ethyl groups" such as ($C_1$-$C_6$ alkoxy)ethyl groups such as a 1-ethoxyethyl group and a 1-(isopropoxy)ethyl group and halogenated ethyl groups such as a 2,2,2-trichloroethyl group; "aralkyl groups" such as $C_1$-$C_6$ alkyl groups that are substituted with 1 to 3 aryl group(s), such as a benzyl group, an α-naphthylmethyl group, a β-naphthylmethyl group, a diphenylmethyl group, a triphenylmethyl group, an α-naphthyldiphenylmethyl group, and a 9-anthrylmethyl group and $C_1$-$C_6$ alkyl groups that are substituted with 1 to 3 aryl group(s) having an aryl ring substituted with a $C_1$-$C_6$ alkoxy group, a nitro group, a halogen atom, or a cyano group, such as a 4-methylbenzyl group, a 2,4,6-trimethylbenzyl group, a 3,4,5-trimethylbenzyl group, a 4-methoxybenzyl group, a 4-methoxyphenyldiphenylmethyl group, a 2-nitrobenzyl group, a 4-nitrobenzyl group, a 4-chlorobenzyl group, a 4-bromobenzyl group, and a 4-cyanobenzyl group; "alkenyloxycarbonyl groups" such as a vinyloxycarbonyl group and an allyloxycarbonyl group; "aralkyloxycarbonyl groups" having an aryl ring that may be substituted with 1 or 2 $C_1$-$C_6$ alkoxy group(s) or nitro groups, such as a benzyloxycarbonyl group, a 4-methoxybenzyloxycarbonyl group, a 3,4-dimethoxybenzyloxycarbonyl group, a 2-nitrobenzyloxycarbonyl group, and a 4-nitrobenzyloxycarbonyl group, and preferably alkylcarbonyl groups, silyl groups or aralkyl groups.

In the above description, a protective group of a carboxyl group is not particularly limited so long as the protective group is a protective group of a carboxyl group used in the field of organic synthetic chemistry. Examples of the protective group of a carboxyl group include the above-described "$C_1$-$C_6$ alkyl groups"; "$C_2$-$C_6$ alkenyl groups" such as an ethenyl group, a 1-propenyl group, a 2-propenyl group, and a 1-methyl-2-propenyl group; "$C_2$-$C_6$ alkynyl groups" such as an ethynyl group, a 1-propynyl group, a 2-propynyl group, and a 1-methyl-2-propynyl group; the above-described "$C_1$-$C_6$ halogenated alkyl groups"; $C_1$-$C_6$ hydroxyalkyl groups such as a hydroxymethyl group and a 2-hydroxyethyl group; ($C_2$-$C_7$ alkylcarbonyl)-($C_1$-$C_6$ alkyl) groups such as an acetylmethyl group; the above-described "aralkyl groups"; or the above-described "silyl groups", and preferably $C_1$-$C_6$ alkyl groups or aralkyl groups.

In the above description, a protective group of an amino group is not particularly limited so long as the protective group is a protective group of an amino group used in the field of organic synthetic chemistry. Examples of the protective group of an amino group include groups similar to "alkylcarbonyl groups", "arylcarbonyl groups", "alkoxycarbonyl groups", "silyl groups", "aralkyl groups", "alkenyloxycarbonyl groups", or "aralkyloxycarbonyl groups" in the above examples of the "protective group of a hydroxy group" or "substituted methylene groups forming a Schiff base" such as N,N-dimethylaminomethylene, benzylidene, 4-methoxybenzylidene, 4-nitrobenzylidene, salicylidene, 5-chlorosalicylidene, diphenylmethylene, and (5-chloro-2-hydroxyphenyl)phenylmethylene, preferably alkylcarbonyl groups, arylcarbonyl groups or alkoxycarbonyl groups, and more preferably alkoxycarbonyl groups.

Examples of the administration method of the compound or a pharmacologically acceptable salt thereof represented by the general formula (I) of the present invention include oral administration by tablet, capsule, granule, powder, syrup, or the like and parenteral administration by injection, suppository, or the like. Further, the compound or a pharmacologically acceptable salt thereof represented by the general formula (I) of the present invention can be administered by pulmonary administration in the form of powder, solution or suspension. Preparations for such administration can be produced by known formulation methods using excipients such as a diluent, a lubricant, a binder, a disintegrating agent, a stabilizer, a flavoring agent, and a dilution agent.

Examples of the diluent include organic diluents such as sugar derivatives such as lactose, sucrose, glucose, mannitol or sorbitol; starch derivatives such as maize starch, potato starch, α-starch, dextrin or carboxymethyl starch; cellulose derivatives such as crystalline cellulose, low-substituted hydroxypropylcellulose, hydroxypropylmethylcellulose, carboxymethylcellulose, carboxymethylcellulose calcium, or internally crosslinked carboxymethylcellulose sodium; gum arabic; dextran; or Pullulan; or inorganic diluents such as silicate derivatives such as light anhydrous silicic acid, synthetic aluminium silicate, or magnesium aluminometasilicate; phosphates such as calcium phosphate; carbonates such as calcium carbonate; or sulfates such as calcium sulfate.

Examples of the lubricant include stearic acid; metal stearates such as calcium stearate or magnesium stearate; talc; colloidal silica; waxes such as veegum or spermaceti; fluoboric acid; adipic acid; sulfates such as sodium sulfate; glycol; fumaric acid; sodium benzoate; DL-leucine; fatty acid sodium salts; lauryl sulfates such as sodium lauryl sulfate or magnesium lauryl sulfate; silicic acids such as anhydrous silicic acid or silicic acid hydrate; or the above-mentioned starch derivatives.

Examples of the binder include polyvinylpyrrolidone or macrogol, or the same compounds as the above diluents.

Examples of the disintegrating agent include the same compounds as the above excipients, or chemically modified starches or celluloses such as croscarmellose sodium, carboxymethyl starch sodium, or crosslinked polyvinylpyrrolidone.

Examples of the stabilizer include paraoxybenzoic acid esters such as methylparaben or propylparaben; alcohols such as chlorobutanol, benzyl alcohol or phenylethyl alcohol; benzalkonium chloride; phenols such as phenol or cresol; thimerosal; dehydroacetic acid; or sorbic acid.

Examples of the flavoring agent include commonly used sweeteners, acidifiers or flavors.

A solution or suspension for pulmonary administration of the compound or a pharmacologically acceptable salt thereof represented by the general formula (I) of the present invention can be produced by, for example, dissolving or suspending the compound of the present invention in water or a mixture of water and an auxiliary solvent (for example, ethanol, propylene glycol or polyethylene glycol). Such a solution or suspension may further contain a preservative (for example, benzalkonium chloride), a solubilizer (for example, polysorbate such as Tween 80 or Span 80 or a surfactant such as benzalkonium chloride), a buffer, an isotonizing agent (for example, sodium chloride), an absorption promoting agent, and/or a thickening agent. Furthermore, a suspension may further contain a suspending agent (for example, microcrystalline cellulose or carboxymethylcellulose sodium).

A composition for pulmonary administration produced as described above is administered directly from the nasal cavity or the oral cavity with common means in the field of inhalants (for example, using a dropper, a pipette, a cannula, or a nebulizer). When an atomizer is used, the compound of the present invention can be sprayed as an aerosol in the form of a pressurized pack with an appropriate propellant (for example, a chlorofluorocarbon gas such as dichlorofluoromethane, trichlorofluoromethane, or dichlorotetrafluoroethane or carbon dioxide) or administered using a nebulizer.

The dose of the compound or a pharmacologically acceptable salt thereof represented by the general formula (I) of the present invention varies depending on the symptom, the age, and the like of a patient (a homeotherm, particularly a human). For example, when the compound is orally administered, the daily dose for adult humans is from 0.1 mg (preferably 1 mg, more preferably 5 mg) as the lower limit to 1000 mg (preferably 100 mg, more preferably 50 mg) as the upper limit, which is recommended to be administered as a single dose or divided into several doses depending on the symptom. When the compound is intravenously administered, the daily dose for adult humans is from 0.01 mg (preferably 0.1 mg) as the lower limit to 100 mg (preferably 10 mg) as the upper limit, which is recommended to be administered as a single dose or divided into several doses depending on the symptom.

When the compound or a pharmacologically acceptable salt thereof represented by the general formula (I) of the present invention is administered by pulmonary administration, the dose varies depending on the symptom, the age, and the like of a patient (a homeotherm, particularly a human). For example, the daily dose for adult humans is from 0.1 µg/kg (preferably 0.5 µg/kg) as the lower limit to 10,000 µg/kg (preferably 1000 µg/kg) as the upper limit, which is recommended to be administered as a single dose or divided into several doses depending on the symptom.

EXAMPLES

Hereafter, the present invention will be described in more detail with reference to the Examples and the Test Examples. However, the scope of the present invention is not limited to these examples.

Elution in column chromatography in the Examples was performed under observation by thin layer chromatography (TLC). In the TLC observation, Silica Gel 60$F_{254}$ produced by Merck & Co., Inc. or TLC Plate NH produced by Fuji Silysia Chemical Ltd. was used as a TLC plate, a solvent used in column chromatography as an elution solvent was used as eluent, and a UV detector was used in a detection method. Silica Gel SK-85 (230 to 400 mesh) or SK-34 (70 to 230 mesh) produced by Kishida Chemical Co., Ltd., Silica Gel 60N (40 to 50 μm) produced by Kanto Chemical Co., Inc., Chromatorex NH DM1020 (100 to 200 mesh) or DM2035SG (200 to 350 mesh) produced by Fuji Silysia Chemical Ltd. or Silica Gel FL100B produced by Fuji Silysia Chemical Ltd. was used as a silica gel for column chromatography. In addition to usual column chromatography, an automated chromatography system (YFLC-prep4) of Yamazen Corporation and disposable columns (Moritex Corporation, Yamazen Corporation, Wako Pure Chemical Industries, Ltd.) were suitably used. A silica Gel 60F$_{254}$ 0.5 mm thick plate 20×20 cm produced by Merck & Co., Inc. was used for purification by preparative TLC. An XTerra Prep MS C18 OBD column (5 μm, 30×100 mm) or XBridge Prep C18 OBD column (5 μm, 30×150 mm) produced by Waters Corporation was used for reversed phase preparative chromatography. Abbreviations used in the Examples have the following meanings:

mg: milligram, g: gram, mL: milliliter, MHz: megahertz, HATU: O-(7-azabenzotriazol-1-yl)-N,N,N',N'-tetramethyl uronium hexafluorophosphate, WSCI HCl: 1-ethyl-3-(3-dimethylaminopropyl)carbodiimide hydrochloride, HOBT H$_2$O: 1-hydroxybenzotriazole monohydrate.

In the following Examples, nuclear magnetic resonance (hereinafter referred to as $^1$H NMR) spectra were described with a chemical shift value as a δ value (ppm) using tetramethylsilane as a reference substance. The coupling patterns were expressed using s for singlet, d for doublet, t for triplet, q for quartet, and br for broad.

Mass spectrometry (hereinafter referred to as MS) was performed by Fast Atom Bombardment (FAB), Electron Ionization (EI), Atmospheric Pressure Chemical Ionization (APCI), or Electron Spray Ionization (ESI).

Example 1

1-{2-[{6-[({5-[{3-[({[(2S)-1'-{2-[(5R)-3-[3,5-Bis (trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl} (methyl)carbamoyl]-2-thienyl}methyl)amino] hexanoyl}(methyl)amino]ethyl}piperidin-4-yl biphenyl-2-ylcarbamate

[Formula 6]

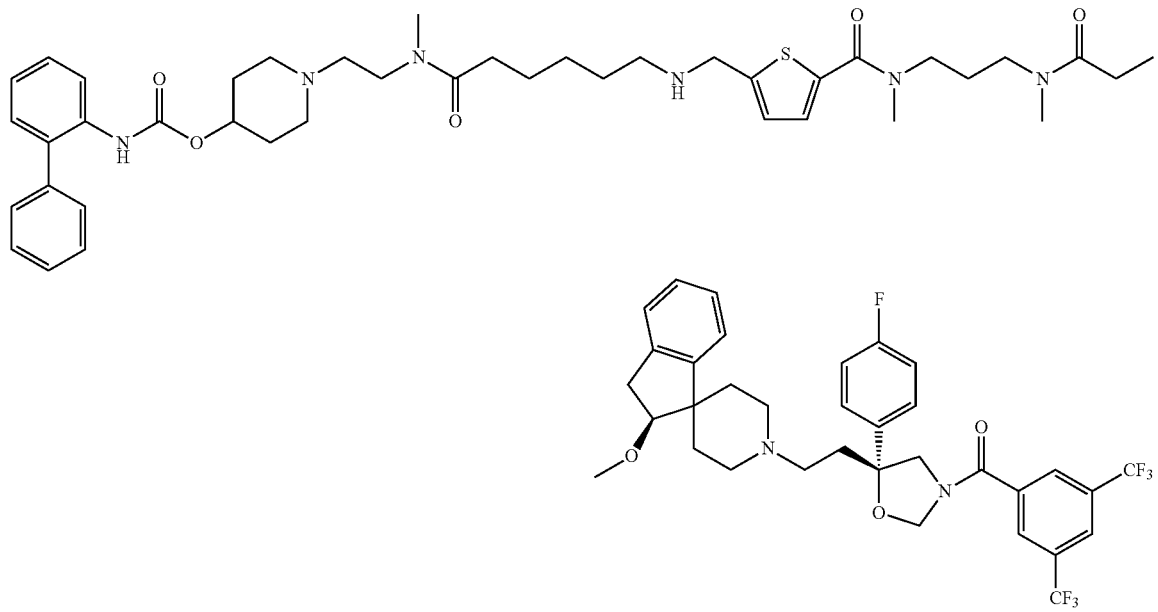

Example 1a

1-{2-[(6-Aminohexanoyl)(methyl)amino] ethyl}piperidin-4-yl biphenyl-2-ylcarbamate 1-[2-(Methylamino)ethyl]piperidin-4-yl biphenyl-2-yl-carbamate (500 mg, 1.41 mmol) was dissolved in methylene chloride (5 mL), triethylamine (0.236 mL, 1.70 mmol) and 6-bromohexanoyl chloride (0.232 mL, 1.56 mmol) were added under ice cooling, and the mixture was stirred at room temperature for 20 minutes. Water was added to the reaction mixture, the reaction mixture was extracted with ethyl acetate (×3), and the organic layer was washed with saturated sodium chloride solution. The organic layer was dried with anhydrous sodium sulfate, then the solvent was evaporated under reduced pressure, the resulting residue was dissolved in N,N-dimethylformamide (3 mL), sodium azide (110 mg, 1.69 mmol) was added, and the mixture was stirred at 60° C. for 5 hours. The reaction mixture was diluted with ethyl acetate, and then the organic layer was washed successively with water (×3) and saturated sodium chloride solution. The organic layer was dried with anhydrous sodium sulfate, and then the solvent was evaporated under reduced pressure. Triphenylphosphine (555 mg, 2.12 mmol) and water (38 μL, 2.12 mmol) were added to a solution of the resulting residue in tetrahydrofuran (14 mL) under ice cooling, and the mixture was stirred overnight at room temperature. The solvent of the reaction mixture was evaporated under reduced pressure, and the resulting residue was purified by NH silica gel column chromatography (ethyl acetate:methanol=100:0→10:1, v/v) to give the title compound (493 mg; yield, 75%) as a yellow oily substance.

MS (FAB) m/z: 467 (M+H)$^+$.

IR (liquid film) $v_{max}$ 2935, 1716, 1634, 1522, 1450, 1303, 1227, 1045, 749, 703 cm$^{-1}$.

Example 1b (5R)-3-[3,5-Bis(trifluoromethyl)benzoyl]-5-(2-{[tert-butyl(dimethyl)silyl]oxy}ethyl)-5-(4-fluorophenyl)-1,3-oxazolidine Paraformaldehyde (18.50 g, 0.617 mol) was added to a solution of (2R)-1-amino-4-{[tert-butyl(dimethyl)silyl]oxy}-2-(4-fluorophenyl)butan-2-ol (128.92 g, 0.411 mol) in benzene (1000 mL), a water separator was mounted, and the mixture was stirred at reflux temperature for 4 hours. The reaction mixture was concentrated under reduced pressure to give 139.43 g of crude (5R)-5-(2-{[tert-butyl(dimethyl)silyl]oxy}ethyl)-5-(4-fluorophenyl)-1,3-oxazolidine as a brown oily substance.

3,5-Bis(trifluoromethyl)benzoyl chloride (100 g, 0.434 mol) was added dropwise to a solution of the resulting crude product (139.43 g), triethylamine (69 mL, 0.495 mol) and 4-(dimethylamino)pyridine (5.02 g, 0.041 mol) in dichloromethane (1000 mL) under ice cooling, and the mixture was stirred at room temperature for 18 hours. The reaction mixture was washed with water and saturated sodium chloride solution, dried with anhydrous sodium sulfate, and then concentrated under reduced pressure. The resulting residue was purified by silica gel column chromatography (ethyl acetate-n-hexane, 10%) to give the title compound (131.76 g; yield, 62%) as a light yellow oily substance.

Example 1c

2-[(5R)-3-[3,5-Bis(trifluoromethyl)benzoyl]-5-(4-fluorophenyl)-1,3-oxazolidin-5-yl]ethanol A solution of tetrabutylammonium fluoride in tetrahydrofuran (1.0 M, 508 mL) and acetic acid (70 mL, 1.27 mol) were added to a solution of the compound (131.76 g, 0.254 mol) obtained in Example 1b in tetrahydrofuran (500 mL), and the mixture was stirred at room temperature for 2 hours. Ethyl acetate (1000 mL) was added to the reaction mixture, washed with a saturated aqueous solution of sodium hydrogencarbonate, water, and saturated sodium chloride solution, dried with anhydrous sodium sulfate, and then concentrated under reduced pressure. The resulting residue was purified by silica gel column chromatography (ethyl acetate-n-hexane, 30%→50%) to give the title compound (102.11 g; yield, 99%) as a colorless oily substance.

Example 1d

2-[(5R)-3-[3,5-Bis(trifluoromethyl)benzoyl]-5-(4-fluorophenyl)-1,3-oxazolidin-5-yl]ethyl methanesulfonate Methanesulfonyl chloride (26 mL, 0.336 mol) was added dropwise to a solution of the compound (102.11 g, 0.226 mol) obtained in Example 1c, triethylamine (63 mL, 0.452 mol) and 4-(dimethylamino)pyridine (2.76 g, 0.0273 mol) in dichloromethane (1000 mL) under ice cooling, and the mixture was stirred under ice cooling for 1 hour. The reaction mixture was washed with water and saturated sodium chloride solution, dried with anhydrous sodium sulfate, and then concentrated under reduced pressure. The residue was purified by silica gel column chromatography (ethyl acetate-n-hexane, 30%→50%) to give the title compound (108.21 g; yield, 90%) as a white solid.

$^1$H NMR (CDCl$_3$, 400 MHz): δ 2.30-2.50 (2H, m), 2.91 (3H, brs), 3.80-4.21 (3H, m), 4.25-4.35 (1H, m), 4.90-5.10 (1H, m), 5.20-5.40 (1H, m), 7.11 (2H, brs), 7.20-7.47 (2H, m), 7.91 (2H, s), 8.00 (1H, s); MS (FAB) m/z: 530 (M+H)$^+$;

IR (ATR) $v_{max}$ 1734, 1646, 1356, 1278, 1171, 1129, 957, 906, 837, 681, 527 cm$^{-1}$.

Example 1e tert-Butyl (2S)-2-(allyloxy)-2,3-dihydro-1'H-spiro[indene-1,4'-piperidine]-1'-carboxylate Sodium hydride (content, 55%; 10.79 g, 247.2 mmol) was added little by little to a solution of tert-butyl (2S)-2-hydroxy-2,3-dihydro-1'H-spiro[indene-1,4'-piperidine]-1'-carboxylate (50.0 g, 164.8 mmol) in dimethylformamide (150 mL) with stirring under ice cooling. After the addition, allyl bromide (28.5 mL, 329.6 mmol) was added dropwise, and the mixture was stirred under ice cooling for 1 hour. Water (400 mL) was added dropwise, and then the mixture was extracted with ethyl acetate (300 mL, 80 mL×2). The organic layer was washed with saturated sodium chloride solution, dried with anhydrous sodium sulfate, and then concentrated under reduced pressure. The resulting residue was purified by silica gel column chromatography (ethyl acetate-n-hexane, 0%→20%) to give the title compound (57.15 g) as a colorless oily substance.

$^1$H NMR (CDCl$_3$, 400 MHz): δ 1.45 (9H, s), 1.65-1.75 (2H, m), 2.05-2.12 (1H, m), 2.95-3.25 (4H, m), 3.80-4.20 (5H, m), 5.13-5.31 (2H, m), 5.86-5.98 (1H, m), 7.11-7.25 (4H, m).

MS (FAB+) m/z: 344 ((M+H)$^+$).

IR (liquid film):
2976, 2929, 1694, 1479, 1425, 1366, 1278, 1237, 1171, 1080, 759 cm$^{-1}$.

Example 1f tert-Butyl (2S)-2-(2-oxoethoxy)-2,3-dihydro-1'H-spiro[indene-1,4'-piperidine]-1'-carboxylate The compound (57.15 g) obtained in Example 1e was dissolved in a mixed solvent of acetone (400 mL), t-butanol (200 mL) and water (200 mL), N-methylmorpholine N-oxide (21.2 g, 181 mmol) and osmium tetraoxide (2.5% by weight %-butanol solution; 8.39 g, 0.825 mmol) were added under ice cooling, and the mixture was stirred at room temperature for 4 hours. An aqueous sodium thiosulfate solution (26 g, 100 mL) was added to the reaction mixture, then the mixture was stirred for 10 minutes, and the organic solvent was evaporated under reduced pressure. The mixture was extracted with ethyl acetate, dried with anhydrous sodium sulfate, and then concentrated under reduced pressure to give 69.58 g of crude tert-butyl (2S)-2-(2,3-dihydroxypropoxy)-2,3-dihydro-1'H-spiro[indene-1,4'-piperidine]-1'-carboxylate as a light yellow amorphous solid.

The resulting crude product was dissolved in a mixed solvent of tetrahydrofuran (400 mL) and water (400 mL), and sodium periodate (52.87 g, 247 mmol) was added little by little with stirring under ice cooling. After the addition, the mixture was stirred at room temperature for 1.5 hours. Water (400 mL) was added to the reaction solution, the reaction solution was extracted with ethyl acetate (300, 150, 100 mL), and the organic layers were combined and washed with saturated sodium chloride solution. The organic layers were dried with anhydrous sodium sulfate and concentrated under reduced pressure to give a crude title compound (59.52 g) as a colorless amorphous solid.

$^1$H NMR (CDCl$_3$, 400 MHz): δ 1.50 (9H, s), 1.62-1.85 (2H, m), 2.15-2.24 (1H, m), 2.92-4.25 (10H, m), 7.19-7.26 (4H, m), 9.74 (1H, s).

MS (FAB+) m/z: 346 ((M+H)$^+$).

IR (liquid film): 2976, 2931, 1686, 1479, 1428, 1367, 1239, 1010, 756 cm$^{-1}$.

Example 1g

{[(2S)-1'-(tert-Butoxycarbonyl)-2,3-dihydrospiro [indene-1,4'-piperidin]-2-yl]oxy}acetic acid The crude product (59.52 g) obtained in Example 1f was dissolved in a mixed solvent of tetrahydrofuran (200 mL) and t-butanol (400 mL), and 2-methyl-2-butene (87.3 mL) was added. An aqueous solution (100 mL) of sodium dihydrogenphosphate dihydrate (64.27 g, 412 mmol) and sodium chlorite (44.7 g, 494 mmol) were successively added with stirring under ice cooling, and the mixture was stirred with water cooling for 2.5 hours. The reaction mixture was ice cooled, and an aqueous 4 N sodium hydroxide solution (206 mL) was added dropwise. Water (200 mL) and ethyl acetate (200 mL) were added, and the resulting white precipitate was separated by filtration, and the residue was washed with water (100 mL) and ethyl acetate (100 mL). The filtrate was ice cooled, and 4 N hydrochloric acid (160 mL) was added to separate and extract the layers. The organic layer was washed with saturated sodium chloride solution, dried with anhydrous sodium sulfate, and then concentrated under reduced pressure to give 59.58 g of a crude title compound as a light yellow amorphous solid. The resulting crude product was recrystallized from a mixed solvent of diethyl ether and n-hexane to give the title compound (50.64 g) as a white solid.

$^1$H NMR (CD$_3$OD, 400 MHz): δ 1.48 (9H, s), 1.52-1.64 (2H, m), 1.68-1.75 (1H, m), 2.12-2.20 (1H, m), 3.00 (1H, dd, J=16.5, 3.0 Hz), 3.15 (1H, dd, J=16.5, 5.4 Hz), 3.20-3.40 (1H, m), 3.41-3.60 (1H, m), 3.86-3.99 (2H, m), 4.15-4.17 (2H, m), 4.32-4.37 (1H, m), 7.10-7.20 (4H, m).

MS (FAB+) m/z: 362 ((M+H)$^+$).

IR (KBr):
2976, 2932, 1756, 1690, 1643, 1479, 1430, 1366, 1279, 1169, 1119, 759 cm$^{-1}$.

Example 1h

Ethyl [(2S)-2,3-dihydrospiro[indene-1,4'-piperidin]-2-yloxy]acetate

Thionyl chloride (12.3 mL, 156 mmol) was added dropwise to a solution of the compound (28.20 g, 78.0 mmol) obtained in Example 1g in ethanol (280 mL) with stirring under ice cooling and heated under reflux for 2 hours. The reaction mixture was left to stand for cooling, and then ethanol was evaporated under reduced pressure. Ethyl acetate was added to the resulting yellow oily substance, and then the organic layer was washed with an aqueous sodium hydrogencarbonate solution. The organic layer was separated, and then ethyl acetate was added to the aqueous layer to extract the mixture. The organic layers were combined and dried with anhydrous magnesium sulfate, and the solvent was evaporated under reduced pressure. Toluene was added to dissolve the resulting residue, and then the solvent was evaporated under reduced pressure to give 32.1 g of a crude title compound as a light yellow oily substance.

MS (FAB+) m/z: 290 ((M+H)$^+$).

Example 1i

Ethyl {[(2S)-1'-{2-[(5R)-3-[3,5-bis(trifluoromethyl) benzoyl]-5-(4-fluorophenyl)-1,3-oxazolidin-5-yl] ethyl}-2,3-dihydrospiro[indene-1,4'-piperidin]-2-yl] oxy}acetate Sodium hydrogencarbonate (7.15 g, 85.11 mmol) was added to a solution of the crude product (32.1 g) obtained in Example 1h and the compound (37.6 g, 70.9 mmol) obtained in Example 1d in acetonitrile (160 mL) with stirring at room temperature, and the mixture was stirred at reflux temperature under a nitrogen atmosphere for 14 hours. The reaction mixture was left to stand for cooling to room temperature, and then the organic solvent was evaporated under reduced pressure. An aqueous sodium hydrogencarbonate solution was added to the resulting residue, and the mixture was extracted with ethyl acetate. The organic layers were combined and dried with anhydrous magnesium sulfate, and the solvent was evaporated under reduced pressure. The resulting residue was purified by silica gel chromatography (hexane:ethyl acetate=2:1→0:1, v/v) to give the title compound (47.8 g; yield, 93%) as a white solid.

$^1$H NMR (CD$_3$OD, 400 MHz): δ 1.26 (3H, t, J=7.1 Hz), 1.45-1.95 (4H, m), 2.05-2.36 (4H, m), 2.37-2.53 (2H, m), 2.57-2.80 (2H, m), 2.92-3.12 (2H, m), 3.75-3.93 (1H, m), 3.97-4.27 (6H, m), 4.84-5.10 (1H, m), 5.20-5.40 (1H, m), 7.02-7.43 (8H, m), 7.93 (2H, s), 7.95 (1H, s).

m/z: 723 ((M+H)$^+$).

IR (KBr): 2927, 1755, 1650, 1431, 1359, 1281, 1182, 1137, 907, 845, 839, 758, 682 cm$^{-1}$.

Example 1j

{[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl] oxy}acetic acid An aqueous 1 N sodium hydroxide solution (71 mL, 71 mmol) was added dropwise to a solution of the compound (34.1 g, 47.1 mmol) obtained in Example 1i in methanol (340 mL) with stirring under ice cooling, and the mixture was stirred at room temperature for 2 hours. 1 N Hydrochloric acid (71 mL, 71 mmol) was added with stirring under ice cooling to neutralize the mixture, and then methanol was evaporated under reduced pressure. Water was added to the residue, and the mixture was extracted with ethyl acetate and dried with anhydrous magnesium sulfate. The solvent was evaporated under reduced pressure, the resulting residue was dissolved in ethyl acetate, and the mixture was filtered through celite. The filtrate was evaporated under reduced pressure to give the title compound (32.6 g; yield, 99%) as a white amorphous solid.

$^1$H NMR (CD$_3$OD, 400 MHz): δ 1.70-2.08 (3H, m), 2.25-2.65 (3H, m), 2.82-3.03 (2H, m), 3.10-3.62 (5H, m), 3.85-4.21 (5H, m), 4.25-4.40 (1H, m), 5.04-5.50 (2H, m), 7.05-7.25 (6H, m), 7.40-7.62 (2H, m), 7.97-8.20 (3H, m).

MS (FAB+) m/z: 695 ((M+H)$^+$).

IR (KBr): 2935, 1651, 1605, 1511, 1432, 1360, 1281, 1179, 1138, 907, 682 cm$^{-1}$.

Example 1k

2-{[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}-N-methyl-N-[3-(methylamino)propyl]acetamide The compound (800 mg, 1.15 mmol) obtained in Example 1j was dissolved in methylene chloride (6 mL), triethylamine (0.240 mL, 1.73 mmol) and pivaloyl chloride (0.156 mL, 1.27 mmol) were added under ice cooling, and the mixture was stirred at room temperature for 15 minutes. The reaction mixture was added dropwise to a solution of N,N'-dimethylpropanediamine (588 mg, 5.75 mmol) in methylene chloride (19 mL) under ice cooling, and the mixture was stirred at room temperature for 1 hour. The solvent was evaporated under reduced pressure, and the resulting residue was purified by NH silica gel column chromatography (ethyl acetate:methanol=30:1→10:1, v/v) to give the title compound (566 mg; yield, 63%) as a light yellow solid.

MS (ESI) m/z: 778 (M$^+$).

IR (ATR) $v_{max}$ 2932, 1645, 1435, 1358, 1279, 1176, 1136, 907, 838, 757 cm$^{-1}$.

Example 1l

N-{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}-5-formyl-N-methylthiophene-2-carboxamide The compound (73 mg, 0.157 mmol) obtained in Example 1k was dissolved in methylene chloride (3 mL), 5-formylthiophene-2-carboxylic acid (40 mg, 0.257 mmol) and 1-ethyl-3-(3-dimethylaminopropyl)carbodiimide hydrochloride (89 mg, 0.464 mmol) were added, and the mixture was stirred at room temperature for 1.5 hours. A saturated aqueous sodium hydrogencarbonate solution was added, and then the mixture was extracted with ethyl acetate (×3) and dried with anhydrous sodium sulfate. The solvent was evaporated under reduced pressure, and the resulting residue was purified by silica gel column chromatography (methylene chloride:methanol=40:1→20:1, v/v) to give the title compound (144 mg; yield, 61%) as a white solid.

$^1$H NMR (CDCl$_3$, 400 MHz): δ 1.67-1.77 (1H, m), 1.83-1.96 (2H, m), 2.02-2.29 (6H, m), 2.35-2.46 (1H, m), 2.56-2.80 (2H, m), 2.85-3.01 (6H, m), 3.03-3.22 (4H, m), 3.28-3.39 (2H, m), 3.44-3.53 (2H, m), 3.75-3.82 (0.5H, m), 3.85-3.91 (0.5H, m), 3.96-4.03 (0.5H, m), 4.03-4.23 (3.5H, m), 4.88 (0.5H, m), 5.05 (0.5H, m), 5.25 (0.5H, m), 5.35 (0.5H, m), 7.04-7.13 (3H, m), 7.14-7.20 (4H, m), 7.35-7.42 (2H, m), 7.65-7.69 (1H, m), 7.90-7.95 (2H, m), 7.98-8.01 (1H, m), 9.93 (1H, s).

MS (ESI) m/z: 916 (M$^+$).

Example 1m

1-{2-[{6-[({5-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-2-thienyl}methyl)amino]hexanoyl}(methyl)amino]ethyl}piperidin-4-yl biphenyl-2-ylcarbamate The compound (73 mg, 0.157 mmol) obtained in Example 1a and the compound (144 mg, 0.157 mmol) obtained in Example 1l were dissolved in methanol (2 mL), and the mixture was stirred at room temperature for 15 minutes. Toluene was added, then the solvent was evaporated under reduced pressure, sodium triacetoxyborohydride (100 mg, 0.471 mmol) was added to a solution of the resulting residue in methanol (2 mL), and the mixture was stirred at room temperature for 2.5 hours. The solvent was evaporated under reduced pressure, and the resulting residue was purified by NH silica gel column chromatography (ethyl acetate:methanol=60:1→20:1, v/v) and further purified by reverse phase preparative column chromatography (Waters; XTerra Prep MS C18 OBD, 5 μm, 30×100 mm) (acetonitrile:0.1% aqueous ammonium acetate solution=40:60→100:0, v/v) to give the title compound (57 mg; yield, 27%) as a light yellow solid.

MS (FAB) m/z: 1367 (M+H)$^+$.

IR (KBr) $v_{max}$ 2931, 1727, 1646, 1511, 1449, 1359, 1281, 1179, 1139, 755 cm$^{-1}$.

Example 2

1-{2-[{6-[({5-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-2-thienyl}methyl)(methyl)amino]hexanoyl}(methyl)amino]ethyl}piperidin-4-yl biphenyl-2-ylcarbamate

[Formula 7]

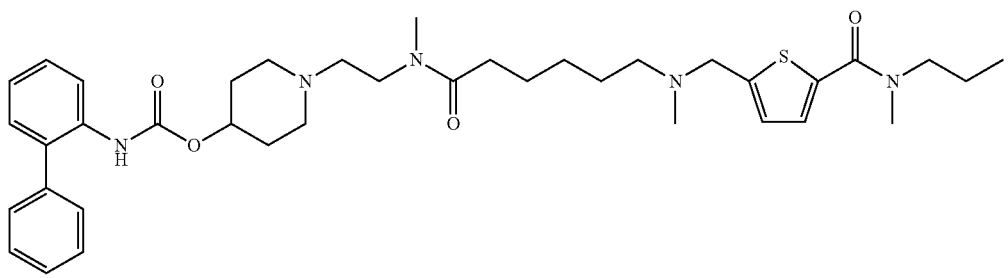

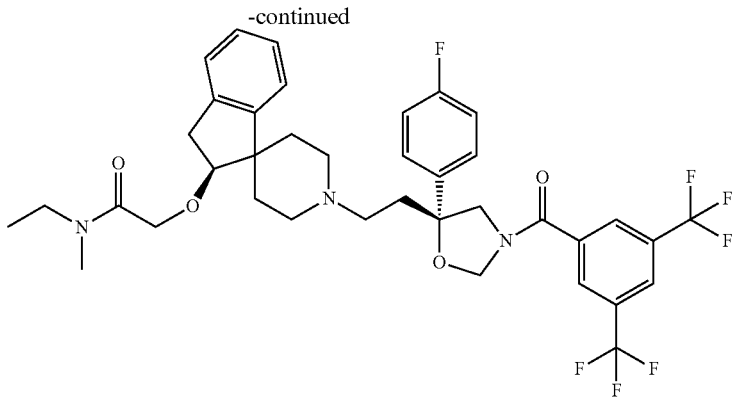

Example 2a

1-(2-{Methyl[6-(methylamino)hexanoyl] amino}ethyl)piperidin-4-yl biphenyl-2-ylcarbamate

1-[2-(Methylamino)ethyl]piperidin-4-yl biphenyl-2-yl-carbamate (500 mg, 1.41 mmol) was dissolved in methylene chloride (5 mL), triethylamine (0.236 mL, 1.70 mmol) and 6-bromohexanoyl chloride (0.232 mL, 1.56 mmol) were added under ice cooling, and the mixture was stirred at room temperature for 30 minutes. Water was added to the reaction mixture, and the mixture was extracted with ethyl acetate (×3) and washed with saturated sodium chloride solution. The organic layer was dried with anhydrous sodium sulfate, then the solvent was evaporated under reduced pressure, the resulting residue was dissolved in methylene chloride (5 mL), a 40% methyl amine-methanol solution (5.76 mL, 56.4 mmol) was added under ice cooling, and the mixture was stirred at room temperature for 7.5 hours. The solvent of the reaction mixture was evaporated under reduced pressure, and the resulting residue was purified by NH silica gel column chromatography (ethyl acetate:methanol=100:0→10:1, v/v) to give the title compound (574 mg; yield, 85%) as a light yellow oily substance.

MS (FAB) m/z: 481 (M+H)$^+$.

IR (KBr) $\nu_{max}$ 2939, 1719, 1638, 1521, 1449, 1303, 1223, 1045, 749, 704 cm$^{-1}$.

Example 2b

1-{2-[{6-[({5-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-2-thienyl}methyl)(methyl)amino]hexanoyl}(methyl)amino]ethyl}piperidin-4-yl biphenyl-2-ylcarbamate

The compound (157 mg, 0.171 mmol) obtained in Example 2a was used to give the title compound (87 mg; yield, 37%) as a white solid according to the method described in Example 1m.

MS (FAB) m/z: 1381 (M+H)$^+$.

IR (KBr) $\nu_{max}$ 2935, 1729, 1646, 1511, 1449, 1359, 1281, 1179, 1138, 755 cm$^{-1}$.

Example 3

1-{2-[{6-[{2-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]benzyl}(methyl)amino]hexanoyl}(methyl)amino]ethyl}piperidin-4-yl biphenyl-2-ylcarbamate

[Formula 8]

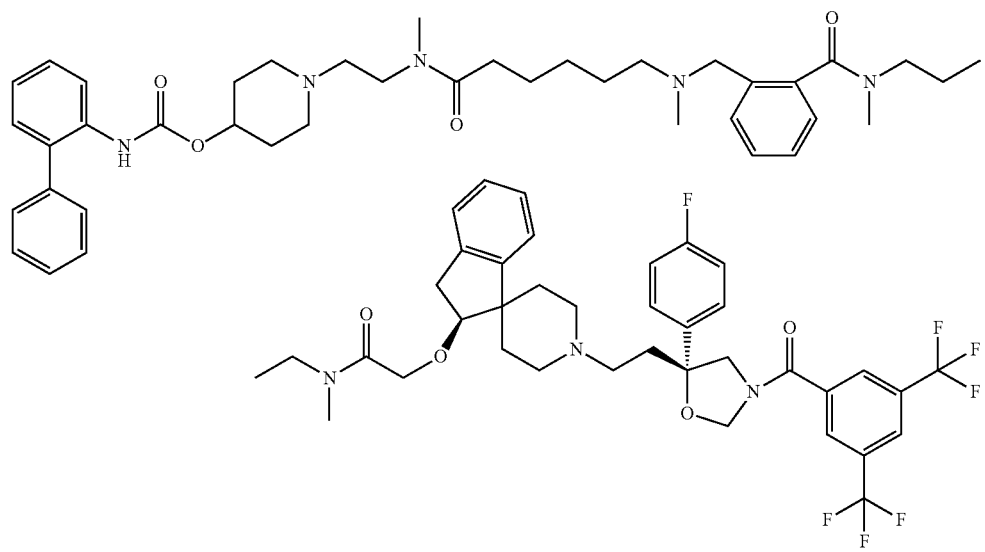

Example 3a

Benzyl 2-formylbenzoate

2-Formylbenzoate (500 mg, 3.33 mmol) was dissolved in N,N-dimethylformamide (3 mL), potassium carbonate (553 mg, 4.00 mmol) and benzyl bromide (0.396 mL, 3.33 mmol) were added, and the mixture was stirred at room temperature for 2 hours. The reaction mixture was diluted with ethyl acetate, and then the organic layer was washed with water (×3) and saturated sodium chloride solution. The organic layer was dried with anhydrous sodium sulfate, and then the solvent was evaporated under reduced pressure to give the title compound (795 mg; yield, 99%) as a colorless oily substance.

$^1$H NMR (CDCl$_3$, 400 MHz): δ 5.42 (2H, s), 7.35-7.42 (4H, m), 7.45-7.46 (1H, m), 7.64 (1H, ddd, J=6.8, 2.4, 2.0 Hz), 7.65 (1H, ddd, J=6.8, 2.4, 2.0 Hz), 7.94 (1H, dd, J=6.8, 2.4 Hz), 8.00 (1H, dd, J=6.8, 2.0 Hz), 10.63 (1H, s).

MS (APCI) m/z: 241 (M+H)$^+$.

Example 3b

Benzyl 2-{[{6-[(2-{4-[(biphenyl-2-ylcarbamoyl)oxy]piperidin-1-yl}ethyl)(methyl)amino]-6-oxohexyl}(methyl)amino]methyl}benzoate The compound (368 mg, 0.766 mmol) obtained in Example 2a and the compound (184 mg, 0.766 mmol) obtained in Example 3a were dissolved in methanol (3 mL), and the mixture was stirred at room temperature for 10 minutes. Toluene was added, then the solvent was evaporated under reduced pressure, sodium triacetoxyborohydride (198 mg, 0.936 mmol) was added to a solution of the resulting residue in methanol (3 mL), and the mixture was stirred at room temperature for 1 hour. The solvent was evaporated under reduced pressure, and the resulting residue was purified by NH silica gel column chromatography (ethyl acetate:methanol=100:0→20:1, v/v) to give the title compound (248 mg; yield, 46%) as a colorless oily substance.

$^1$H NMR (CDCl$_3$, 400 MHz): δ 1.26-1.32 (2H, m), 1.42-1.49 (2H, m), 1.54-1.68 (4H, m), 1.88-1.95 (2H, m), 2.11 (3H, s), 2.23-2.32 (6H, m), 2.44-2.47 (2H, m), 2.66-2.75 (2H, m), 2.92 (1.5H, s), 2.97 (1.5H, s), 3.35 (1H, t, J=7.0 Hz), 3.46 (2H, t, J=7.0 Hz), 3.76 (2H, s), 5.32 (2H, s), 6.58 (1H, s), 7.11-7.15 (1H, m), 7.21-7.23 (1H, m), 7.29-7.33 (1H, m), 7.35-7.39 (5H, m), 7.41-7.45 (2H, m), 7.46-7.50 (2H, m), 7.57-7.63 (2H, m), 7.68-7.77 (2H, m), 7.91-7.89 (1H, m), 8.11-8.09 (1H, m).

MS (ESI) m/z: 704 (M$^+$).

Example 3c

1-{2-[{6-[{2-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]benzyl}(methyl)amino]hexanoyl}(methyl)amino]ethyl}piperidin-4-yl biphenyl-2-ylcarbamate A solution of the compound (248 mg, 0.352 mmol) obtained in Example 3b in ethyl acetate (20 mL) was added to 10% palladium-carbon (dry; 50 mg), the atmosphere in the system was replaced with a hydrogen atmosphere, and then the mixture was stirred at room temperature for 4 hours. The atmosphere in the system was replaced with a nitrogen atmosphere, and the mixture was filtered through celite. The solvent was evaporated under reduced pressure, and moisture was removed from the resulting residue azeotropically with tetrahydrofuran and toluene (×2). The residue was dissolved in methylene chloride (6 mL), the compound (274 mg, 0.352 mmol) obtained in Example 1k and 1-ethyl-3-(3-dimethylaminopropyl)carbodiimide hydrochloride (101 mg, 0.528 mmol) were added, and the mixture was stirred overnight at room temperature. A saturated aqueous sodium hydrogencarbonate solution was added, and then the mixture was extracted with ethyl acetate (×3) and dried with anhydrous sodium sulfate. The solvent was evaporated under reduced pressure, and the resulting residue was purified by NH silica gel column chromatography (hexane:ethyl acetate=1:1→ethyl acetate:methanol=40:1, v/v) and further purified by reverse phase preparative column chromatography (Waters; XTerra Prep MS C18 OBD, 5 μm, 30×100 mm) (acetonitrile: 0.1% aqueous ammonium acetate solution=40:60→90:10, v/v) to give the title compound (119 mg; yield, 25%) as a white solid.

MS (FAB) m/z: 1375 (M+H)$^+$.

IR (KBr) ν$_{max}$ 2939, 1730, 1643, 1513, 1449, 1359, 1281, 1180, 1139, 753 cm$^{-1}$.

Example 4

1-(2-{[6-({5-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-2-thienyl}amino)hexanoyl](methyl)amino}ethyl)piperidin-4-yl biphenyl-2-ylcarbamate

[Formula 9]

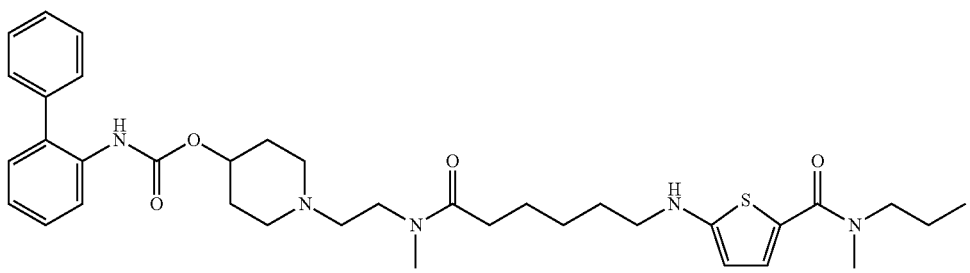

-continued

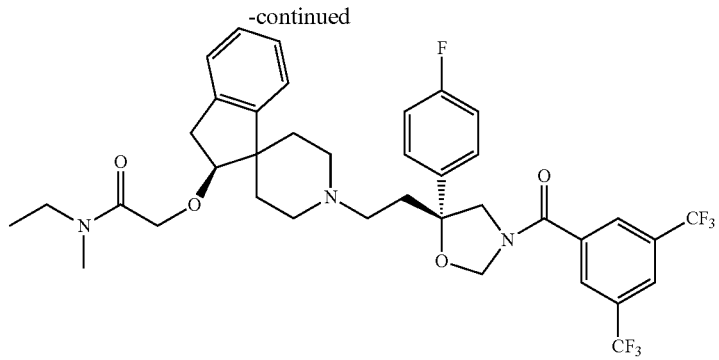

Example 4a

Methyl 5-aminothiophene-2-carboxylate

5-Aminothiophene-2-carboxylic acid (1.00 g, 5.78 mmol) instead of 2-formylbenzoic acid and methyl iodide (1.44 mL, 23.1 mmol) instead of benzyl bromide were used to give the title compound (1.04 g; yield, 97%) as a dark brown solid according to the method described in Example 3a.

$^1$H NMR (CDCl$_3$, 400 MHz): δ 3.81 (3H, s), 6.09 (1H, d, J=3.9 Hz), 7.45 (1H, d, J=3.9 Hz).

ZMS (EI) m/z: 157 (M$^+$)

Example 4b

Methyl 5-[tert-butoxycarbonyl)amino]thiophene-2-carboxylate

The compound (947 mg, 5.58 mmol) obtained in Example 4a was dissolved in tetrahydrofuran (19 mL), di-tert-butyl dicarbonate (1.58 g, 7.25 mmol) was added, and then the mixture was stirred with heating to reflux for 48 hours. The solvent was evaporated under reduced pressure, and the resulting residue was purified by silica gel column chromatography (hexane:ethyl acetate=6:1→4:1, v/v) to give the title compound (971 mg; yield, 68%) as a brown solid.

$^1$H NMR (CDCl$_3$, 400 MHz): δ 1.53 (9H, s), 3.84 (3H, s), 6.44 (1H, d, J=3.9 Hz), 7.21 (1H, brs), 7.56 (1H, d, J=3.9 Hz).

MS (EI) m/z: 257 (M$^+$).

Example 4c

5-[(tert-Butoxycarbonyl)amino]thiophene-2-carboxylic acid

The compound (568 mg, 2.21 mmol) obtained in Example 4b was dissolved in methanol (4.5 mL), an aqueous 1 N sodium hydroxide solution (8.82 mL, 8.82 mmol) was added, and the mixture was stirred at 50° C. for 4 hours. The solvent was evaporated under reduced pressure, methylene chloride and 1 N hydrochloric acid were added to the resulting residue, and the mixture was extracted with methylene chloride (×3) and dried with anhydrous sodium sulfate. The solvent was evaporated under reduced pressure to give the title compound (493 mg; yield, 92%) as a light brown solid.

$^1$H NMR (CDCl$_3$, 400 MHz): δ 1.54 (9H, s), 6.53 (1H, d, J=3.9 Hz), 7.53 (1H, d, J=3.9 Hz), 9.24 (1H, s).

MS (APCI) m/z: 244 (M+H)$^+$.

Example 4d tert-Butyl {5-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-2-thienyl}carbamate The compound (94 mg, 0.385 mmol) obtained in Example 4c was dissolved in methylene chloride (4 mL), triethylamine (80 μL, 0.578 mmol) and pivaloyl chloride (52 μL, 0.424 mmol) were added under ice cooling, and the mixture was stirred at room temperature for 15 minutes. The compound (300 mg, 0.385 mmol) obtained in Example 1k was added to the reaction mixture under ice cooling, and the mixture was stirred at room temperature for 1 hour. The solvent was evaporated under reduced pressure, and the resulting residue was purified by NH silica gel column chromatography (hexane:ethyl acetate=1:2→0:100, v/v) to give the title compound (366 mg; yield, 94%) as a white solid.

MS (FAB) m/z: 1004 (M+H)$^+$.

IR (KBr) ν$_{max}$ 3436, 2931, 1648, 1509, 1359, 1281, 1160, 1141, 758 cm$^{-1}$.

Example 4e

5-Amino-N-{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}-N-methylthiophene-2-carboxamide The compound (343 mg, 0.342 mmol) obtained in Example 4d was dissolved in methylene chloride (6 mL), trifluoroacetic acid (2 mL) was added under ice cooling, and the mixture was stirred at room temperature for 2 hours. The solvent was evaporated under reduced pressure, and the resulting residue was purified by NH silica gel column chromatography (ethyl acetate:methanol=100:0→20:1, v/v) to give the title compound (267 mg; yield, 86%) as a white solid.

MS (FAB) m/z: 904 (M+H)$^+$.

IR (KBr) ν$_{max}$ 3320, 2928, 1647, 1604, 1470, 1359, 1281, 1180, 1138, 758 cm$^{-1}$.

Example 4f

1-{2-[(6-Hydroxyhexanoyl)(methyl)amino]ethyl}piperidin-4-yl biphenyl-2-ylcarbamate 1-[2-(Methylamino)ethyl]piperidin-4-yl biphenyl-2-ylcarbamate (5.00 g, 14.1 mmol) was dissolved in methylene chloride (141 mL), triethylamine (2.35 mL, 16.9 mmol) and 6-bromohexanoyl chloride (2.32 mL, 15.6 mmol) were added under ice cooling, and the mixture was stirred at room temperature for 20 minutes. The solvent was evaporated under reduced pressure, water was added to the resulting residue, the mixture was extracted with ethyl acetate (×3), and the organic layer was washed with saturated sodium chloride solution. The organic layer was dried with anhydrous sodium sulfate, the solvent was evaporated under reduced pressure, the resulting residue was dissolved in N,N-dimethylformamide (47 mL), potassium acetate (2.08 g, 21.2 mmol) and 18-crown-6 (373 mg, 1.41 mmol) were added, and the mixture was stirred at 60° C. for 15.5 hours. Methanol (47 mL) and potassium carbonate (5.85 g, 42.3 mmol) were added to the reaction mixture, and the mixture was stirred at room temperature for 2 hours. The mixture was diluted with methylene chloride, water and saturated sodium chloride solution were added, and the mixture was extracted with methylene chloride (×3). The organic layer was dried with anhydrous sodium sulfate, the solvent was evaporated under reduced pressure, and the resulting residue was purified by NH silica gel column chromatography (ethyl acetate:methanol=100:0→20:1, v/v) to give the title compound (5.93 g; yield, 90%) as a white solid.

MS (FAB) m/z: 468 (M+H)$^+$.

IR (KBr) $\nu_{max}$ 2929, 1723, 1627, 1530, 1359, 1282, 1232, 1058, 1045, 746, 707 cm$^{-1}$.

Example 4g

1-{2-[Methyl(6-oxohexanoyl)amino]ethyl}piperidin-4-yl biphenyl-2-ylcarbamate

The compound (2.50 g, 5.35 mmol) obtained in Example 4f, dimethyl sulfoxide (3.80 mL, 53.5 mmol) and N,N-diisopropylethylamine (4.58 mL, 26.7 mmol) were dissolved in methylene chloride (54 mL), a sulfur trioxide-pyridine complex (4.17 g, 26.7 mmol) was added under ice cooling, and the mixture was stirred at room temperature for 1 hour. A saturated aqueous sodium hydrogencarbonate solution was added to the reaction mixture, the mixture was extracted with ethyl acetate (×3), and the organic layer was washed with saturated sodium chloride solution. The organic layer was dried with anhydrous sodium sulfate, the solvent was evaporated under reduced pressure, and the resulting residue was purified by silica gel column chromatography (ethyl acetate:methanol=30:0→10:1, v/v) to give the title compound (2.32 g; yield, 93%) as a yellow oily substance.

$^1$H NMR (CDCl$_3$, 400 MHz): δ 1.66-1.69 (6H, m), 1.90-1.94 (2H, m), 2.24-2.35 (4H, m), 2.44-2.49 (4H, m), 2.68-2.73 (2H, m), 2.93 (1H, s), 3.00 (2H, s), 3.37 (1H, t, J=7.1 Hz), 3.47 (2H, t, J=7.1 Hz), 4.70-4.75 (1H, m), 6.58-6.59 (1H, m), 7.11-7.15 (1H, m), 7.21-7.23 (1H, m), 7.33-7.40 (3H, m), 7.41-7.43 (1H, m), 7.47-7.52 (2H, m), 8.09-8.11 (1H, m), 9.77 (1H, s).

MS (FAB) m/z: 466 (M+H)$^+$.

Example 4h 1-(2-{[6-({5-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-2-thienyl}amino)hexanoyl](methyl)amino}ethyl)piperidin-4-yl biphenyl-2-ylcarbamate The compound (135 mg, 0.289 mmol) obtained in Example 4g and the compound (218 mg, 0.289 mmol) obtained in Example 4e were dissolved in ethanol (3 mL), and the mixture was stirred at room temperature for 10 minutes. Toluene was added, and then the solvent was evaporated under reduced pressure (×2). The resulting residue was dissolved in methylene chloride (3 mL), acetic acid (43 µL) and sodium triacetoxyborohydride (153 mg, 0.723 mmol) were added, and the mixture was stirred at room temperature for 4.5 hours. Sodium borohydride (36 mg, 1.16 mmol) was added, and the mixture was stirred at room temperature for 20 minutes. The solvent was evaporated under reduced pressure, and the resulting residue was purified by NH silica gel column chromatography (ethyl acetate:methanol=100:1→20:1, v/v). Of the resulting crude product (170 mg), 75 mg was further purified by reverse phase preparative column chromatography (Waters; XTerra Prep MS C18 OBD, 5 µm, 30×100 mm) (acetonitrile:0.1% aqueous ammonium acetate solution=40:60→100:0, v/v) to give the title compound (43 mg; yield, 25%) as a light red solid.

MS (FAB) m/z: 1353 (M+H)$^+$.

IR (KBr) $\nu_{max}$ 3290, 2932, 1729, 1646, 1450, 1359, 1281, 1065, 756 cm$^{-1}$.

Example 5

1-{2-[{6-[({6-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]pyridin-3-yl}methyl)(methyl)amino]hexanoyl}(methyl)amino]ethyl}piperidin-4-yl biphenyl-2-ylcarbamate

[Formula 10]

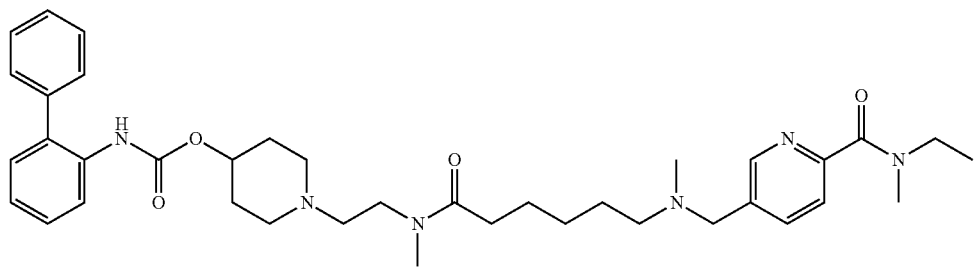

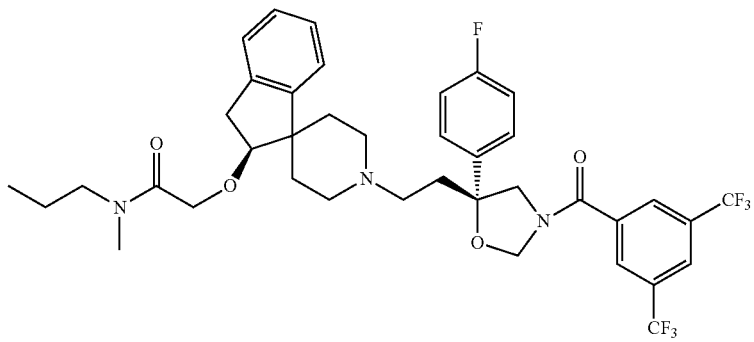

Example 5a

Methyl 6-[(3-{[(benzyloxy)carbonyl](methyl)amino}propyl)(methyl)carbamoyl]pyridine-3-carboxylate 5-(Methoxycarbonyl)pyridine-2-carboxylic acid (700 mg, 3.86 mmol) was dissolved in methylene chloride (40 mL), triethylamine (0.805 mL, 5.79 mmol) and pivaloyl chloride (0.524 mL, 4.25 mmol) were added under ice cooling, and the mixture was stirred at room temperature for 15 minutes. The reaction mixture was added dropwise to a solution of N,N'-dimethylpropanediamine (1.18 g, 11.6 mmol) in methylene chloride (40 mL) under ice cooling, and the mixture was stirred overnight at room temperature. Triethylamine (4.03 mL, 29.0 mmol) and benzyloxycarbonyl chloride (4.14 mL, 29.0 mmol) were added under ice cooling, and the mixture was stirred at room temperature for 2 hours. The solvent was evaporated under reduced pressure, and the resulting residue was purified by silica gel column chromatography (hexane:ethyl acetate=2:3→0:100, v/v) to give the title compound (1.23 g; yield, 80%) as a colorless oily substance.

$^1$H NMR (CDCl$_3$, 400 MHz): δ 1.89-2.00 (2H, m), 2.87 (2H, brs), 2.94-2.98 (3H, m), 3.04 (1H, brs), 3.13 (1H, brs), 3.22-3.23 (1H, m), 3.30-3.42 (2H, m), 3.52-3.60 (1H, m), 3.95-3.98 (2H, m), 5.05 (1H, s), 5.13 (1H, s), 7.27-7.36 (5H, m), 7.63-7.72 (1H, m), 8.37-8.39 (1H, m), 9.11-9.17 (1H, m).

MS (ESI) m/z: 399 (M$^+$).

Example 5b

6-[(3-{[(Benzyloxy)carbonyl](methyl)amino}propyl)(methyl)carbamoyl]pyridine-3-carboxylic acid The compound (1.23 g, 3.08 mmol) obtained in Example 5a was dissolved in methanol (9 mL), a 1 N aqueous sodium hydroxide solution (9.24 mL, 9.24 mmol) was added, and then the mixture was stirred at 50° C. for 10 hours. The solvent was evaporated under reduced pressure, ethyl acetate was added to the resulting residue, the mixture was extracted with water (×2), the aqueous layer was adjusted to pH 3 with 1 N hydrochloric acid, and the mixture was extracted with methylene chloride (×3) and dried with anhydrous sodium sulfate. The solvent was evaporated under reduced pressure to give the title compound (799 mg; yield, 68%) as a colorless oily substance.

$^1$H NMR (CDCl$_3$, 400 MHz): δ 2.02-1.96 (2H, m), 2.89 (1H, brs), 2.95 (2H, brs), 2.99 (1H, brs), 3.05 (1H, brs), 3.14 (1H, brs), 3.25-3.28 (2H, m), 3.33-3.43 (1H, m), 3.53-3.62 (1H, m), 5.07 (1H, s), 5.14 (1H, s), 7.24-7.38 (5H, m), 7.66-7.75 (1H, m), 8.39-8.44 (1H, m), 9.16-9.23 (1H, m).

MS (ESI) m/z: 385 (M$^+$).

Example 5c

Benzyl {3-[{[5-(hydroxymethyl)pyridin-2-yl]carbonyl}(methyl)amino]propyl}methylcarbamate The compound (350 mg, 0.908 mmol) obtained in Example 5b was dissolved in tetrahydrofuran (4 mL), a borane-tetrahydrofuran complex (1.0 M tetrahydrofuran solution; 3.18 mL, 3.18 mmol) was added under ice cooling, and then the mixture was stirred at room temperature for 45 minutes. Methanol (1 mL) was added under ice cooling, and the mixture was stirred at room temperature for 1 hour. The solvent was evaporated under reduced pressure, and the resulting residue was purified by NH silica gel column chromatography (ethyl acetate:methanol=100:0→20:1, v/v) to give the title compound (124 mg; yield, 37%) as a colorless oily substance.

$^1$H NMR (CDCl$_3$, 400 MHz): δ 1.81-1.98 (2H, m), 2.78-2.85 (2H, m), 2.96-2.97 (2H, m), 3.05-3.17 (3H, m), 3.20-3.27 (1H, m), 3.39-3.40 (1H, m), 3.51-3.58 (1H, m), 4.69-4.76 (2H, m), 4.98-5.13 (2H, m), 7.28-7.36 (5H, m), 7.45-7.61 (1H, m), 7.70-7.79 (1H, m), 8.48 (0.6H, s), 8.53 (0.4H, s).

MS (ESI) m/z: 371 (M$^+$).

Example 5d

N-{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}-5-(hydroxymethyl)-N-methylpyridine-2-carboxamide An ethyl acetate-methanol solution (1:1; 12 mL) of the compound (124 mg, 0.334 mmol) obtained in Example 5c was added to 10% palladium-carbon (dry; 80 mg), and the mixture was stirred at room temperature under a hydrogen atmosphere for 1 hour. The atmosphere in the system was replaced with a nitrogen atmosphere, and the mixture was filtered through celite. The solvent was evaporated under reduced pressure, and moisture was removed from the resulting residue azeotropically with ethyl acetate (×2) to give a CbZ-deprotected compound. The compound (232 mg, 0.334 mmol) obtained in Example 1j was dissolved in methylene chloride (5 mL), triethylamine (70 μL, 0.501 mmol) and pivaloyl chloride (45 μL, 0.367 mmol) were added under ice cooling, and the mixture was stirred at room temperature for 15 minutes. The reaction mixture was added dropwise to a solution of the obtained CbZ-deprotected compound in methylene chloride (5 mL) under ice cooling, and the mixture was stirred at room temperature for 1 hour. The solvent was evaporated under reduced pressure, and the resulting residue was purified by NH silica gel column chromatography (ethyl acetate:methanol=40:1→30:1, v/v) to give the title compound (189 mg; yield, 62%) as a colorless oily substance.

MS (ESI) m/z: 913 (M+).

Example 5e

1-{2-[{6-[({6-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]pyridin-3-yl}methyl)(methyl)amino]hexanoyl}(methyl)amino]ethyl}piperidin-4-yl biphenyl-2-ylcarbamate The compound (189 mg, 0.207 mmol) obtained in Example 5d was dissolved in ethyl acetate (4 mL), triethylamine (43 μL, 0.248 mmol) and methanesulfonyl chloride (19 μL, 0.248 mmol) were added under ice cooling, and the mixture was stirred at the same temperature for 15 minutes. Insoluble matter was removed by filtration through celite, the solvent was evaporated under reduced pressure, the resulting residue and the compound (50 mg, 0.104 mmol) obtained in Example 2a were dissolved in acetonitrile (5 mL), N,N-diisopropylethylamine (27 μL, 0.156 mmol) was added, and the mixture was stirred with heating to reflux for 5 hours. The solvent was evaporated under reduced pressure, and the resulting residue was purified by NH silica gel column chromatography (ethyl acetate:methanol=100:0→30:1, v/v) and further purified by reverse phase preparative column chromatography (Waters; XTerra Prep MS C18 OBD, 5 μm, 30×100 mm) (acetonitrile:0.1% aqueous ammonium acetate solution=60:40→70:30, v/v) to give the title compound (39 mg; yield, 27%) as a white solid.

MS (FAB) m/z: 1376 (M+H)+.
IR (KBr) $v_{max}$ 2934, 1729, 1645, 1512, 1449, 1359, 1281, 1180, 1139, 755 cm$^{-1}$.

Example 6

1-{2-[{6-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]pyridin-3-yl}(methyl)amino]hexanoyl}(methyl)amino]ethyl}piperidin-4-yl biphenyl-2-ylcarbamate

[Formula 11]

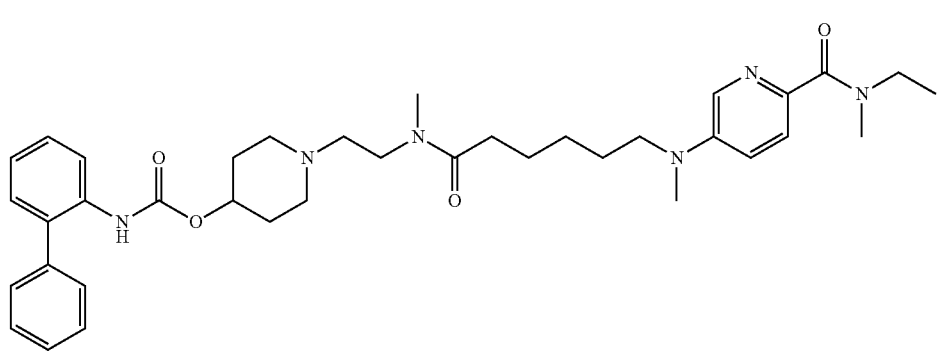

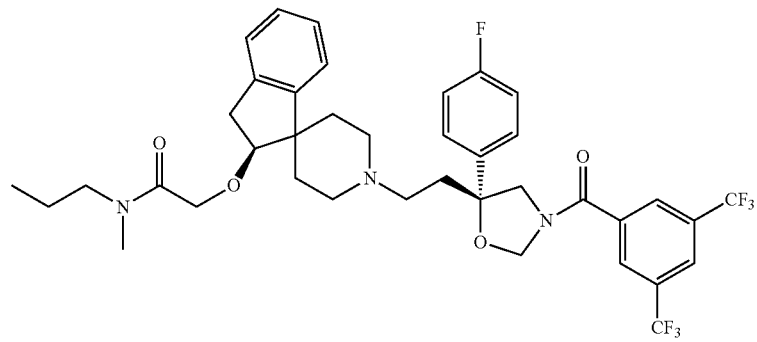

Example 6a

Benzyl {3-[({5-[(tert-butoxycarbonyl)amino]pyridin-2-yl}carbonyl)(methyl)amino]propyl}methylcarbamate The compound (449 mg, 1.16 mmol) obtained in Example 5b was dissolved in tert-butanol (6 mL), triethylamine (1.78 mL, 1.28 mmol) and diphenylphosphate azide (0.251 mL, 1.16 mmol) were added, and the mixture was stirred with heating to reflux for 3 hours. The solvent was evaporated under reduced pressure, and the resulting residue was purified by silica gel column chromatography (hexane:ethyl acetate=1:2→0:100, v/v) to give the title compound (339 mg; yield, 64%) as a colorless oily substance.

$^1$H NMR (CDCl$_3$, 400 MHz): δ 1.54 (9H, s), 1.94-1.97 (2H, m), 2.88-3.10 (6H, m), 3.23-3.25 (1H, m), 3.36-3.44 (1H, m), 3.47-3.57 (2H, m), 5.09 (1H, s), 5.13 (1H, s), 6.54-6.66 (1H, m), 7.33-7.41 (5H, m), 7.60-7.68 (1H, m), 8.02 (1H, brs), 8.20-8.44 (1H, m).

MS (ESI) m/z: 456 (M$^+$).

Example 6b

Benzyl {3-[({5-[(tert-butoxycarbonyl)(methyl)amino]pyridin-2-yl}carbonyl)(methyl)amino]propyl}methylcarbamate The compound (170 mg, 0.372 mmol) obtained in Example 6a was dissolved in tetrahydrofuran (4 mL), sodium hydride (55%; 20 mg, 0.447 mmol) was added under ice cooling, and the mixture was stirred at room temperature for 15 minutes. Methyl iodide (35 μL, 0.558 mmol) was added, and then the mixture was stirred overnight at room temperature. Water was added to the reaction mixture, the mixture was extracted with ethyl acetate (×3), and the organic layer was washed with saturated sodium chloride solution. The organic layer was dried with anhydrous sodium sulfate, and then the solvent was evaporated under reduced pressure to give the title compound (178 mg; yield, 100%) as a yellow oily substance.

$^1$H NMR (CDCl$_3$, 400 MHz): δ 1.48 (9H, s), 1.92-1.98 (2H, m), 2.88-3.10 (6H, m), 3.24-3.31 (4H, m), 3.36-3.49 (2H, m), 3.50-3.58 (1H, m), 5.08 (1H, s), 5.13 (1H, s), 6.54-6.66 (1H, m), 7.33-7.36 (5H, m), 7.59-7.70 (1H, m), 8.43-8.52 (1H, m).

MS (ESI) m/z: 470 (M$^+$).

Example 6c tert-Butyl {6-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]pyridin-3-yl}methylcarbamate The compound (178 mg, 0.372 mmol) obtained in Example 6b was used to give the title compound (163 mg; yield, 56%) as a white solid according to the method described in Example 5d.

$^1$H NMR (CDCl$_3$, 400 MHz): δ 1.48 (9H, s), 1.76-1.82 (1H, m), 1.91-1.96 (2H, m), 2.05-2.29 (6H, m), 2.38-2.45 (1H, m), 2.59-2.78 (3H, m), 2.84 (1H, brs), 2.89-2.91 (3H, m), 2.97-3.01 (2H, m), 3.04-3.13 (3H, m), 3.27-3.31 (3H, m), 3.40-3.44 (2H, m), 3.51-3.55 (2H, m), 3.76-3.80 (0.5H, m), 3.87-3.91 (0.5H, m), 3.98-4.03 (0.5H, m), 4.07-4.24 (3.5H, m), 4.86-4.89 (0.5H, brs), 5.04-5.06 (0.5H, brs), 5.24-5.26 (0.5H, brs), 5.32-5.35 (0.5H, brs), 7.07-7.11 (3H, m), 7.15-7.19 (4H, m), 7.38 (1H, brs), 7.64-7.70 (2H, m), 7.93 (2H, brs), 7.99 (1H, brs), 8.52-8.44 (1H, m).

MS (ESI) m/z: 1013 (M$^+$).

Example 6d

N-{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}-N-methyl-5-(methylamino)pyridine-2-carboxamide The compound (163 mg, 0.161 mmol) obtained in Example 6c was dissolved in methanol (2 mL), 4 N hydrochloric acid-dioxane (0.805 mL, 3.22 mmol) was added, and then the mixture was stirred at room temperature for 2 hours. A saturated aqueous sodium hydrogencarbonate solution was added to the reaction mixture, and the mixture was extracted with methylene chloride (×3) and dried with anhydrous sodium sulfate. The solvent was evaporated under reduced pressure, and the resulting residue was purified by silica gel column chromatography (methylene chloride:methanol=20:1→10:1, v/v) to give the title compound (127 mg; yield, 86%) as a white solid.

MS (FAB) m/z: 913 (M+H)$^+$.

IR (KBr) ν$_{max}$ 2927, 1648, 1591, 1359, 1281, 1180, 1139, 847, 758, 682 cm$^{-1}$.

Example 6e

1-{2-[{6-[{6-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]pyridin-3-yl}(methyl)amino]hexanoyl}(methyl)amino]ethyl}piperidin-4-yl biphenyl-2-ylcarbamate The compound (107 mg, 0.117 mmol) obtained in Example 6d was used to give the title compound (69 mg; yield, 43%) as a white solid according to the method described in Example 4h.

MS (FAB) m/z: 1362 (M+H)$^+$.

IR (KBr) ν$_{max}$ 2930, 1728, 1646, 1585, 1359, 1281, 1139, 847, 754 cm$^{-1}$.

Example 7

1-{2-[{6-[({6-[{3-[({[(2S)-1'-{2-[(5R)-3-[3,5-Bis (trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methy)amino]propyl} (methyl)carbamoyl]pyridin-3-yl}methyl)amino] hexanoyl}(methyl)amino]ethyl}piperidin-4-yl biphenyl-2-ylcarbamate

[Formula 12]

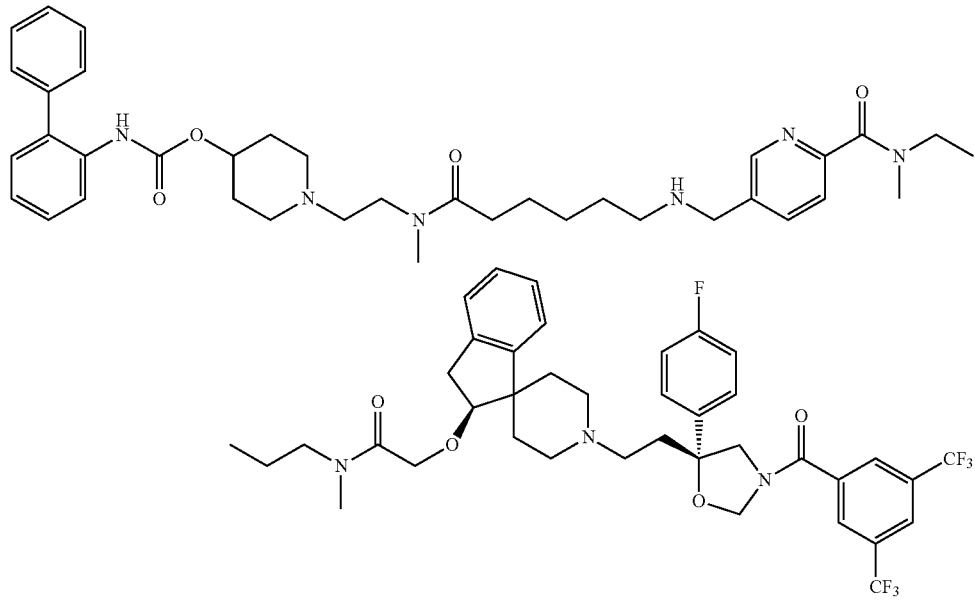

The compound (68 mg, 0.146 mmol) obtained in Example 1a was used to give the title compound (40 mg; yield, 20%) as a white solid according to the method described in Example 5e.

MS (FAB) m/z: 1362 (M+H)$^+$.

IR (KBr) $\nu_{max}$ 2929, 1726, 1643, 1512, 1359, 1281, 1180, 1139, 848, 753 cm$^{-1}$.

Example 8

1-{2-[{6-[{5-[{3-[({[(2S)-1'-{2-[(5R)-3-[3,5-Bis (trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl} (methyl)carbamoyl]-2-thienyl}(methyl)amino] hexanoyl}(methyl)amino]ethyl}piperidin-4-yl biphenyl-2-ylcarbamate

[Formula 13]

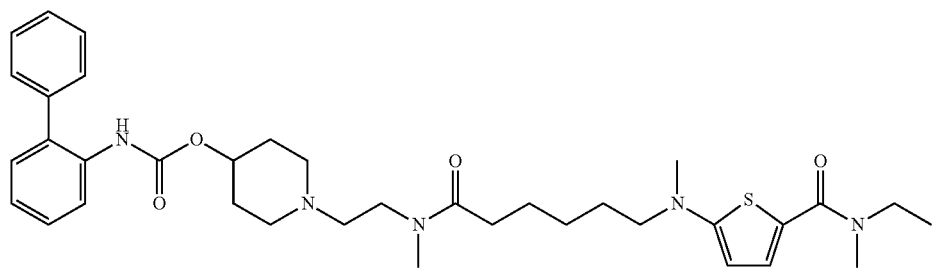

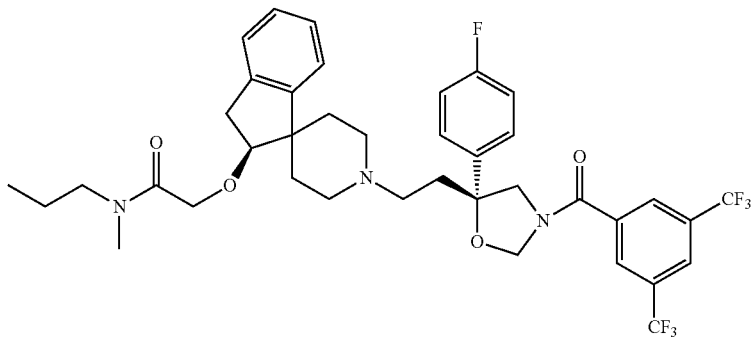

Example 8a tert-Butyl {5-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methy)amino]propyl}(methyl)carbamoyl]-2-thienyl}methylcarbamate The compound (500 mg, 1.94 mmol) obtained in Example 4b was dissolved in tetrahydrofuran (4 mL), sodium hydride (55%; 102 mg, 2.33 mmol) was added under ice cooling, and then the mixture was stirred at room temperature for 15 minutes. Methyl iodide (0.181 mL, 2.91 mmol) was added, and then the mixture was stirred overnight at room temperature. Water was added to the reaction mixture, the mixture was extracted with ethyl acetate (×3), and the organic layer was washed with saturated sodium chloride solution. The organic layer was dried with anhydrous sodium sulfate, then the solvent was evaporated under reduced pressure, the resulting residue was dissolved in methanol (8 mL), a 1 N aqueous sodium hydroxide solution (7.76 mL, 7.76 mmol) was added, and the mixture was stirred at 50° C. for 1.5 hours. The solvent was evaporated under reduced pressure, ethyl acetate and 1 N hydrochloric acid were added to the resulting residue, the mixture was extracted with ethyl acetate (×3), and the organic layer was dried with anhydrous sodium sulfate. The solvent was evaporated under reduced pressure to give a carboxylic acid compound (427 mg). The resulting carboxylic acid compound (56 mg, 0.218 mmol) was dissolved in methylene chloride (2 mL), triethylamine (45 μL, 0.327 mmol) and pivaloyl chloride (28 μL, 0.229 mmol) were added under ice cooling, and the mixture was stirred at room temperature for 15 minutes. A solution of the compound (170 mg, 0.218 mmol) obtained in Example 1k in methylene chloride (2 mL) was added dropwise under ice cooling, and the mixture was stirred at room temperature for 1 hour. The solvent was evaporated under reduced pressure, and the resulting residue was purified by NH silica gel column chromatography (hexane:ethyl acetate=1:1→0:100, v/v) to give the title compound (159 mg; yield, 72%) as a white solid.

$^1$H NMR (CDCl$_3$, 400 MHz): δ 1.57 (9H, s), 1.69-1.76 (1H, m), 1.85-1.92 (2H, m), 2.07-2.27 (6H, m), 2.37-2.45 (1H, m), 2.58-2.79 (3H, m), 2.88 (3H, brs), 2.94 (1H, brs), 2.97-3.01 (2H, m), 3.04-3.07 (3H, m), 3.18-3.22 (3H, m), 3.34-3.36 (2H, m), 3.48-3.53 (1H, m), 3.77-3.83 (1H, m), 3.87-3.92 (1H, m), 3.96-4.01 (0.5H, m), 4.05-4.24 (3.5H, m), 4.86-4.88 (0.5H, brs), 5.04-5.06 (0.5H, brs), 5.24-5.26 (0.5H, brs), 5.32-5.35 (0.5H, brs), 6.40-6.43 (1H, m), 7.04-7.12 (3H, m), 7.16-7.21 (4H, m), 7.35-7.40 (2H, m), 7.92 (2H, brs), 7.99 (1H, brs).

MS (ESI) m/z: 1018 (M+H)$^+$.

Example 8b

N-{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}-N-methyl-5-(methylamino)thiophene-2-carboxamide The compound (159 mg, 0.156 mmol) obtained in Example 8a was used to give the title compound (141 mg; yield, 98%) as a white solid according to the method described in Example 4e.

$^1$H NMR (CDCl$_3$, 400 MHz): δ 1.71-1.76 (1H, m), 1.85-1.91 (2H, m), 2.09-2.26 (6H, m), 2.38-2.43 (1H, m), 2.60-2.76 (3H, m), 2.88 (3H, brs), 2.94 (1H, brs), 2.97-3.01 (2H, m), 3.03-3.06 (2H, m), 3.17-3.21 (3H, m), 3.30-3.36 (3H, m), 3.47-3.50 (1H, m), 3.76-3.79 (1H, m), 3.89-3.91 (1H, m), 3.97-4.02 (0.5H, m), 4.06-4.25 (3.5H, m), 4.29-4.32 (1H, m), 4.87 (0.5H, brs), 5.05 (0.5H, brs), 5.25 (0.5H, brs), 5.34 (0.5H, brs), 5.86-5.88 (1H, m), 7.05-7.13 (3H, m), 7.15-7.18 (4H, m), 7.36-7.40 (2H, m), 7.92 (2H, brs), 7.99 (1H, brs).

MS (ESI) m/z: 917 (M$^+$).

Example 8c

1-{2-[{6-[{5-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-2-thienyl}(methyl)amino]hexanoyl}(methyl)amino]ethyl}piperidin-4-yl biphenyl-2-ylcarbamate The compound (141 mg, 0.154 mmol) obtained in Example 8b was used to give the title compound (45 mg; yield, 21%) as a white solid according to the method described in Example 4h.

MS (FAB) m/z: 1367 (M+H)$^+$.

IR (KBr) ν$_{max}$ 2929, 1729, 1648, 1495, 1359, 1281, 1180, 1139, 755 cm$^{-1}$.

Example 9

1-(2-{[6-({6-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]pyridin-3-yl}amino)hexanoyl](methyl)amino}ethyl)piperidin-4-yl biphenyl-2-ylcarbamate

[Formula 14]

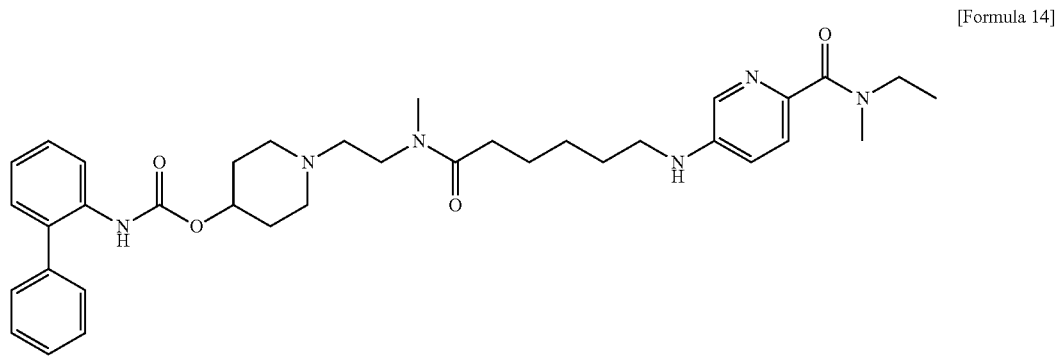

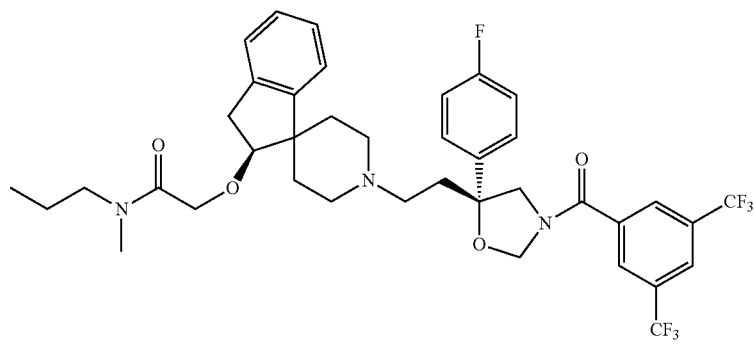

Example 9a

5-Amino-N-{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}-N-methylpyridine-2-carboxamide The compound (163 mg, 0.357 mmol) obtained in Example 6a was used to give a condensed compound (196 mg) according to the method described in Example 5d.

The resulting condensed compound was used to give the title compound (148 mg; yield, 64%) as a white solid according to the method described in Example 6d.

$^1$H NMR (CDCl$_3$, 400 MHz): δ 1.73-1.80 (1H, m), 1.89-1.95 (2H, m), 2.07-2.25 (3H, m), 2.38-2.43 (1H, m), 2.59-2.76 (3H, m), 2.86-2.90 (2H, m), 2.93-3.02 (2H, m), 3.06-3.08 (2H, m), 3.14-3.15 (1H, m), 3.26-3.34 (3H, m), 3.48-3.55 (2H, m), 3.63-3.67 (0.5H, m), 3.69-3.71 (4H, m), 3.76-3.79 (0.5H, m), 3.89 (2H, brs), 4.06-4.24 (1H, m), 4.29-4.32 (1H, m), 4.88 (0.5H, brs), 5.05 (0.5H, brs), 5.24 (0.5H, brs), 5.35 (0.5H, brs), 6.97-7.02 (1H, m), 7.05-7.12 (2H, m), 7.15-7.20 (4H, m), 7.36-7.39 (2H, m), 7.59-7.57 (2H, m), 7.92 (2H, brs), 7.99 (1H, brs).

MS (ESI) m/z: 898 (M$^+$).

Example 9b 1-(2-{[6-({6-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]pyridin-3-yl}amino)hexanoyl](methyl)amino}ethyl)piperidin-4-yl biphenyl-2-ylcarbamate The compound (205 mg, 0.228 mmol) obtained in Example 9a was used to give the title compound (83 mg; yield, 27%) as a light yellow solid according to the method described in Example 4h.

MS (FAB) m/z: 1348 (M+H)$^+$.

IR (KBr) ν$_{max}$ 2933, 1729, 1645, 1588, 1512, 1359, 1281, 1139, 847, 754 cm$^{-1}$.

Example 10

1-(2-{[6-({5-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]pyridin-2-yl}amino)hexanoyl](methyl)amino}ethyl)piperidin-4-yl biphenyl-2-ylcarbamate

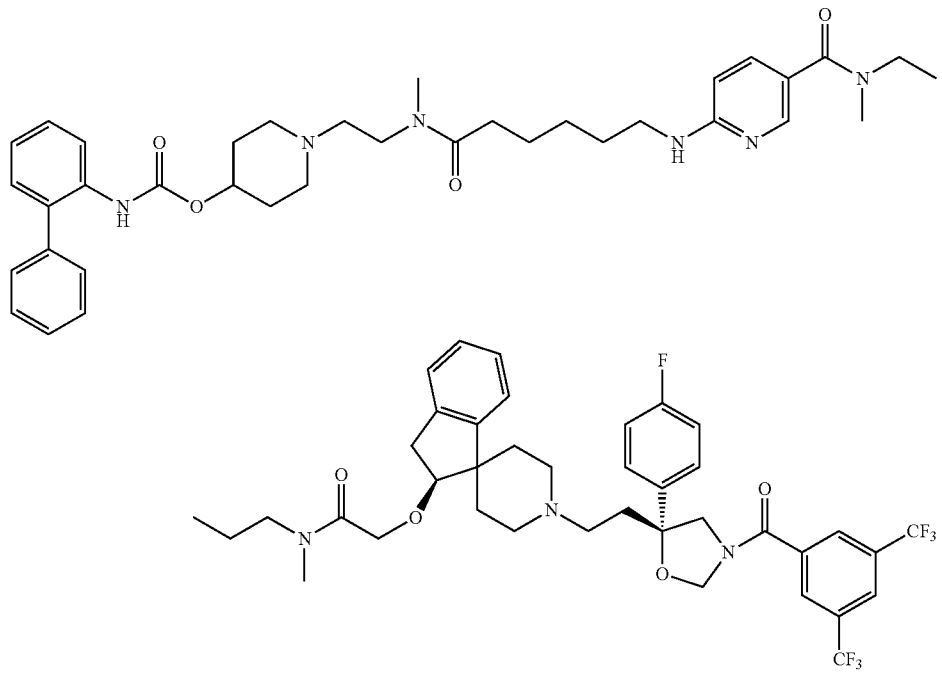

[Formula 15]

Example 10a

6-Amino-N-{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}-N-methylnicotinamide The compound (200 mg, 0.257 mmol) obtained in Example 1k was dissolved in methylene chloride (3 mL)-N,N-dimethylformamide (2 mL), 6-aminopyridine-3-carboxylic acid (36 mg, 0.257 mmol), 1-ethyl-3-(3-dimethylaminopropyl)carbodiimide hydrochloride (74 mg, 0.386 mmol) and 4-dimethylaminopyridine (4 mg, 0.0258 mmol) were added, and the mixture was stirred overnight at room temperature. The solvent was evaporated under reduced pressure, and the resulting residue was purified by NH silica gel column chromatography (ethyl acetate:methanol=40:1, v/v) to give the title compound (196 mg; yield, 85%) as a white solid.

$^1$H NMR (CDCl$_3$, 400 MHz): δ 1.73-1.80 (1H, m), 1.86-1.96 (2H, m), 2.06-2.28 (3H, m), 2.39-2.44 (1H, m), 2.59-2.76 (3H, m), 2.85-2.93 (5H, m), 2.97-3.00 (2H, m), 3.05-3.12 (3H, m), 3.19-3.18 (1H, m), 3.34-3.43 (3H, m), 3.48-3.54 (2H, m), 3.75-3.80 (0.5H, m), 3.85-3.89 (0.5H, m), 3.96-4.23 (4H, m), 4.87 (0.5H, brs), 5.05 (0.5H, brs), 5.26 (0.5H, brs), 5.34 (0.5H, brs), 6.33-6.82 (1H, m), 7.06-7.11 (2H, m), 7.15-7.19 (4H, m), 7.34-7.40 (2H, m), 7.59-7.69 (2H, m), 7.93 (2H, brs), 7.99 (1H, brs).

MS (ESI) m/z: 898 (M$^+$).

Example 10b 1-(2-{[6-({5-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]pyridin-2-yl}amino)hexanoyl](methyl)amino}ethyl)piperidin-4-yl biphenyl-2-ylcarbamate The compound (205 mg, 0.228 mmol) obtained in Example 10a was used to give the title compound (83 mg; yield, 27%) as a light yellow solid according to the method described in Example 4h.

MS (FAB) m/z: 1348 (M+H)$^+$.

IR (KBr) ν$_{max}$ 2931, 1728, 1645, 1605, 1519, 1359, 1281, 1180, 1139, 754 cm$^{-1}$.

Example 11

1-(2-{[6-({6-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]pyridazin-3-yl}amino)hexanoyl](methyl)amino}ethyl)piperidin-4-yl biphenyl-2-ylcarbamate

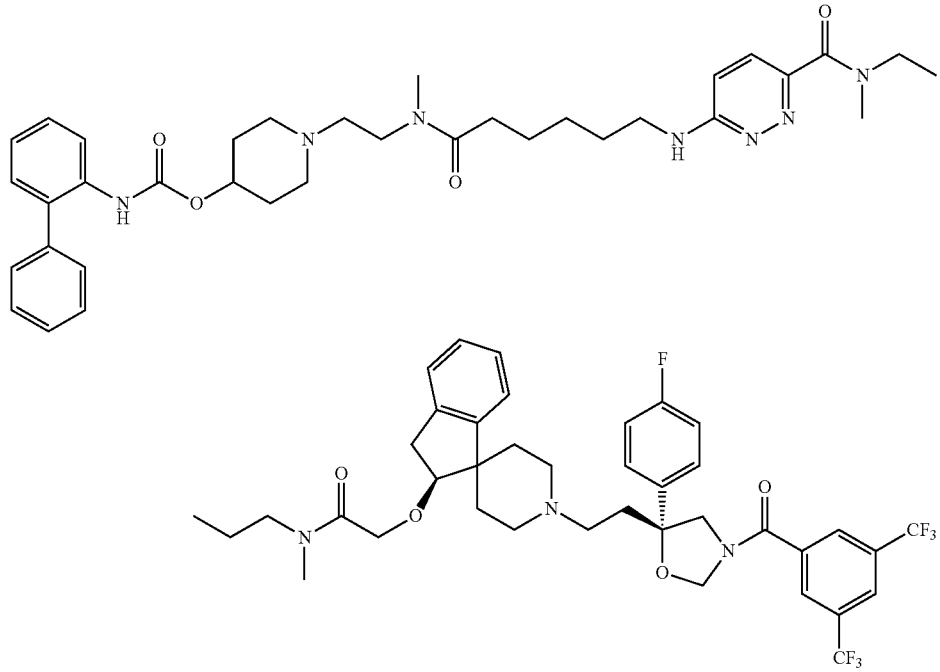

[Formula 16]

Example 11a

6-Chloropyridazine-3-carboxylic acid

3-Chloro-6-methylpyridazine (3.00 g, 23.3 mmol) was dissolved in concentrated sulfuric acid (23 mL), and potassium dichromate (8.24 g, 28.0 mmol) was added little by little under ice cooling. The mixture was stirred at room temperature for 1.5 hours, and the mixture was further stirred at 50° C. for 60 hours. The reaction mixture was slowly poured into ice water, and the mixture was extracted with diethyl ether (×3). The organic layer was washed with saturated sodium chloride solution and dried with anhydrous sodium sulfate, and then the solvent was evaporated under reduced pressure to give the title compound (1.27 g; yield, 34%) as a white solid.

$^1$H NMR (CDCl$_3$, 400 MHz): δ 7.80 (1H, d, J=7.8 Hz), 8.32 (1H, d, J=7.8 Hz).
MS (ESI) m/z: 159 (M+H)$^+$.

Example 11b

1-{2-[{6-[(tert-Butoxycarbonyl)amino]hexanoyl}(methyl)amino]ethyl}piperidin-4-yl biphenyl-2-yl-carbamate 6-[(tert-Butoxycarbonyl)amino]hexanoic acid (720 mg, 3.11 mmol) was dissolved in methylene chloride (14 mL), triethylamine (0.590 mL, 4.25 mmol) and pivaloyl chloride (0.418 mL, 3.40 mmol) were added under ice cooling, and the mixture was stirred at room temperature for 15 minutes. 1-[2-(Methylamino)ethyl]piperidin-4-yl biphenyl-2-ylcarbamate (1.00 g, 2.83 mmol) was added, and the mixture was stirred at room temperature for 2 hours. The solvent was evaporated under reduced pressure, and the resulting residue was purified by NH silica gel column chromatography (hexane:ethyl acetate=1:1→40:100, v/v) to give the title compound (1.59 g; yield, 99%) as a white solid.

$^1$H NMR (CDCl$_3$, 400 MHz): δ 1.33-1.43 (2H, m), 1.43 (9H, s), 1.48-1.55 (2H, m), 1.60-1.69 (4H, m), 1.88-1.94 (2H, m), 2.24-2.34 (4H, m), 2.45-2.48 (2H, m), 2.68-2.72 (2H, m), 2.93 (1.3H, s), 3.00 (1.7H, s), 3.08-3.12 (2H, m), 3.34-3.38 (1H, m), 3.45-3.48 (1H, m), 4.52-4.56 (1H, m), 4.69-4.75 (1H, m), 6.58 (1H, brs), 7.11-7.15 (1H, m), 7.21-7.26 (1H, m), 7.31-7.38 (3H, m), 7.40-7.43 (1H, m), 7.47-7.51 (2H, m), 8.08-8.11 (1H, m).

Example 11c

1-{2-[(6-Aminohexanoyl)(methyl)amino]ethyl}piperidin-4-yl biphenyl-2-ylcarbamate dihydrochloride The compound (1.59 g, 2.80 mmol) obtained in Example 11b was dissolved in 1,4-dioxane (7 mL), 4 N hydrochloric acid-dioxane (7.00 mL, 28.0 mmol) was added under ice cooling, and the mixture was stirred at room temperature for 20 minutes. Since insoluble material was precipitated, methanol (4 mL) was added, and the mixture was stirred at room temperature for 40 minutes. The solvent was evaporated under reduced pressure to give the title compound (1.60 g; yield, 100%) as a white solid.

MS (APCI) m/z: 467 (M+H)$^+$.

Example 11d

1-[2-(Methyl{6-[(6-{methyl[3-(methylamino)propyl]carbamoyl}pyridazin-3-yl)amino]hexanoyl}amino)ethyl]piperidin-4-yl biphenyl-2-ylcarbamate The compound (100 mg, 0.631 mmol) obtained in Example 11a was dissolved in methylene chloride (6 mL), triethylamine (0.105 mL, 0.757 mmol) and pivaloyl chloride (78 µL, 0.631 mmol) were added under ice cooling, and the mixture was stirred at room temperature for 15 minutes. A solution of tert-butyl methyl[3-(methylamino)propyl]carbamate (described in J. Med. Chem. 1990, 33, 97-101) (128 mg, 0.631 mmol) in methylene chloride (3 mL) was added dropwise under ice cooling, and the mixture was stirred at room temperature for 1 hour. The solvent was evaporated under reduced pressure, and the resulting residue was purified by silica gel column chromatography (methylene chloride:methanol=20:1, v/v) to give a crude Boc compound (202 mg).

The resulting crude Boc compound, the compound (263 mg, 0.487 mmol) obtained in Example 11c and the compound (47 mg, 0.102 mmol) obtained in Example 1a were dissolved in n-butanol (5 mL), triethylamine (0.196 mL, 1.41 mmol) was added, and the mixture was stirred with heating to reflux for 36 hours. The solvent was evaporated under reduced pressure, and the resulting residue was purified by NH silica gel column chromatography (ethyl acetate:methanol=40:1→20:1, v/v) to give a crude aminoalkylated compound (108 mg).

The crude aminoalkylated compound was dissolved in methanol (1 mL), 4 N hydrochloric acid-dioxane (2.50 mL, 4.19 mmol) was added, and the mixture was stirred at room temperature for 2 hours. A saturated aqueous sodium hydrogencarbonate solution was added to the reaction mixture, and the mixture was extracted with methylene chloride (×3) and dried with anhydrous sodium sulfate. The solvent was evaporated under reduced pressure, and the resulting residue was purified by NH silica gel column chromatography (ethyl acetate:methanol=20:1→methylene chloride:methanol=10:1, v/v) to give the title compound (59 mg; yield, 15%) as a light yellow oily substance.

$^1$H NMR (CDCl$_3$, 400 MHz): δ 1.30-1.33 (2H, m), 1.44-1.72 (14H, m), 1.88-1.96 (2H, m), 2.24-2.38 (3H, m), 2.46-2.48 (4H, m), 2.68-2.72 (2H, m), 2.94-3.00 (2H, m), 3.08-3.11 (1H, m), 3.27-3.29 (1H, m), 3.35-3.39 (1H, m), 3.46-3.49 (3H, m), 3.62-3.67 (1H, m), 3.72-3.75 (1H, m), 4.69-4.75 (1H, m), 6.61-6.73 (2H, m), 7.11-7.16 (2H, m), 7.21-7.26 (2H, m), 7.35-7.43 (2H, m), 7.46-7.52 (1H, m), 7.60-7.65 (1H, m), 8.06-8.10 (1H, m).

MS (FAB) m/z: 673 (M+H)$^+$.

Example 11e 1-(2-{[6-({6-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]pyridazin-3-yl}amino)hexanoyl](methyl)amino}ethyl)piperidin-4-yl biphenyl-2-ylcarbamate The compound (67 mg, 0.097 mmol) obtained in Example 1j was dissolved in methylene chloride (2 mL), triethylamine (18 µL, 0.13 mmol) and pivaloyl chloride (12 µL, 0.097 mmol) were added under ice cooling, and the mixture was stirred at room temperature for 15 minutes. A solution of the compound (59 mg, 0.088 mmol) obtained in Example 11d in methylene chloride (2 mL) was added dropwise under ice cooling, and the mixture was stirred at room temperature for 2 hours. The solvent was evaporated under reduced pressure, and the resulting residue was purified by NH silica gel column chromatography (ethyl acetate:methanol=40:1→20:1, v/v) and further purified by reverse phase preparative column chromatography (Waters; XTerra Prep MS C18 OBD, 5 µm, 30×100 mm) (acetonitrile:0.1% aqueous ammonium formate solution=50:50→60:40, v/v) to give the title compound (53 mg; yield, 41%) as a light yellow solid.

MS (FAB) m/z: 1349 (M+H)$^+$.

IR (KBr) $v_{max}$ 2931, 1727, 1643, 1449, 1359, 1281, 1181, 1139, 753 cm$^{-1}$.

Example 12

1-(2-{[6-({4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-3-fluorophenyl}amino)hexanoyl](methyl)amino}ethyl)piperidin-4-yl biphenyl-2-ylcarbamate

[Formula 17]

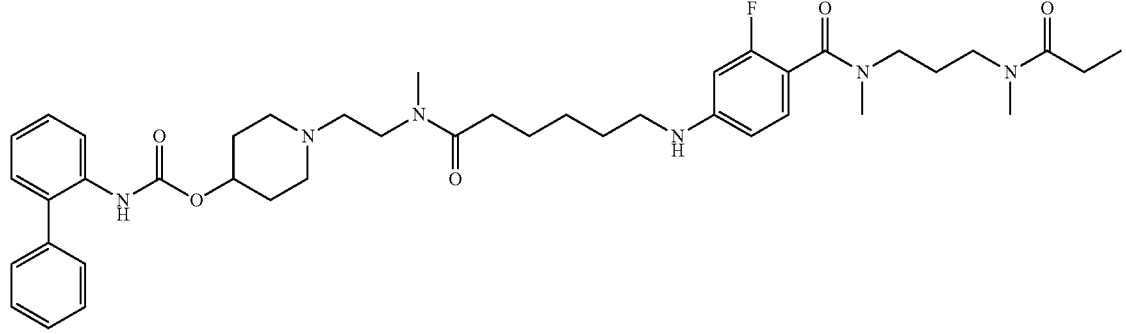

-continued

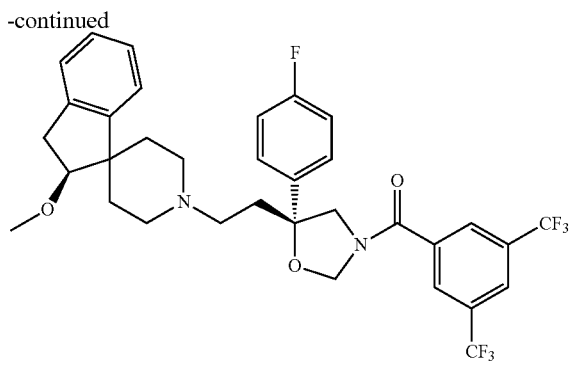

Example 12a tert-Butyl (3-{[(2-fluoro-4-nitrophenyl)carbonyl](methyl)amino}propyl)methylcarbamate 2-Fluoro-4-nitrobenzoic acid (150 mg, 0.810 mmol) was dissolved in methylene chloride (8 mL), triethylamine (0.135 mL, 0.972 mmol) and pivaloyl chloride (0.100 mL, 0.810 mmol) were added under ice cooling, and the mixture was stirred at room temperature for 15 minutes. A solution of tert-butyl methyl[3-(methylamino)propyl]carbamate (described in J. Med. Chem. 1990, 33, 97-101) (164 mg, 0.810 mmol) in methylene chloride (4 mL) was added dropwise under ice cooling, and the mixture was stirred at room temperature for 2 hours. The solvent was evaporated under reduced pressure, and the resulting residue was purified by NH silica gel column chromatography (hexane:ethyl acetate=1:2→0:100, v/v) to give the title compound (300 mg; yield, 100%) as a yellow oily substance.

$^1$H NMR (CDCl$_3$, 400 MHz): δ 1.37 (3H, s), 1.47 (6H, s), 1.72-1.80 (1H, m), 1.88-1.94 (1H, m), 2.71 (1H, brs), 2.85-2.91 (4H, m), 3.04-3.17 (3H, m), 3.30-3.33 (1H, m), 3.56-3.59 (1H, m), 7.52-7.61 (1H, m), 8.00 (1H, dd, J=8.8, 2.0 Hz), 8.11 (1H, dd, J=8.8, 2.0 Hz).

MS (ESI) m/z: 269 (M+H)$^+$ (form with Boc removed).

Example 12b tert-Butyl (3-{[(4-amino-2-fluorophenyl)carbonyl](methyl)amino}propyl)methylcarbamate A solution of the compound (300 mg, 0.810 mmol) obtained in Example 12a in methanol (8 mL) was added to 10% palladium-carbon (dry; 30 mg), the atmosphere in the system was replaced with a hydrogen atmosphere, and then the mixture was stirred at room temperature for 30 minutes. The atmosphere in the system was replaced with a nitrogen atmosphere, then 10% palladium-carbon (dry; 90 mg) was further added, the atmosphere in the system was replaced with a hydrogen atmosphere, and the mixture was stirred at room temperature for 30 minutes. The atmosphere in the system was replaced with a nitrogen atmosphere, and then the mixture was filtered through celite. The solvent was evaporated under reduced pressure to give the title compound (260 mg; yield, 95%) as a light brown oily substance.

IR (KBr) ν$_{max}$ 3405, 3238, 1689, 1628, 1611, 1483, 1407, 1327, 1167, 534 cm$^{-1}$.

Example 12c

1-{2-[{6-[(3-Fluoro-4-{methyl[3-(methylamino)propyl]carbamoyl}phenyl)amino]hexanoyl}(methyl)amino]ethyl}piperidin-4-yl biphenyl-2-ylcarbamate The compound (274 mg, 0.589 mmol) obtained in Example 4g and the compound (200 mg, 0.589 mmol) obtained in Example 12b were dissolved in methylene chloride (6 mL), acetic acid (100 µL) and sodium triacetoxyborohydride (187 mg, 0.884 mmol) were added, and the mixture was stirred overnight at room temperature. Sodium borohydride (22 mg, 0.589 mmol) was added, and the mixture was stirred at room temperature for 1 hour. The solvent was evaporated under reduced pressure, and the resulting residue was purified by NH silica gel column chromatography (hexane:ethyl acetate=1:1→0:100, v/v) to give a crude Boc compound (226 mg).

The resulting crude Boc compound was dissolved in methanol (2 mL), 4 N hydrochloric acid-dioxane (2.15 mL, 8.60 mmol) was added, and the mixture was stirred at room temperature for 1.5 hours. 4 N Hydrochloric acid-dioxane (1.08 mL, 4.32 mmol) was further added, and then the mixture was stirred at room temperature for 2.5 hours. The solvent was evaporated under reduced pressure, and the resulting residue was purified by NH silica gel column chromatography (ethyl acetate:methanol=30:1→methylene chloride:methanol=10:1, v/v) to give the title compound (186 mg; yield, 46%) as a white solid.

$^1$H NMR (CDCl$_3$, 400 MHz): δ 1.43-1.45 (2H, m), 1.62-1.71 (6H, m), 1.85-1.93 (4H, m), 2.25-2.37 (4H, m), 2.45-2.49 (4H, m), 2.68-2.71 (3H, m), 2.94 (3H, s), 3.00-3.05 (3H, m), 3.09-3.14 (2H, m), 3.29-3.39 (2H, m), 3.46-3.49 (2H, m), 3.60-3.63 (2H, m), 4.69-4.75 (1H, m), 6.22 (1H, dd, J=12.7, 2.0 Hz), 6.36 (1H, d, J=8.5 Hz), 6.59 (1H, brs), 7.11-7.17 (2H, m), 7.21-7.23 (1H, m), 7.34-7.39 (2H, m), 7.42 (1H, d, J=8.5 Hz), 7.47-7.50 (2H, m), 8.08-8.10 (1H, m).

MS (APCI) m/z: 689 (M+H)$^+$.

Example 12d 1-(2-{[6-({4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-3-fluorophenyl}amino)hexanoyl](methyl)amino}ethyl)piperidin-4-yl biphenyl-2-ylcarbamate The compound (120 mg, 0.174 mmol) obtained in Example 12c was used to give the title compound (108 mg; yield, 45%) as a yellow solid according to the method described in Example 11e.

MS (FAB) m/z: 1365 (M+H)$^+$.

IR (KBr)ν$_{max}$ 2930, 1729, 1628, 1512, 1449, 1359, 1281, 1179, 1139, 756 cm$^{-1}$.

Example 13

1-(2-{[6-({4-[{3-[({[(2S)-1'-{2-[(5R)-3-[3,5-Bis (trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl} (methyl)carbamoyl]-2-fluorophenyl}amino) hexanoyl](methyl)amino}ethyl)piperidin-4-yl biphenyl-2-ylcarbamate trihydrochloride

[Formula 18]

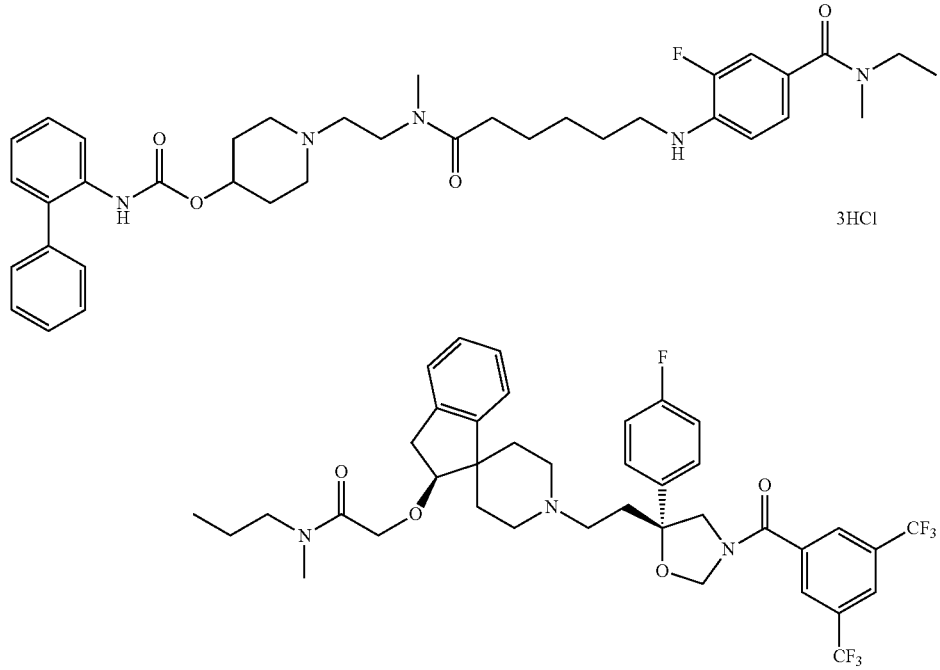

Example 13a tert-Butyl (3-{[(3-fluoro-4-nitrophenyl)carbonyl] (methyl)amino}propyl)methylcarbamate 3-Fluoro-4-nitrobenzoic acid (150 mg, 0.810 mmol) was used to give the title compound (275 mg; yield, 92%) as a light yellow oily substance according to the method described in Example 12a.

$^1$H NMR (CDCl$_3$, 400 MHz): δ 1.38 (4H, s), 1.47 (5H, s), 1.74-1.80 (1H, m), 1.88-1.92 (1H, m), 2.74 (1H, brs), 2.85-2.95 (4H, m), 3.04-3.12 (2H, m), 3.18-3.22 (1H, m), 3.30-3.34 (1H, m), 3.52-3.56 (1H, m), 7.28-7.38 (2H, m), 8.10-8.13 (1H, m).

MS (ESI) m/z: 269 (M+H)$^+$ (form with Boc removed).

Example 13b tert-Butyl (3-{[(4-amino-3-fluorophenyl)carbonyl] (methyl)amino}propyl)methylcarbamate The compound (275 mg, 0.744 mmol) obtained in Example 13a was used to give the title compound (245 mg, yield 97%) as a light yellow oily substance according to the method described in Example 12b.

$^1$H NMR (CDCl$_3$, 400 MHz): δ 1.44 (9H, s), 1.82-1.84 (2H, m), 2.83 (3H, brs), 3.03 (3H, s), 3.17-3.25 (2H, m), 3.37-3.45 (2H, m), 3.90 (2H, s), 6.75 (1H, t, J=8.4 Hz), 7.04 (1H, d, J=8.1 Hz), 7.09-7.12 (1H, m).

MS (APCI) m/z: 339 (M+H)$^+$.

Example 13c

1-{2-[{6-[(2-Fluoro-4-{methyl[3-(methylamino) propyl]carbamoyl}phenyl)amino]hexanoyl}(methyl) amino]ethyl}piperidin-4-yl biphenyl-2-ylcarbamate The compound (275 mg, 0.744 mmol) obtained in Example 13b was used to give the title compound (203 mg; yield, 50%) as a white solid according to the method described in Example 12c.

$^1$H NMR (CDCl$_3$, 400 MHz): δ 1.43-1.49 (2H, m), 1.62-1.72 (6H, m), 1.88-1.94 (4H, m), 2.25-2.37 (4H, m), 2.45-2.48 (4H, m), 2.58-2.64 (1H, m), 2.68-2.74 (2H, m), 2.94-3.03 (6H, m), 3.15-3.20 (2H, m), 3.29-3.39 (2H, m), 3.37 (1H, t, J=7.3 Hz), 3.48 (1H, t, J=7.3 Hz), 3.49-3.54 (2H, m), 4.70-4.74 (1H, m), 6.59-6.65 (2H, m), 7.08-7.15 (3H, m), 7.20-7.23 (1H, m), 7.34-7.43 (3H, m), 7.47-7.52 (2H, m), 8.08-8.10 (1H, m).

MS (APCI) m/z: 689 (M+H)$^+$.

Example 13d 1-(2-{[6-({4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-2-fluorophenyl}amino)hexanoyl](methyl)amino}ethyl)piperidin-4-yl biphenyl-2-ylcarbamate The compound (120 mg, 0.174 mmol) obtained in Example 13c was used to give the title compound (148 mg; yield, 62%) as a white solid according to the method described in Example 11e.

MS (FAB) m/z: 1365 (M+H)+.

IR (KBr) $v_{max}$ 2937, 1731, 1647, 1438, 1359, 1282, 1224, 1178, 1138, 753 cm$^{-1}$.

Example 14

1-(2-{[6-({5-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]pyrimidin-2-yl}amino)hexanoyl](methyl)amino}ethyl)piperidin-4-yl biphenyl-2-ylcarbamate trihydrochloride

[Formula 19]

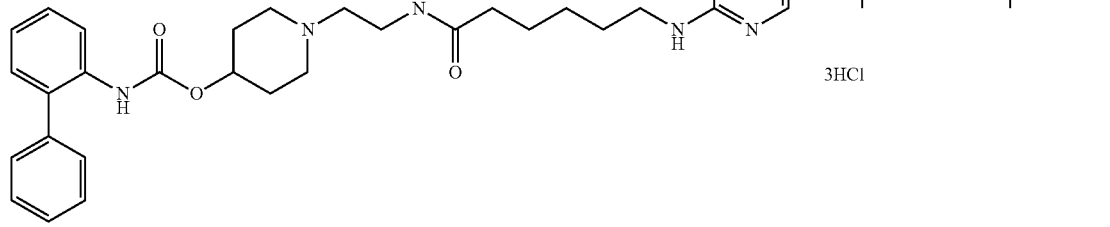

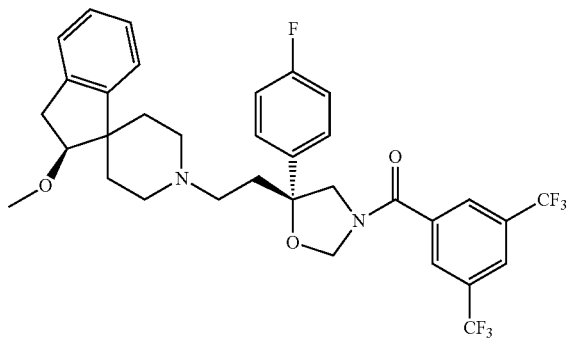

Example 13e 1-(2-{[6-({4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-2-fluorophenyl}amino)hexanoyl](methyl)amino}ethyl)piperidin-4-yl biphenyl-2-ylcarbamate trihydrochloride The compound (148 mg) obtained in Example 13d was dissolved in methanol (1 mL), 4 N hydrochloric acid-dioxane (0.108 mL, 0.434 mmol) was added, and the solvent was evaporated under reduced pressure to give the title compound (127 mg; yield, 80%) as a white solid.

MS (FAB) m/z: 1365 (M+H)+ (free form).

Example 14a

1-{2-[{6-[(5-Bromopyrimidin-2-yl)amino]hexanoyl}(methyl)amino]ethyl}piperidin-4-yl biphenyl-2-yl-carbamate 5-Bromo-2-chloropyrimidine (124 mg, 0.643 mmol) and the compound (300 mg, 0.643 mmol) obtained in Example 1a were dissolved in n-butanol (5 mL), triethylamine (0.134 mL, 0.965 mmol) was added, and the mixture was stirred with heating to reflux for 19 hours. The solvent was evaporated under reduced pressure, and the resulting residue was purified by NH silica gel column chromatography (hexane:ethyl acetate=1:1→0:100, v/v) to give the title compound (299 mg; yield, 75%) as a yellow solid.

$^1$H NMR (CDCl$_3$, 400 MHz): δ 1.39-1.45 (2H, m), 1.59-1.73 (6H, m), 1.86-1.95 (2H, m), 2.25-2.36 (4H, m), 2.46 (2H, t, J=6.8 Hz), 2.67-2.74 (2H, m), 2.93-3.00 (3H, m), 3.35-3.40 (3H, m), 3.47 (1H, t, J=7.3 Hz), 4.69-4.74 (1H, m), 5.18-5.22

(1H, m), 6.62-6.75 (1H, m), 7.11-7.16 (1H, m), 7.20-7.23 (1H, m), 7.34-7.43 (4H, m), 7.46-7.50 (2H, m), 8.07-8.10 (1H, m), 8.22-8.24 (1H, m).

MS (APCI) m/z: 623 (M+H)$^+$.

Example 14b

Benzyl 2-({6-[(2-{4-[(biphenyl-2-ylcarbamoyl)oxy]piperidin-1-yl}ethyl)(methyl)amino]-6-oxohexyl}amino)pyrimidine-5-carboxylate The compound (279 mg, 0.447 mmol) obtained in Example 14a was dissolved in N,N-dimethylformamide (3 mL), and palladium acetate (15 mg, 0.0671 mmol), 1,1'-bis(diphenylphosphino)ferrocene (74 mg, 0.134 mmol), triethylamine (1.24 mL, 8.94 mmol) and benzyl alcohol (0.926 mL, 8.94 mmol) were added. The atmosphere in the system was replaced with a carbon monoxide atmosphere, the mixture was stirred at 90° C. for 17.5 hours, then palladium acetate (30 mg, 0.134 mmol) and 1,1'-bis(diphenylphosphino)ferrocene (148 mg, 0.268 mmol) were added, and the mixture was stirred at 90° C. under the carbon monoxide atmosphere for 29 hours. Palladium acetate (30 mg, 0.134 mmol) and 1,1'-bis(diphenylphosphino)ferrocene (148 mg, 0.268 mmol) were added, and the mixture was stirred at 90° C. under the carbon monoxide atmosphere for 60 hours. The reaction mixture was diluted with ethyl acetate, insoluble matter was removed by filtration through celite, then the solvent was evaporated under reduced pressure, and the resulting residue was purified by NH silica gel column chromatography (hexane:ethyl acetate=1:1→1:2, v/v) to give the title compound (182 mg; yield, 60%) as a brown oily substance.

$^1$H NMR (CDCl$_3$, 400 MHz): δ 1.39-1.46 (2H, m), 1.59-1.71 (6H, m), 1.89-1.93 (2H, m), 2.24-2.37 (4H, m), 2.46 (2H, t, J=6.8 Hz), 2.68-2.74 (2H, m), 2.93-3.00 (3H, m), 3.34-3.38 (1H, m), 3.46-3.51 (3H, m), 4.70-4.75 (1H, m), 5.32 (2H, s), 6.68-6.71 (1H, m), 6.63-6.75 (1H, m), 7.11-7.16 (1H, m), 7.20-7.23 (1H, m), 7.34-7.42 (8H, m), 7.45-7.49 (2H, m), 8.06-8.10 (1H, m), 8.75-8.89 (1H, m).

MS (APCI) m/z: 679 (M+H)$^+$.

Example 14c 1-(2-{[6-({5-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methy)amino]propyl}(methyl)carbamoyl]pyrimidin-2-yl}amino)hexanoyl](methyl)amino}ethyl)piperidin-4-yl biphenyl-2-ylcarbamate trihydrochloride The compound (182 mg, 0.268 mmol) obtained in Example 14b was used to give a free form of a crude title compound according to the method described in Example 5d, and the product was purified by reverse phase preparative column chromatography (Waters; XTerra Prep MS C18 OBD, 5 30×100 mm) (acetonitrile:0.1% aqueous ammonium formate solution=60:40→65:35, v/v). The resulting free form (154 mg) of the title compound was dissolved in methanol (1 mL), 4 N hydrochloric acid-dioxane (0.685 mL, 2.74 mmol) was added, and the solvent was evaporated under reduced pressure to give the title compound (176 mg; yield, 57%) as a light brown solid.

MS (FAB) m/z: 1349 (M+H)$^+$ (free form).

IR (KBr) ν$_{max}$ 2936, 1726, 1649, 1450, 1360, 1282, 1224, 1174, 1138, 753 cm$^{-1}$.

Example 15

1-(2-{[6-({4-[{2-[({[(2S)-1-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]ethyl}(methyl)carbamoyl]phenyl}amino)hexanoyl](methyl)amino}ethyl)piperidin-4-yl biphenyl-2-ylcarbamate

[Formula 20]

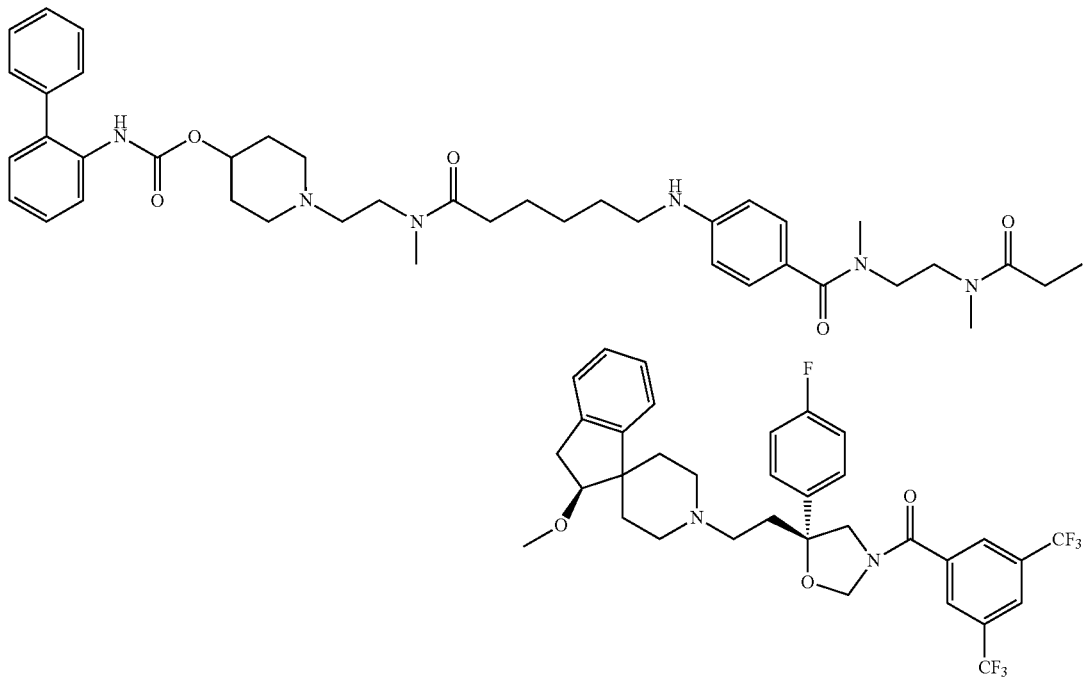

Example 15a

2-{[(2S)-1'-{2-[(5R)-3-[3,5-Bis(trifluoromethyl)
benzoyl]-5-(4-fluorophenyl)-1,3-oxazolidin-5-yl]
ethyl}-2,3-dihydrospiro[indene-1,4'-piperidin]-2-yl]
oxy}-N-methyl-N-[2-(methylamino)ethyl]acetamide N,N'-Dimethylethylenediamine (57 mg, 0.648 mmol) was used to give the title compound (71 mg; yield, 43%) as a yellow solid according to the method described in Example 1k.

MS (APCI) m/z: 765 (M+H)$^+$.

IR (KBr) $v_{max}$ 2929, 1649, 1510, 1435, 1359, 1281, 1181, 1138, 848, 758 cm$^{-1}$.

Example 15b tert-Butyl 4-[(6-ethoxy-6-oxohexyl)amino]benzoate

Ethyl 6-bromohexanoate (8.44 mL, 49.7 mmol) and tert-butyl 4-aminobenzoate (6.41 g, 33.2 mmol) were dissolved in N,N-dimethylformamide (33 mL), N,N-diisopropylethylamine (8.64 mL, 49.7 mmol) was added, and the mixture was stirred at 50° C. for 3 days. Potassium iodide (8.25 g, 49.7 mmol) was added, and the mixture was further stirred at 50° C. for 4 days. A saturated aqueous sodium hydrogencarbonate solution was added, and the mixture was extracted with ethyl acetate (×2). The resulting organic layer was washed with water (×3) and saturated sodium chloride solution and dried with anhydrous sodium sulfate. The solvent was evaporated under reduced pressure, and the resulting residue was purified by silica gel column chromatography (hexane:ethyl acetate=9:1→4:1, v/v). A mixed solvent of hexane and dichloromethane was added to the resulting white solid, and the mixture was filtered to give the title compound (5.54 g; yield, 50%) as a white solid.

$^1$H NMR (CDCl$_3$, 500 MHz): δ 1.26 (2H, t, J=7.3 Hz), 1.39-1.48 (2H, m), 1.56 (9H, s), 1.59-1.73 (4H, m), 2.32 (2H, t, J=7.3 Hz), 3.17 (2H, t, J=7.1 Hz), 4.04 (1H, s), 4.13 (2H, q, J=7.0 Hz), 6.52 (2H, d, J=8.8 Hz), 7.81 (2H, d, J=8.8 Hz).

MS (FAB) m/z: 335 (M)$^+$.

IR (KBr) $v_{max}$ 3385, 1727, 1682, 1602, 1288, 1269, 1158, 1113, 842, 772 cm$^{-1}$.

Example 15c tert-Butyl 4-({6-[(2-{4-[(biphenyl-2-ylcarbamoyl)
oxy]piperidin-1-yl}ethyl)(methyl)amino]-6-
oxohexyl}amino)benzoate The compound (310 mg, 0.925 mmol) obtained in Example 15b was dissolved in a mixed solvent of ethanol (20 mL) and water (10 mL), a 1 N aqueous sodium hydroxide solution (1.39 mL, 1.39 mmol) was added at room temperature, and the mixture was stirred at the same temperature for 3.5 hours. A 1 N aqueous hydrochloric acid solution (1.5 mL, 1.5 mmol) was added, then the mixture was extracted with dichloromethane (×3), and the organic layer was washed with saturated sodium chloride solution. The solvent was evaporated under reduced pressure, the resulting residue was dissolved in dichloromethane (6 mL), 1-[2-(methylamino)ethyl]piperidin-4-yl biphenyl-2-ylcarbamate (218 mg, 0.616 mmol), 1-ethyl-3-(3-dimethylaminopropyl)carbodiimide hydrochloride (235 mg, 1.23 mmol) and 4-N,N-dimethylaminopyridine (5 mg, 0.04 mmol) were added, and the mixture was stirred at room temperature for 1 hour. After the reaction was completed, a saturated aqueous sodium hydrogencarbonate solution was added, and the mixture was extracted with dichloromethane and dried with anhydrous sodium sulfate. The desiccant was removed by filtration through celite, and then the solvent was evaporated under reduced pressure. The residue was purified by NH silica gel column chromatography (hexane:ethyl acetate=9:1→ethyl acetate:methanol=9:1, v/v) to give the title compound (133 mg; yield, 34%) as a white solid.

MS (FAB) m/z: 643 (M+H)$^+$.

IR (KBr) $v_{max}$ 2932, 1696, 1605, 1523, 1292, 1160, 1045, 772, 749, 702 cm$^{-1}$.

Example 15d 1-(2-{[6-({4-[{2-[({[(2S)-1'-{2-[(5R)-3-[3,5-Bis
(trifluoromethyl)benzoyl]-5-(4-fluorophenyl)-1,3-
oxazolidin-5-yl]ethyl}-2,3-dihydrospiro[indene-1,4'-
piperidin]-2-yl]oxy}acetyl)(methyl)amino]ethyl}
(methyl)carbamoyl]phenyl}amino)hexanoyl]
(methyl)amino}ethyl)piperidin-4-yl biphenyl-2-
ylcarbamate The compound (219 mg, 0.340 mmol) obtained in Example 15c was dissolved in 1,4-dioxane (5 mL), 4 N hydrochloric acid-dioxane (5.10 mL, 20.4 mmol) was added, and the mixture was stirred at room temperature for 15 hours. The solvent was evaporated under reduced pressure and moisture was removed azeotropically with toluene (×2) to give crude carboxylic acid (230 mg). The resulting crude carboxylic acid (74 mg) and the compound (71 mg, 0.0929 mmol) obtained in Example 15a were used according to the method described in Example 11e to give the title compound (31 mg; yield, 25%) as a white solid.

MS (FAB) m/z: 1333 (M+H)$^+$.

IR (KBr) $v_{max}$ 2932, 1729, 1647, 1610, 1449, 1359, 1281, 1179, 1140, 762 cm$^{-1}$.

Example 16

1-(2-{[6-({4-[{2-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]ethyl}(methyl)carbamoyl]phenyl}amino)hexanoyl](methyl)amino}ethyl)piperidin-4-yl biphenyl-2-ylcarbamate trihydrochloride

[Formula 21]

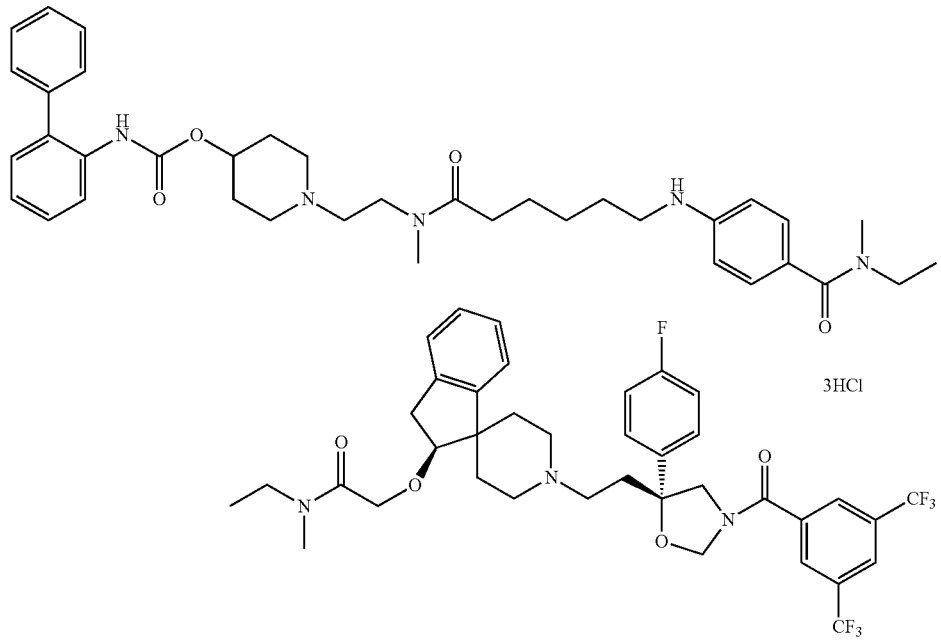

3HCl

The compound (31 mg, 0.0232 mmol) obtained in Example 15d was used to give the title compound (31 mg; yield, 93%) as a white solid according to the method described in Example 13e.

MS (FAB) m/z: 1333 (M+H)$^+$ (free form).

IR (KBr) $v_{max}$ 2958, 1738, 1649, 1512, 1451, 1360, 1225, 1180, 1139, 754 cm$^{-1}$.

Example 17

1-{2-[{6-[({5-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-2-thienyl}methyl)(cyclopropylmethyl)amino]hexanoyl}(methyl)amino]ethyl}piperidin-4-yl biphenyl-2-ylcarbamate trihydrochloride

[Formula 22]

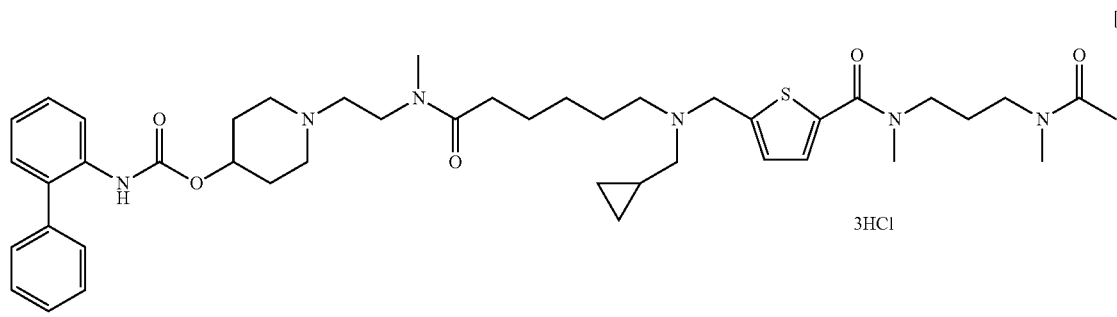

3HCl

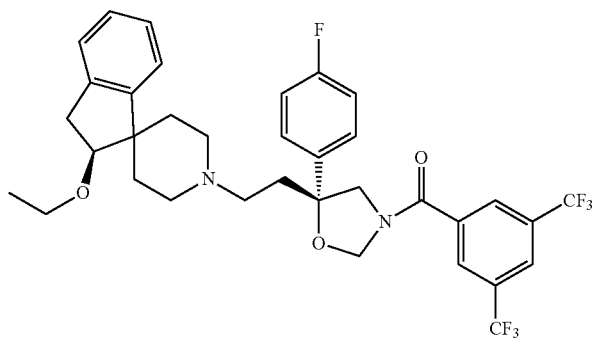

The compound (49 mg, 0.0358 mmol) obtained in Example 1m and cyclopropane carboxaldehyde (8 μL, 0.107 mmol) were dissolved in ethanol-methylene chloride (1:1; 2 mL), and the mixture was stirred at room temperature for 1 hour. The solvent was evaporated under reduced pressure, the resulting residue was dissolved in methylene chloride (2 mL), cyclopropane carboxaldehyde (32 μL, 0.428 mmol) was added, and the mixture was stirred overnight. Ethanol (1.5 mL) and sodium triacetoxyborohydride (11 mg, 0.0537 mmol) were added, and the mixture was stirred at room temperature for 30 minutes. The solvent was evaporated under reduced pressure, and the resulting residue was purified by NH silica gel column chromatography (ethyl acetate: methanol=40:1, v/v) to give a free form (48 mg) of the title compound.

The free form of the title compound was dissolved in methanol (1 mL), 4 N hydrochloric acid-dioxane (34 μL, 0.135 mmol) was added, and the solvent was evaporated under reduced pressure to give the title compound (47 mg; yield, 85%) as a white solid.

MS (FAB) m/z: 1421 (M+H)$^+$ (free form).

IR (KBr) ν$_{max}$ 2958, 1737, 1644, 1451, 1360, 1282, 1226, 1179, 1139, 753 cm$^{-1}$.

Example 18

1-(2-{[6-({4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-3-methylphenyl}amino)hexanoyl](methyl)amino}ethyl)piperidin-4-yl biphenyl-2-ylcarbamate trihydrochloride

[Formula 23]

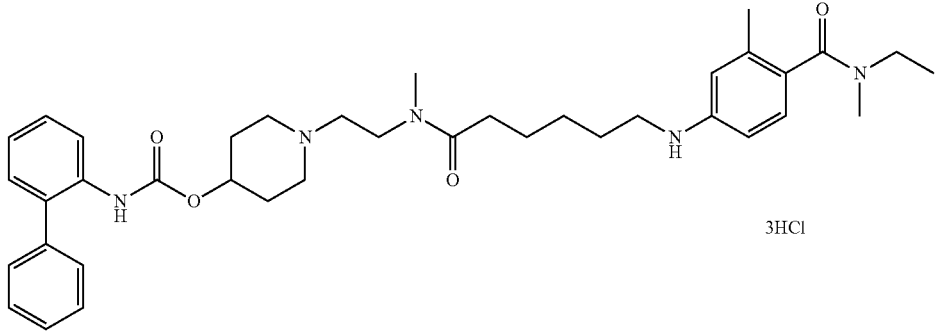

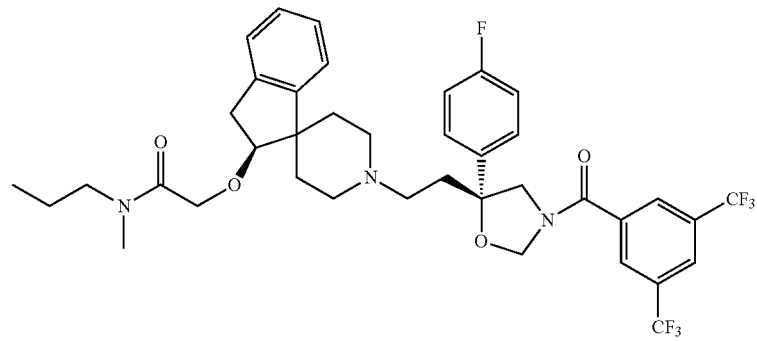

Example 18a tert-Butyl 4-amino-2-methylbenzoate

2-Methyl-4-nitrobenzoic acid (700 mg, 3.86 mmol) was dissolved in pyridine (8 mL), p-toluenesulfonyl chloride (1.47 g, 7.74 mmol) was added, then tert-butanol (0.369 mL, 3.86 mmol) was added under ice cooling, and the mixture was stirred at 0° C. for 2 hours and at room temperature for 2 hours. tert-Butanol (0.369 mL, 3.86 mmol) was further added, and the mixture was stirred overnight at room temperature. The solvent was evaporated under reduced pressure, water was added, then the mixture was extracted with ethyl acetate (×3), and the organic layer was washed with 1 N hydrochloric acid, a 1 N aqueous sodium hydroxide solution, water, and saturated sodium chloride solution. The organic layer was dried with anhydrous sodium sulfate, the solvent was evaporated under reduced pressure, a solution of the resulting residue in ethyl acetate (40 mL) was added to 10% palladium-carbon (dry; 222 mg), the atmosphere in the system was replaced with a hydrogen atmosphere, and then the mixture was stirred at room temperature for 2 hours. The atmosphere in the system was replaced with a nitrogen atmosphere, and then the mixture was filtered through celite. The solvent was evaporated under reduced pressure to give the title compound (835 mg; yield, 100%) as a brown solid.

$^1$H NMR (CDCl$_3$, 400 MHz): δ 1.57 (9H, s), 2.52 (3H, s), 6.70-6.72 (2H, m), 7.78 (1H, d, J=8.1 Hz).

MS (APCI) m/z: 208 (M+H)$^+$.

Example 18b tert-Butyl 4-({6-[(2-{4-[(biphenyl-2-ylcarbamoyl)oxy]piperidin-1-yl}ethyl)(methyl)amino]-6-oxohexyl}amino)-2-methylbenzoate The compound (135 mg, 0.289 mmol) obtained in Example 4g and the compound (103 mg, 0.473 mmol) obtained in Example 18a were dissolved in methylene chloride (4 mL), acetic acid (73 μL) and sodium triacetoxyborohydride (137 mg, 0.645 mmol) were added, and the mixture was stirred overnight at room temperature. Sodium borohydride (16 mg, 0.430 mmol) was added, and the mixture was stirred at room temperature for 20 minutes. The solvent was evaporated under reduced pressure, and the resulting residue was purified by NH silica gel column chromatography (hexane:ethyl acetate=1:1→1:2, v/v) to give the title compound (114 mg; yield, 40%) as a white solid.

$^1$H NMR (CDCl$_3$, 400 MHz): δ 1.40-1.48 (2H, m), 1.56 (9H, s), 1.59-1.72 (5H, m), 1.91-1.95 (2H, m), 2.26-2.37 (4H, m), 2.45-2.50 (2H, m), 2.53 (3H, s), 2.68-2.75 (2H, m), 2.94-3.05 (3H, m), 3.16 (2H, t, J=7.1 Hz), 3.37 (1H, t, J=6.8 Hz), 3.49 (1H, t, J=6.8 Hz), 3.99-4.04 (1H, m), 4.71-4.75 (1H, m), 6.34-6.39 (1H, m), 6.59 (1H, brs), 7.12-7.16 (1H, m), 7.21-7.23 (1H, m), 7.35-7.44 (4H, m), 7.48-7.53 (2H, m), 7.78 (1H, d, J=8.6 Hz), 8.09-8.12 (1H, m).

MS (APCI) m/z: 657 (M+H)$^+$.

Example 18c 1-(2-{[6-({4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-3-methylphenyl}amino)hexanoyl](methyl)amino}ethyl)piperidin-4-yl biphenyl-2-ylcarbamate trihydrochloride The compound (100 mg, 0.152 mmol) obtained in Example 18b was dissolved in 1,4-dioxane (2.5 mL), 4 N hydrochloric acid-dioxane (2.30 mL, 9.13 mmol) was added, and then the mixture was stirred at room temperature for 15 hours. The solvent was evaporated under reduced pressure and moisture was removed azeotropically with toluene (×2) to give a crude carboxylic acid compound. The resulting crude carboxylic acid compound and the compound (108 mg, 0.139 mmol) obtained in Example 1k were used according to the methods described in Examples 11e and 13e to give the title compound (40 mg; yield, 20%) as a white solid.

MS (FAB) m/z: 1361 (M+H)$^+$ (free form).

IR (KBr) $v_{max}$ 2935, 1726, 1639, 1450, 1360, 1282, 1225, 1174, 1138, 752 cm$^{-1}$.

Example 19

1-(2-{[6-({4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}methyl)carbamoyl]-2-methylphenyl}amino)hexanoyl](methyl)amino}ethyl)piperidin-4-yl biphenyl-2-ylcarbamate trihydrochloride

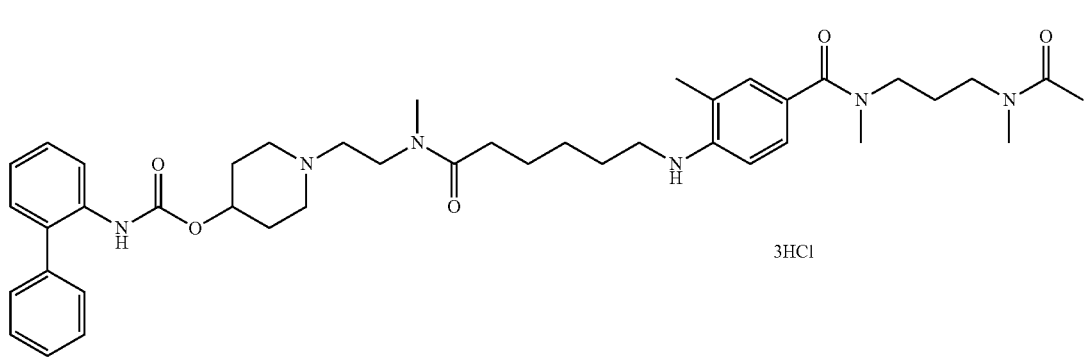

[Formula 24]

3HCl

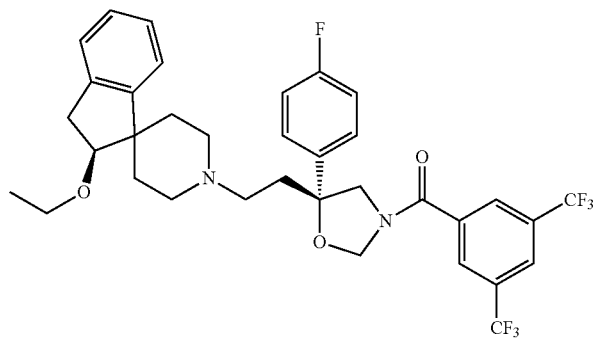

Example 19a tert-Butyl 4-({6-[(2-{4-[(biphenyl-2-ylcarbamoyl)oxy]piperidin-1-yl}ethyl)(methyl)amino]-6-oxohexyl}amino)-3-methylbenzoate 3-Methyl-4-nitrobenzoic acid (700 mg, 3.86 mmol) was used to give a crude aniline compound according to the method described in Example 18a.

The resulting crude aniline compound (98 mg, 0.473 mmol) was used to give the title compound (117 mg; yield, 41%) as a white solid according to the method described in Example 18b.

$^1$H NMR (CDCl$_3$, 400 MHz): δ 1.44-1.50 (2H, m), 1.56 (9H, s), 1.58-1.61 (1H, m), 1.67-1.73 (4H, m), 1.90-1.95 (2H, m), 2.13 (3H, s), 2.24-2.37 (4H, m), 2.45-2.49 (2H, m), 2.68-2.75 (2H, m), 2.94-3.05 (3H, m), 3.21-3.24 (2H, m), 3.37 (1H, t, J=7.1 Hz), 3.48 (1H, t, J=7.1 Hz), 3.89-4.00 (1H, m), 4.69-4.76 (1H, m), 6.53 (1H, d, J=8.8 Hz), 6.58 (1H, brs), 7.11-7.16 (1H, m), 7.21-7.25 (1H, m), 7.35-7.43 (4H, m), 7.47-7.52 (2H, m), 7.67 (1H, s), 7.76-7.78 (1H, m), 8.09-8.11 (1H, m).

MS (APCI) m/z: 657 (M+H)$^+$.

Example 19b 1-(2-{[6-({4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-2-methylphenyl}amino)hexanoyl](methyl)amino}ethyl)piperidin-4-yl biphenyl-2-ylcarbamate trihydrochloride The compound (117 mg, 0.178 mmol) obtained in Example 19a was used to give the title compound (81 mg; yield, 53%) as a white solid according to the method described in Example 18c.

MS (FAB) m/z: 1361 (M+H)$^+$ (free form).

IR (KBr) ν$_{max}$ 2934, 1727, 1644, 1449, 1360, 1282, 1224, 1176, 1139, 753 cm$^{-1}$.

Example 20

1-(2-{[6-({4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-3-methoxyphenyl}amino)hexanoyl](methyl)amino}ethyl)piperidin-4-yl biphenyl-2-ylcarbamate trihydrochloride

[Formula 25]

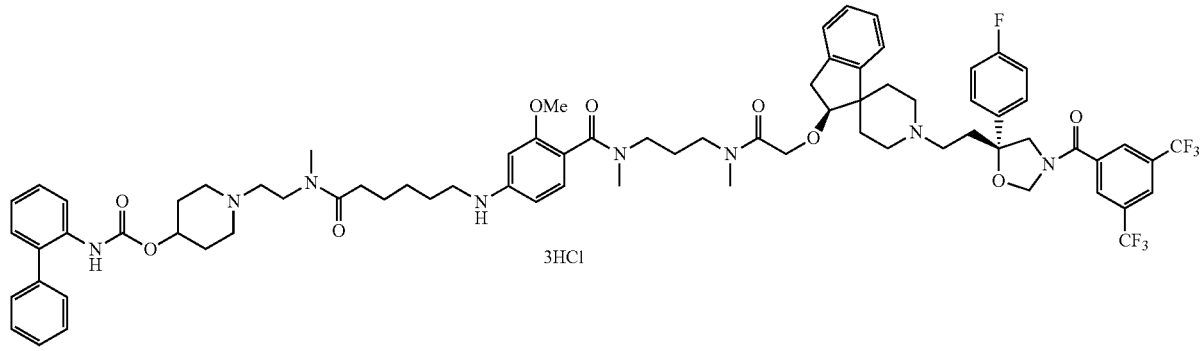

Example 20a tert-Butyl 4-amino-2-methoxybenzoate

2-Methoxy-4-nitrobenzoic acid (700 mg, 3.55 mmol) was used to give the title compound (735 mg; yield, 95%) as a light brown solid according to the method described in Example 18a.

$^1$H NMR (CDCl$_3$, 400 MHz): δ 1.55 (9H, s), 3.85 (3H, s), 3.98 (2H, brs), 6.19-6.22 (2H, m), 7.69 (1H, d, J=8.1 Hz).

MS (APCI) m/z: 168 (M+H)$^+$ (form with tBu removed).

Example 20b tert-Butyl 4-({6-[(2-{4-[(biphenyl-2-ylcarbamoyl)oxy]piperidin-1-yl}ethyl)(methyl)amino]-6-oxohexyl}amino)-2-methoxybenzoate The compound (106 mg, 0.473 mmol) obtained in Example 20a was used to give the title compound (191 mg; yield, 66%) as a white solid according to the method described in Example 18b.

$^1$H NMR (CDCl$_3$, 400 MHz): δ 1.42-1.49 (2H, m), 1.58 (9H, s), 1.62-1.71 (5H, m), 1.88-1.95 (2H, m), 2.25-2.37 (4H, m), 2.47 (2H, t, J=6.8 Hz), 2.68-2.75 (2H, m), 2.94-3.00 (3H, m), 3.14-3.19 (2H, m), 3.37 (1H, t, J=7.1 Hz), 3.48 (1H, t, J=7.1 Hz), 3.86 (3H, s), 4.11-4.16 (1H, m), 4.69-4.76 (1H, m), 6.06-6.13 (2H, m), 6.59 (1H, brs), 7.11-7.16 (1H, m), 7.20-7.21 (1H, m), 7.34-7.43 (3H, m), 7.47-7.52 (2H, m), 7.70 (1H, d, J=8.8 Hz), 8.08-8.11 (1H, m).

MS (APCI) m/z: 673 (M+H)$^+$.

Example 20c 1-(2-{[6-({4-[{3-[(tert-Butoxycarbonyl)(methyl)amino]propyl}(methyl)carbamoyl]-3-methoxyphenyl}amino)hexanoyl](methyl)amino}ethyl)piperidin-4-yl biphenyl-2-ylcarbamate The compound (191 mg, 0.284 mmol) obtained in Example 20b was dissolved in 1,4-dioxane (4.3 mL), 4 N hydrochloric acid-dioxane (4.30 mL, 17.0 mmol) was added, and then the mixture was stirred at room temperature for 13.5 hours. The solvent was evaporated under reduced pressure and moisture was removed azeotropically with toluene (×2) to give a crude carboxylic acid compound. The resulting crude carboxylic acid compound was used to give the title compound (198 mg; yield, 87%) as a white solid according to the method described in Example 12a.

$^1$H NMR (CDCl$_3$, 400 MHz): δ 1.40-1.46 (11H, m), 1.60-1.72 (8H, m), 1.84-1.95 (2H, m), 2.25-2.37 (4H, m), 2.45-2.47 (2H, m), 2.69-2.74 (3H, m), 2.85-2.88 (4H, m), 2.94-3.05 (6H, m), 3.11-3.14 (2H, m), 3.27-3.32 (1H, m), 3.38 (1H, t, J=7.3 Hz), 3.48 (1H, t, J=7.3 Hz), 3.50-3.54 (1H, m), 3.76-3.78 (3H, m), 4.70-4.74 (1H, m), 6.08-6.19 (2H, m), 6.58-6.70 (1H, m), 6.97-7.05 (1H, m), 7.11-7.15 (1H, m), 7.20-7.23 (1H, m), 7.34-7.43 (4H, m), 7.47-7.52 (2H, m), 8.08-8.11 (1H, m).

MS (APCI) m/z: 801 (M+H)$^+$.

Example 20d

1-{2-[{6-[(3-Methoxy-4-{methyl[3-(methylamino)propyl]carbamoyl}phenyl)amino]hexanoyl}(methyl)amino]ethyl}piperidin-4-yl biphenyl-2-ylcarbamate The compound (198 mg, 0.247 mmol) obtained in Example 20c was used to give the title compound (165 mg; yield, 95%) as a white solid according to the method described in Example 6d.

$^1$H NMR (CDCl$_3$, 400 MHz): δ 1.43-1.49 (2H, m), 1.62-1.72 (6H, m), 1.91-1.98 (4H, m), 2.24-2.37 (5H, m), 2.46-2.51 (4H, m), 2.68-2.76 (2H, m), 2.86-2.96 (3H, m), 3.05-3.15 (3H, m), 3.05-3.15 (3H, m), 3.20-3.25 (1H, m), 3.38 (1H, t, J=7.3 Hz), 3.48 (1H, t, J=7.3 Hz), 3.59-3.66 (1H, m), 3.77-3.79 (3H, m), 3.90-3.92 (1H, m), 4.69-4.75 (1H, m), 6.10-6.20 (2H, m), 6.58-6.61 (1H, m), 6.99-7.04 (1H, m), 7.11-7.16 (1H, m), 7.21-7.22 (1H, m), 7.36-7.43 (3H, m), 7.47-7.52 (2H, m), 8.08-8.10 (1H, m).

MS (APCI) m/z: 701 (M+H)$^+$.

Example 20e 1-(2-{[6-({4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-3-methoxyphenyl}amino)hexanoyl](methyl)amino}ethyl)piperidin-4-yl biphenyl-2-ylcarbamate trihydrochloride The compound (140 mg, 0.200 mmol) obtained in Example 20d was used to give the title compound (163 mg; yield, 55%) as a white solid according to the methods described in Examples 11e and 13e.

MS (FAB) m/z: 1377 (M+H)$^+$ (free form).

IR (KBr) ν$_{max}$ 2935, 1727, 1644, 1449, 1360, 1282, 1224, 1174, 1138, 753 cm$^{-1}$.

Example 21

1-{2-[(6-{[4-({2-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]ethyl}carbamoyl)phenyl]amino}hexanoyl)(methyl)amino]ethyl}piperidin-4-yl biphenyl-2-ylcarbamate trihydrochloride

[Formula 26]

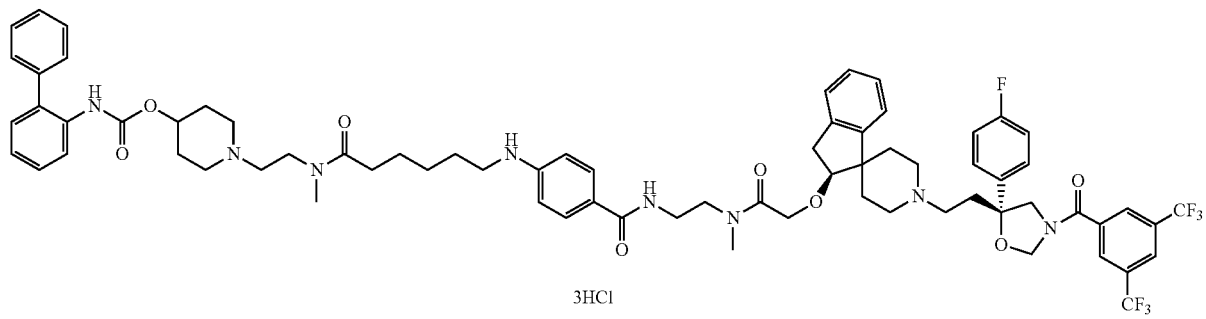

Example 21a tert-Butyl {2-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]ethyl}carbamate The compound (135 mg, 0.194 mmol) obtained in Example 1j was dissolved in methylene chloride (3 mL), triethylamine (81 μL, 0.583 mmol) and pivaloyl chloride (25 μL, 0.204 mmol) were added under ice cooling, and the mixture was stirred at room temperature for 15 minutes. tert-Butyl [2-(methylamino)ethyl]carbamate hydrochloride (45 mg, 0.214 mmol) was added to the reaction mixture, and the mixture was stirred overnight at room temperature. The solvent was evaporated under reduced pressure, and the resulting residue was purified by NH silica gel column chromatography (hexane:ethyl acetate=1:1→1:2, v/v) to give the title compound (150 mg; yield, 91%) as a white solid.

MS (APCI) m/z: 851 (M+H)$^+$.

Example 21b

N-(2-Aminoethyl)-2-{[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}-N-methylacetamide The compound (150 mg, 0.176 mmol) obtained in Example 21a was used to give the title compound (125 mg; yield, 95%) as a white solid according to the method described in Example 6d.

MS (APCI) m/z: 751 (M+H)$^+$.

Example 21c

1-{2-[(6-{[4-({2-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]ethyl}carbamoyl)phenyl]amino}hexanoyl)(methyl)amino]ethyl}piperidin-4-yl biphenyl-2-ylcarbamate trihydrochloride The compound (96 mg, 0.150 mmol) obtained in Example 15c was dissolved in 1,4-dioxane (2.3 mL), 4 N hydrochloric acid-dioxane (2.30 mL, 9.00 mmol) was added, and then the mixture was stirred at room temperature for 15 hours. The solvent was evaporated under reduced pressure and moisture was removed azeotropically with toluene (×2) to give a crude carboxylic acid compound. The resulting crude carboxylic acid compound and the compound (124 mg, 0.165 mmol) obtained in Example 21b were used according to the methods described in Examples 11e and 13e to give the title compound (86 mg; yield, 40%) as a white solid.

MS (FAB) m/z: 1319 (M+H)$^+$ (free form).

IR (KBr) $\nu_{max}$ 2939, 1724, 1636, 1513, 1449, 1361, 1282, 1176, 1139, 754 cm$^{-1}$.

Example 22

1-{2-[{6-[{4-[{2-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]ethyl}(methyl)carbamoyl]phenyl}(methyl)amino]hexanoyl}(methyl)amino]ethyl}piperidin-4-yl biphenyl-2-ylcarbamate trihydrochloride

[Formula 27]

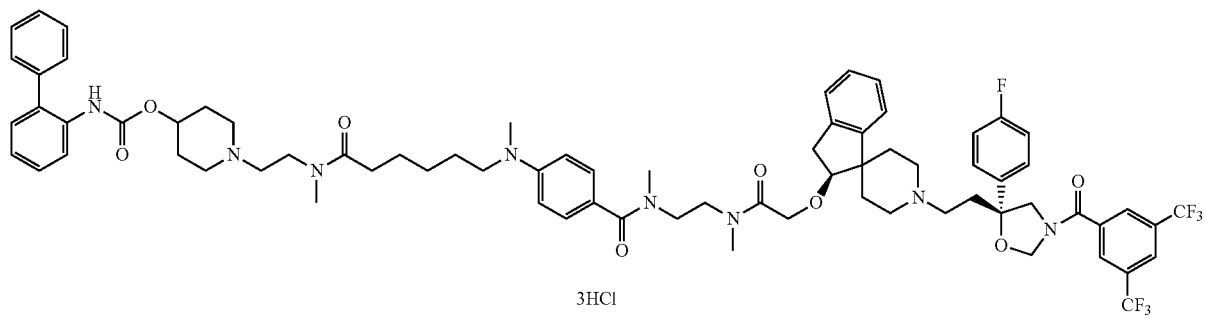

Example 22a tert-Butyl 4-[{6-[(2-{4-[(biphenyl-2-ylcarbamoyl)oxy]piperidin-1-yl}ethyl)(methyl)amino]-6-oxo-hexyl}(methyl)amino]benzoate The compound (151 mg, 0.235 mmol) obtained in Example 15c was dissolved in ethanol (2 mL), a 35% aqueous formaldehyde solution (0.590 mL, 6.89 mmol) was added, and the mixture was stirred at room temperature for 20 minutes. Toluene was added, and then the solvent was evaporated under reduced pressure (×2). The resulting residue was dissolved in methylene chloride-ethanol (1:1; 2 mL), sodium borohydride (10 mg, 0.230 mmol) was added, and the mixture was stirred at room temperature for 20 minutes. The solvent was evaporated under reduced pressure, and the resulting residue purified by NH silica gel column chromatography (hexane:ethyl acetate=1:2, v/v) and further purified by reverse phase preparative column chromatography (Waters; XTerra Prep MS C18 OBD, 5 μm, 30×100 mm) (acetonitrile:0.1% aqueous ammonium acetate solution=55:45→60:40, v/v) to give the title compound (72 mg; yield, 47%) as a white solid.

MS (APCI) m/z: 657 (M+H)$^+$.

IR (KBr) $v_{max}$ 2933, 1732, 1696, 1644, 1605, 1293, 1161, 770, 701 cm$^{-1}$.

Example 22b

1-{2-[{6-[{4-[{2-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]ethyl}(methyl)carbamoyl]phenyl}(methyl)amino]hexanoyl}(methyl)amino]ethyl}piperidin-4-yl biphenyl-2-ylcarbamate trihydrochloride The compound (72 mg, 0.110 mmol) obtained in Example 22a was dissolved in 1,4-dioxane (1.6 mL), 4 N hydrochloric acid-dioxane (1.60 mL, 6.58 mmol) was added, and then the mixture was stirred at room temperature for 18 hours. The solvent was evaporated under reduced pressure and moisture was removed azeotropically with toluene (×2) to give a crude carboxylic acid compound. The resulting crude carboxylic acid compound and the compound (84 mg, 0.110 mmol) obtained in Example 21b were used according to the methods described in Examples 11e and 13e to give the title compound (69 mg; yield, 43%) as a white solid.

MS (FAB) m/z: 1347 (M+H)$^+$ (free form).

IR (KBr) $v_{max}$ 2933, 1726, 1645, 1450, 1360, 1282, 1225, 1138, 753 cm$^{-1}$.

Example 23

1-(2-{[6-({4-[{3-[({[(2S)-1'-{2-[(2R)-4-[3,5-Bis(trifluoromethyl)benzoyl]-2-(3,4-dichlorophenyl)morpholin-2-yl]ethyl}-2,3-dihydrospiro[indene-1,4'-piperidin]-2-yl]oxy}acetyl)(methyl)amino]propyl}(methyl)carbamoyl]phenyl}amino)hexanoyl](methyl)amino}ethyl)piperidin-4-yl biphenyl-2-ylcarbamate

[Formula 28]

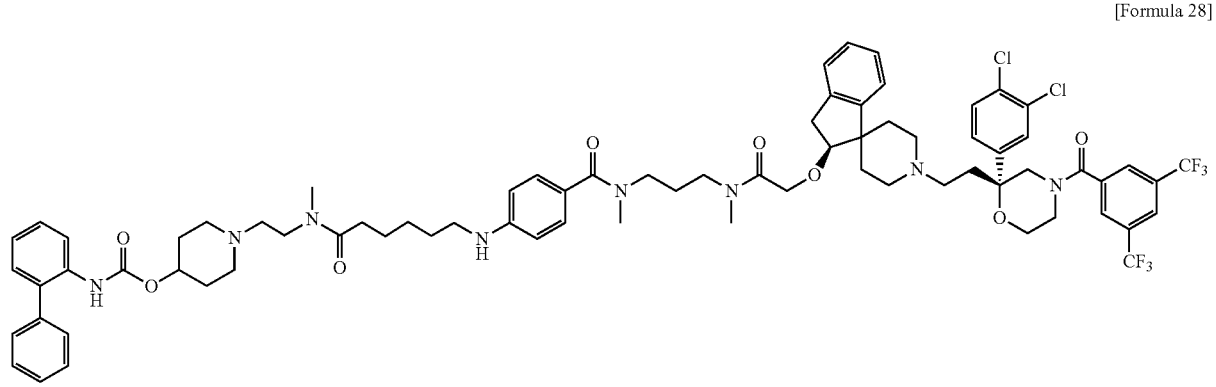 [SMILES: CN(CCN1CCC(OC(=O)Nc2ccccc2-c2ccccc2)CC1)C(=O)CCCCCNc1ccc(C(=O)N(C)CCCN(C)C(=O)CO[C@H]2Cc3ccccc3C23CCN(CC[C@@]2(c4ccc(Cl)c(Cl)c4)CN(C(=O)c4cc(C(F)(F)F)cc(C(F)(F)F)c4)CCO2)CC3)cc1]

Example 23a tert-Butyl {3-[({[(2S)-1'-{2-[(2R)-4-[3,5-bis(trifluoromethyl)benzoyl]-2-(3,4-dichlorophenyl)morpholin-2-yl]ethyl}-2,3-dihydrospiro[indene-1,4'-piperidin]-2-yl]oxy}acetyl)(methyl)amino]propyl}methylcarbamate {[(2S)-1'-{2-[(2R)-4-[3,5-Bis(trifluoromethyl)benzoyl]-2-(3,4-dichlorophenyl)morpholin-2-yl]ethyl}-2,3-dihydrospiro[indene-1,4'-piperidin]-2-yl]oxy}acetic acid (described in EP1746095 A1) (1.20 g, 1.58 mmol) was used to give the title compound (1.03 g; yield, 69%) as a white solid according to the method described in Example 12a.

MS (FAB) m/z: 943 (M+H)$^+$.

IR (KBr) $\nu_{max}$ 2930, 1693, 1645, 1476, 1375, 1281, 1138, 905, 756, 681 cm$^{-1}$.

Example 23b

2-{[(2S)-1'-{2-[(2R)-4-[3,5-Bis(trifluoromethyl)benzoyl]-2-(3,4-dichlorophenyl)morpholin-2-yl]ethyl}-2,3-dihydrospiro[indene-1,4'-piperidin]-2-yl]oxy}-N-methyl-N-[3-(methylamino)propyl]acetamide dihydrochloride The compound (972 mg, 1.03 mmol) obtained in Example 23a was used to give a free form (750 mg) of the title compound according to the method described in Example 6d. The resulting free compound was used to give the title compound (203 mg; yield, 50%) as a white solid according to the method described in Example 13e.

MS (FAB) m/z: 843 (M+H)$^+$ (free form).

IR (KBr) $\nu_{max}$ 2931, 2724, 1646, 1474, 1441, 1376, 1282, 1137, 905, 759, 681 cm$^{-1}$.

Example 23c 1-(2-{[6-({4-[{3-[({[(2S)-1'-{2-[(2R)-4-[3,5-Bis(trifluoromethyl)benzoyl]-2-(3,4-dichlorophenyl)morpholin-2-yl]ethyl}-2,3-dihydrospiro[indene-1,4'-piperidin]-2-yl]oxy}acetyl)(methyl)amino]propyl}(methyl)carbamoyl]phenyl}amino)hexanoyl](methyl)amino}ethyl)piperidin-4-yl biphenyl-2-ylcarbamate The compound (96 mg, 0.150 mmol) obtained in Example 15c was dissolved in 1,4-dioxane (2.3 mL), 4 N hydrochloric acid-dioxane (2.30 mL, 9.00 mmol) was added, and then the mixture was stirred at room temperature for 18 hours. The solvent was evaporated under reduced pressure and moisture was removed azeotropically with toluene (×2) to give a crude carboxylic acid. The resulting crude carboxylic acid and the compound (138 mg, 0.150 mmol) obtained in Example 23b were used according to the method described in Example 15d to give the title compound (114 mg; yield, 54%) as a white solid.

MS (FAB) m/z: 1411 (M+H)$^+$.

Example 24

1-(2-{[6-({4-[{3-[({[(2S)-1'-{2-[(2R)-4-[3,5-Bis(trifluoromethyl)benzoyl]-2-(3,4-dichlorophenyl)morpholin-2-yl]ethyl}-2,3-dihydrospiro[indene-1,4'-piperidin]-2-yl]oxy}acetyl)(methyl)amino]propyl}(methyl)carbamoyl]phenyl}amino)hexanoyl](methyl)amino}ethyl)piperidin-4-yl biphenyl-2-ylcarbamate trihydrochloride

[Formula 29]

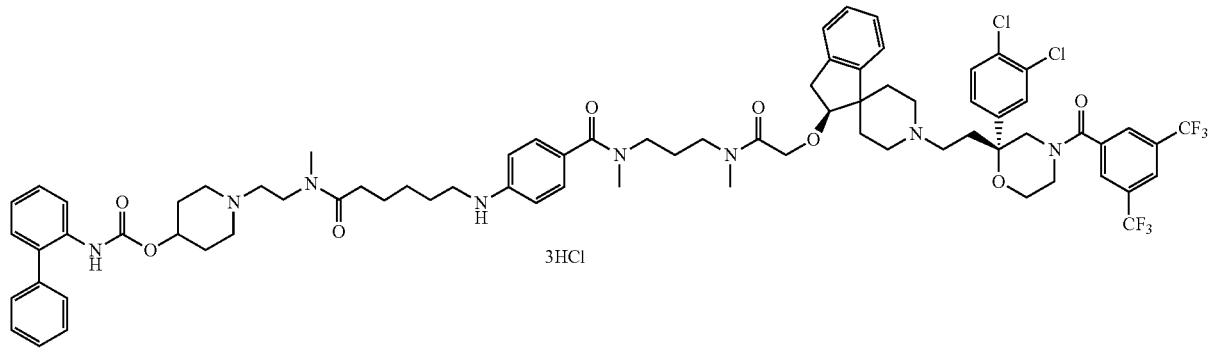

The compound (114 mg) obtained in Example 23c was used to give the title compound (111 mg; yield, 90%) as a light yellow solid according to the method described in Example 13e.

MS (FAB) m/z: 1411 (M+H)$^+$ (free form).

IR (KBr) $v_{max}$ 2931, 1727, 1638, 1521, 1477, 1450, 1282, 1138, 753, 681 cm$^{-1}$.

Example 25

1-(2-{[6-({4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(cyclopropyl)carbamoyl]phenyl}amino)hexanoyl](methyl)amino}ethyl)piperidin-4-yl biphenyl-2-ylcarbamate trihydrochloride

Example 25a

3-{[tert-Butyl(dimethyl)silyl]oxy}-N-methylpropan-1-amine (3-Bromopropoxy)(tert-butyl)dimethylsilane (1.65 g, 6.52 mmol) was dissolved in methanol (13 mL), and the mixture was added to a 40% methyl amine-methanol solution (13.3 mL, 130.0 mmol) under ice cooling, and the mixture was stirred overnight at room temperature. The solvent was evaporated under reduced pressure, and the resulting residue was purified by silica gel column chromatography (ethyl acetate:methanol=10:1→methylene chloride:methanol=10:1, v/v) to give the title compound (864 mg; yield, 65%) as a yellow oily substance.

$^1$H NMR (CDCl$_3$, 400 MHz): δ 0.06 (6H, s), 0.89 (9H, s), 1.78 (2H, tt, J=6.8, 6.1 Hz), 2.49 (3H, s), 2.77 (2H, t, J=6.8 Hz), 3.73 (2H, t, J=6.1 Hz).

[Formula 30]

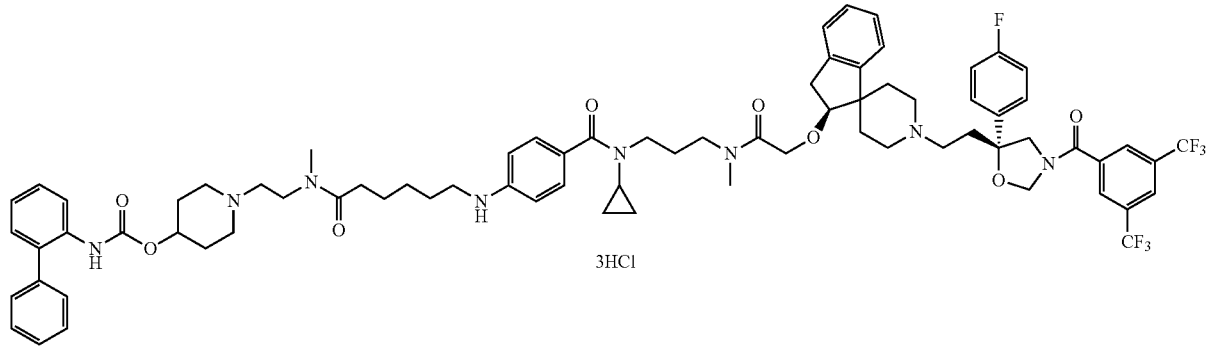

Example 25b tert-Butyl (3-hydroxypropyl)methylcarbamate

The compound (864 mg, 4.25 mmol) obtained in Example 25a was dissolved in methylene chloride (4 mL), a solution of di-tert-butyl dicarbonate (1.02 g., 4.67 mmol) in methylene chloride (5 mL) and 4-dimethylaminopyridine (52 mg, 0.425 mmol) were added, and then the mixture was stirred at room temperature for 1 hour. The solvent was evaporated under reduced pressure, ethyl acetate and 1 N hydrochloric acid were added to the resulting residue, and the mixture was extracted with ethyl acetate (×3). The organic layer was washed with saturated sodium chloride solution and dried with anhydrous sodium sulfate, then the solvent was evaporated under reduced pressure, the resulting residue was dissolved in tetrahydrofuran (4 mL), tetrabutylammonium fluoride (1 M tetrahydrofuran solution, 6.38 mL, 6.38 mmol) was added, and then the mixture was stirred at room temperature for 2 hours. The solvent was evaporated under reduced pressure, and ethyl acetate and water were added to the resulting residue, and the mixture was extracted with ethyl acetate (×3). The organic layer was washed with saturated sodium chloride solution and dried with anhydrous sodium sulfate, then the solvent was evaporated under reduced pressure, and the resulting residue was purified by silica gel column chromatography (hexane:ethyl acetate=4:1→0:100, v/v) to give the title compound (739 mg; yield, 92%) as a light yellow oily substance.

$^1$H NMR (CDCl$_3$, 400 MHz): δ 1.47 (9H, s), 1.66-1.69 (2H, m), 2.84 (3H, s), 3.38-3.40 (2H, m), 3.52-3.65 (2H, m), 3.76 (1H, brs).

Example 25c tert-Butyl [3-(cyclopropylamino)propyl]methylcarbamate

The compound (300 mg, 1.59 mmol) obtained in Example 25b was dissolved in ethyl acetate (16 mL), triethylamine (0.323 mL, 2.39 mmol) and methanesulfonyl chloride (0.147 mL, 1.90 mmol) were added under ice cooling, and the mixture was stirred at the same temperature for 10 minutes. Insoluble matter was removed by filtration through celite, the solvent was evaporated under reduced pressure, the resulting residue was added dropwise to a solution of cyclopropylamine (1.82 g, 31.8 mmol) in methanol (3 mL) under ice cooling, and the mixture was stirred at 60° C. for 72 hours. The solvent was evaporated under reduced pressure, 1 N sodium hydroxide was added to the resulting residue, and the mixture was extracted with ethyl acetate (×3). The organic layer was dried with anhydrous sodium sulfate, then the solvent was evaporated under reduced pressure, and the resulting residue was purified by silica gel column chromatography (methylene chloride:methanol=20:1→10:1, v/v) to give the title compound (215 mg; yield, 59%) as a yellow oily substance.

$^1$H NMR (CDCl$_3$, 400 MHz): δ 0.33-0.46 (4H, m), 1.46 (9H, s), 1.62-1.68 (2H, m), 2.09-2.14 (1H, m), 2.69 (2H, t, J=6.8 Hz), 2.84 (3H, s), 3.26-3.28 (2H, m).

MS (APCI) m/z: 229 (M+H)$^+$.

Example 25d

1-(2-{[6-({4-[{3-([tert-Butoxycarbonyl)(methyl)amino]propyl}(cyclopropyl)carbamoyl]phenyl}amino) hexanoyl](methyl)amino}ethyl)piperidin-4-yl biphenyl-2-ylcarbamate The compound (180 mg, 0.280 mmol) obtained in Example 15c was dissolved in 1,4-dioxane (4.2 mL), 4 N hydrochloric acid-dioxane (4.20 mL, 16.9 mmol) was added, and then the mixture was stirred at room temperature for 15 hours. The solvent was evaporated under reduced pressure and moisture was removed azeotropically with toluene (×2). The resulting residue was dissolved in methylene chloride (3 mL), triethylamine (0.234 mL, 1.68 mmol) and pivaloyl chloride (36 μL, 0.294 mmol) were added under ice cooling, and the mixture was stirred at room temperature for 45 minutes. A solution of the compound (141 mg, 0.616 mmol) obtained in Example 25c in dichloroethane (3 mL) was added dropwise under ice cooling, and the mixture was stirred with heating to reflux for 24 hours. The solvent was evaporated under reduced pressure, and the resulting residue was purified by NH silica gel column chromatography (ethyl acetate:methanol=40:1, v/v) to give the title compound (185 mg; yield, 83%) as a white solid.

$^1$H NMR (CDCl$_3$, 400 MHz): δ 0.48-0.50 (2H, m), 0.68-0.69 (2H, m), 1.47 (9H, s), 1.65-1.74 (6H, m), 1.90-1.96 (4H, m), 2.27-2.39 (4H, m), 2.49 (2H, t, J=6.8 Hz), 2.70-2.77 (2H, m), 2.85-2.87 (4H, m), 2.96-3.02 (3H, m), 3.17 (2H, t, J=6.8 Hz), 3.27-3.32 (2H, m), 3.39 (1H, t, J=6.8 Hz), 3.52 (4H, quint, J=6.8 Hz), 3.87-3.90 (1H, m), 4.71-4.76 (1H, m), 6.54 (2H, d, J=8.6 Hz), 6.61 (1H, brs), 7.12-7.17 (1H, m), 7.22-7.25 (2H, m), 7.36-7.45 (5H, m), 7.49-7.54 (2H, m), 8.10-8.12 (1H, m).

MS (APCI) m/z: 797 (M+H)$^+$.

Example 25e

1-{2-[{6-[(4-{Cyclopropyl[3-(methylamino)propyl]carbamoyl}phenyl)amino]hexanoyl}(methyl)amino]ethyl}piperidin-4-yl biphenyl-2-ylcarbamate The compound (185 mg, 0.232 mmol) obtained in Example 25d was used to give the title compound (149 mg; yield, 92%) as a light yellow solid according to the method described in Example 6d.

MS (APCI) m/z: 697 (M+H)$^+$.

Example 25f

1-(2-{[6-({4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(cyclopropyl)carbamoyl]phenyl}amino)hexanoyl](methyl)amino}ethyl)piperidin-4-yl biphenyl-2-ylcarbamate trihydrochloride The compound (100 mg, 0.143 mmol) obtained in Example 25e was used to give the title compound (61 mg; yield, 29%) as a white solid according to the methods described in Examples 11e and 13e.

MS (FAB) m/z: 1373 (M+H)$^+$ (free form).

IR (KBr) ν$_{max}$ 2935, 1728, 1641, 1512, 1438, 1360, 1282, 1138, 848, 753 cm$^{-1}$.

Example 26

1-{2-[{[3-({4-[{3-[({[(2S)-1'-{2-[(5R)-3-[3,5-Bis
(trifluoromethyl)benzoyl]-5-(4-fluorophenyl)-1,3-
oxazolidin-5-yl]ethyl}-2,3-dihydrospiro[indene-1,4'-
piperidin]-2-yl]oxy}acetyl)(methyl)amino]propyl}
(methyl)carbamoyl]phenyl}amino)propoxy]acetyl}
(methyl)amino]ethyl}piperidin-4-yl biphenyl-2-
ylcarbamate

[Formula 31]

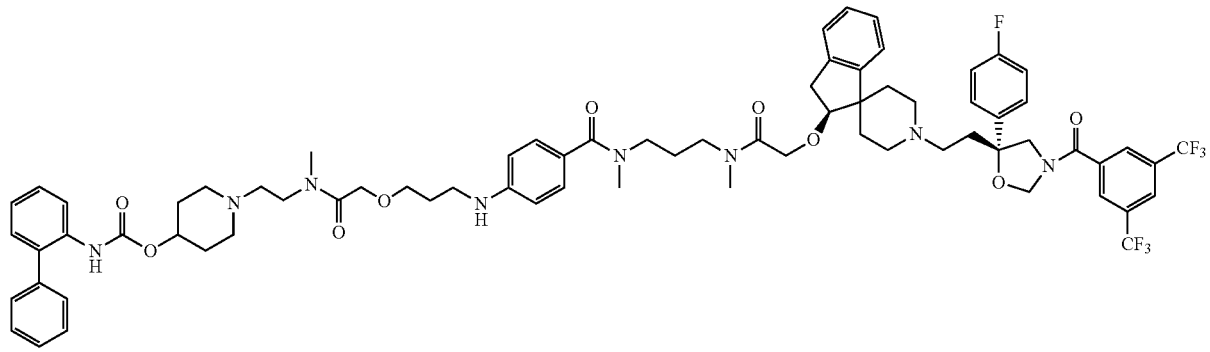

Example 26a

Ethyl (3-{[tert-butyl(dimethyl)silyl]oxy}propoxy)
acetate

Ethyl hydroxyacetate (600 mg, 5.76 mmol) was dissolved in N,N-dimethylformamide (6 mL), sodium hydride (55%; 277 mg, 0.447 mmol) was added under ice cooling, and then the mixture was stirred at room temperature for 30 minutes. (3-Bromopropoxy)(tert-butyl)dimethylsilane (1.46 mL, 6.34 mmol) was added, and the mixture was stirred at room temperature for 6.5 hours. Ethyl acetate was added to the reaction mixture, and the organic layer was washed with water (×3) and saturated sodium chloride solution. The organic layer was dried with anhydrous sodium sulfate, then the solvent was evaporated under reduced pressure, and the resulting residue was purified by silica gel column chromatography (hexane: ethyl acetate=9:1, v/v) to give the title compound (842 mg; yield, 53%) as a colorless oily substance.

$^1$H NMR (CDCl$_3$, 400 MHz): δ 0.05 (6H, s), 0.89 (9H, s), 1.29 (3H, t, J=7.1 Hz), 1.83 (2H, tt, J=6.3, 6.1 Hz), 3.62 (2H, t, J=6.3 Hz), 3.72 (2H, t, J=6.1 Hz), 4.06 (2H, s), 4.22 (2H, q, J=7.1 Hz).

MS (APCI) m/z: 277 (M+H)$^+$.

Example 26b 1-(2-{[(3-Hydroxypropoxy)acetyl](methyl)
amino}ethyl)piperidin-4-yl biphenyl-2-ylcarbamate The compound (166 mg, 0.600 mmol) obtained in Example 26a was dissolved in ethanol (1.8 mL), a 1 N aqueous sodium hydroxide solution (1.80 mL, 1.80 mmol) was added, and the mixture was stirred at room temperature for 1.5 hours. Ethyl acetate and 1 N hydrochloric acid were added to the reaction mixture, and the mixture was extracted with ethyl acetate (×3). The organic layer was washed with saturated sodium chloride solution and dried with anhydrous sodium sulfate, and then the solvent was evaporated under reduced pressure to give a carboxylic acid compound (127 mg; yield, 85%) as a colorless oily substance.

The resulting carboxylic acid compound was dissolved in methylene chloride (5 mL), triethylamine (0.107 mL, 0.511 mmol) and pivaloyl chloride (69 μL, 0.562 mmol) were added under ice cooling, and the mixture was stirred at room temperature for 15 minutes. 1-[2-(Methylamino)ethyl]piperidin-4-yl biphenyl-2-ylcarbamate (181 mg, 0.511 mmol) was added under ice cooling, and the mixture was stirred at room temperature for 1 hour. The solvent was evaporated under reduced pressure, and the resulting residue was purified by NH silica gel column chromatography (hexane:ethyl acetate=1:1, v/v) to give a colorless oily condensed compound (275 mg; yield, 92%).

The condensed compound was dissolved in tetrahydrofuran (1 mL), tetrabutylammonium fluoride (1 M tetrahydrofuran solution; 1.13 mL, 1.13 mmol) was added, and then the mixture was stirred at room temperature for 2 hours. 1 N Sodium hydroxide was added to the reaction mixture, and the mixture was extracted with ethyl acetate (×3). The organic layer was washed with saturated sodium chloride solution and dried with anhydrous sodium sulfate, then the solvent was evaporated under reduced pressure, and the resulting residue was purified by NH silica gel column chromatography (hexane:ethyl acetate=1:2→ethyl acetate:methanol=20:1, v/v) to give the title compound (175 mg; yield, 79%) as a colorless oily substance.

$^1$H NMR (CDCl$_3$, 400 MHz): δ 1.64-1.67 (2H, m), 1.83 (2H, tt, J=5.8, 5.6 Hz), 1.89-1.95 (2H, m), 2.23-2.31 (2H, m), 2.48 (2H, t, J=6.8 Hz), 2.67-2.74 (2H, m), 2.95 (3H, s), 3.29 (1H, t, J=6.4 Hz), 3.49 (2H, t, J=6.4 Hz), 3.67 (2H, t, J=5.6 Hz), 3.81 (2H, t, J=5.6 Hz), 4.14-4.22 (2H, m), 4.70-4.74 (1H, m) 6.60 (1H, s), 7.11-7.16 (1H, m), 7.21-7.23 (1H, m), 7.34-7.44 (3H, m), 7.48-7.52 (2H, m), 8.09-8.11 (1H, m).

MS (APCI) m/z: 470 (M+H)$^+$.

Example 26c 1-(2-{Methyl[(3-oxopropoxy)acetyl]amino}ethyl) piperidin-4-yl biphenyl-2-ylcarbamate The compound (275 mg, 0.586 mmol) obtained in Example 26b was used to give the title compound (222 mg; yield, 81%) as a light yellow oily substance according to the method described in Example 4g.

$^1$H NMR (CDCl$_3$, 400 MHz): δ 1.62-1.70 (2H, m), 1.91-1.95 (2H, m), 2.25-2.30 (2H, m), 2.46-2.53 (2H, m), 2.67-2.75 (3H, m), 2.89-3.02 (3H, m), 3.35 (1H, t, J=6.6 Hz), 3.46-3.50 (2H, m), 3.86-3.90 (2H, m), 4.10-4.22 (2H, m), 4.69-4.76 (1H, m), 6.59 (1H, s), 7.13 (1H, t, J=7.1 Hz), 7.21-7.23 (1H, m), 7.34-7.44 (3H, m), 7.49 (2H, t, J=7.1 Hz), 8.09-8.11 (1H, m), 9.82 (1H, s).

MS (APCI) m/z: 468 (M+H)$^+$.

Example 26d tert-Butyl 4-[(3-{2-[(2-{4-[(biphenyl-2-ylcarbamoyl) oxy]piperidin-1-yl}ethyl)(methyl)amino]-2-oxoethoxy}propyl)amino]benzoate The compound (222 mg, 0.475 mmol) obtained in Example 26c and tert-butyl 4-aminobenzoate (92 mg, 0.475 mmol) were used according to the method described in Example 18b to give the title compound (192 mg; yield, 63%) as a white solid.

$^1$H NMR (CDCl$_3$, 400 MHz): δ 1.59 (9H, s), 1.59-1.68 (2H, m), 1.88-1.93 (4H, m), 2.24-2.30 (2H, m), 2.49 (2H, quint, J=6.8 Hz), 2.66-2.75 (2H, m), 2.97 (3H, s), 3.29-3.36 (2H, m), 3.50 (2H, t, J=6.8 Hz), 3.61 (2H, q, J=5.1 Hz), 4.13-4.20 (2H, m), 4.69-4.74 (1H, m), 5.17-5.20 (1H, m), 6.55-6.60 (3H, m), 7.13 (1H, t, J=7.3 Hz), 7.21-7.23 (1H, m), 7.34-7.43 (4H, m), 7.47-7.50 (2H, m), 7.79 (2H, d, J=8.8 Hz), 8.08-8.10 (1H, m).

MS (APCI) m/z: 645 (M+H)$^+$.

Example 26e

1-{2-[{[3-({4-[{3-([tert-Butoxycarbonyl)(methyl) amino]propyl}(methyl)carbamoyl]phenyl}amino) propoxy]acetyl}(methyl)amino]ethyl}piperidin-4-yl biphenyl-2-ylcarbamate The compound (192 mg, 0.298 mmol) obtained in Example 26d was dissolved in 1,4-dioxane (4.5 mL), 4 N hydrochloric acid-dioxane (4.50 mL, 17.9 mmol) was added, and the mixture was stirred at room temperature for 17.5 hours. The solvent was evaporated under reduced pressure and then removed azeotropically with toluene (×2) to give a crude carboxylic acid compound. The resulting crude carboxylic acid compound was used to give the title compound (177 mg; yield, 77%) as a light yellow solid according to the method described in Example 12a.

MS (APCI) m/z: 773 (M+H)$^+$.

IR (KBr) ν$_{max}$ 2930, 1689, 1606, 1520, 1448, 1393, 1205, 1160, 1043, 747 cm$^{-1}$.

Example 26f 1-(2-{[6-({4-[{3-[({[(2S)-1'-{2-[(5R)-3-[3,5-Bis (trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl} (cyclopropyl)carbamoyl]phenyl}amino)hexanoyl] (methyl)amino}ethyl)piperidin-4-yl biphenyl-2-ylcarbamate The compound (120 mg, 0.155 mmol) obtained in Example 26e was used to give a Boc-deprotected compound according to the method described in Example 6d. The resulting Boc-deprotected compound was used to give the title compound (85 mg; yield, 41%) as a white solid according to the method described in Example 11e.

MS (FAB) m/z: 1349 (M+H)$^+$.

IR (KBr) ν$_{max}$ 2932, 1730, 1649, 1512, 1359, 1281, 1179, 1138, 838, 756 cm$^{-1}$.

Example 27

1-{2-[{[3-({4-[{3-[({[(2S)-1'-{2-[(5R)-3-[3,5-Bis (trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl} (methyl)carbamoyl]phenyl}amino)propoxy]acetyl} (methyl)amino]ethyl}piperidin-4-yl biphenyl-2-ylcarbamate trihydrochloride

[Formula 32]

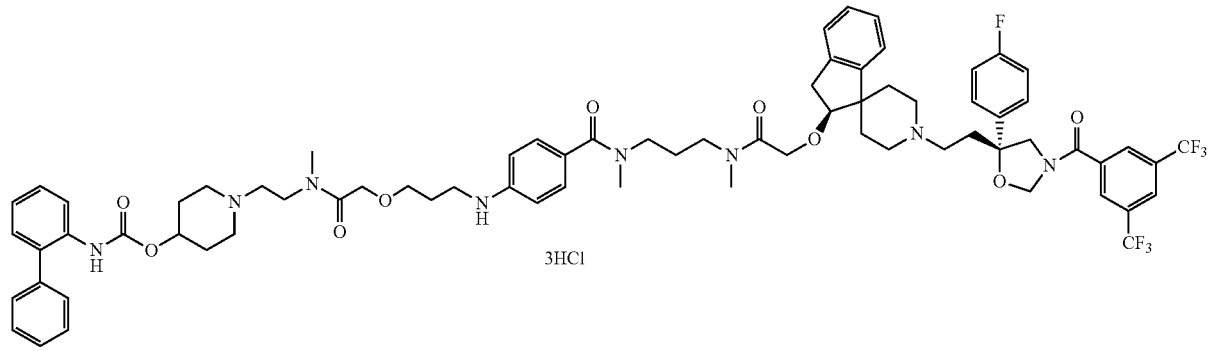

The compound (85 mg) obtained in Example 26f was used to give the title compound (88 mg; yield, 96%) as a white solid according to the method described in Example 13e.

MS (FAB) m/z: 1349 (M+H)⁺ (free form).

IR (KBr) $v_{max}$ 2932, 1731, 1639, 1438, 1360, 1282, 1225, 1178, 1138, 753 cm⁻¹.

Example 28

1-{2-[{3-[2-({4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}amino)ethoxy]propanoyl}(methyl)amino]ethyl}piperidin-4-yl biphenyl-2-ylcarbamate

Example 28c tert-Butyl methyl(3-{methyl[(4-nitrophenyl)carbonyl]amino}propyl)carbamate 4-Nitrobenzoic acid (93 mg, 0.500 mmol) was used to give the title compound (162 mg; yield, 92%) as a colorless oily substance according to the method described in Example 12a.

¹H NMR (CDCl₃, 400 MHz): δ 1.37 (4.5H, s), 1.47 (4.5H, s), 1.75-1.79 (1H, m), 1.90-1.93 (1H, m), 2.69-2.73 (2H, m), 2.90 (1.5H, s), 2.94 (1.5H, s), 3.08-3.11 (2H, m), 3.18-3.22 (1H, m), 3.32-3.34 (1H, m), 3.54-3.58 (1H, m), 7.54-7.60 (2H, m), 8.28 (2H, d, J=8.8 Hz).

MS (APCI) m/z: 252 (M+H)⁺ (from with Boc removed).

[Formula 33]

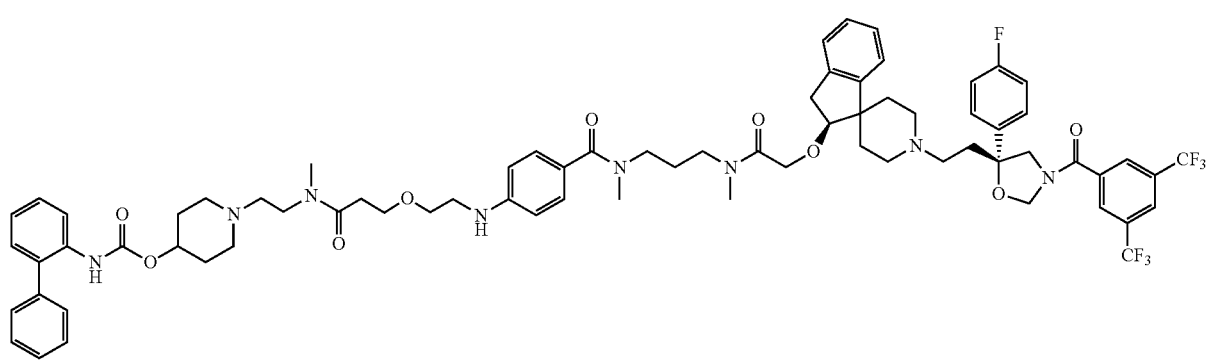

Example 28a tert-Butyl 3-(2-hydroxyethoxy)propanoate tert-Butyl acrylate (5.72 mL, 39.0 mmol) was added to a mixture of ethylene glycol (2.42 g, 39.0 mmol), tetrabutylammonium bromide (377 mg, 1.17 mmol) and potassium hydroxide (77 mg; purity, 85%; 1.17 mmol), and the mixture was stirred at room temperature for 4 days. The reaction mixture was purified by silica gel column chromatography (hexane:ethyl acetate=4:1→2:1, v/v) to give the title compound (1.66 g; yield, 22%) as a colorless oily substance.

¹H NMR (CDCl₃, 400 MHz): δ 1.47 (9H, s), 2.44 (1H, brs), 2.52 (2H, t, J=6.1 Hz), 3.59 (2H, t, J=5.6 Hz), 3.73-3.76 (4H, m).

Example 28b tert-Butyl 3-(2-oxoethoxy)propanoate

The compound (199 mg, 1.05 mmol) obtained in Example 28a was used to give the title compound (169 mg; yield, 86%) as a light brown oily substance according to the method described in Example 4g.

¹H NMR (CDCl₃, 400 MHz): δ 1.46 (9H, s), 2.56 (2H, t, J=6.1 Hz), 3.80 (2H, t, J=6.1 Hz), 4.10 (2H, s), 9.73 (1H, s).

Example 28d tert-Butyl (3-{[(4-aminophenyl)carbonyl](methyl)amino}propyl)methylcarbamate A solution of the compound (162 mg, 0.461 mmol) obtained in Example 28c in methanol (5 mL) was added to 10% palladium-carbon (dry; 16 mg), and the atmosphere in the system was replaced with a hydrogen atmosphere, and then the mixture was stirred at room temperature for 1.5 hours. The atmosphere in the system was replaced with a nitrogen atmosphere, and the mixture was filtered through celite. The solvent was evaporated under reduced pressure to give the title compound (150 mg; yield, 100%) as a colorless oily substance.

¹H NMR (CDCl₃, 400 MHz): δ 1.44 (9H, s), 1.81-1.85 (2H, m), 2.80-2.83 (3H, m), 3.03 (3H, s), 3.17-3.24 (2H, m), 3.39-3.44 (2H, m), 3.81-3.83 (2H, m), 6.65 (2H, d, J=8.3 Hz), 7.25 (2H, d, J=8.3 Hz).

MS (APCI) m/z: 322 (M+H)⁺.

Example 28e tert-Butyl 3-[2-({4-[{3-([tert-butoxycarbonyl)(methyl)amino]propyl}(methyl)carbamoyl]phenyl}amino)ethoxy]propanoate The compound (87 mg, 0.461 mmol) obtained in Example 28b and the compound (150 mg, 0.461 mmol) obtained in Example 28d were used to give the title compound (188 mg; yield, 83%) as a colorless oily substance according to the method described in Example 18b.

¹H NMR (CDCl₃, 400 MHz): δ 1.44 (9H, s), 1.47 (9H, s), 1.54-1.58 (2H, m), 1.82-1.86 (1H, m), 2.51 (2H, t, J=6.1 Hz), 2.80-2.86 (3H, m), 3.03 (3H, s), 3.18-3.23 (2H, m), 3.30 (2H, t, J=5.1 Hz), 3.40-3.45 (2H, m), 3.69 (2H, t, J=5.1 Hz), 3.72 (2H, t, J=6.1 Hz), 6.61 (2H, d, J=8.3 Hz), 7.28 (2H, d, J=8.3 Hz).
MS (APCI) m/z: 494 (M+H)⁺.

Example 28f

1-{2-[{3-[2-({4-[{3[(tert-Butoxycarbonyl)(methyl)amino]propyl}(methyl)carbamoyl]phenyl}amino)ethoxy]propanoyl}(methyl)amino]ethyl}piperidin-4-yl biphenyl-2-ylcarbamate The compound (188 mg, 0.381 mmol) obtained in Example 28e was dissolved in methylene chloride (4 mL), trifluoroacetic acid (2 mL) was added under ice cooling, and the mixture was stirred at room temperature for 2.5 hours. The solvent was evaporated under reduced pressure, and moisture was removed from the resulting residue azeotropically with toluene (×2). The resulting residue was dissolved in methylene chloride (4 mL), triethylamine (0.318 mL, 2.29 mmol) and di-tert-butyl dicarbonate (183 mg, 0.838 mmol) were added, and the mixture was stirred at room temperature for 18.5 hours. The solvent was evaporated under reduced pressure, the resulting residue was dissolved in methylene chloride (4 mL), triethylamine (79 μL, 0.572 mmol) and pivaloyl chloride (49 μL, 0.400 mmol) were added under ice cooling, and the mixture was stirred at room temperature for 20 minutes. 1-[2-(Methylamino)ethyl]piperidin-4-yl biphenyl-2-ylcarbamate (296 mg, 0.838 mmol) was added under ice cooling, and the mixture was stirred at room temperature for 2 hours. The solvent was evaporated under reduced pressure, and the resulting residue was purified by NH silica gel column chromatography (ethyl acetate:methanol=50:1, v/v) to give the title compound (196 mg; yield, 66%) as a white solid.
¹H NMR (CDCl₃, 400 MHz): δ 1.44 (9H, s), 1.53-1.67 (6H, m), 1.98-2.05 (4H, m), 2.24-2.30 (2H, m), 2.46-2.50 (2H, m), 2.56-2.65 (2H, m), 2.67-2.73 (2H, m), 2.80-2.84 (2H, m), 2.97-3.03 (3H, m), 3.19-3.28 (3H, m), 3.37-3.51 (4H, m), 3.67-3.71 (2H, m), 3.78-3.82 (2H, m), 4.56-4.63 (1H, m), 4.68-4.74 (1H, m), 6.58-6.60 (2H, m), 7.11-7.15 (1H, m), 7.21-7.27 (2H, m), 7.34-7.43 (5H, m), 7.47-7.52 (2H, m), 8.07-8.11 (1H, m).
MS (APCI) m/z: 773 (M+H)⁺.

Example 28g

1-{2-[Methyl(3-{2-[(4-{methyl[3-(methylamino)propyl]carbamoyl}phenyl)amino]ethoxy}propanoyl)amino]ethyl}piperidin-4-yl biphenyl-2-ylcarbamate The compound (195 mg, 0.252 mmol) obtained in Example 28f was used to give the title compound (159 mg; yield, 94%) as a white solid according to the method described in Example 6d.
¹H NMR (CDCl₃, 400 MHz): δ 1.64-1.71 (6H, m), 1.82-1.93 (4H, m), 2.24-2.29 (2H, m), 2.49 (2H, t, J=7.1 Hz), 2.59 (2H, t, J=7.1 Hz), 2.63 (2H, t, J=6.8 Hz), 2.67-2.75 (2H, m), 2.97-3.03 (4H, m), 3.26-3.30 (2H, m), 3.39 (1H, t, J=6.6 Hz), 3.51 (3H, t, J=7.1 Hz), 3.69-3.72 (2H, m), 3.79-3.82 (2H, m), 4.62-4.75 (2H, m), 6.58-6.63 (3H, m), 7.11-7.21 (2H, m), 7.23-7.24 (1H, m), 7.34-7.43 (4H, m), 7.47-7.53 (2H, m), 8.08-8.10 (1H, m).
MS (APCI) m/z: 673 (M+H)⁺.

Example 28h

1-{2-[{3-[2-({4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}amino)ethoxy]propanoyl}(methyl)amino]ethyl}piperidin-4-yl biphenyl-2-ylcarbamate The compound (159 mg, 0.236 mmol) obtained in Example 28g was used to give the title compound (190 mg; yield, 56%) as a white solid according to the method described in Example 11e.
MS (FAB) m/z: 1349 (M+H)⁺.
IR (KBr) ν_max 2929, 1729, 1644, 1512, 1359, 1281, 1179, 1138, 839, 755 cm⁻¹.

Example 29

1-{2-[{3-[2-({4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methy)amino]propyl}(methyl)carbamoyl]phenyl}amino)ethoxy]propanoyl}(methyl)amino]ethyl}piperidin-4-yl biphenyl-2-ylcarbamate trihydrochloride

[Formula 34]

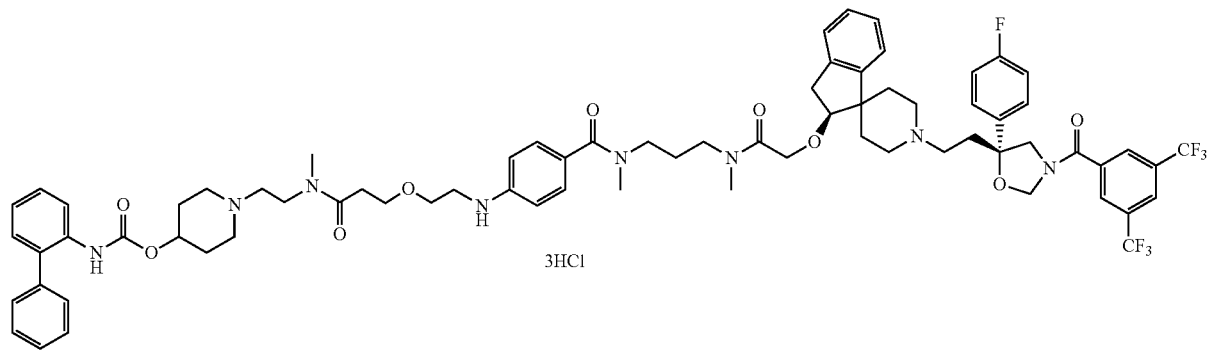

3HCl

The compound (190 mg) obtained in Example 28h was used to give the title compound (201 mg; yield, 98%) as a white solid according to the method described in Example 13e.

MS (FAB) m/z: 1349 (M+H)+ (free form).

IR (KBr) $v_{max}$ 2931, 1726, 1642, 1438, 1360, 1282, 1225, 1175, 1137, 753 cm$^{-1}$.

Example 30

1-(2-{[6-({5-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-4-methyl-2-thienyl}amino)hexanoyl](methyl)amino}ethyl)piperidin-4-yl biphenyl-2-ylcarbamate trihydrochloride

[Formula 35]

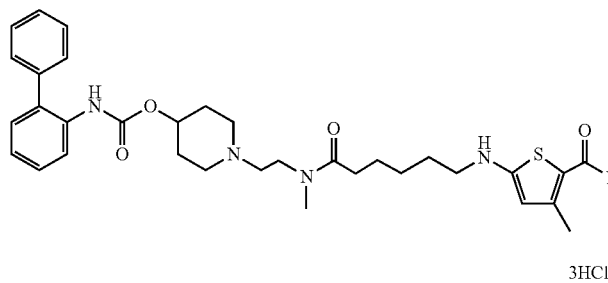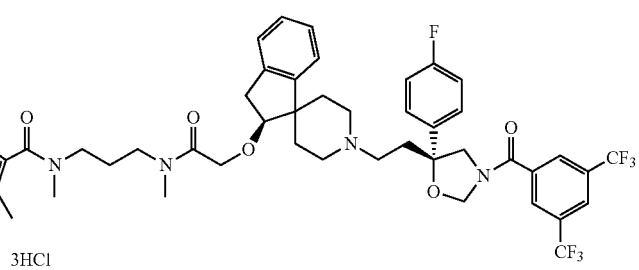

3HCl

Example 30a

Methyl 5-amino-3-methylthiophene-2-carboxylate

Cyanoacetic acid (2.50 g, 29.4 mmol) was dissolved in toluene (14 mL), methyl 3-oxobutanoate (2.97 mL, 27.5 mmol), ammonium acetate (530 mg, 6.89 mmol) and acetic acid (0.787 mL, 13.8 mmol) were added, and the mixture was stirred with heating to reflux using a Dean-Stark apparatus for 31 hours. A saturated aqueous sodium hydrogencarbonate solution was added to the reaction mixture, and the mixture was extracted with ethyl acetate (×3). The organic layer was washed with saturated sodium chloride solution and dried with anhydrous sodium sulfate, then the solvent was evaporated under reduced pressure, the resulting residue was dissolved in ethanol (16 mL), diethylamine (3.12 mL, 29.9 mmol) and sulfur (959 mg, 29.9 mmol) were added, and the mixture was stirred at room temperature for 36 hours. Saturated sodium chloride solution was added to the reaction mixture, the mixture was extracted with ethyl acetate (×3), and the organic layer was washed with saturated sodium chloride solution and dried with anhydrous sodium sulfate. The solvent was evaporated under reduced pressure, and the resulting residue was purified by silica gel column chromatography (hexane:ethyl acetate=6:1→4:1, v/v) to give the title compound (2.40 g; yield, 61%) as a brown oily substance.

$^1$H NMR (CDCl$_3$, 400 MHz): δ 2.42 (3H, s), 3.78 (3H, s), 4.23 (2H, brs), 5.95 (1H, s).

MS (APCI) m/z: 172 (M+H)+.

Example 30b

Methyl 5-[(tert-butoxycarbonyl)amino]-3-methylthiophene-2-carboxylate

The compound (342 mg, 2.00 mmol) obtained in Example 30a was used to give the title compound (449 mg; yield, 83%) as a light brown solid according to the method described in Example 4b.

$^1$H NMR (CDCl$_3$, 400 MHz): δ 1.53 (9H, s), 2.47 (3H, s), 3.80 (3H, s), 6.32 (1H, s).

MS (APCI) m/z: 272 (M+H)+.

Example 30c tert-Butyl {3-[({5-[(tert-butoxycarbonyl)amino]-3-methylthiophen-2-yl}carbonyl)(methyl)amino]propyl}methylcarbamate The compound (449 mg, 1.66 mmol) obtained in Example 30b was used to give a crude carboxylic acid compound (341 mg) according to the method described in Example 4c. The resulting crude carboxylic acid compound (194 mg, 0.754 mmol) was used to give the title compound (129 mg; yield, 31%) as a white solid according to the method described in Example 12a.

MS (APCI) m/z: 442 (M+H)+.

Example 30d tert-Butyl (3-{[(5-amino-3-methylthiophen-2-yl)carbonyl](methyl)amino}propyl)methylcarbamate The compound (129 mg, 0.292 mmol) obtained in Example 30c was dissolved in methylene chloride (3 mL), trifluoroacetic acid (1.5 mL) was added under ice cooling, and the mixture was stirred at room temperature for 1 hour. The solvent was evaporated under reduced pressure, toluene (×2) was added to the resulting residue, and the solvent was evaporated under reduced pressure. The resulting residue was dissolved in methylene chloride (3 mL), triethylamine (0.318 mL, 2.29 mmol) and di-tert-butyl dicarbonate (244 mg, 1.75 mmol) were added, and the mixture was stirred at room temperature for 15 hours. The solvent was evaporated under reduced pressure, and the resulting residue was purified by NH silica gel column chromatography (hexane:ethyl acetate=1:2→0:100, v/v) to give the title compound (78 mg; yield, 78%) as a yellow oily substance.

MS (APCI) m/z: 342 (M+H)$^+$.

Example 30e

1-{2-[{3-[2-({4-[{3-([tert-Butoxycarbonyl)(methyl)amino]propyl}(methyl)carbamoyl]phenyl}amino)ethoxy]propanoyl}(methyl)amino]ethyl}piperidin-4-yl biphenyl-2-ylcarbamate The compound (78 mg, 0.228 mmol) obtained in Example 30d was used to give the title compound (112 mg; yield, 62%) as a yellow solid according to the method described in Example 18b.

MS (FAB) m/z: 1367 (M+H)$^+$ (free form).

IR (KBr) $v_{max}$ 2936, 1725, 1646, 1439, 1360, 1282, 1225, 1175, 1138, 753 cm$^{-1}$.

Example 31

1-(2-{[5-({4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}amino)pentanoyl](methyl)amino}ethyl)piperidin-4-yl biphenyl-2-ylcarbamate

[Formula 36]

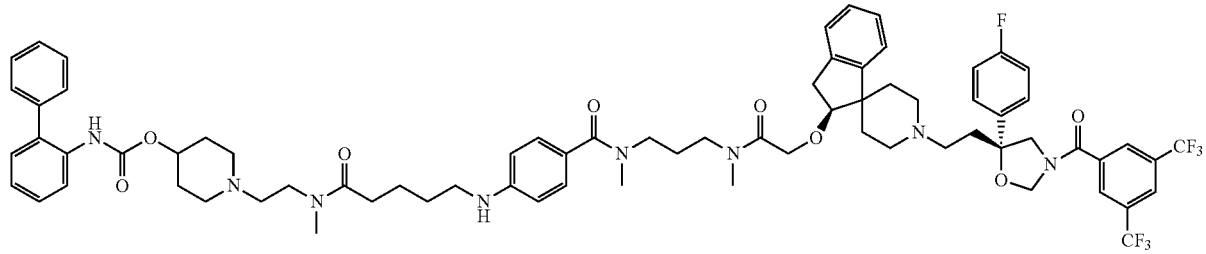

$^1$H NMR (CDCl$_3$, 400 MHz): δ 1.44 (9H, s), 1.61-1.69 (6H, m), 1.80-1.85 (2H, m), 1.89-1.95 (2H, m), 2.14 (3H, s), 2.24-2.35 (4H, m), 2.46 (2H, t, J=7.1 Hz), 2.61 (2H, s), 2.68-2.75 (2H, m), 2.82 (3H, s), 2.93-3.03 (6H, m), 3.08-3.11 (2H, m), 3.19-3.23 (2H, m), 3.36 (1H, t, J=7.3 Hz), 3.41-3.49 (3H, m), 4.70-4.74 (1H, m), 6.58-6.59 (1H, m), 7.10-7.14 (1H, m), 7.19-7.22 (1H, m), 7.32-7.43 (4H, m), 7.46-7.51 (2H, m), 8.08-8.10 (1H, m).

MS (APCI) m/z: 791 (M+H)$^+$.

Example 30f 1-(2-{[6-({5-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-4-methyl-2-thienyl}amino)hexanoyl](methyl)amino}ethyl)piperidin-4-yl biphenyl-2-ylcarbamate trihydrochloride The compound (112 mg, 0.142 mmol) obtained in Example 30e was used to give a crude Boc-deprotected compound (80 mg) according to the method described in Example 6d. The resulting crude Boc-deprotected compound was used according to the methods described in Examples 11e and 13e to give the title compound (34 mg; yield, 20%) as a light yellow solid.

Example 31a

1-{2-[(5-Hydroxypentanoyl)(methyl)amino]ethyl}piperidin-4-yl biphenyl-2-ylcarbamate 5-Bromopentanoyl chloride (0.125 mL, 0.934 mmol) was used to give the title compound (242 mg; yield, 63%) as a colorless oily substance according to the method described in Example 4f.

$^1$H NMR (CDCl$_3$, 400 MHz): δ 1.59-1.69 (3H, m), 1.77 (3H, quint, J=7.1 Hz), 1.90-1.94 (3H, m), 2.25-2.32 (2H, m), 2.36 (2H, quint, J=6.8 Hz), 2.46-2.49 (2H, m), 2.69-2.75 (2H, m), 2.94-3.01 (3H, m), 3.38 (1H, t, J=6.8 Hz), 3.50 (1H, t, J=6.8 Hz), 3.60-3.64 (2H, m), 4.71-4.74 (1H, m), 6.59 (1H, brs), 7.11-7.15 (1H, m), 7.21-7.23 (1H, m), 7.34-7.38 (3H, m), 7.42-7.44 (1H, m), 7.47-7.51 (2H, m), 8.09-8.10 (1H, m).

MS (APCI) m/z: 454 (M+H)$^+$.

Example 31b tert-Butyl-4-({5-[(2-{4-[(biphenyl-2-ylcarbamoyl)oxy]piperidin-1-yl}ethyl)(methyl)amino]-5-oxopentyl}amino)benzoate The compound (242 mg, 0.534 mmol) obtained in Example 31a was used to give a crude aldehyde compound (252 mg) according to the method described in Example 4g. The resulting crude aldehyde compound and tert-butyl 4-aminobenzoate (92 mg, 0.475 mmol) were used to give the title compound (231 mg; yield, 69%) as a white solid according to the method described in Example 18b.

$^1$H NMR (CDCl$_3$, 400 MHz): δ 1.56 (9H, s) 1.64-1.72 (4H, m), 1.74-1.79 (2H, m), 1.89-1.94 (2H, m), 2.24-2.30 (2H, m), 2.34-2.40 (2H, m), 2.45-2.49 (2H, m), 2.67-2.75 (2H, m), 2.94-3.00 (3H, m), 3.17-3.20 (2H, m), 3.37 (1H, t, J=6.8 Hz), 3.49 (1H, t, J=6.8 Hz), 4.27-4.29 (1H, m), 4.69-4.75 (1H, m), 6.52 (2H, d, J=6.8 Hz), 6.58-6.60 (1H, m), 7.11-7.16 (1H, m), 7.21-7.24 (1H, m), 7.34-7.41 (3H, m), 7.41-7.43 (1H, m), 7.47-7.51 (2H, m), 7.81 (2H, d, J=8.8 Hz), 8.09-8.11 (1H, m).

MS (APCI) m/z: 629 (M+H)$^+$.

Example 31c 1-(2-{[5-({4-[{3-([tert-Butoxycarbonyl)(methyl)amino]propyl}(methyl)carbamoyl]phenyl}amino)pentanoyl](methyl)amino}ethyl)piperidin-4-yl biphenyl-2-ylcarbamate The compound (231 mg, 0.367 mmol) obtained in Example 31b was dissolved in 1,4-dioxane (5.5 mL), 4 N hydrochloric acid-dioxane (5.50 mL, 22.0 mmol) was added, and then the mixture was stirred at room temperature for 18 hours. The solvent was evaporated under reduced pressure and moisture was removed azeotropically with toluene (×2) to give a crude carboxylic acid compound. The resulting crude carboxylic acid compound was used to give the title compound (199 mg; yield, 72%) as a white solid according to the method described in Example 12a.

$^1$H NMR (CDCl$_3$, 400 MHz): δ 1.44 (9H, s), 1.53-1.57 (3H, m), 1.64-1.69 (3H, m), 1.72-1.79 (1H, m), 1.82-1.86 (1H, m), 1.90-1.94 (1H, m), 2.25-2.30 (2H, m), 2.33-2.40 (2H, m), 2.46-2.49 (2H, m), 2.68-2.76 (2H, m), 2.82-2.84 (3H, m), 2.94-3.03 (6H, m), 3.14-3.18 (2H, m), 3.20-3.24 (2H, m), 3.36-3.50 (5H, m), 4.70-4.75 (1H, m), 6.54 (2H, d, J=8.5 Hz), 6.58-6.60 (1H, m), 7.11-7.16 (2H, m), 7.21-7.23 (1H, m), 7.34-7.38 (3H, m), 7.40-7.43 (1H, m), 7.47-7.52 (2H, m), 8.08-8.11 (1H, m).

MS (APCI) m/z: 757 (M+H)$^+$.

Example 31d 1-(2-{[5-({4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}amino)pentanoyl](methyl)amino}ethyl)piperidin-4-yl biphenyl-2-ylcarbamate The compound (199 mg, 0.263 mmol) obtained in Example 31c was used to give a crude Boc-deprotected compound according to the method described in Example 6d. The resulting crude Boc-deprotected compound was used to give the title compound (232 mg; yield, 66%) as a white solid according to the method described in Example 11e.

MS (FAB) m/z: 1333 (M+H)$^+$.

IR (KBr) $v_{max}$ 2930, 1728, 1644, 1512, 1359, 1281, 1179, 1139, 838, 755 cm$^{-1}$.

Example 32

1-(2-{[5-({4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}amino)pentanoyl](methyl)amino}ethyl)piperidin-4-yl biphenyl-2-ylcarbamate trihydrochloride

[Formula 37]

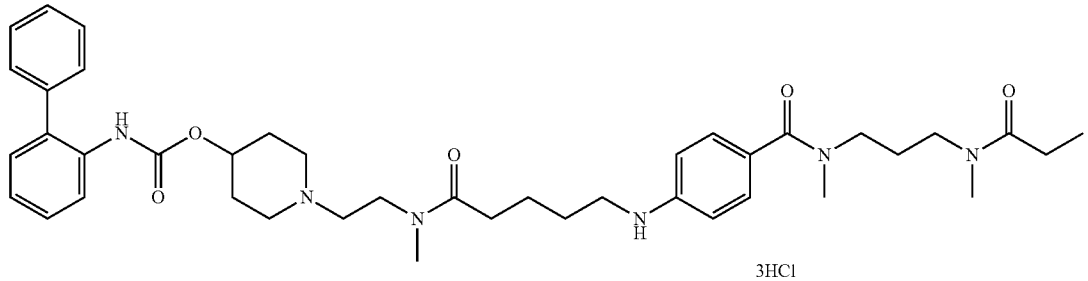

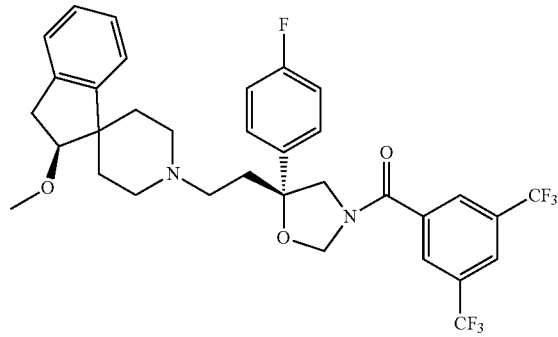

The compound (90 mg) obtained in Example 31d was used to give the title compound (95 mg; yield, 98%) as a white solid according to the method described in Example 13e.

MS (FAB) m/z: 1333 (M+H)+ (free form).
IR (KBr) ν$_{max}$ 2933, 1730, 1642, 1450, 1360, 1282, 1224, 1177, 1138, 753 cm$^{-1}$.

Example 33

1-(2-{[4-({4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}amino)butanoyl](methyl)amino}ethyl)piperidin-4-yl biphenyl-2-ylcarbamate MS (FAB) m/z: 484 (M+H)+.
IR (KBr) ν$_{max}$ 2948, 1724, 1651, 1528, 1280, 1233, 1124, 1057, 748 cm$^{-1}$.

Example 33b

1-{2-[Methyl(4-oxobutanoyl)amino]ethyl}piperidin-4-yl biphenyl-2-ylcarbamate

The compound (300 mg, 0.620 mmol) obtained in Example 33a was dissolved in dichloromethane (6 mL), trifluoroacetic acid (3 mL) was added at room temperature, and the mixture was stirred for 2 hours. The solvent was evaporated under reduced pressure, the resulting residue was dissolved in ethyl acetate, and the organic layer was washed with a 1 N aqueous sodium hydroxide solution, water, and satu-

[Formula 38]

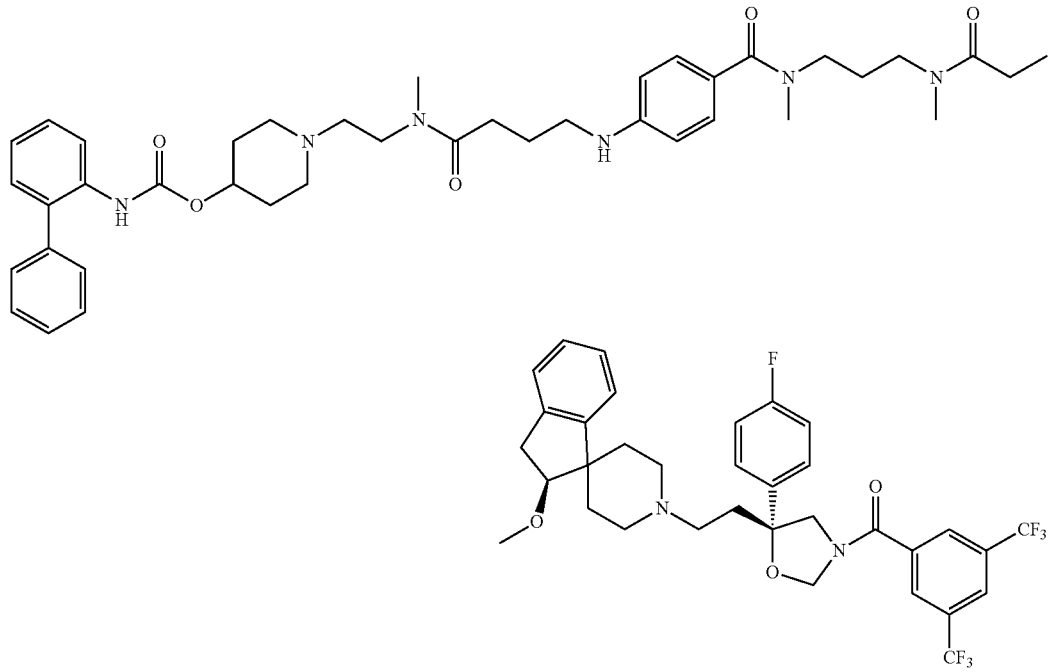

Example 33a

1-{2-[(4,4-Dimethoxybutanoyl)(methyl)amino]ethyl}piperidin-4-yl biphenyl-2-ylcarbamate Methyl 4,4-dimethoxybutanoate (600 mg, 3.70 mmol) was dissolved in methanol (6 mL), a 1 N aqueous sodium hydroxide solution (5.55 mL, 5.55 mmol) was added, and then the mixture was stirred at room temperature for 5.5 hours. 1 N Hydrochloric acid was added to the reaction mixture to adjust the mixture to pH 4, and then the mixture was extracted with ethyl acetate (×3). The organic layer was washed with saturated sodium chloride solution and dried with anhydrous sodium sulfate. The solvent was evaporated under reduced pressure to give a carboxylic acid compound (499 mg). The resulting carboxylic acid compound (168 mg, 1.13 mmol) and 1-[2-(methylamino)ethyl]piperidin-4-yl biphenyl-2-ylcarbamate (400 mg, 1.13 mmol) were used to give the title compound (499 mg; yield, 91%) as a colorless oily substance according to the method described in Example 12a.

rated sodium chloride solution. The organic layer was dried with anhydrous sodium sulfate and filtered through celite. The filtrate was concentrated under reduced pressure to give a crude title compound (261 mg; yield, 98%) as a colorless oily substance.

$^1$H NMR (CDCl$_3$, 400 MHz): δ 1.62-1.70 (2H, m), 1.90-1.94 (2H, m), 2.24-2.33 (2H, m), 2.45-2.48 (1H, m), 2.51 (1H, t, J=6.8 Hz), 2.61-2.72 (4H, m), 2.79-2.84 (2H, m), 2.94 (1.2H, s), 3.05 (1.8H, s), 3.41 (0.8H, t, J=6.8 Hz), 3.48 (1.2H, t, J=6.8 Hz), 4.70-4.76 (1H, m), 6.59 (1H, s), 7.11-7.16 (1H, m), 7.34-7.40 (3H, m), 7.42-7.44 (1H, m), 7.47-7.51 (2H, m), 8.09-8.11 (1H, m), 9.86 (1H, s).

Example 33c tert-Butyl 4-({4-[(2-{4-[(biphenyl-2-ylcarbamoyl)oxy]piperidin-1-yl}ethyl)(methyl)amino]-4-oxobutyl}amino)benzoate The compound (130 mg, 0.297 mmol) obtained in Example 33b and tert-butyl 4-aminobenzoate (92 mg, 0.475 mmol) were used to give the title compound (151 mg; yield, 83%) as a white solid according to the method described in Example 18b.

$^1$H NMR (CDCl$_3$, 400 MHz): δ 1.55 (3.9H, s), 1.56 (5.1H, s), 1.62-1.67 (1H, m), 1.89-1.93 (2H, m), 1.98-2.02 (2H, m), 2.22-2.29 (2H, m), 2.40-2.48 (4H, m), 2.61-2.65 (1H, m), 2.71-2.76 (1H, m), 2.95 (1.3H, s), 2.99 (1.7H, s), 3.21-3.24 (2H, m), 3.35 (1.3H, t, J=7.1 Hz), 3.49 (1.7H, t, J=7.1 Hz), 4.55-4.61 (1H, m), 4.70-4.74 (1H, m), 6.51 (2H, d, J=8.5 Hz), 6.58-6.61 (1H, m), 7.11-7.16 (1H, m), 7.21-7.23 (1H, m), 7.34-7.40 (3H, m), 7.41-7.43 (1H, m), 7.47-7.50 (2H, m), 7.78-7.81 (2H, m), 8.08-8.11 (1H, m).

MS (APCI) m/z: 615 (M+H)$^+$.

Example 33d 1-(2-{[4-({4-[{3-([tert-Butoxycarbonyl)(methyl) amino]propyl}(methyl)carbamoyl]phenyl}amino) butanoyl](methyl)amino}ethyl)piperidin-4-yl biphenyl-2-ylcarbamate The compound (151 mg, 0.246 mmol) obtained in Example 33c was dissolved in 1,4-dioxane (4 mL), 4 N hydrochloric acid-dioxane (3.68 mL, 14.7 mmol) was added, and then the mixture was stirred at room temperature for 20 hours. The solvent was evaporated under reduced pressure and moisture was removed azeotropically with toluene (×2) to give a crude carboxylic acid compound. The resulting crude carboxylic acid compound was used to give the title compound (147 mg; yield, 80%) as a white solid according to the method described in Example 12a.

$^1$H NMR (CDCl$_3$, 400 MHz): δ 1.33 (9H, s), 1.62-1.67 (2H, m), 1.81-1.85 (2H, m), 1.89-1.93 (2H, m), 1.97-2.02 (2H, m), 2.24-2.29 (2H, m), 2.40-2.49 (4H, m), 2.64-2.75 (2H, m), 2.82 (3H, s), 2.95-3.03 (6H, m), 3.18-3.22 (3H, m), 3.34-3.41 (4H, m), 4.25-4.32 (1H, m), 4.70-4.74 (1H, m), 6.54 (2H, d, J=8.8 Hz), 6.58-6.62 (1H, m), 7.11-7.16 (2H, m), 7.21-7.24 (1H, m), 7.34-7.38 (4H, m), 7.42-7.43 (1H, m), 7.47-7.52 (2H, m), 8.08-8.10 (1H, m).

MS (APCI) m/z: 743 (M+H)$^+$.

Example 33e 1-(2-{[4-({4-[{3-[({[(2S)-1'-{2-[(5R)-3-[3,5-Bis (trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl} (methyl)carbamoyl]phenyl}amino)butanoyl](methyl) amino}ethyl)piperidin-4-yl biphenyl-2-ylcarbamate The compound (147 mg, 0.198 mmol) obtained in Example 33d was used to give a crude Boc-deprotected compound according to the method described in Example 6d. The resulting Boc-deprotected compound was used to give the title compound (144 mg; yield, 55%) as a white solid according to the method described in Example 13e.

MS (FAB) m/z: 1319 (M+H)$^+$.

IR (KBr) ν$_{max}$ 2930, 1731, 1644, 1512, 1359, 1281, 1178, 1138, 838, 755 cm$^{-1}$.

Example 34

1-(2-{[4-({4-[{3-[({[(2S)-1'-{2-[(5R)-3-[3,5-Bis (trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl} (methyl)carbamoyl]phenyl}amino)butanoyl](methyl) amino}ethyl)piperidin-4-yl biphenyl-2-ylcarbamate trihydrochloride

[Formula 39]

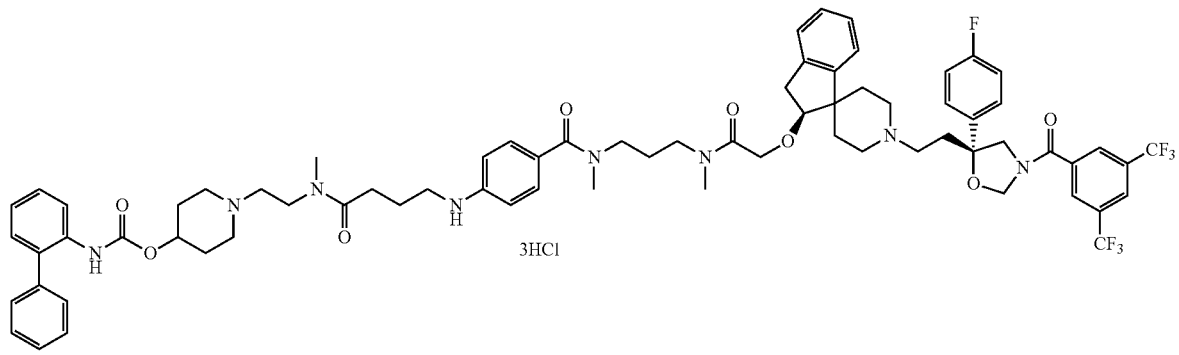

The compound (144 mg, 0.109 mmol) obtained in Example 33e was used to give the title compound (149 mg; yield, 96%) as a white solid according to the method described in Example 13e.

MS (FAB) m/z: 1319 (M+H)+ (free form).

IR (KBr) $v_{max}$ 2932, 1726, 1642, 1438, 1360, 1282, 1225, 1175, 1139, 753 cm$^{-1}$.

Example 35

1-{2-[{4-[{4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}(methyl)amino]butanoyl}(methyl)amino]ethyl}piperidin-4-yl biphenyl-2-ylcarbamate

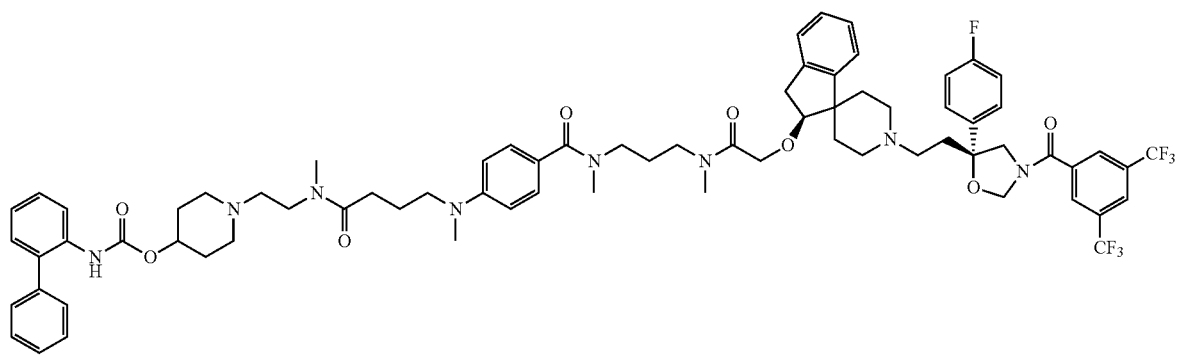

Example 35a tert-Butyl 4-(methylamino)benzoate 4-(Methylamino)benzoate (2.00 g, 13.2 mmol) was dissolved in tert-butanol (66 mL), 1-ethyl-3-(3-dimethylaminopropyl)carbodiimide hydrochloride (89 mg, 0.464 mmol) and 4-dimethylaminopyridine (81 mg, 0.660 mmol) were added, and the mixture was stirred at room temperature for 17 hours. The solvent was evaporated under reduced pressure, and the resulting residue was purified by silica gel column chromatography (hexane:ethyl acetate=6:1, v/v) to give the title compound (2.14 g; yield, 78%) as a yellow oily substance.

$^1$H NMR (CDCl$_3$, 400 MHz): δ 1.57 (9H, s), 2.88 (3H, s), 6.54 (2H, d, J=8.8 Hz), 7.83 (2H, d, J=8.8 Hz).

MS (APCI) m/z: 208 (M+H)+.

Example 35b tert-Butyl 4-[{4-[(2-{4-[(biphenyl-2-ylcarbamoyl)oxy]piperidin-1-yl}ethyl)(methyl)amino]-4-oxobutyl}(methyl)amino]benzoate The compound (130 mg, 0.297 mmol) obtained in Example 33b and the compound (62 mg, 0.297 mmol) obtained in Example 35a were used to give the title compound (94 mg; yield, 50%) as a white solid according to the method described in Example 18b.

$^1$H NMR (CDCl$_3$, 400 MHz): δ 1.55-1.56 (9H, m), 1.62-1.67 (2H, m), 1.89-1.96 (4H, m), 2.18-2.39 (5H, m), 2.45-2.49 (1H, m), 2.59-2.65 (1H, m), 2.71-2.74 (1H, m), 2.94 (3H, d, J=2.7 Hz), 2.99 (3H, d, J=2.7 Hz), 3.27-3.34 (1H, m), 3.43-3.50 (3H, m), 4.69-4.75 (1H, m), 6.59-6.65 (3H, m), 7.11-7.15 (1H, m), 7.21-7.23 (1H, m), 7.34-7.39 (3H, m), 7.41-7.43 (1H, m), 7.47-7.50 (2H, m), 7.81-7.85 (2H, m), 8.09-8.11 (1H, m).

MS (APCI) m/z: 629 (M+H)+.

Example 35c

1-{2-[{4-[{4-[{3-[tert-Butoxycarbonyl)(methyl)amino]propyl}(methyl)carbamoyl]phenyl}(methyl)amino]butanoyl}(methyl)amino]ethyl}piperidin-4-yl biphenyl-2-ylcarbamate The compound (94 mg, 0.149 mmol) obtained in Example 35b was dissolved in 1,4-dioxane (2.5 mL), 4 N hydrochloric acid-dioxane (2.24 mL, 8.97 mmol) was added, and then the mixture was stirred at room temperature for 20 hours. The solvent was evaporated under reduced pressure and moisture

[Formula 40]

was removed azeotropically with toluene (×2) to give a crude carboxylic acid compound. The resulting crude carboxylic acid compound was used to give the title compound (81 mg; yield, 72%) as a white solid according to the method described in Example 12a.

$^1$H NMR (CDCl$_3$, 400 MHz): δ 1.44 (9H, s), 1.59-1.66 (2H, m), 1.82-1.85 (2H, m), 1.90-1.95 (4H, m), 2.22-2.36 (4H, m), 2.40-2.49 (2H, m), 2.64-2.76 (2H, m), 2.83 (3H, s), 2.94-3.03 (9H, m), 3.19-3.23 (2H, m), 3.30-3.41 (1H, m), 3.40-3.50 (6H, m), 4.49-4.74 (1H, m), 6.59-6.67 (3H, m), 7.12-7.15 (2H, m), 7.20-7.23 (1H, m), 7.30-7.38 (4H, m), 7.41-7.43 (1H, m), 7.47-7.52 (2H, m), 8.08-8.10 (1H, m).

MS (APCI) m/z: 757 (M+H)+.

Example 35d

1-{2-[{4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}(methyl)amino]butanoyl}(methyl)amino]ethyl}piperidin-4-yl biphenyl-2-ylcarbamate The compound (81 mg, 0.107 mmol) obtained in Example 35c was used to give a crude Boc-deprotected compound according to the method described in Example 6d. The resulting crude Boc-deprotected compound was used to give the title compound (118 mg; yield, 83%) as a white solid according to the method described in Example 11e.

MS (FAB) m/z: 1333 (M+H)+.

IR (KBr) $v_{max}$ 2929, 1728, 1645, 1522, 1359, 1281, 1181, 1138, 839, 755 cm$^{-1}$.

Example 36

1-{2-[{4-[{4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}(methyl)amino]butanoyl}(methyl)amino]ethyl}piperidin-4-yl biphenyl-2-ylcarbamate trihydrochloride

[Formula 41]

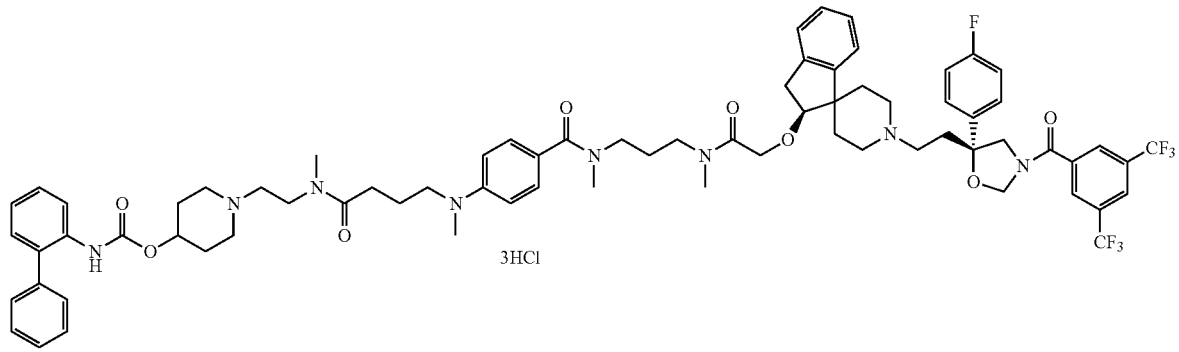

The compound (118 mg) obtained in Example 35d was used to give the title compound (125 mg; yield, 98%) as a white solid according to the method described in Example 13e.

MS (FAB) m/z: 1333 (M+H)$^+$.

IR (KBr) $v_{max}$ 2935, 1725, 1642, 1438, 1360, 1282, 1225, 1175, 1138, 753 cm$^{-1}$.

Example 37

1-{2-[{5-[{4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methy)amino]propyl}(methyl)carbamoyl]phenyl}(methyl)amino]pentanoyl}(methyl)amino]ethyl}piperidin-4-yl biphenyl-2-ylcarbamate

[Formula 42]

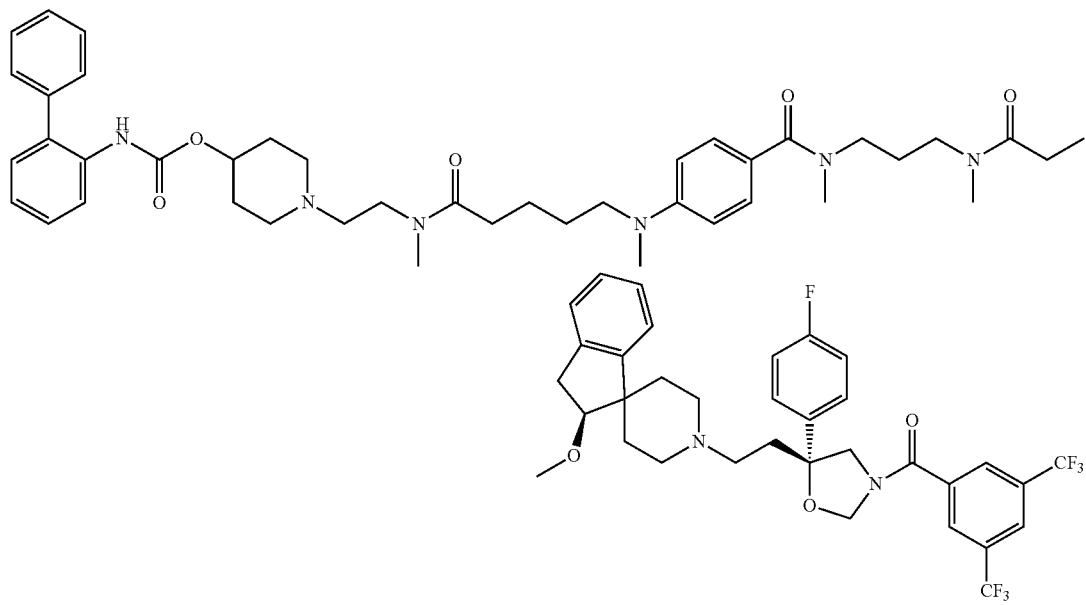

Example 37a tert-Butyl 4-[{5-[(2-{4-[(biphenyl-2-ylcarbamoyl)oxy]piperidin-1-yl}ethyl)(methyl)amino]-5-oxopentyl}(methyl)amino]benzoate The compound (114 mg, 0.252 mmol) obtained in Example 31a was used to give a crude aldehyde compound (115 mg) according to the method described in Example 4g. The resulting crude aldehyde compound and the compound (52 mg, 0.252 mmol) obtained in Example 35a were used to give the title compound (73 mg; yield, 45%) as a white solid according to the method described in Example 18b.

$^1$H NMR (CDCl$_3$, 400 MHz): δ 1.56 (9H, s) 1.64-1.65 (6H, m), 1.90-1.93 (2H, m), 2.24-2.36 (4H, m), 2.43-2.48 (2H, m), 2.65-2.74 (2H, m), 2.93-3.01 (6H, m), 3.35 (1H, t, J=6.8 Hz), 3.40 (2H, t, J=6.8 Hz), 3.47 (1H, t, J=6.8 Hz), 4.69-4.75 (1H, m), 6.60 (3H, d, J=8.6 Hz), 7.13 (1H, t, J=7.1 Hz), 7.22 (1H, d, J=8.1 Hz), 7.34-7.39 (3H, m), 7.42 (1H, d, J=7.1 Hz), 7.47-7.52 (2H, m), 7.84 (2H, d, J=8.6 Hz), 8.09-8.11 (1H, m).
MS (APCI) m/z: 643 (M+H)$^+$.

Example 37b

1-{2-[{5-[{4-[{3-([tert-Butoxycarbonyl)(methyl)amino]propyl}(methyl)carbamoyl]phenyl}(methyl)amino]pentanoyl}(methyl)amino]ethyl}piperidin-4-yl biphenyl-2-ylcarbamate The compound (73 mg, 0.114 mmol) obtained in Example 37a was dissolved in 1,4-dioxane (1.7 mL), 4 N hydrochloric acid-dioxane (1.70 mL, 6.81 mmol) was added, and then the mixture was stirred at room temperature for 15.5 hours. The solvent was evaporated under reduced pressure and moisture was removed azeotropically with toluene (×2) to give a crude carboxylic acid compound. The resulting crude carboxylic acid compound was used to give the title compound (67 mg; yield, 76%) as a white solid according to the method described in Example 12a.

$^1$H NMR (CDCl$_3$, 400 MHz): δ 1.44 (9H, s), 1.53-1.57 (4H, m), 1.61-1.67 (4H, m), 1.82-1.86 (1H, m), 1.88-1.93 (1H, m), 2.24-2.36 (4H, m), 2.44-2.48 (2H, m), 2.68-2.74 (2H, m), 2.82-2.84 (3H, m), 2.93-3.04 (12H, m), 3.20-3.24 (1H, m), 3.35-3.38 (2H, m), 3.42-3.49 (2H, m), 4.70-4.74 (1H, m), 6.61 (3H, d, J=8.8 Hz), 7.11-7.15 (1H, m), 7.21-7.23 (2H, m), 7.31-7.44 (5H, m), 7.47-7.53 (2H, m), 8.09-8.11 (1H, m).
MS (APCI) m/z: 771 (M+H)$^+$.

Example 37c

1-{2-[{5-[{4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}(methyl)amino]pentanoyl}(methyl)amino]ethyl}piperidin-4-yl biphenyl-2-ylcarbamate The compound (67 mg, 0.0869 mmol) obtained in Example 37b was used to give a crude Boc-deprotected compound according to the method described in Example 6d. The resulting crude Boc-deprotected compound was used to give the title compound (96 mg; yield, 82%) as a white solid according to the method described in Example 11e.
MS (FAB) m/z: 1347 (M+H)$^+$.
IR (KBr) ν$_{max}$ 2930, 1729, 1645, 1522, 1359, 1281, 1181, 1138, 847, 756 cm$^{-1}$.

Example 38

1-{2-[{5-[{4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methy)amino]propyl}(methyl)carbamoyl]phenyl}(methyl)amino]pentanoyl}(methyl)amino]ethyl}piperidin-4-yl biphenyl-2-ylcarbamate trihydrochloride

[Formula 43]

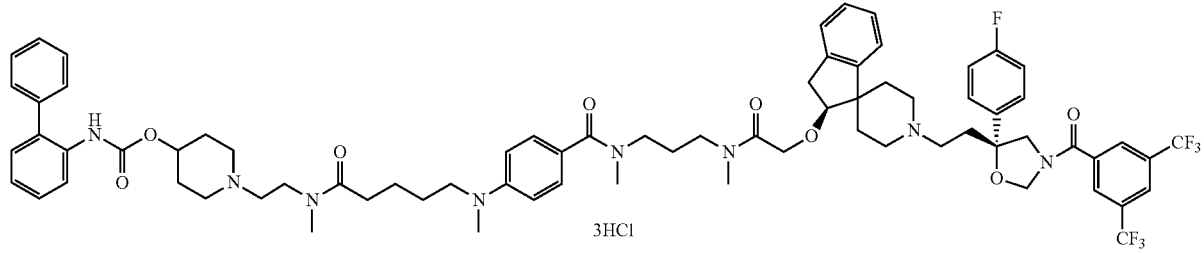

The compound (96 mg, 0.071 mmol) obtained in Example 37c was used to give the title compound (103 mg; yield, 99%) as a white solid according to the method described in Example 13e.
MS (FAB) m/z: 1347 (M+H)$^+$ (free form).
IR (KBr) ν$_{max}$ 2937, 1725, 1641, 1450, 1360, 1282, 1225, 1174, 1138, 753 cm$^{-1}$.

Example 39

1-(2-{[7-({4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}methyl)carbamoyl]phenyl}amino)heptanoyl](methyl)amino}ethyl)piperidin-4-yl biphenyl-2-ylcarbamate trihydrochloride

[Formula 44]

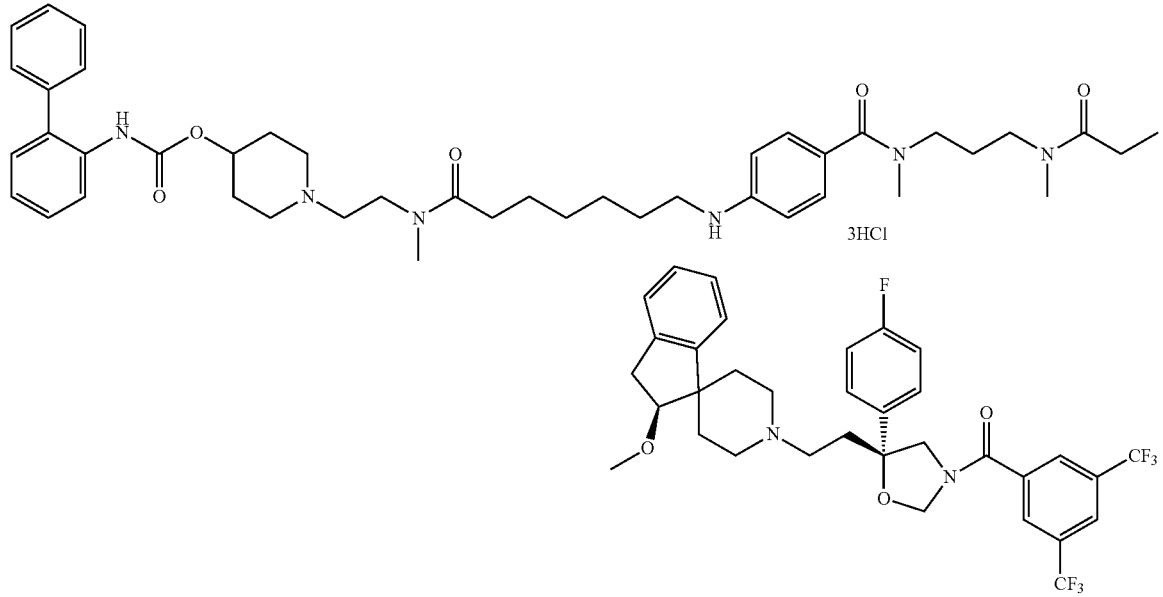

Example 39a

Methyl 7-[(2-{4-[(biphenyl-2-ylcarbamoyl)oxy]piperidin-1-yl}ethyl)(methyl)amino]-7-oxoheptanoate Monomethyl pimelate (79 mg, 0.450 mmol) and 1-[2-(methylamino)ethyl]piperidin-4-yl biphenyl-2-ylcarbamate (159 mg, 0.450 mmol) were used to give the title compound (235 mg; yield, 100%) as a colorless oily substance according to the method described in Example 12a.

$^1$H NMR (CDCl$_3$, 400 MHz): δ 1.35-1.41 (2H, m), 1.63-1.68 (5H, m), 1.90-1.94 (2H, m), 2.27-2.346 (6H, m), 2.47 (2H, t, J=6.8 Hz), 2.68-2.75 (2H, m), 2.93-3.00 (3H, m), 3.37 (1H, t, J=6.8 Hz), 3.45-3.49 (2H, t, J=6.8 Hz), 3.66 (3H, s), 4.70-4.75 (1H, m), 6.59-6.60 (1H, m), 7.11-7.15 (1H, m), 7.21-7.22 (1H, m), 7.34-7.38 (3H, m), 7.42-7.44 (1H, m), 7.49 (2H, t, J=7.3 Hz), 8.09-8.11 (1H, m).
MS (APCI) m/z: 510 (M+H)$^+$.

Example 39b

1-{2-[(7-Hydroxyheptanoyl)(methyl)amino]ethyl}piperidin-4-yl biphenyl-2-ylcarbamate Lithium borohydride (39 mg, 1.80 mmol) was suspended in tetrahydrofuran (6 mL), methanol (73 μL, 1.80 mmol) and a solution of the compound (235 mg, 0.450 mmol) obtained in Example 39a in tetrahydrofuran (7 mL) was added, and the mixture was stirred at room temperature for 2 days. A 1 N aqueous sodium hydroxide solution was added to the reaction mixture, and the mixture was extracted with ethyl acetate (×3). The organic layer was washed with saturated sodium chloride solution and dried with anhydrous sodium sulfate. The solvent was evaporated under reduced pressure, and the resulting residue was purified by NH silica gel column chromatography (ethyl acetate:methanol=50:1, v/v) to give the title compound (163 mg; yield, 75%) as a white solid.
MS (APCI) m/z: 482 (M+H)$^+$.

Example 39c tert-Butyl 4-({7-[(2-{4-[(biphenyl-2-ylcarbamoyl)oxy]piperidin-1-yl}ethyl)(methyl)amino]-7-oxoheptyl}amino)benzoate The compound (94 mg, 0.195 mmol) obtained in Example 39b was used to give a crude aldehyde compound according to the method described in Example 4g. The resulting crude aldehyde compound and tert-butyl 4-aminobenzoate (62 mg, 0.293 mmol) were used to give the title compound (66 mg; yield, 52%) as a white solid according to the method described in Example 18b.

$^1$H NMR (CDCl$_3$, 400 MHz): δ 1.38-1.45 (4H, m), 1.56 (9H, s) 1.62-1.68 (6H, m), 1.91-1.94 (2H, m), 2.24-2.35 (4H, m), 2.47 (2H, t, J=6.8 Hz), 2.68-2.75 (2H, m), 2.93 (1.2H, s), 3.00 (1.8H, m), 3.12-3.16 (2H, m), 3.37 (0.8H, t, J=6.8 Hz), 3.48 (1.2H, t, J=6.8 Hz), 4.04-4.08 (1H, m), 4.70-4.75 (1H, m), 6.52 (2H, d, J=8.8 Hz), 6.59 (1H, brs), 7.11-7.16 (1H, m), 7.21-7.23 (1H, m), 7.34-7.40 (2H, m), 7.42 (1H, d, J=7.1 Hz), 7.47-7.52 (2H, m), 7.80 (2H, d, J=8.8 Hz), 8.09-8.11 (1H, m).
MS (APCI) m/z: 657 (M+H)⁺.

Example 39d 1-(2-{[7-({4-[{3-[(tert-Butoxycarbonyl)(methyl) amino]propyl}(methyl)carbamoyl]phenyl}amino) heptanoyl](methyl)amino}ethyl)piperidin-4-yl biphenyl-2-ylcarbamate The compound (66 mg, 0.100 mmol) obtained in Example 39c was dissolved in 1,4-dioxane (1.5 mL), 4 N hydrochloric acid-dioxane (1.51 mL, 6.03 mmol) was added, and then the mixture was stirred at room temperature for 19.5 hours. The solvent was evaporated under reduced pressure and moisture was removed azeotropically with toluene (×2) to give a crude carboxylic acid compound. The resulting crude carboxylic acid compound was used to give the title compound (63 mg; yield, 80%) as a white solid according to the method described in Example 12a.

¹H NMR (CDCl₃, 400 MHz): δ 1.44 (9H, s), 1.61-1.68 (8H, m), 1.81-1.85 (2H, m), 1.88-1.94 (2H, m), 2.26-2.35 (4H, m), 2.47 (2H, t, J=6.8 Hz), 2.68-2.74 (2H, m), 2.82 (3H, brs), 2.94-3.03 (8H, m), 3.12 (2H, t, J=6.8 Hz), 3.18-3.23 (2H, m), 3.36-3.48 (4H, m), 4.70-4.73 (1H, m), 6.54 (2H, d, J=8.5 Hz), 6.59 (1H, brs), 7.11-7.15 (1H, m), 7.21-7.30 (3H, m), 7.34-7.40 (3H, m), 7.42-7.43 (1H, m), 7.47-7.52 (2H, m), 8.09-8.11 (1H, m).
MS (APCI) m/z: 785 (M+H)⁺.

Example 39e 1-(2-{[7-({4-[{3-[({[(2S)-1'-{2-[(5R)-3-[3,5-Bis (trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl} (methyl)carbamoyl]phenyl}amino)heptanoyl] (methyl)amino}ethyl)piperidin-4-yl biphenyl-2-ylcarbamate trihydrochloride The compound (67 mg, 0.0803 mmol) obtained in Example 39d was used according to the method described in Example 6d to give a crude Boc-deprotected compound. The resulting crude Boc-deprotected compound was used to give the title compound (85 mg; yield, 72%) as a white solid according to the methods described in Examples 11e and 13e.

MS (FAB) m/z: 1361 (M+H)⁺ (free form).
IR (KBr) ν_max 2935, 1727, 1642, 1449, 1360, 1282, 1224, 1176, 1138, 753 cm⁻¹.

Example 40

1-{2-[{7-[{4-[{3-[({[(2S)-1'-{2-[(5R)-3-[3,5-Bis (trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl} (methyl)carbamoyl]phenyl}(methyl)amino] heptanoyl}(methyl)amino]ethyl}piperidin-4-yl biphenyl-2-ylcarbamate trihydrochloride

[Formula 45]

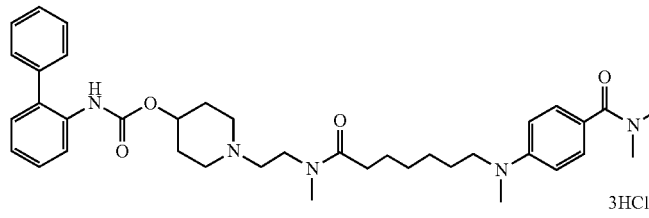
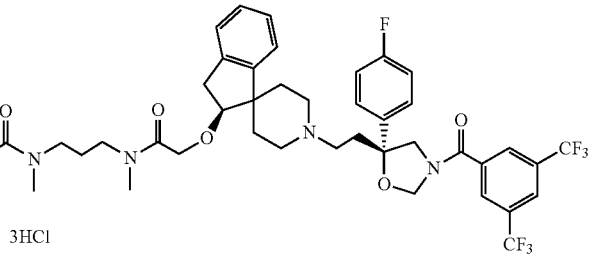

Example 40a tert-Butyl-4-[{7-[(2-{4-[(biphenyl-2-ylcarbamoyl) oxy]piperidin-1-yl}ethyl)(methyl)amino]-7-oxoheptyl}(methyl)amino]benzoate The compound (163 mg, 0.338 mmol) obtained in Example 39b was used according to the method described in Example 4g to give a crude aldehyde compound (160 mg). The resulting crude aldehyde compound and the compound (69 mg, 0.334 mmol) obtained in Example 35a were used a to give the title compound (58 mg; yield, 26%) as a white solid according to the method described in Example 18b.

¹H NMR (CDCl₃, 400 MHz): δ 1.34-1.36 (4H, m), 1.56 (9H, s) 1.57-1.68 (6H, m), 1.88-1.94 (2H, m), 2.25-2.33 (4H, m), 2.44-2.49 (2H, m), 2.68-2.74 (2H, m), 2.93-3.01 (6H, m), 3.33-3.38 (2H, m), 3.45-3.53 (2H, m), 4.70-4.75 (1H, m), 6.59 (2H, d, J=9.1 Hz), 7.11-7.15 (2H, m), 7.21-7.23 (1H, m), 7.35-7.38 (3H, m), 7.42 (1H, d, J=6.1 Hz), 7.47-7.50 (2H, m), 7.82-7.88 (2H, m), 8.09-8.11 (1H, m).
MS (APCI) m/z: 671 (M H)⁺.

Example 40b

1-[2-(Methyl{7-[methyl(4-{methyl[3-(methylamino) propyl]carbamoyl}phenyl)amino]heptanoyl}amino) ethyl]piperidin-4-yl biphenyl-2-ylcarbamate The compound (58 mg, 0.0865 mmol) obtained in Example 40a was dissolved in 1,4-dioxane (1.3 mL), 4 N hydrochloric acid-dioxane (1.30 mL, 5.19 mmol) was added, and then the mixture was stirred at room temperature for 19.5 hours. The solvent was evaporated under reduced pressure and moisture was removed azeotropically with toluene (×2) to give a crude carboxylic acid compound. The resulting crude carboxylic acid compound was used to give a crude Boc compound (43 mg) according to the method described in Example 12a. The resulting crude Boc compound was used to give the title compound (31 mg; yield, 51%) as a white solid according to the method described in Example 6d.

MS (APCI) m/z: 699 (M+H)⁺.

Example 40c

1-{2-[{7-[{4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}(methyl)amino]heptanoyl}(methyl)amino]ethyl}piperidin-4-yl biphenyl-2-ylcarbamate trihydrochloride The compound (31 mg, 0.0444 mmol) obtained in Example 40b was used according to the methods described in Examples 11e and 13e to give the title compound (49 mg; yield, 74%) as a white solid.

MS (FAB) m/z: 1333 (M+H)⁺ (free form).
IR (KBr) $v_{max}$ 2937, 1725, 1641, 1450, 1360, 1282, 1225, 1174, 1138, 753 cm$^{-1}$.

Example 41

1-{2-[{6-[{3-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]benzyl}(methyl)amino]hexanoyl}(methyl)amino]ethyl}piperidin-4-yl biphenyl-2-ylcarbamate trihydrochloride aqueous sodium hydrogencarbonate solution was added to the reaction mixture under ice cooling, and ethyl acetate was further added to separate the layers. The resulting organic layer was separated, washed with saturated sodium chloride solution, and then dried with anhydrous sodium sulfate, and the solvent was evaporated under reduced pressure. The resulting residue was purified by silica gel column chromatography (ethyl acetate:methanol, 10:1, v/v) to give the title compound (147 mg; yield, 83.8%) as a colorless oily substance.

MS (ESI): m/z 911 (M+H)⁺.

Example 41b

1-{2-[{6-[{3-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]benzyl}(methyl)amino]hexanoyl}(methyl)amino]ethyl}piperidin-4-yl biphenyl-2-ylcarbamate The compound (164 mg, 0.341 mmol) obtained in Example 2a and sodium triacetoxyborohydride (50 mg, 0.235

[Formula 46]

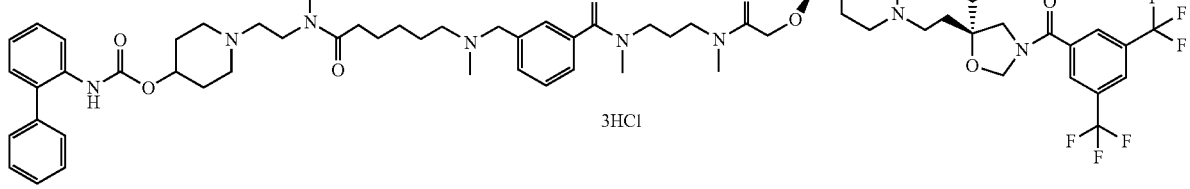

Example 41a

N-{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}-3-formyl-N-methylbenzamide The compound (150 mg, 0.193 mmol) obtained in Example 1k was dissolved in dichloromethane (6 mL), 3-formylbenzoic acid (43 mg, 0.289 mmol), 1-ethyl-3-(3-dimethylaminopropyl)carbodiimide hydrochloride (63 mg, 0.289 mmol) and 4-N,N-dimethylaminopyridine (2 mg, 19.3 µmol) were added under ice cooling, and the mixture was stirred at the same temperature under a nitrogen atmosphere for 15 hours. After the reaction was completed, a saturated mmol) were added to a solution of the compound (147 mg, 0.193 mmol) obtained in Example 41a in ethanol (6 mL) under ice cooling, and the mixture was stirred at room temperature under a nitrogen atmosphere for 16 hours. After the reaction was completed, a saturated aqueous sodium hydrogencarbonate solution was added to the reaction mixture under ice cooling, and ethyl acetate was further added to separate the layers. The resulting organic layer was separated, washed with saturated sodium chloride solution, and then dried with anhydrous sodium sulfate. The solvent was evaporated under reduced pressure, and the resulting residue was purified by NH silica gel column chromatography (ethyl acetate:methanol, 10:1, v/v) and then further purified by reverse phase preparative column chromatography (XTerra Prep MS C18 OBD, 5 µm, 30ϕ×100 mm) (acetonitrile:0.1% aqueous ammonium acetate solution, 50:50→acetonitrile) to give the title compound (60.0 mg; yield, 20%) as a white solid.

Example 41c

1-{2-[{6-[{3-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]benzyl}(methyl)amino]hexanoyl}(methyl)amino]ethyl}piperidin-4-yl biphenyl-2-ylcarbamate trihydrochloride The compound (60.0 mg, 43.6 µmol) obtained in Example 41b was dissolved in dichloromethane (6 mL), a 4 N hydrochloric acid-1,4-dioxane solution (33 µL, 0.131 mmol) was added, and the mixture was stirred for 10 minutes and then concentrated under reduced pressure to give the title compound (32.4 mg; yield, 50%) as a white solid.

MS (FAB): m/z 1375 (M+H)⁺ (free form).
IR (KBr) ν max 3423, 2940, 1730, 1645, 1281, 1225, 1175, 1138, 848, 752 cm⁻¹.

Example 42

1-(2-{[6-({3-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]benzyl}amino)hexanoyl](methyl)amino}ethyl)piperidin-4-yl biphenyl-2-ylcarbamate trihydrochloride

[Formula 47]

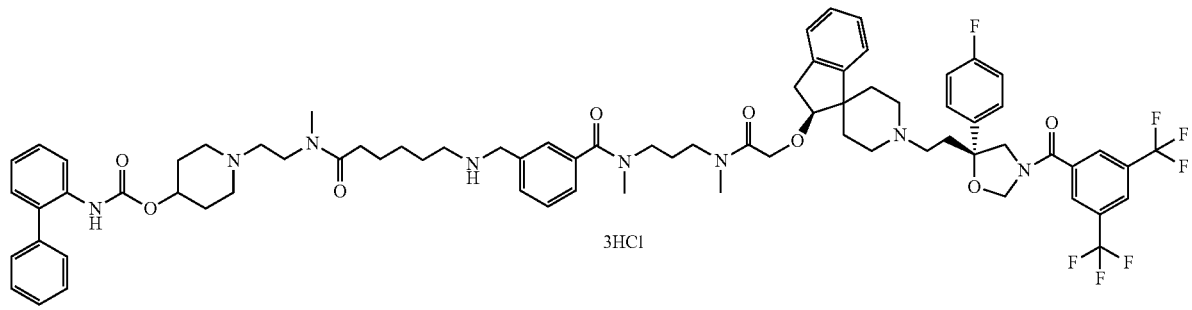

The compound (85.0 mg, 0.181 mmol) obtained in Example 1a was used according to the methods described in Examples 41b and 41c to give the title compound (60.0 mg; yield, 22%) as a white solid.

MS (FAB): m/z 1361 (M+H)⁺ (free form).
IR (KBr) ν max 3424, 2935, 1729, 1644, 1449, 1359, 1281, 1138, 752, 704 cm⁻¹.

Example 43

1-(2-{[6-({3-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}amino)hexanoyl](methyl)amino}ethyl)piperidin-4-yl biphenyl-2-ylcarbamate trihydrochloride

[Formula 48]

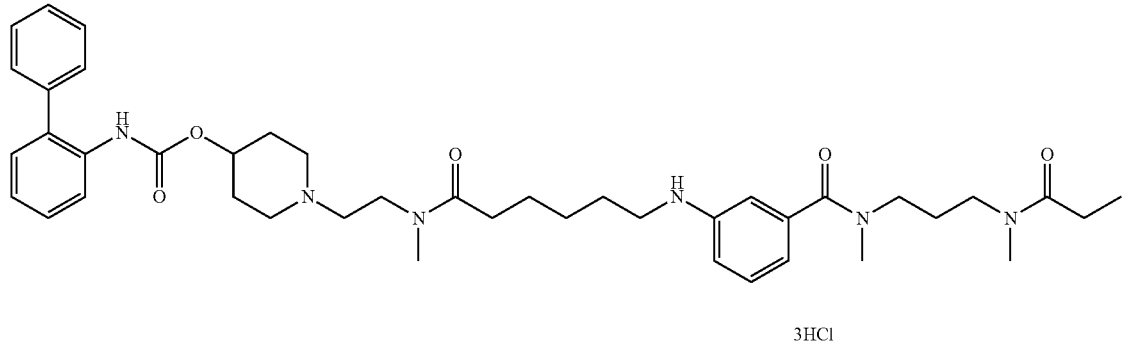

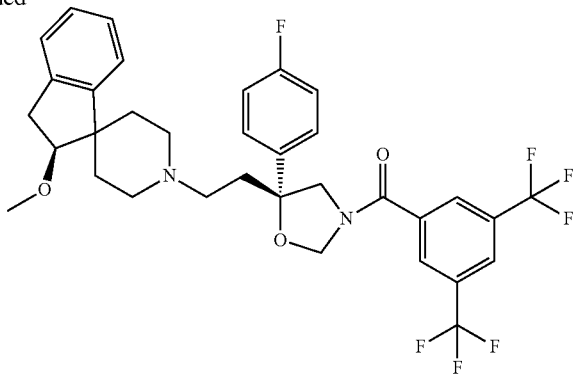

Example 43a tert-Butyl 3-({6-[(2-{4-[(biphenyl-2-ylcarbamoyl)oxy]piperidin-1-yl}ethyl)(methyl)amino]-6-oxohexyl}amino)benzoate The compound (100 mg, 0.215 mmol) obtained in Example 4g was dissolved in ethanol (6 mL), tert-butyl 3-aminobenzoate (54 mg, 0.279 mmol) and sodium triacetoxyborohydride (59 mg, 0.279 mmol) were added under ice cooling, and the mixture was stirred at room temperature under a nitrogen atmosphere for 16 hours. After the reaction was completed, a saturated aqueous sodium hydrogencarbonate solution was added, and ethyl acetate was further added to separate the layers. The organic layer was separated, washed with saturated sodium chloride solution, and then dried with anhydrous sodium sulfate. The solvent was evaporated under reduced pressure, and the resulting residue was purified by NH silica gel column chromatography (ethyl acetate:methanol, 10:1, v/v) to give the title compound (80.0 mg; yield, 58%) as a colorless oily substance.

MS (ESI): m/z 643 (M+H)$^+$.

Example 43b 3-({6-[(2-{4-[(Biphenyl-2-ylcarbamoyl)oxy]piperidin-1-yl}ethyl)(methyl)amino]-6-oxohexyl}amino)benzoic acid The compound (80.0 mg, 0.124 mmol) obtained in Example 43a was dissolved in dichloromethane (6 mL), trifluoroacetic acid (1 mL) was added under ice cooling, and the mixture was stirred at room temperature under a nitrogen atmosphere for 1.5 hours. After the reaction was completed, the mixture was concentrated under reduced pressure to give a crude title compound.

Example 43c 1-(2-{[6-({3-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}amino)hexanoyl](methyl)amino}ethyl)piperidin-4-yl biphenyl-2-ylcarbamate The crude product obtained in Example 43b was dissolved in dichloromethane (4 mL), the compound (93 mg, 0.149 mmol) obtained in Example 1k, 1-ethyl-3-(3-dimethylaminopropyl)carbodiimide hydrochloride (33.0 mg, 0.149 mmol) and 4-N,N-dimethylaminopyridine (2 mg, 19.3 μmol) were added under ice cooling, and the mixture was stirred at room temperature under a nitrogen atmosphere for 15 hours. After the reaction was completed, a saturated aqueous sodium hydrogencarbonate solution was added, and ethyl acetate was further added to separate the layers. The resulting organic layer was separated, washed with saturated sodium chloride solution, and then dried with anhydrous sodium sulfate, and the solvent was evaporated under reduced pressure. The residue was purified by NH silica gel column chromatography (ethyl acetate→ethyl acetate:methanol, 10:1, v/v) and then purified by reverse phase preparative column chromatography (XTerra Prep MS C18 OBD, 5 μm (30φ×100 mm) (acetonitrile:0.1% aqueous ammonium acetate solution, 50:50→acetonitrile) to give the title compound (51.0 mg; yield, 24%) as a white solid.

Example 43d 1-(2-{[6-({3-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}amino)hexanoyl](methyl)amino}ethyl)piperidin-4-yl biphenyl-2-ylcarbamate trihydrochloride The compound (51.0 mg) obtained in Example 43c was used to give the title compound (39.1 mg; yield, 71%) as a white solid according to the method described in Example 41c.

MS (FAB): m/z 1347 (M+H)$^+$ (free form).
IR (KBr) ν max 3421, 2936, 1728, 1646, 1360, 1282, 1225, 1176, 1139, 752 cm$^{-1}$.

Example 44

1-{2-[{6-[{3-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}(methyl)amino]hexanoyl}(methyl)amino]ethyl}piperidin-4-yl biphenyl-2-ylcarbamate trihydrochloride

[Formula 49]

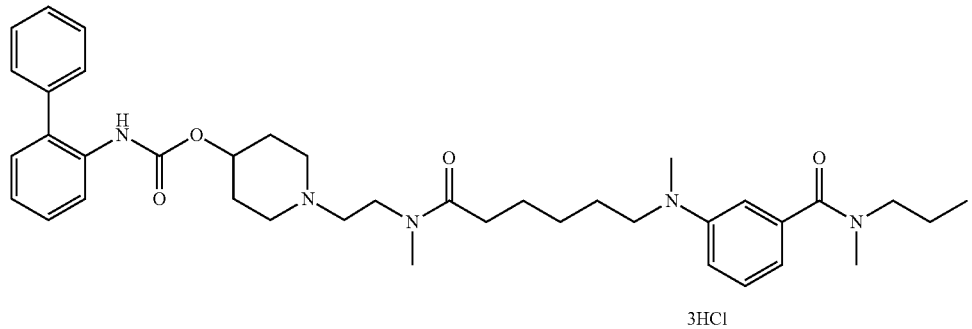

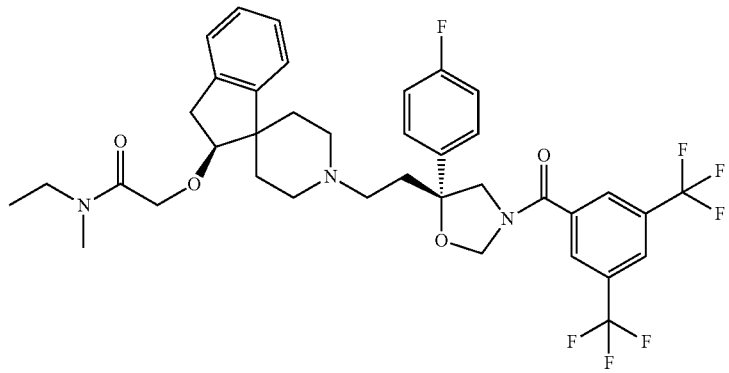

Example 44a tert-Butyl 3-[{6-[(2-{4-[(biphenyl-2-ylcarbamoyl)oxy]piperidin-1-yl}ethyl)(methyl)amino]-6-oxohexyl}(methyl)amino]benzoate Moisture was removed from a mixture of the compound (120 mg, 0.205 mmol) obtained in Example 43a and a 35% aqueous formaldehyde solution (85 μL, 1.02 mmol) azeotropically with toluene 3 times. The resulting mixture was dissolved in ethanol (6 mL), sodium triacetoxyborohydride (65 mg, 0.307 mmol) was added under ice cooling, and the mixture was stirred at room temperature under a nitrogen atmosphere for 16 hours. After the reaction was completed, a saturated aqueous sodium hydrogencarbonate solution was added, and ethyl acetate was further added to separate the layers. The resulting organic layer was separated, washed with saturated sodium chloride solution, and then dried with anhydrous sodium sulfate, and the solvent was evaporated under reduced pressure. The residue was purified by NH silica gel column chromatography (ethyl acetate:methanol, 10:1, v/v) to give the title compound (118 mg; yield, 96%) as a colorless oily substance.

MS (ESI): m/z 657 (M+H)$^+$.

Example 44b

1-{2-[{6-[{3-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}(methyl)amino]hexanoyl}(methyl)amino]ethyl}piperidin-4-yl biphenyl-2-ylcarbamate trihydrochloride The compound (118 mg, 0.180 mmol) obtained in Example 44a was used according to the methods described in Examples 43b, 43c, and 41c to give the title compound (43.0 mg; yield, 11%) as a white solid.

MS (FAB): m/z 1361 (M+H)$^+$ (free form).

IR (KBr) ν max 3423, 1730, 1646, 1359, 1281, 1223, 1175, 1282, 1224, 1175 cm$^{-1}$.

Example 45

1-(2-{[6-(Benzyl{4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]benzyl}amino)hexanoyl](methyl)amino}ethyl)piperidin-4-yl biphenyl-2-ylcarbamate trihydrochloride

[Formula 50]

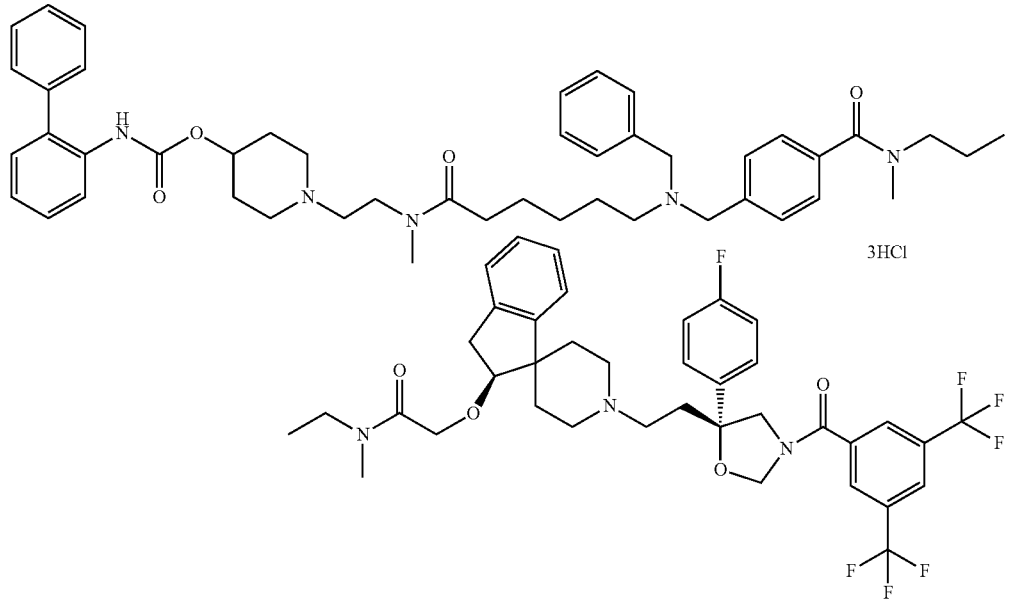

3HCl

Example 45a

N-{3-[({[(2S)-1-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}-4-formyl-N-methylbenzamide 4-Formylbenzoic acid (174 mg, 1.16 mmol) was used to give the title compound (663 mg; yield, 95%) as a white solid according to the method described in Example 41a.

MS (FAB) m/z: 911 (M+H)$^+$.

IR (KBr) $v_{max}$ 2931, 1704, 1644, 1359, 1281, 1177, 1138, 846, 758, 682 cm$^{-1}$.

Example 45b

4-[(Benzylamino)methyl]-N-{3-[({[(2S)-1-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}-N-methylbenzamide Moisture was removed from a mixture of the compound (150 mg, 0.165 mmol) obtained in Example 45a and benzylamine (20 μL, 0.181 mmol) azeotropically with toluene 3 times. The resulting mixture was dissolved in ethanol (6 mL), sodium triacetoxyborohydride (38 mg, 0.181 mmol) was added under ice cooling, and the mixture was stirred at room temperature under a nitrogen atmosphere for 16 hours. After the reaction was completed, a saturated aqueous sodium hydrogencarbonate solution was added to the reaction mixture under ice cooling, and ethyl acetate was further added to separate the layers. The resulting organic layer was separated, washed with saturated sodium chloride solution, and then dried with anhydrous sodium sulfate, and the solvent was evaporated under reduced pressure. The residue was purified by NH silica gel column chromatography (hexane:ethyl acetate, 10:1, v/v) to give the title compound (151 mg; yield, 92%) as a colorless oily substance.

MS (ESI): m/z 1003 (M+H)$^+$.

Example 45c 1-(2-{[6-(Benzyl{4-[{3-[({[(2S)-1-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]benzyl}amino)hexanoyl](methyl)amino}ethyl)piperidin-4-yl biphenyl-2-ylcarbamate trihydrochloride The compound (151 mg, 0.151 mmol) obtained in Example 45b and the compound (77.0 mg, 0.166 mmol) obtained in Example 4g were used to give a free form (130 mg; yield, 59%) of the title compound as a white solid according to the method described in Example 41b.

The resulting free compound (130 mg, 89.6 μmol) was used to give the title compound (100 mg; yield, 72%) as a white solid according to the method described in Example 41c.

MS (FAB): m/z 1451 (M+H)$^+$ (free form).

IR (KBr) v max 3423, 2934, 1727, 1645, 1360, 1281, 1224, 1177, 1139, 754 cm$^{-1}$.

Example 46

1-(2-{[6-(Isopropyl{-4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]benzyl}amino)hexanoyl](methyl)amino}ethyl)piperidin-4-yl biphenyl-2-ylcarbamate trihydrochloride

[Formula 51]

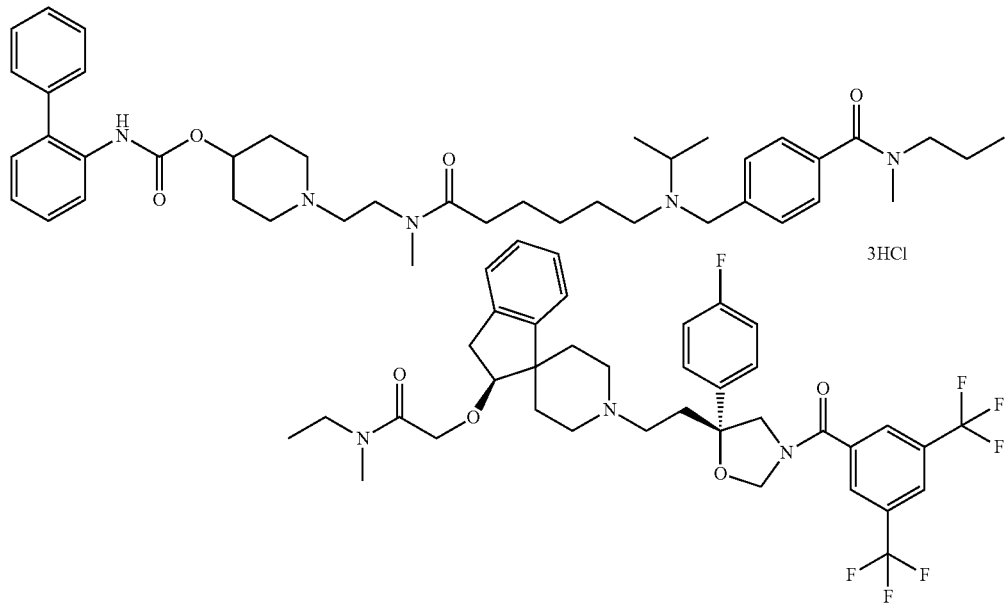

The compound (90 mg, 0.094 mmol) obtained in Example 45a and isopropylamine (21 µL, 0.247 mmol) were used according to the methods described in Example 45b and 45c to give the title compound (60.0 mg; yield, 24%) as a pale yellow solid.

MS (FAB): m/z 1403 (M+H)$^+$ (free form).
IR (KBr) ν max 3424, 2936, 1730, 1645, 1360, 1281, 1224, 1174, 1139, 754 cm$^{-1}$.

Example 47

1-{2-[(3-{[{4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]benzyl}(methyl)amino]methyl}benzoyl)(methyl)amino]ethyl}piperidin-4-yl biphenyl-2-ylcarbamate trihydrochloride

[Formula 52]

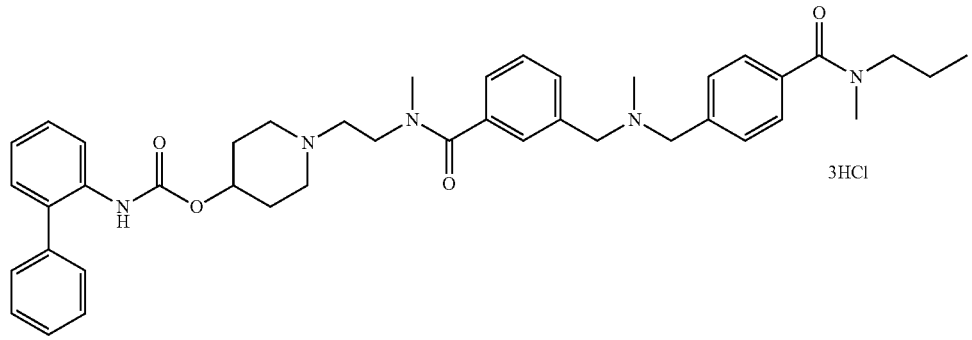

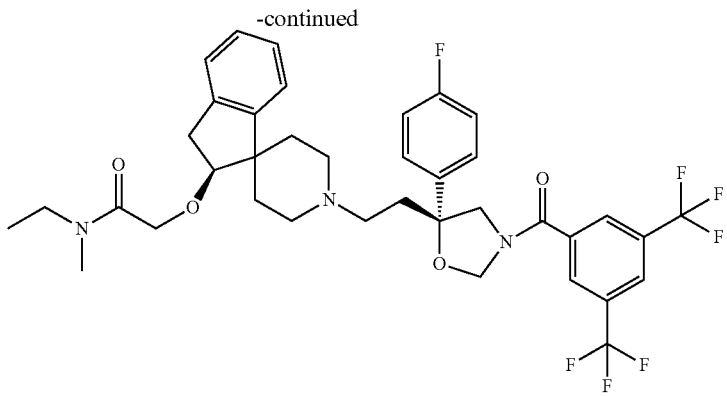

Example 47a 1-(2-{[(3-Formylphenyl)carbonyl](methyl)
amino}ethyl)piperidin-4-yl biphenyl-2-ylcarbamate 1-[2-(Methylamino)ethyl]piperidin-4-yl biphenyl-2-yl-carbamate (1.00 g, 2.83 mmol) was dissolved in dichloromethane (20 mL), 3-formylbenzoic acid (425 mg, 2.83 mmol), O-(benzotriazol-1-yl)-N,N,N',N'-tetramethyluroniumhexafluorophosphate (1.08 g, 2.83 mmol) and diisopropylethylamine (1.48 mL, 8.49 mmol) were added under ice cooling, and the mixture was stirred at room temperature under a nitrogen atmosphere for 16 hours. After the reaction was completed, a saturated aqueous sodium hydrogencarbonate solution was added, and ethyl acetate was further added to separate the layers. The resulting organic layer was separated, washed with saturated sodium chloride solution, and then dried with anhydrous sodium sulfate, and the solvent was evaporated under reduced pressure. The residue was purified by NH silica gel column chromatography (ethyl acetate: methanol, 10:1, v/v) to give the title compound (1.54 g; yield, 100%) as a colorless oily substance.

$^1$H HMR (CDCl$_3$, 400 MHz): δ1.5-3.7 (15H, m), 6.6 (1H, s), 7.0-7.1 (1H, m), 7.1-7.2 (2H, m), 7.3-7.4 (3H, m), 7.4-7.5 (2H, m), 7.5-7.6 (1H, m), 7.7-7.8 (1H, m), 7.9-8.0 (2H, m), 10.0 (1H, s).

Example 47b

1-{2-[Methyl({3-[(methylamino)methyl]
phenyl}carbonyl)amino]ethyl}piperidin-4-yl biphenyl-2-ylcarbamate The compound (150 mg, 0.309 mol) obtained in Example 47a was dissolved in a 40% methyl amine-methanol solution (5 mL), sodium triacetoxyborohydride (72 mg, 0.340 mmol) was added under ice cooling, and the mixture was stirred at room temperature under a nitrogen atmosphere for 16 hours. After the reaction was completed, a saturated aqueous sodium hydrogencarbonate solution was added, and ethyl acetate was further added to separate the layers. The resulting organic layer was separated, washed with saturated sodium chloride solution, and dried with anhydrous sodium sulfate, and the solvent was evaporated under reduced pressure. The residue was purified by NH silica gel column chromatography (ethyl acetate:methanol, 10:1, v/v) to give the title compound (108 mg; yield, 70%) as a colorless oily substance.

MS (ESI): m/z 501 (M+H)$^+$.

Example 47c

1-{2-[(3-{[{4-[{3-[({[(2S)-1'-{2-[(5R)-3-[3,5-Bis
(trifluoromethyl)benzoyl]-5-(4-fluorophenyl)-1,3-
oxazolidin-5-yl]ethyl}-2,3-dihydrospiro[indene-1,4'-
piperidin]-2-yl]oxy}acetyl)(methyl)amino]propyl}
(methyl)carbamoyl]benzyl}(methyl)amino]
methyl}benzoyl)(methyl)amino]ethyl}piperidin-4-yl
biphenyl-2-ylcarbamate trihydrochloride The compound (108 mg, 0.165 mmol) obtained in Example 47b and the compound (100 mg, 0.110 mmol) obtained in Example 45a were used to give a free form (40 mg; yield, 26%) of the title compound as a white solid according to the method described in Example 41b.

The resulting free compound (40 mg, 28.7 μmol) was used to give the title compound (30 mg; yield, 70%) as a white solid according to the method described in Example 41c.

MS (FAB): m/z 1395 (M+H)$^+$ (free form).

IR (KBr) ν max 3423, 2937, 1731, 1638, 1359, 1281, 1180, 1139, 848, 753 cm$^{-1}$.

Example 48

1-{2-[{6-[{4-[{3-[({[(2S)-1'-{2-[(5R)-3-[3,5-Bis
(trifluoromethyl)benzoyl]-5-(4-fluorophenyl)-1,3-
oxazolidin-5-yl]ethyl}-2,3-dihydrospiro[indene-1,4'-
piperidin]-2-yl]oxy}acetyl)(methyl)amino]propyl}
(methyl)carbamoyl]-2,6-dimethylbenzyl}(methyl)
amino]hexanoyl}(methyl)amino]ethyl}piperidin-4-yl
biphenyl-2-ylcarbamate trihydrochloride

[Formula 53]

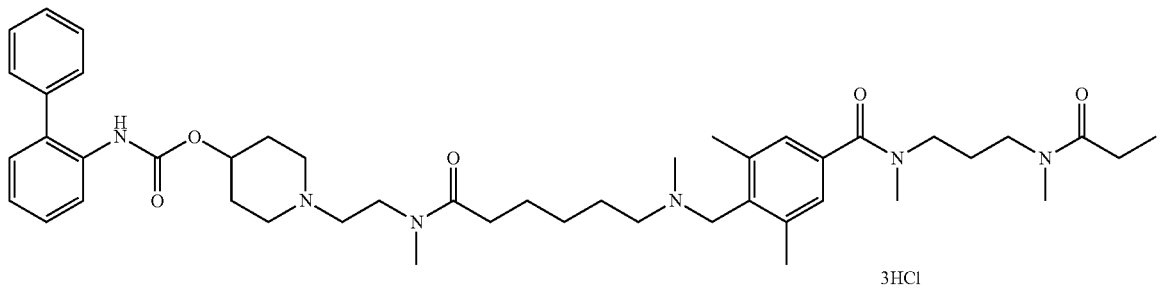

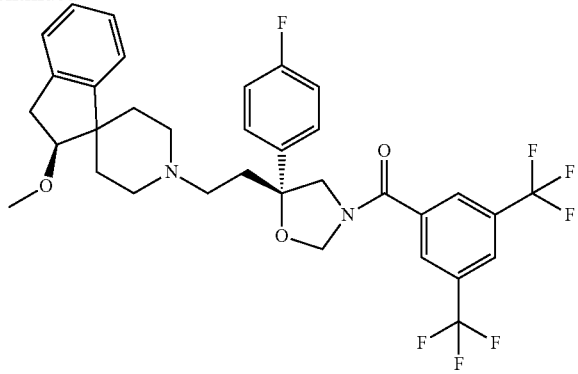

Example 48a

4-{([tert-Butoxycarbonyl)(methyl)amino]methyl}-3,5-dimethylbenzoic acid 4-(Bromomethyl)-3,5-dimethylbenzonitrile (500 mg, 2.23 mmol) was dissolved in a 2 M methylamine-tetrahydrofuran solution (5 mL), and the mixture was stirred at room temperature under a nitrogen atmosphere for 3 hours. After the reaction was completed, the solvent was evaporated under reduced pressure, ethyl acetate was added under ice cooling, and a saturated aqueous sodium hydrogencarbonate solution was further added to neutralize the mixture and separate the layers. The resulting organic layer was separated, washed with saturated sodium chloride solution, and then dried with anhydrous sodium sulfate, and the solvent was evaporated under reduced pressure. The resulting residue was dissolved in tetrahydrofuran (10 mL), di-tert-butyl dicarbonate (584 mg, 2.68 mmol) was added under ice cooling, and the mixture was stirred at the same temperature under a nitrogen atmosphere for 16 hours. After the reaction was completed, the solvent was evaporated under reduced pressure. The residue was purified by NH silica gel column chromatography (hexane:ethyl acetate, 10:1, v/v) to give tert-butyl (4-cyano-2,6-dimethylbenzyl)methylcarbamate (550 mg; yield, 90%) as a colorless oily substance.

The resulting tert-butyl (4-cyano-2,6-dimethyl benzyl)methylcarbamate (200 mg, 1.15 mmol) was dissolved in ethanol (2 mL), a 5 N aqueous sodium hydroxide solution (2 mL) was added at room temperature, and the mixture was heated to reflux for 16 hours. After the reaction was completed, a 1 N aqueous hydrochloric acid solution was added to the reaction mixture under ice cooling, and ethyl acetate was further added to separate the layers. The resulting organic layer was separated, washed with saturated sodium chloride solution, and then dried with anhydrous sodium sulfate, and the solvent was evaporated under reduced pressure to give the title compound (184 mg; yield, 89%) as a white solid.

MS (ESI): m/z 294 (M+H)$^+$.

Example 48b tert-Butyl {4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methy)amino]propyl}(methyl)carbamoyl]-2,6-dimethylbenzyl}methylcarbamate The compound (45 mg, 0.231 mmol) obtained in Example 48a and the compound (150 mg, 0.193 mmol) obtained in Example 1k were used to give the title compound (129 mg; yield, 64%) as a colorless oily substance according to the method described in Example 41a.

MS (ESI): m/z 1054 (M+H)$^+$.

Example 48c

N-{3-[({[(2S)-1-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}-N,3,5-trimethyl-4-[(methylamino)methyl]benzamide The compound (129 mg, 0.182 mol) obtained in Example 48b was used to give the title compound (124 mg; yield, 71%) as a colorless oily substance according to the method described in Example 6d.

MS (ESI): m/z 954 (M+H)$^+$.

Example 48d

1-{2-[{6-[{4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-2,6-dimethylbenzyl}(methyl)amino]hexanoyl}(methyl)amino]ethyl}piperidin-4-yl biphenyl-2-ylcarbamate trihydrochloride Moisture was removed from a mixture of the compound (124 mg, 0.130 mmol) obtained in Example 48c and the compound (66.6 mg, 0.143 mol) obtained in Example 4g azeotropically with toluene 3 times. The resulting mixture was used to give a free form (80 mg; yield, 44%) of the title compound as a white solid according to the method described in Example 41b.

The resulting free compound (80 mg, 57.0 μmol) was used to give the title compound (73 mg; yield, 85%) as a pale yellow solid according to the method described in Example 41c.

MS (FAB): m/z 1403 (M+H)$^+$ (free form).

IR (KBr) ν max 3415, 2932, 1727, 1642, 1360, 1282, 1225, 1178, 1138, 753 cm$^{-1}$.

Example 49

1-{2-[{6-[{4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]benzyl}(2,2-dimethylpropyl)amino]hexanoyl}(methyl)amino]ethyl}piperidin-4-yl biphenyl-2-ylcarbamate trihydrochloride

[Formual 54]

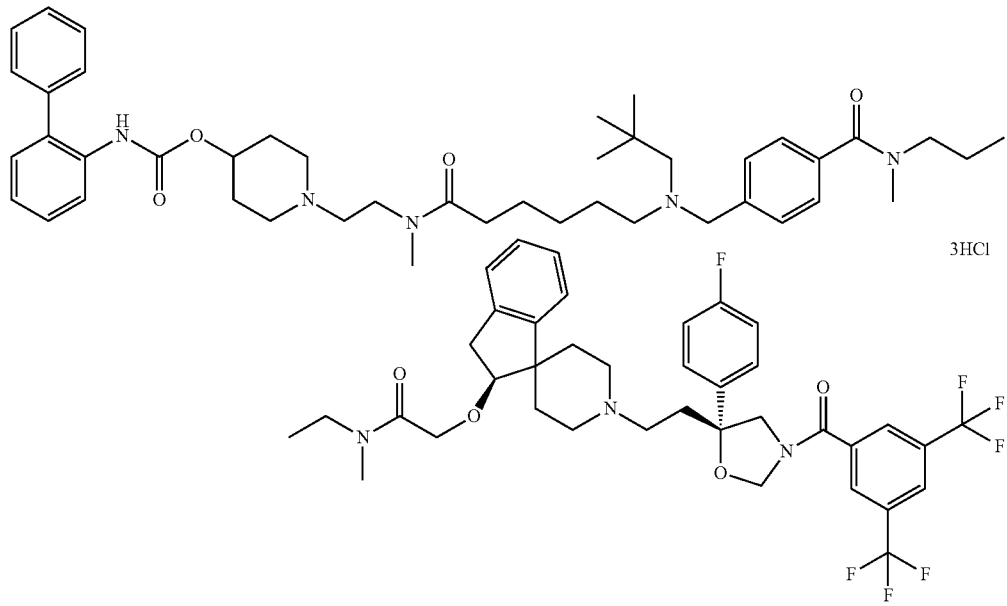

The compound obtained in Example 45a and 2,2-dimethylpropan-1-amine (28 mg, 0.325 mmol) were used according to the methods described in Examples 45b and 45c to give the title compound (17.0 mg; yield, 7%) as a white solid.

MS (FAB): m/z 1431 (M+H)$^+$ (free form).
IR (KBr) ν max 3422, 2924, 1726, 1644, 1360, 1224, 1139, 848, 753 cm$^{-1}$.

Example 50

1-{2-[{6-[(2-{4-[{3-[({[(2S)-1-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}ethyl)(methyl)amino]hexanoyl}(methyl)amino]ethyl}piperidin-4-yl biphenyl-2-ylcarbamate trihydrochloride

[Formula 55]

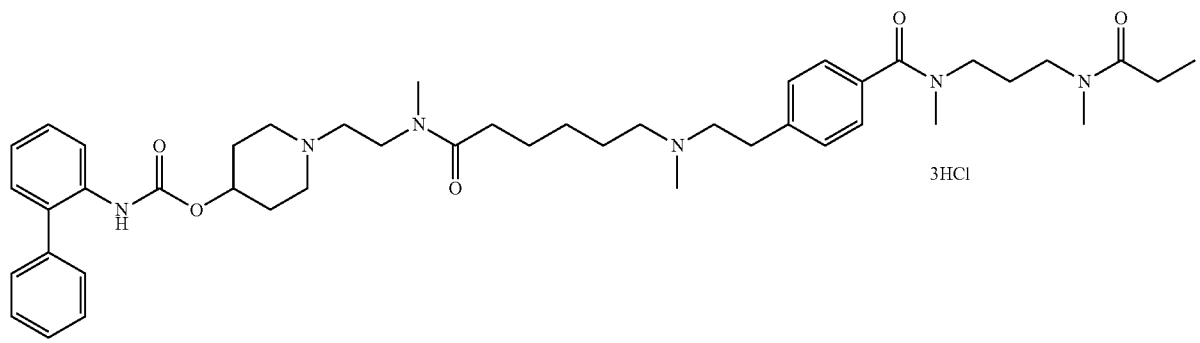

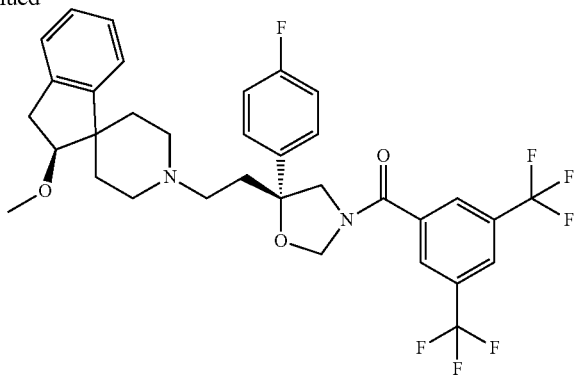

Example 50a

4-{2-[(tert-Butoxycarbonyl)(methyl)amino]ethyl}benzoic acid

4-{2-[(tert-Butoxycarbonyl)amino]ethyl}benzoic acid (400 mg, 1.51 mmol) was dissolved in N,N'-dimethylformamide (12 mL), methyl iodide (0.94 mL, 15.1 mmol) and 55% sodium hydride (198 mg, 4.53 mmol) were added under ice cooling, and the mixture was stirred at room temperature under a nitrogen atmosphere for 16 hours. After the reaction was completed, a saturated aqueous sodium hydrogencarbonate solution was added, and ethyl acetate was further added to separate the layers. The resulting organic layer was separated, washed with saturated sodium chloride solution, and then dried with anhydrous sodium sulfate, and the solvent was evaporated under reduced pressure. The residue was purified by silica gel column chromatography (hexane:ethyl acetate, 10:1, v/v) to give methyl 4-{2-([tert-butoxycarbonyl)(methyl)amino]ethyl}benzoate (384 mg; yield, 87%) as a colorless oily substance.

The resulting methyl 4-{2-[(tert-butoxycarbonyl)(methyl)amino]ethyl}benzoate (200 mg, 0.682 mmol) was dissolved in tetrahydrofuran (4 mL), a 1 N aqueous sodium hydroxide solution (1 mL) was added under ice cooling, and the mixture was stirred at room temperature for 16 hours. After the reaction was completed, the aqueous layer was washed with ethyl acetate, the aqueous layer was adjusted to pH 3 with a 1 N aqueous hydrochloric acid solution, and then ethyl acetate was further added to separate the layers. The resulting organic layer was separated, washed with saturated sodium chloride solution, and then dried with anhydrous sodium sulfate, and the solvent was evaporated under reduced pressure to give a crude title compound (140 mg; yield, 74%) as a colorless oily substance.

MS (FAB): m/z 280 (M+H)$^+$.

Example 50b tert-Butyl (2-{4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}ethyl)methylcarbamate

The compound (140 mg, 0.501 mmol) obtained in Example 50a and the compound (260 mg, 334 mol) obtained in Example 1k were used to give the title compound (320 mg; yield, 92%) as a white solid according to the method described in Example 41a.

Example 50c

N-{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}-N-methyl-4-[2-(methylamino)ethyl]benzamide

The compound (320 mg, 0.308 mmol) obtained in Example 50b was used to give the title compound (277 mg; yield, 96%) as a white solid according to the method described in Example 6d.

Example 50d

1-{2-[{6-[(2-{4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}ethyl)(methyl)amino]hexanoyl}(methyl)amino]ethyl}piperidin-4-yl biphenyl-2-ylcarbamate trihydrochloride

Moisture was removed from a mixture of the compound (135 mg, 0.144 mmol) obtained in Example 50c and the compound (67 mg, 0.144 mol) obtained in Example 4g azeotropically with toluene 3 times. The resulting mixture was used to give a free form (77 mg; yield, 39%) of the title compound as a white solid according to the method described in Example 41b.

The resulting free compound (77 mg, 55.4 μmol) was used to give the title compound (56 mg; yield, 84%) as a white solid according to the method described in Example 41c.

MS (FAB): m/z 1389 (M+H$^+$) (free form).

IR (KBr) ν max 3424, 2959, 2930, 1729, 1645, 1463, 1281, 1136, 1072, 746 cm$^{-1}$.

Example 51

1-{2-[(3-{[(2-{4-[{3-[({[(2S)-1'-{2-[(5R)-3-[3,5-Bis
(trifluoromethyl)benzoyl]-5-(4-fluorophenyl)-1,3-
oxazolidin-5-yl]ethyl}-2,3-dihydrospiro[indene-1,4'-
piperidin]-2-yl]oxy}acetyl)(methyl)amino]propyl}
(methyl)carbamoyl]phenyl}ethyl)(methyl)amino]
methyl}benzoyl)(methyl)amino]ethyl}piperidin-4-yl
biphenyl-2-ylcarbamate trihydrochloride

[Formula 56]

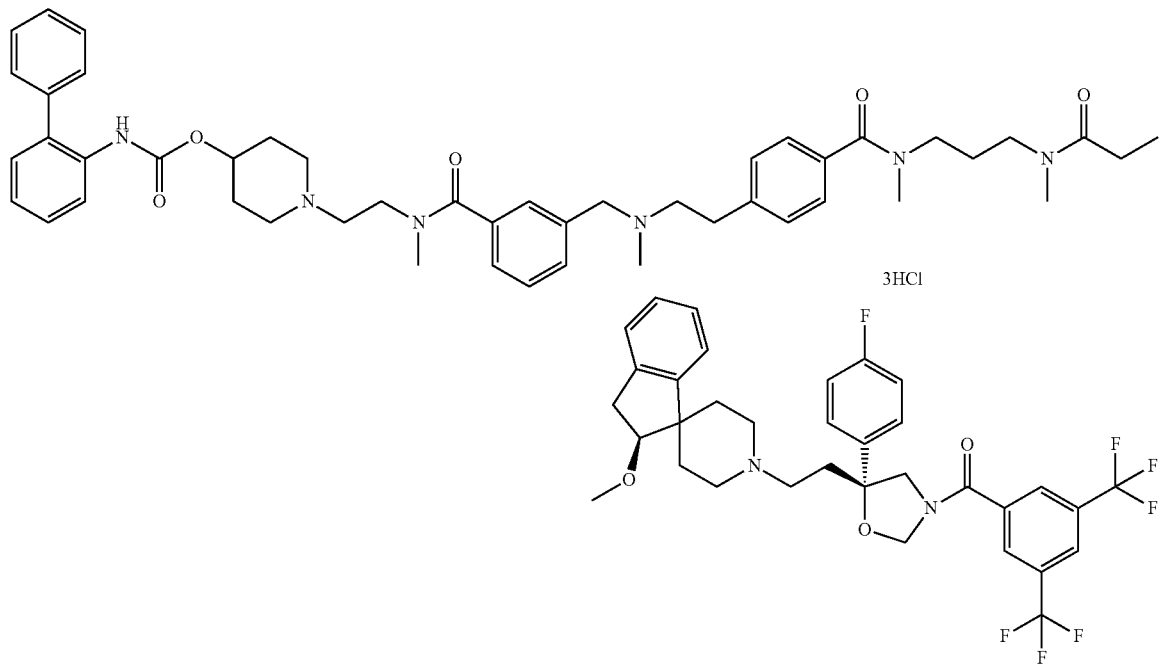

The compound (60 mg, 0.124 mmol) obtained in Example 47a and the compound obtained in Example 50c were used to give the title compound (47 mg; yield, 28%) as a white solid according to the method described in Example 50d.

MS (FAB): m/z 1409 (M+H)$^+$ (free form).
IR (KBr) ν max 3423, 2934, 1638, 1282, 1225, 1181, 1138, 752 cm$^{-1}$.

Example 52

1-(2-{[6-({4-[({-4-[({[(2S)-1-{2-[(5R)-3-[3,5-Bis
(trifluoromethyl)benzoyl]-5-(4-fluorophenyl)-1,3-
oxazolidin-5-yl]ethyl}-2,3-dihydrospiro[indene-1,4'-
piperidin]-2-yl]oxy}acetyl)(methyl)amino]
butoxy}carbonyl)amino]benzyl}amino)hexanoyl]
(methyl)amino}ethyl)piperidin-4-yl biphenyl-2-
ylcarbamate trihydrochloride

[Formula 57]

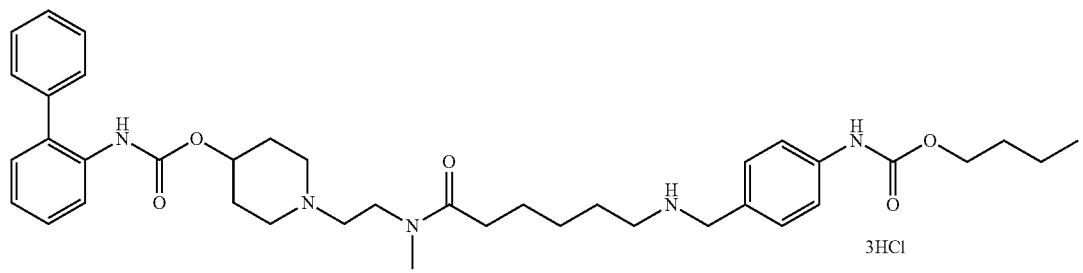

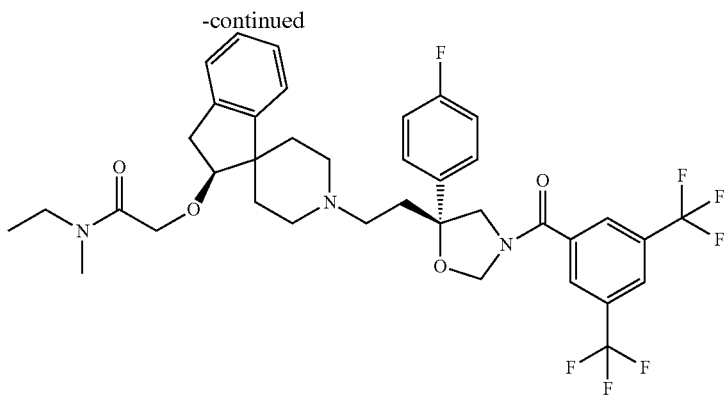

Example 52a

2-{[(2S)-1'-{2-[(5R)-3-[3,5-Bis(trifluoromethyl) benzoyl]-5-(4-fluorophenyl)-1,3-oxazolidin-5-yl] ethyl}-2,3-dihydrospiro[indene-1,4'-piperidin]-2-yl] oxy}-N-(4-hydroxybutyl)-N-methylacetamide The compound (400 mg, 0.576 mmol) obtained in Example 1j was dissolved in dichloromethane (30 mL), triethylamine (0.12 mL, 1.04 mmol) and pivaloyl chloride (0.11 mL, 0.864 mmol) were added under ice cooling, and the mixture was stirred at the same temperature under a nitrogen atmosphere for 15 minutes. Subsequently, a solution of 4-(methylamino)butan-1-ol (178 mg, 1.73 mmol) in dichloromethane (2 mL) was added under ice cooling, and the mixture was stirred at room temperature under a nitrogen atmosphere for 16 hours. After the reaction was completed, a saturated aqueous sodium hydrogencarbonate solution was added, and ethyl acetate was further added to separate the layers. The resulting organic layer was separated, washed with saturated sodium chloride solution, and then dried with anhydrous sodium sulfate, and the solvent was evaporated under reduced pressure. The residue was purified by NH silica gel column chromatography (hexane:ethyl acetate, 10:1, v/v) to give the title compound (347 mg; yield, 77%) as a colorless oily substance.

Example 52b

4-[({[(2S)-1'-{2-[(5R)-3-[3,5-Bis(trifluoromethyl) benzoyl]-5-(4-fluorophenyl)-1,3-oxazolidin-5-yl] ethyl}-2,3-dihydrospiro[indene-1,4'-piperidin]-2-yl] oxy}acetyl)(methyl)amino]butyl(4-formylphenyl) carbamate The compound (347 mg, 0.445 mmol) obtained in Example 52a was dissolved in toluene (10 mL), 4-isocyanate benzaldehyde (90 mg, 0.667 mmol) was added, and the mixture was stirred at 110° C. under a nitrogen atmosphere for 16 hours. After the reaction was completed, water was added, and ethyl acetate was further added to separate the layers. The resulting organic layer was separated, washed with saturated sodium chloride solution, and then dried with anhydrous sodium sulfate, and the solvent was evaporated under reduced pressure. The residue was purified by silica gel column chromatography (ethyl acetate:methanol, 15:1, v/v) to give the title compound (301 mg; yield, 73%) as a colorless oily substance.

Example 52c 1-(2-{[6-({4-[({4-[({[(2S)-1'-{2-[(5R)-3-[3,5-Bis (trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino] butoxy}carbonyl)amino]benzyl}amino)hexanoyl] (methyl)amino}ethyl)piperidin-4-yl biphenyl-2-ylcarbamate trihydrochloride Moisture was removed from a mixture of the compound (301 mg, 0.330 mmol) obtained in Example 52b and the compound (197 mg, 0.422 mmol) obtained in Example 4g azeotropically with toluene 3 times. The resulting mixture was used to give a free form (44 mg; yield, 10%) of the title compound as a white solid according to the method described in Example 41b.

The resulting free compound (44 mg, 31.9 μmol) was used to give the title compound (35 mg; yield, 73%) as a white solid according to the method described in Example 41c.

MS (FAB): m/z 1377 (M+H)$^+$ (free form).

IR (KBr) v max 3421, 2936, 1725, 1647, 1528, 1360, 1281, 1225, 1139, 753 cm$^{-1}$.

Example 53

1-(2-{[6-({4-[({3-[({[(2S)-1'-{2-[(5R)-3-[3,5-Bis (trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino] propoxy}carbonyl)amino]benzyl}amino)hexanoyl] (methyl)amino}ethyl)piperidin-4-yl biphenyl-2-ylcarbamate trihydrochloride

[Formula 58]

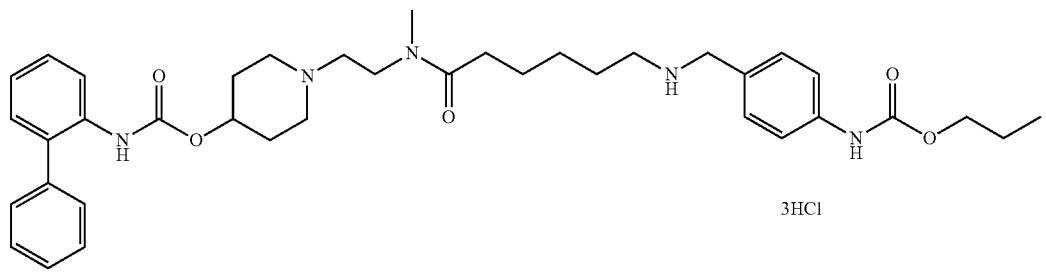

3HCl

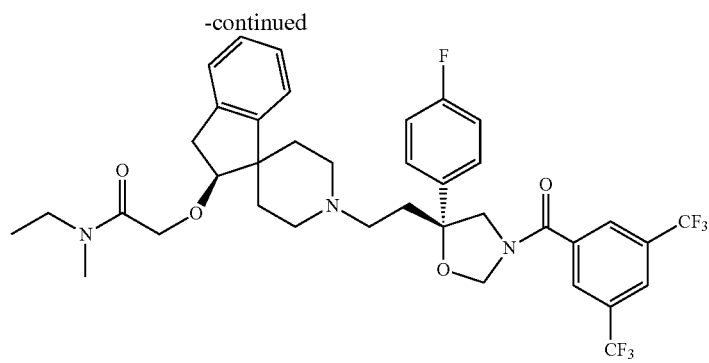

3-(Methylamino)propan-1-ol (154 mg, 1.78 mmol) was used to give the title compound (58 mg; yield, 15%) as a white solid according to the method described in Example 52.

MS (FAB): m/z 1363 (M+H)$^+$ (free form).

IR (KBr) ν max 2944, 1726, 1648, 1525, 1359, 1281, 1226, 1139, 847, 754 cm$^{-1}$.

Example 54

1-{2-[{6-[({5-[{3-[({[(2S)-1'-{2-[(5R)-3-[3,5-Bis (trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methy)amino]propyl} (methyl)carbamoyl]-2-thienyl}methyl)amino] hexanoyl}(methyl)amino]ethyl}piperidin-4-yl biphenyl-2-ylcarbamate trihydrochloride

[Formula 59]

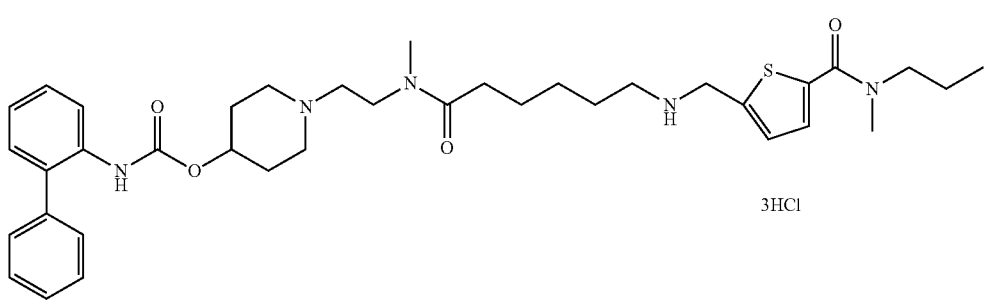

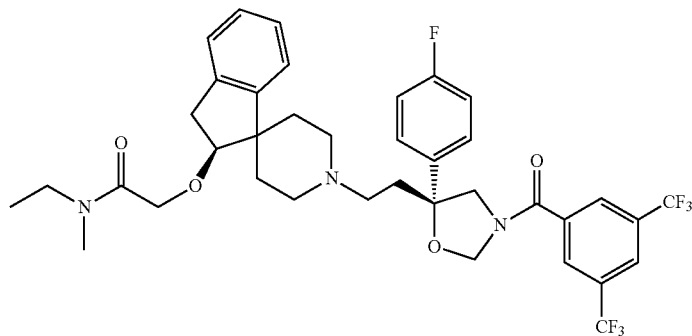

The compound (43 mg, 31.4 μmol) obtained in Example 1m was used to give the title compound (30 mg; yield, 65%) as a pale yellow solid according to the method described in Example 41c.

MS (FAB): m/z 1367 (M+H)$^+$ (free form).

IR (KBr) ν max 2934, 1728, 1647, 1449, 1359, 1281, 1224, 1177, 1139, 753 cm$^{-1}$.

Example 55

1-{2-[{6-[({5-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-2-thienyl}methyl)(2,2-dimethylpropyl)amino]hexanoyl}(methyl)amino]ethyl}piperidin-4-yl biphenyl-2-ylcarbamate trihydrochloride

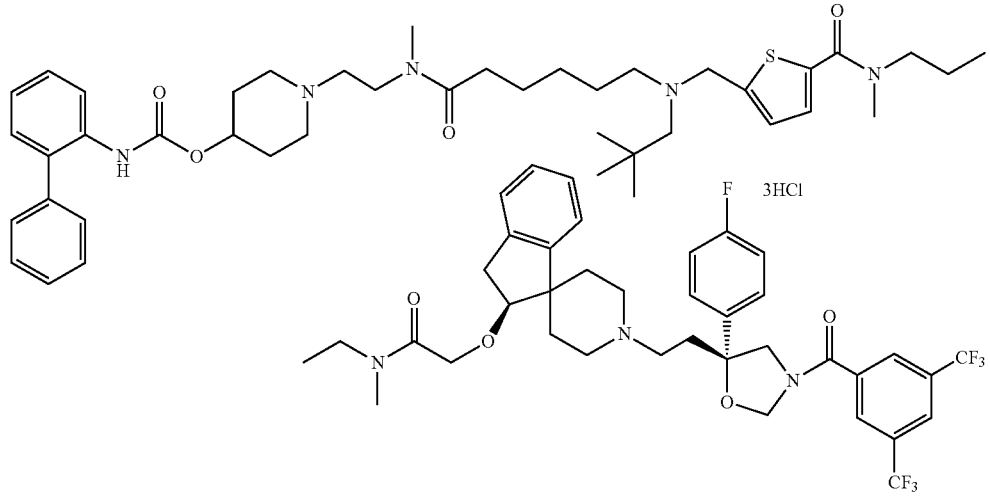

[Formula 60]

Example 55a tert-Butyl (3-{[(5-formyl-2-thienyl)carbonyl](methyl)amino}propyl)methylcarbamate 5-Formylthiophene-2-carboxylic acid (300 mg, 1.92 mmol) and tert-butyl methyl[3-(methylamino)propyl]carbamate (466 mg, 2.31 mmol) were used to give the title compound (517 mg; yield, 83%) as a colorless oily substance according to the method described in Example 41a.
MS (FAB): m/z 240 (M+H)$^+$.
IR (KBr) v max 2975, 1681, 1626, 1486, 1400, 1211, 1162, 1040, 822, 739 cm$^{-1}$.

Example 55b tert-Butyl (3-{[(5-{[(2,2-dimethylpropyl)amino]methyl}-2-thienyl)carbonyl](methyl)amino}propyl)methylcarbamate Moisture was removed from a mixture of the compound (150 mg, 0.460 mmol) obtained in Example 55a and 2,2-dimethylpropan-1-amine (80 mg, 0.919 mmol) azeotropically with toluene 3 times. The resulting mixture was used to give the title compound (122 mg; yield, 67%) as a colorless oily substance according, to the method described in Example 45b.

Example 55c

1-{2-[{6-[({5-[{3-[(tert-Butoxycarbonyl)(methyl)amino]propyl}(methyl)carbamoyl]-2-thienyl}methyl)(2,2-dimethylpropyl)amino]hexanoyl}(methyl)amino]ethyl}piperidin-4-yl biphenyl-2-ylcarbamate The compound (122 mg, 0.307 mol) obtained in Example 55b and the compound (171 mg, 0.368 mmol) obtained in Example 4g were used to give the title compound (181 mg; yield, 69%) as a colorless oily substance according to the method described in Example 45b.

Example 55d

1-{2-[(6-{(2,2-Dimethylpropyl)[(5-{methyl[3-(methylamino)propyl]carbamoyl}-2-thienyl)methyl]amino}hexanoyl)(methy)amino]ethyl}piperidin-4-yl biphenyl-2-ylcarbamate The compound (181 mg, 0.210 mmol) obtained in Example 55c was used according to the description in Example 6d to give the title compound (160 mg; yield, 100%) as a colorless oily substance.
MS (ESI): m/z 761 (M+H)$^+$.

Example 55e

1-{2-[{6-[({5-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-2-thienyl}methyl)(2,2-dimethylpropyl)amino]hexanoyl}(methyl)amino]ethyl}piperidin-4-yl biphenyl-2-ylcarbamate trihydrochloride The compound (160 mg, 0.210 mmol) obtained in Example 55d was used according to the description in Example 11e to give a free form (134 mg; yield, 61%) of the title compound as a white solid.
The resulting free compound (134 mg, 93.2 µmol) was used according to the method described in Example 41c to give the title compound (134 mg; yield, 67%) as a white solid.
MS (FAB): m/z 1437 (M+H)$^+$ (free form).
IR (KBr) v max 2936, 1735, 1649, 1359, 1281, 1224, 1179, 1139, 847, 753 cm$^{-1}$.

Example 56

1-{2-[{6-[({5-[{3-[({[(2S)-1'-{2-[(5R)-3-[3,5-Bis (trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl} (methyl)carbamoyl]-2-thienyl}methyl)(propyl) amino]hexanoyl}(methyl)amino]ethyl}piperidin-4-yl biphenyl-2-ylcarbamate trihydrochloride

[Formula 61]

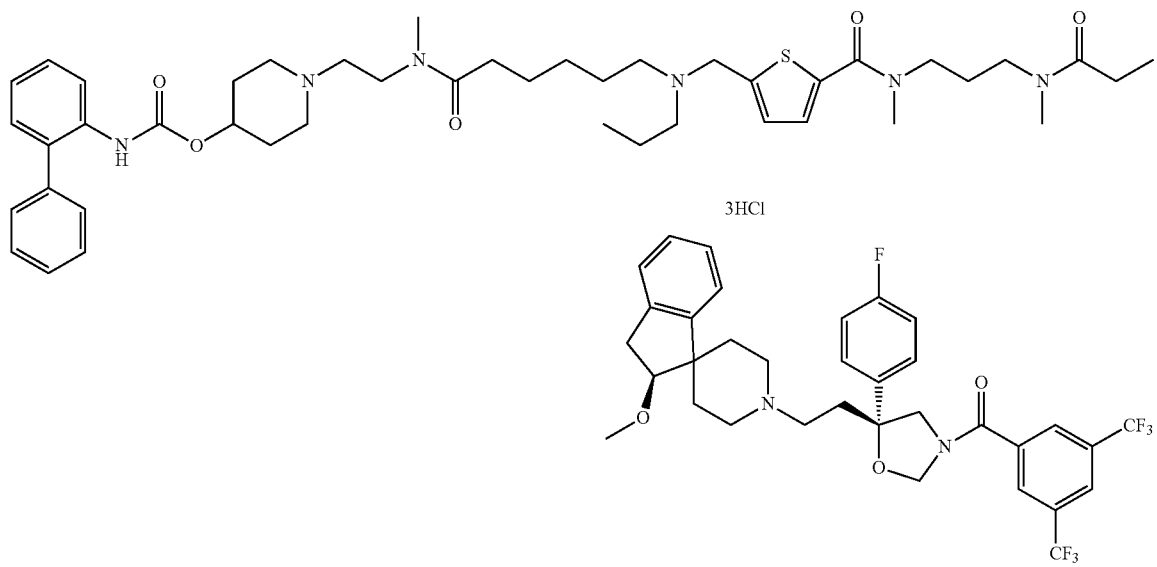

Propan-1-amine (54 mg, 0.919 mmol) was used to give the title compound (94 mg; yield, 30%) as a white solid according to the method described in Example 55.

MS (FAB): m/z 1409 (M+H)$^+$ (free form).

IR (KBr) ν max 2933, 1735, 1649, 1359, 1280, 1224, 1178, 1139, 847, 753 cm$^{-1}$.

Example 57

1-{2-[{6-[(4-{2-[{3-[({[(2S)-1'-{2-[(5R)-3-[3,5-Bis (trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl} (methyl)amino]-2-oxoethyl}phenyl)amino] hexanoyl}(methyl)amino]ethyl}piperidin-4-yl biphenyl-2-ylcarbamate trihydrochloride

[Formula 62]

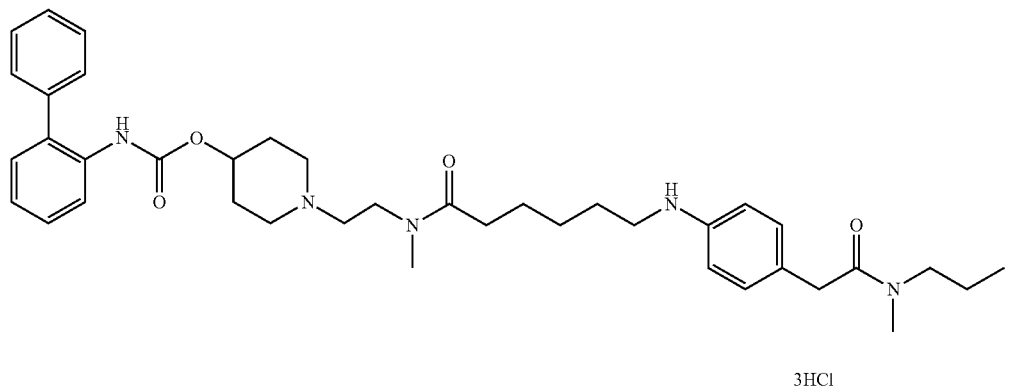

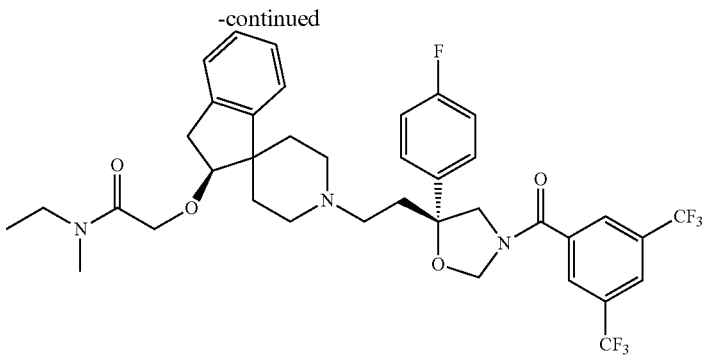

Example 57a

2-{[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}-N-methyl-N-(3-{methyl[(4-nitrophenyl)acetyl]amino}propyl)acetamide (4-Nitrophenyl)acetic acid (52 mg, 0.287 mmol) and the compound (186 mg, 0.239 mmol) obtained in Example 1k were used to give the title compound (212 mg; yield, 94%) as a colorless oily substance according to the method described in Example 41a.

Example 57b 2-(4-Aminophenyl)-N-{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}-N-methylacetamide The compound (212 mg, 0.225 mmol) obtained in Example 57a was dissolved in ethanol (10 mL), 10% palladium-carbon (42 mg, 20% by weight) was added, and the mixture was stirred at room temperature under a hydrogen atmosphere for 5 hours. The reaction mixture was filtered through celite, and the solvent was evaporated under reduced pressure. The residue was purified by NH silica gel column chromatography (ethyl acetate:methanol, 10:1, v/v) to give the title compound (194 mg; yield, 98%) as a yellow oily substance.

Example 57c

1-{2-[{6-[(4-{2-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)amino]-2-oxoethyl}phenyl)amino]hexanoyl}(methyl)amino]ethyl}piperidin-4-yl biphenyl-2-ylcarbamate The compound (194 mg, 0.219 mmol) obtained in Example 57b and the compound (102 mg, 0.219 mmol) obtained in Example 4g were used to give the title compound (95 mg; yield, 32%) as a white solid according to the method described in Example 41b.

Example 57d

1-{2-[{6-[(4-{2-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)amino]-2-oxoethyl}phenyl)amino]hexanoyl}(methyl)amino]ethyl}piperidin-4-yl biphenyl-2-ylcarbamate trihydrochloride The compound (30 mg, 22.0 μmol) obtained in Example 57c was used to give the title compound (23 mg; yield, 70%) as a white solid according to the method described in Example 41c.

MS (FAB): m/z 1361 (M+H)$^+$ (free form).
IR (KBr) ν max 2937, 1724, 1644, 1513, 1438, 1360, 1281, 1224, 1174, 1138 cm$^{-1}$.

Example 58

1-{2-[{6-[(4-{2-[{3-[({[(2S)-1'-{2-[(5R)-3-[3,5-Bis(trifluoromethyl)benzoyl]-5-(4-fluorophenyl)-1,3-oxazolidin-5-yl]ethyl}-2-dihydrospiro[indene-1,4'-piperidin]-2-yl]oxy}acetyl)(methyl)amino]propyl}(methyl)amino]-2-oxoethyl}phenyl)(methyl)amino]hexanoyl}(methyl)amino]ethyl}piperidin-4-yl biphenyl-2-ylcarbamate trihydrochloride

[Formula 63]

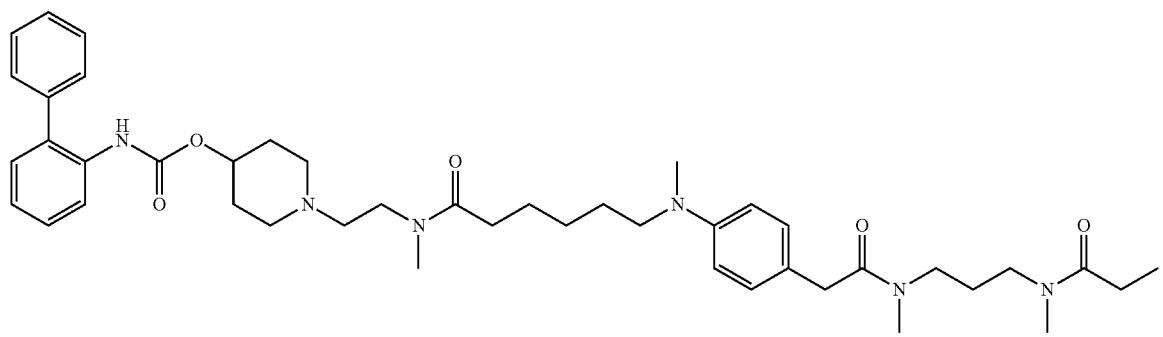

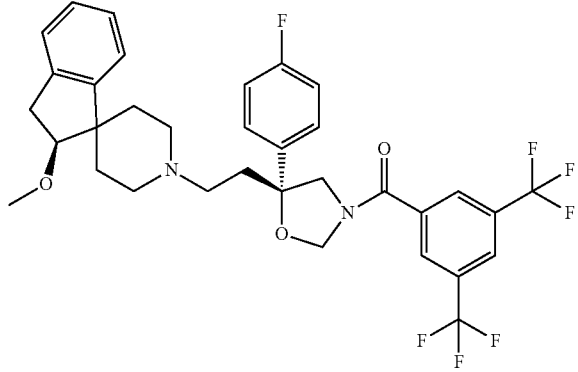

Moisture was removed from a mixture of the compound (95 mg, 69.8 μmol) obtained in Example 57c and a 35% aqueous formaldehyde solution (6 μL, 76.8 μmol) azeotropically with toluene 3 times. The resulting mixture was used to give a free form (40 mg; yield, 42%) of the title compound as a white solid according to the method described in Example 41b.

The resulting free compound (40 mg, 29.1 μmol) was used to give the title compound (35 mg; yield, 81%) as a white solid according to the method described in Example 41c.

MS (FAB): m/z 1375 (M+H)$^+$ (free form).

IR (KBr) ν max 3425, 2933, 1725, 1645, 1360, 1282, 1224, 1175, 1138, 752 cm$^{-1}$.

Example 59

1-{2-[(6-{5-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-2,3-dihydro-1H-indol-1-yl}hexanoyl)(methyl)amino]ethyl}piperidin-4-yl biphenyl-2-ylcarbamate trihydrochloride

[Formula 64]

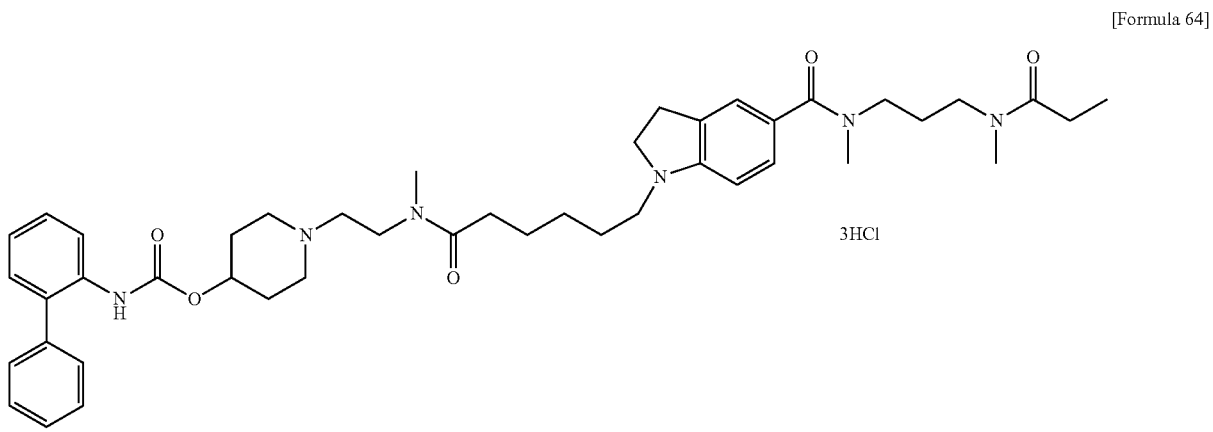

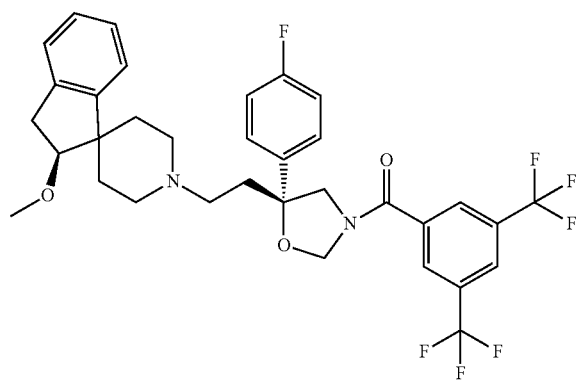

Example 59a tert-Butyl 5-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]indolin-1-carboxylate 1-(tert-Butoxycarbonyl)-2,3-dihydro-1H-indole-5-carboxylic acid (WO2004/69792 A2 [19, Aug. 2004]) (51 mg, 0.193 mmol) and the compound (100 mg, 0.128 mmol) obtained in Example 1k were used to give the title compound (144 mg; yield, 100%) as a colorless oily substance according to the method described in Example 41a.

Example 59b

N-{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}-N-methylindoline-5-carboxamide The compound (144 mg, 0.141 mmol) obtained in Example 59a was used to give the title compound (102 mg; yield, 86%) as a colorless oily substance according to the method described in Example 6d.

Example 59c

1-{2-[(6-{5-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-2,3-dihydro-1H-indol-1-yl}hexanoyl)(methyl)amino]ethyl}piperidin-4-yl biphenyl-2-ylcarbamate trihydrochloride The compound (102 mg, 0.110 mmol) obtained in Example 59b and the compound (61 mg, 0.132 mmol) obtained in Example 4g were used to give a free form (45 mg; yield, 30%) of the title compound as a white solid according to the method described in Example 41b.

The resulting free compound (45 mg, 32.8 µmol) was used to give the title compound (21 mg; yield, 58%) as a white solid according to the method described in Example 41c.

MS (FAB): m/z 1373 (M+H)$^+$ (free form).

IR (KBr) ν max 3418, 2933, 1726, 1449, 1360, 1281, 1224, 1174, 1137, 752 cm$^{-1}$.

Example 60

1-{2-[(6-{6-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-3,4-dihydroisoquinolin-2(1H)-yl}hexanoyl)(methyl)amino]ethyl}piperidin-4-yl biphenyl-2-ylcarbamate trihydrochloride

[Formula 65]

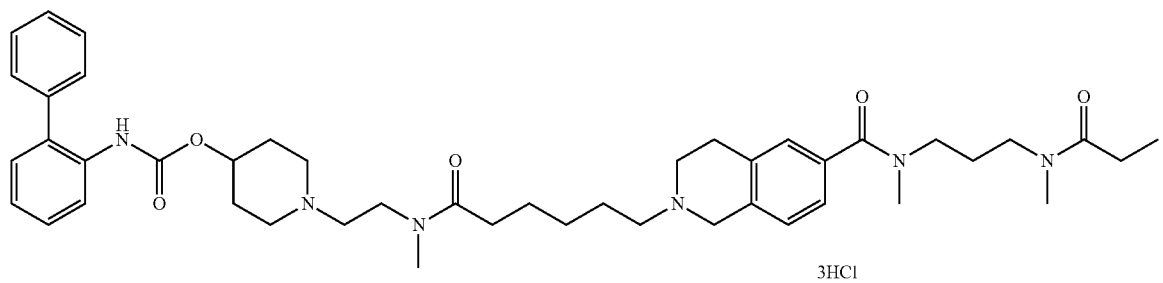

3HCl

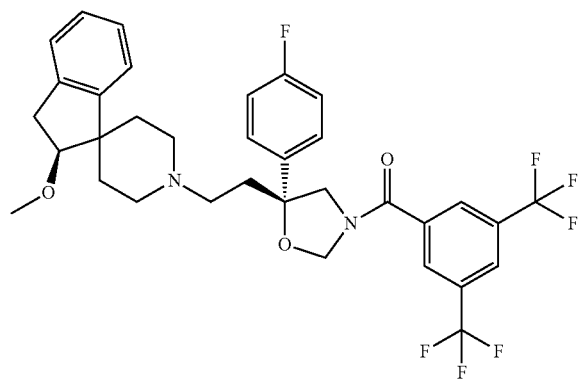

1-(tert-Butoxycarbonyl)-1,2,3,4-tetrahydroquinoline-6-carboxylic acid (63 mg, 0.229 mmol) was used to give the title compound (82 mg; yield, 33%) as a white solid according to the method described in Example 59.

MS (FAB): m/z 1387 (M+H)+ (free form).

IR (KBr) ν max 3417, 1721, 1639, 1438, 1360, 1282, 1225, 1174, 1137, 752 cm−1.

Example 61

1-{2-[{6-[(2-{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}-1-oxo-1,2,3,4-tetrahydroisoquinolin-6-yl)amino]hexanoyl}(methyl)amino]ethyl}piperidin-4-yl biphenyl-2-ylcarbamate trihydrochloride sodium chloride solution, and then dried with anhydrous sodium sulfate, and the solvent was evaporated under reduced pressure. The resulting residue was dissolved in tetrahydrofuran (5 mL), a 1.0 M tetrabutylammonium fluoride-tetrahydrofuran solution (22.5 mL, 22.5 mmol) was added under ice cooling, and the mixture was stirred at room temperature under a nitrogen atmosphere for 2 hours. After the reaction was completed, saturated aqueous ammonium chloride was added to the reaction mixture under ice cooling, and ethyl acetate was further added to separate the layers. The resulting organic layer was separated, washed with saturated sodium chloride solution, and then dried with anhydrous sodium sulfate, and the solvent was evaporated under reduced pressure. The residue was purified by silica gel column chromatography (ethyl acetate:methanol, 10:1, v/v) to give the title compound (1.93 g; yield, 100%) as a colorless oily substance.

MS (ESI): m/z 235 (M+H)+.

[Formula 66]

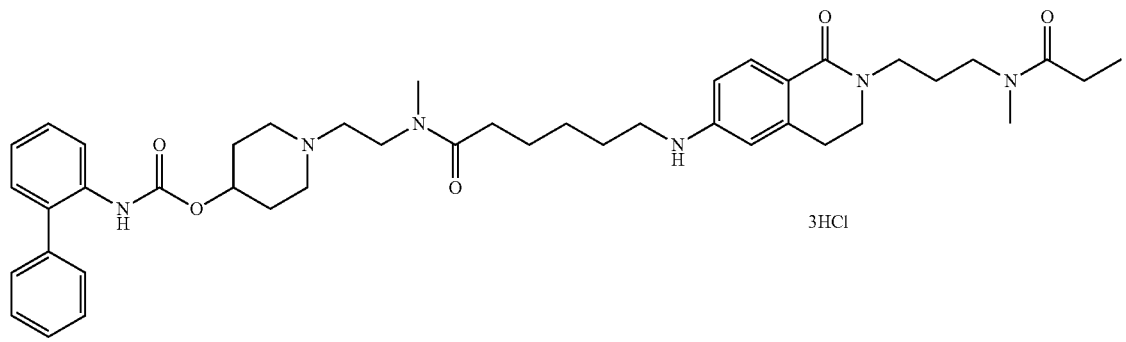

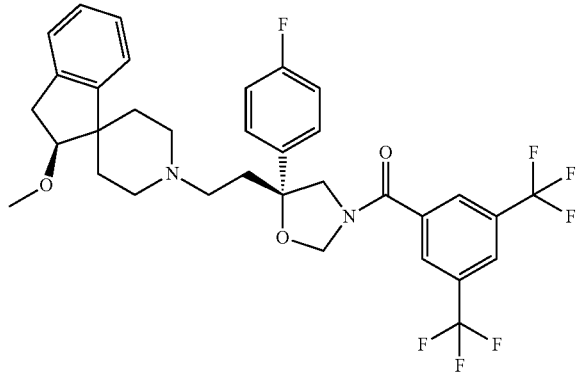

Example 61a 2-(3-Hydroxypropyl)-6-methoxy-3,4-dihydroisoquinolin-1(2H)-one

6-Methoxy-3,4-dihydroisoquinolin-1(2H)-one (1.0 g, 5.64 mmol) was dissolved in N,N-dimethylformamide (15 mL), (3-bromopropoxy)(tert-butyl)dimethylsilane (2.62 mL, 11.3 mmol) and 55% sodium hydride (259 mg, 5.93 mmol) were added under ice cooling, and the mixture was stirred at room temperature under a nitrogen atmosphere for 2 hours. After the reaction was completed, saturated aqueous ammonium chloride was added to the reaction mixture under ice cooling, and ethyl acetate was further added to separate the layers. The resulting organic layer was separated, washed with saturated

Example 61b tert-Butyl [3-(6-hydroxy-1-oxo-3,4-dihydroisoquinolin-2(1H)-yl)propyl]methylcarbamate The compound (1.93 g, 5.64 mmol) obtained in Example 61a was dissolved in ethyl acetate (20 mL), methanesulfonyl chloride (0.655 mL, 8.47 mmol) and triethylamine (1.42 mL, 10.2 mmol) were added under ice cooling, and the mixture was stirred at the same temperature under a nitrogen atmosphere for 15 minutes. After the reaction was completed, a saturated aqueous sodium hydrogencarbonate solution was added to the reaction mixture under ice cooling, and ethyl acetate was further added to separate the layers. The resulting organic layer was separated, washed with saturated sodium chloride solution, and then dried with anhydrous sodium sulfate, and the solvent was evaporated under reduced pressure.

A 40% methylamine-methanol solution was added to the resulting residue under ice cooling, and the mixture was stirred at room temperature under a nitrogen atmosphere for 7 hours. After the reaction was completed, the solvent was evaporated under reduced pressure. The residue was purified by NH silica gel column chromatography (ethyl acetate: methanol, 10:1, v/v) to give 6-methoxy-2-[3-(methylamino) propyl]-3,4-dihydroisoquinolin-1(2H)-one (1.0 g; yield, 72%) as a colorless oily substance.

A 47% aqueous hydrogen bromide solution (16 mL) was added to the resulting 6-methoxy-2-[3-(methylamino)propyl]-3,4-dihydroisoquinolin-1(2H)-one (1.0 g, 4.06 mmol) under ice cooling, and the mixture was stirred at 120° C. for 16 hours. After the reaction was completed, the solvent was evaporated under reduced pressure.

The resulting residue was dissolved in ethyl acetate (30 mL), a saturated aqueous sodium hydrogencarbonate solution (30 mL) and di-tert-butyl dicarbonate (967 mg, 4.43 mmol) were added under ice cooling, and the mixture was stirred at room temperature for 16 hours. After the reaction was completed, water was added to the reaction mixture under ice cooling, and ethyl acetate was further added to separate the layers. The resulting organic layer was separated, washed with saturated sodium chloride solution, and then dried with anhydrous sodium sulfate, and the solvent was evaporated under reduced pressure. The residue was purified by silica gel column chromatography (hexane:ethyl acetate, 10:1, v/v) to give the title compound (971 mg; yield, 72%) as a white solid.

MS (ESI): m/z 235 (M+H)$^+$. (form with Boc removed).

Example 61c

Methyl 2-{3-([tert-butoxycarbonyl)(methyl)amino] propyl}-1-oxo-1,2,3,4-tetrahydroisoquinoline-6-carboxylate The compound (0.471 g, 1.41 mol) obtained in Example 61b was dissolved in pyridine (6 mL), anhydrous trifluoromethanesulfonic acid (0.355 mL, 2.11 mmol) was added under ice cooling, and the mixture was stirred at the same temperature under a nitrogen atmosphere for 15 minutes. After the reaction was completed, the solvent was evaporated under reduced pressure. The residue was purified by silica gel column chromatography (hexane:ethyl acetate, 1:1, v/v) to give tert-butyl [3-(6-hydroxy-1-oxo-3,4-dihydroisoquinolin-2(1H)-yl)propyl]methylcarbamate as a white solid.

The resulting tert-butyl [3-(6-hydroxy-1-oxo-3,4-dihydroisoquinolin-2(1H)-yl)propyl]methylcarbamate was dissolved in a mixed solvent (11 mL) of N,N-dimethylformamide and methanol (10:1), palladium acetate (65 mg, 0.291 mmol), 1,3-diphenylphosphinopropane (120 mg, 0.291 mmol) and triethylamine (0.405 mL, 2.91 mmol) were added, and the mixture was stirred at 65° C. under a carbon monoxide atmosphere for 16 hours. After the reaction was completed, water was added to the reaction mixture, and ethyl acetate was further added to separate the layers. The resulting organic layer was separated, washed with saturated sodium chloride solution, and then dried with anhydrous sodium sulfate, and the solvent was evaporated under reduced pressure. The residue was purified by silica gel column chromatography (hexane:ethyl acetate, 1:1, v/v) to give the title compound (535 mg; yield, 100%) as a colorless oily substance.

$^1$H HMR (CDCl$_3$, 400 MHz): δ 1.5 (9H, s), 1.8-1.9 (2H, m), 2.87 (3H, s), 3.0-3.1 (2H, m), 3.2-3.3 (2H, m), 3.5-3.6 (2H, m), 3.9 (3H, s), 7.9 (1H, s), 8.0 (1H, d, J=8.5 Hz), 8.1 (1H, d, J=8.5 Hz).

Example 61d tert-Butyl [3-(6-amino-1-oxo-3,4-dihydroisoquinolin-2(1H)-yl)propyl]methylcarbamate The compound (535 mg, 1.41 mmol) obtained in Example 61c was dissolved in a mixed solvent (6 mL) of tetrahydrofuran and methanol (1:1), a 1 N aqueous sodium hydroxide solution (1 mL) was added, and the mixture was stirred at 60° C. for 5 hours. After the reaction was completed, a 1 N aqueous hydrochloric acid solution (10 mL) was added to the reaction mixture under ice cooling, and ethyl acetate was further added to separate the layers. The resulting organic layer was separated, washed with saturated sodium chloride solution, and then dried with anhydrous sodium sulfate, and the solvent was evaporated under reduced pressure. The resulting residue was dissolved in 1,4-dioxane (6 mL), diphenyl phosphate azide (0.238 mL, 1.10 mmol), triethylamine (0.154 mL, 1.10 mmol) and benzyl alcohol (0.228 mL, 2.21 mmol) were added under ice cooling, and the mixture was stirred at 100° C. under a nitrogen atmosphere for 16 hours. After the reaction was completed, the solvent was evaporated under reduced pressure. The resulting residue was dissolved in a mixed solvent (12 mL) of ethyl acetate and methanol (1:2), 10% palladium-carbon (53 mg) was added, and the mixture was stirred at room temperature under a hydrogen atmosphere for 1 hour. After the reaction was completed, the reaction mixture was filtered through celite, the filtrate was washed with ethanol, and the solvent was evaporated under reduced pressure. The residue was purified by NH silica gel column chromatography (ethyl acetate:methanol, 10:1, v/v) to give the title compound (149 mg; yield, 81%) as a colorless oily substance.

$^1$H HMR (CDCl$_3$, 400 MHz): δ 1.5 (9H, s), 1.8-1.9 (2H, m), 2.8-2.9 (5H, m), 3.2-3.3 (2H, m), 3.5-3.6 (4H, m), 3.9-4.0 (2H, m), 6.4 (1H, s), 6.6 (1H, d, J=8.5 Hz), 7.9 (1H, d, J=8.5 Hz).

Example 61e

1-{2-[{6-[(2-{3-[(tert-Butoxycarbonyl)(methyl) amino]propyl}-1-oxo-1,2,3,4-tetrahydroisoquinolin-6-yl)amino]hexanoyl}(methyl)amino] ethyl}piperidin-4-yl biphenyl-2-ylcarbamate The compound (149 mg, 0.447 mmol) obtained in Example 61d and the compound (250 mg, 0.536 mmol) obtained in Example 4g were used to give the title compound (85 mg; yield, 24%) as a colorless oily substance according to the method described in Example 45b.

MS (ESI): m/z 783 (M+H)$^+$.

Example 61f

1-{2-[{6-[(2-{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}-1-oxo-1,2,3,4-tetrahydroisoquinolin-6-yl)amino] hexanoyl}(methyl)amino]ethyl}piperidin-4-yl biphenyl-2-ylcarbamate trihydrochloride The compound (85 mg, 0.109 mmol) obtained in Example 61e was used to give a Boc-deprotected compound 1-(2-{methyl[6-({2-[3-(methylamino)propyl]-1-oxo-1,2,3,4-tetrahydroisoquinolin-6-yl}amino)hexanoyl]amino}ethyl)piperidin-4-yl biphenyl-2-ylcarbamate (52 mg; yield, 70%) as a colorless oily substance according to the method described in Example 6d.

The resulting Boc-deprotected compound was used to give a free form (82 mg; yield, 71%) of the title compound as a white solid according to the method described in Example 11e.

The resulting free compound (82 mg, 60.3 μmol) was used to give the title compound (59 mg; yield, 67%) as a white solid according to the method described in Example 41c.

MS (FAB): m/z 1359 (M+H)⁺ (free form).
IR (KBr) ν max 3422, 2932, 1735, 1642, 1602, 1478, 1359, 1281, 1139, 752 cm⁻¹.

Example 62

1-{2-[{6-[(2-{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}-1-oxo-1,2,3,4-tetrahydroisoquinolin-6-yl)(methyl)amino]hexanoyl}(methyl)amino]ethyl}piperidin-4-yl biphenyl-2-ylcarbamate trihydrochloride solution (1 mL) was added, and the mixture was stirred at 60° C. for 5 hours. After the reaction was completed, a 1 N aqueous hydrochloric acid solution (10 mL) was added to the reaction mixture under ice cooling, and ethyl acetate was further added to separate the layers. The resulting organic layer was separated, washed with saturated sodium chloride solution, and then dried with anhydrous sodium sulfate, and the solvent was evaporated under reduced pressure. The resulting residue was dissolved in 1,4-dioxane (6 mL), diphenyl phosphate azide (0.238 mL, 1.10 mmol), triethylamine (0.154 mL, 1.10 mmol) and benzyl alcohol (0.228 mL, 2.21 mmol) were added under ice cooling, and the mixture was stirred at 100° C. under a nitrogen atmosphere for 16 hours. After the reaction was completed, the solvent was evaporated under reduced pressure, the resulting crude benzyl (2-{3-([tert-butoxycarbonyl)(methyl)amino]propyl}-1-oxo-1,2,3,4-tetrahydroisoquinolin-6-yl)carbamate (354 mg, 0.757 mmol) was dissolved in N,N-dimethylformamide (7 mL), methyl iodide (0.236 mL, 3.79 mmol) and 55% sodium hydride (40 mg, 0.909 mmol) were added under ice cooling, and the mixture was stirred at room temperature under a nitrogen atmosphere for 1 hour. After the reaction was completed, water was added to the reaction mixture under ice

[Formula 67]

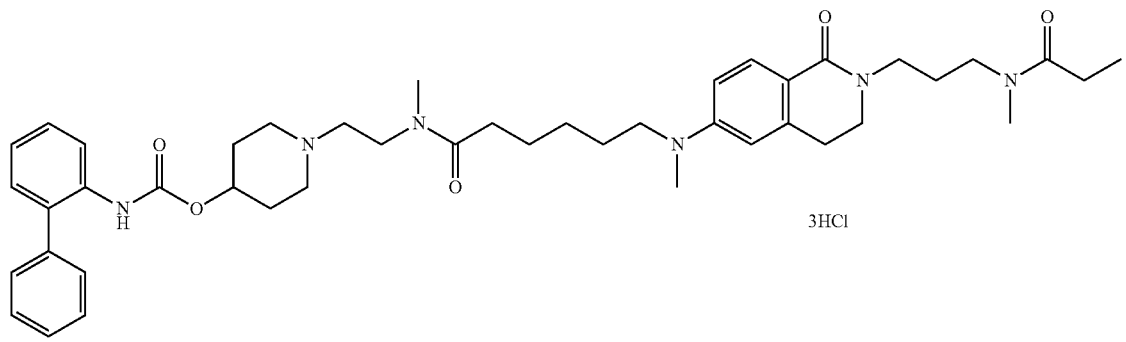

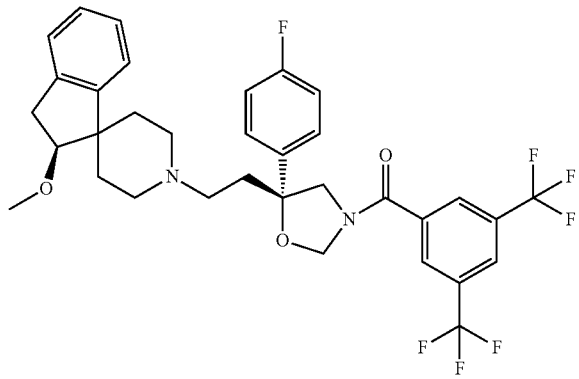

Example 62a

Benzyl (2-{3-([tert-butoxycarbonyl)(methyl)amino] propyl}-1-oxo-1,2,3,4-tetrahydroisoquinolin-6-yl) methylcarbamate The compound (535 mg, 1.41 mmol) obtained in Example 61c was dissolved in a mixed solvent (6 mL) of tetrahydrofuran and methanol (1:1), a 1 N aqueous sodium hydroxide cooling, and ethyl acetate was further added to separate the layers. The resulting organic layer was separated, washed with saturated sodium chloride solution, and then dried with anhydrous sodium sulfate, and the solvent was evaporated under reduced pressure. The residue was purified by silica gel column chromatography (hexane:ethyl acetate, 1:5, v/v) to give the title compound (320 mg; yield, 88%) as a colorless oily substance.

MS (ESI): m/z 382 (M+H)⁺ (form with Boc removed).

Example 62b tert-Butyl methyl{3-[6-(methylamino)-1-oxo-3,4-dihydroisoquinolin-2(1H)-yl]propyl}carbamate The compound (320 mg, 0.664 mmol) obtained in Example 62a was dissolved in ethanol (6 mL), 10% palladium-carbon (64 mg, 20% by weight) was added, and the mixture was stirred at room temperature under a hydrogen atmosphere for 5 hours. After the reaction was completed, the reaction mixture was filtered through celite, the filtrate was washed with ethanol, and the solvent was evaporated under reduced pressure. The residue was purified by NH silica gel column chromatography (ethyl acetate) to give the title compound (213 mg; yield, 92%) as a yellow oily substance.

$^1$H HMR (CDCl$_3$, 400 MHz): δ 1.4 (9H, s), 1.8-1.9 (2H, m), 2.8-2.9 (8H, m), 3.2-3.3 (2H, m), 3.5-3.6 (4H, m), 4.0-4.1 (2H, m), 6.3 (1H, s), 6.5 (1H, d, J=8.5 Hz), 7.9 (1H, d, J=8.5 Hz).

Example 62c

1-{2-[{6-[(2-{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}-1-oxo-1,2,3,4-tetrahydroisoquinolin-6-yl)(methyl)amino]hexanoyl}(methyl)amino]ethyl}piperidin-4-yl biphenyl-2-ylcarbamate trihydrochloride The compound (213 mg, 0.613 mmol) obtained in Example 62b and the compound obtained in Example 4g were used according to the methods described in Examples 45b and 61f to give the title compound (27 mg; yield, 23%) as a white solid.

MS (FAB): m/z 1373 (M+H)$^+$ (free form).

IR (KBr) ν max 3415, 2934, 1644, 1615, 1507, 1360, 1282, 1230, 1136, 752 cm$^{-1}$.

Example 63

1-{2-[{6-[(2-{-4-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]butanoyl}-1,2,3,4-tetrahydroisoquinolin-6-yl)amino]hexanoyl}(methyl)amino]ethyl}piperidin-4-yl biphenyl-2-ylcarbamate trihydrochloride

[Formula 68]

Example 63a tert-Butyl 6-({6-[(2-{4-[(biphenyl-2-ylcarbamoyl)oxy]piperidin-1-yl}ethyl)(methyl)amino]-6-oxohexyl}amino)-3,4-dihydroisoquinoline-2(1H)-carboxylate tert-Butyl 6-amino-3,4-dihydroisoquinoline-2(1H)-carboxylate (227 mg, 0.914 mmol) and the compound (638 mg, 1.37 mmol) obtained in Example 4g were used to give the title compound (122 mg; yield, 19%) as a colorless oily substance according to the method described in Example 45b.

MS (ESI): m/z 698 (M+H)+.

Example 63b 1-(2-{Methyl[6-(1,2,3,4-tetrahydroisoquinolin-6-ylamino)hexanoyl]amino}ethyl)piperidin-4-yl biphenyl-2-ylcarbamate The compound (122 mg, 0.175 mmol) obtained in Example 63a was used to give the title compound (94 mg; yield, 90%) as a colorless oily substance according to the method described in Example 6d.

MS (ESI): m/z 598 (M+H)+.

Example 63c

Methyl 4-(methylamino)butanoate hydrochloride 4-(Methylamino)butanoic acid hydrochloride (22.1 g, 144 mmol) was dissolved in methanol (560 mL), thionyl chloride (42 mL) was added under ice cooling, and then the mixture was stirred at room temperature for 24 hours. After the reaction was completed, the solvent was evaporated under reduced pressure, and the resulting white solid was washed with a mixed solvent of dichloromethane (30 mL) and hexane (300 mL) to give the title compound (21.2 g; yield, 88%) as a white solid.

$^1$H NMR (CDCl$_3$, 400 MHz): δ 2.13-2.29 (2H, m), 2.53 (2H, t, J=7.04 Hz), 2.66-2.79 (3H, m), 3.00-3.12 (2H, m), 3.69 (3H, s), 9.32-9.83 (2H, m).

MS (EI) m/z: 131 (M)+ (free form).

IR (KBr) ν$_{max}$ 2962, 1735, 1456, 1427, 1286, 1211, 1017, 895, 884, 752 cm$^{-1}$.

Example 63d

Methyl 4-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]butanoate The compound (240 mg, 1.44 mmol) obtained in Example 63c and the compound (200 mg, 0.288 mmol) obtained in Example 1j were used to give the title compound (172 mg; yield, 74%) as a colorless oily substance according to the method described in Example 12a.

MS (FAB) m/z: 808 (M+H)+.

IR (KBr) ν$_{max}$ 2930, 1738, 1650, 1437, 1359, 1281, 1178, 1138, 758, 682 cm$^{-1}$.

Example 63e

4-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]butanoic acid The compound (172 mg, 0.213 mmol) obtained in Example 63d was dissolved in a mixed solvent of methanol (12 mL) and water (6 mL), then a 1 N aqueous sodium hydroxide solution (0.84 mL, 0.84 mmol) was added at room temperature, and the mixture was stirred at the same temperature for 4 hours. After the reaction was completed, 1 N hydrochloric acid was added, and the organic layer was extracted with dichloromethane 3 times. The organic layer was dried with anhydrous sodium sulfate, and the solvent was evaporated under reduced pressure. The resulting residue was purified by silica gel column chromatography (elution solvents, hexane:ethyl acetate:methanol=9:1:0→0:10:0→0:8:2, v/v/v) to give the title compound (83 mg; yield, 49%).

MS (FAB) m/z: 794 (M+H)+.

IR (KBr) ν$_{max}$ 2934, 1652, 1433, 1360, 1282, 1139, 907, 848, 759, 682 cm$^{-1}$.

Example 63f

1-{2-[{6-[(2-{4-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]butanoyl}-1,2,3,4-tetrahydroisoquinolin-6-yl)amino]hexanoyl}(methyl)amino]ethyl}piperidin-4-yl biphenyl-2-ylcarbamate trihydrochloride The compound (83 mg, 0.105 mmol) obtained in Example 63e and the compound (93 mg, 0.157 mmol) obtained in Example 63b were used according to the descriptions in Examples 43c and 41c to give the title compound (77 mg; yield, 50%) as a yellow solid.

MS (FAB): m/z 1373 (M+H)+ (free form).

IR (KBr) ν max 3414, 2938, 1643, 1438, 1359, 1281, 1224, 1174, 1137, 752 cm$^{-1}$.

Example 64

1-{2-[{6-[(2-{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}-1,2,3,4-tetrahydroisoquinolin-6-yl)amino]hexanoyl}(methyl)amino]ethyl}piperidin-4-yl biphenyl-2-ylcarbamate tetrahydrochloride

[Formula 69]

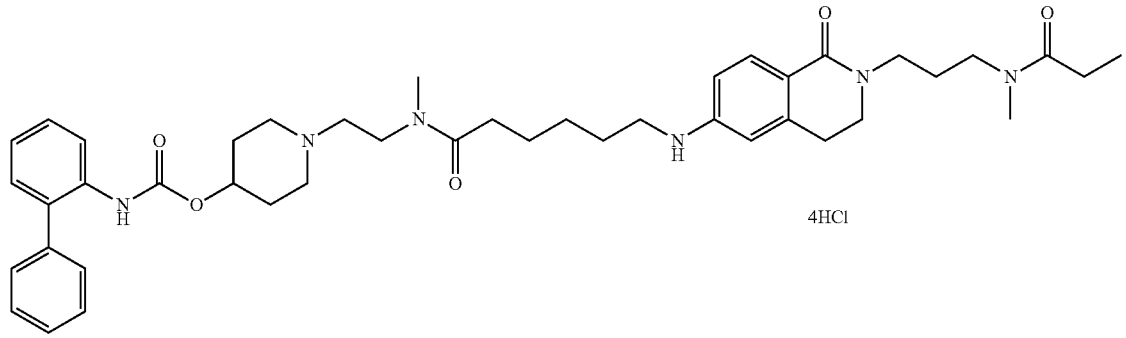

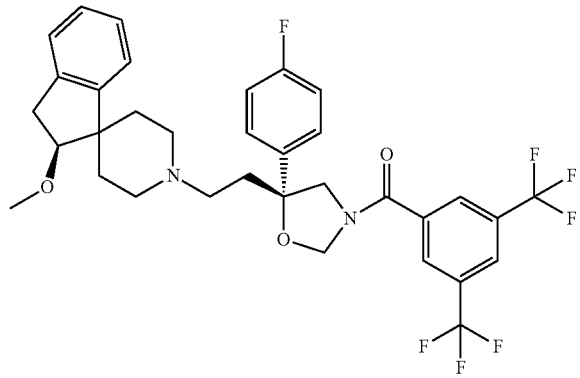

Example 64a

1-{2-[{6-[(2-{3-([tert-Butoxycarbonyl)(methyl)amino]propyl}-1,2,3,4-tetrahydroisoquinolin-6-yl)amino]hexanoyl}(methyl)amino]ethyl}piperidin-4-yl biphenyl-2-ylcarbamate The compound (47 mg, 78.6 μmol) obtained in Example 63b and tert-butyl methyl(3-oxopropyl)carbamate (Bioorg. Med. Chem., 12, 19, 2004, 5147-5160) (18 mg, 94.3 μmol) were used to give the title compound (48 mg; yield, 79%) as a colorless oily substance according to the method described in Example 41a.

Example 64b 1-(2-{Methyl[6-({2-[3-(methylamino)propyl]-1,2,3,4-tetrahydroisoquinolin-6-yl}amino)hexanoyl]amino}ethyl)piperidin-4-yl biphenyl-2-ylcarbamate The compound (48 mg, 62.4 μmol) obtained in Example 64a was used to give the title compound (37 mg; yield, 88%) as a colorless oily substance according to the method described in Example 6d.

Example 64c

1-{2-[{6-[(2-{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}-1,2,3,4-tetrahydroisoquinolin-6-yl)amino]hexanoyl}(methyl)amino]ethyl}piperidin-4-yl biphenyl-2-ylcarbamate tetrahydrochloride The compound (37 mg, 0.055 mmol) obtained in Example 64b and the compound (58 mg, 0.083 mmol) obtained in Example 1j were used to give a free form (37 mg; yield, 33%) of the title compound as a white solid according to the method described in Example 11e.

The resulting free compound (37 mg, 27.5 μmol) was used to give the title compound (25 mg; yield, 61%) as a white solid according to the method described in Example 41c.

MS (FAB): m/z 1345 (M+H)$^+$ (free form).

IR (KBr) v max 3420, 2934, 1643, 1512, 1438, 1360, 1282, 1177, 1137, 753 cm$^{-1}$.

Example 65

1-(2-{[3-(1-{4-[{3-[({[(2S)-1-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}piperidin-4-yl)propanoyl](methyl)amino}ethyl)piperidin-4-yl biphenyl-2-ylcarbamate trihydrochloride

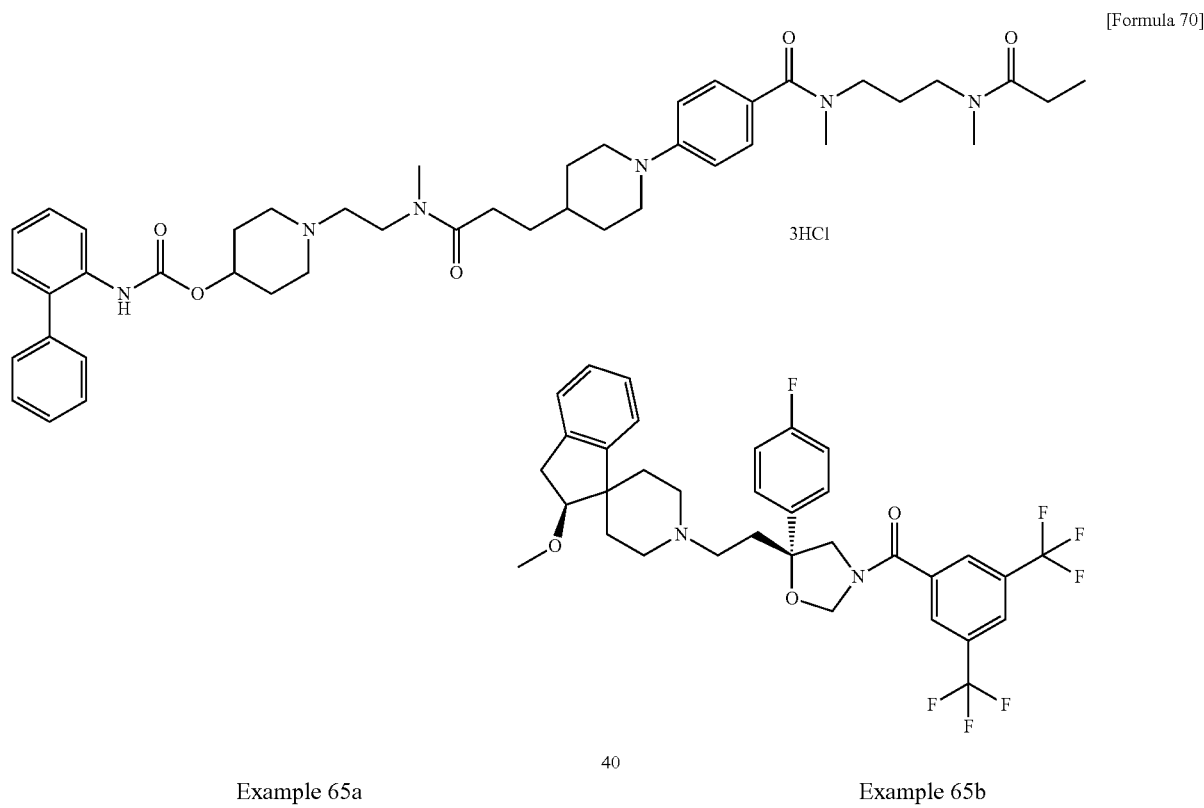

[Formula 70]

Example 65a tert-Butyl 4-[4-(3-methoxy-3-oxopropyl)piperidin-1-yl]benzoate

Methyl 3-(piperidin-4-yl)propanoate (WO2004/92124 A2) (206 mg, 1.11 mmol) was dissolved in N,N-dimethylformamide (10 mL), tert-butyl 4-fluorobenzoate (141 mg, 1.11 mmol) and potassium carbonate (100 mg, 1.11 mmol) were added, and the mixture was stirred at 120° C. under a nitrogen atmosphere for 16 hours. After the reaction was completed, a saturated aqueous sodium hydrogencarbonate solution was added to the reaction mixture under ice cooling, and ethyl acetate was further added to separate the layers. The resulting organic layer was separated, washed with saturated sodium chloride solution, and then dried with anhydrous sodium sulfate, and the solvent was evaporated under reduced pressure. The residue was purified by NH silica gel column chromatography (hexane:ethyl acetate, 10:1, v/v) to give the title compound (126 mg; yield, 31%) as a colorless oily substance.

$^1$H HMR (CDCl$_3$, 400 MHz): δ 1.2-1.4 (2H, m), 1.5-1.6 (10H, m), 1.6-1.7 (2H, m), 1.7-1.8 (2H, m), 2.4-2.5 (2H, m), 2.7-2.8 (2H, m), 3.7 (3H, s), 3.8-3.9 (2H, m), 6.8-6.9 (2H, m), 7.7-7.8 (1H, m), 7.8-7.9 (2H, m).

Example 65b tert-Butyl 4-(4-{3-[(2-{4-[(biphenyl-2-ylcarbamoyl)oxy]piperidin-1-yl}ethyl)(methyl)amino]-3-oxopropyl}piperidin-1-yl)benzoate The compound (126 mg, 0.349 mmol) obtained in Example 65a was dissolved in methanol (6 mL), a 1 N aqueous sodium hydroxide solution (0.697 mL) was added under ice cooling, and the mixture was stirred at 50° C. for 16 hours. After the reaction was completed, a 1 N aqueous hydrochloric acid solution (1.04 mL, 1.04 mmol) was added under ice cooling, and the solvent was evaporated under reduced pressure. The resulting residue was used to give the title compound (178 mg; yield, 75%) as a colorless oily substance according to the method described in Example 12a.

Example 65c 1-(2-{[3-(1-{4-[{3-([tert-Butoxycarbonyl)(methyl)amino]propyl}(methyl)carbamoyl]phenyl}piperidin-4-yl)propanoyl](methyl)amino}ethyl)piperidin-4-yl biphenyl-2-ylcarbamate A 4 N hydrochloric acid-1,4-dioxane solution (4 mL) was added to the compound (178 mg, 0.261 mmol) obtained in Example 65b, and the mixture was stirred under a nitrogen atmosphere for 16 hours. After the reaction was completed, the solvent was evaporated under reduced pressure.

The residue was dissolved in dichloromethane (5 mL), triethylamine (1 mL) and pivaloyl chloride (34 μL, 0.274 mmol) were added under ice cooling, and the mixture was stirred at the same temperature under a nitrogen atmosphere for 15 minutes. Subsequently, a solution of tert-butyl methyl [3-(methylamino)propyl]carbamate (63 mg, 0.313 mmol) in dichloromethane (2 mL) was added dropwise under ice cooling, and the mixture was stirred at room temperature under a nitrogen atmosphere for 16 hours. After the reaction was completed, a saturated aqueous sodium hydrogencarbonate solution was added to the reaction mixture under ice cooling, and ethyl acetate was further added to separate the layers. The resulting organic layer was separated, washed with saturated sodium chloride solution, and then dried with anhydrous sodium sulfate, and the solvent was evaporated under reduced pressure. The residue was purified by NH silica gel column chromatography (hexane:ethyl acetate, 1:9, v/v) to give the title compound (161 mg; yield, 57%) as a colorless oily substance.

MS (ESI): m/z 797 (M+H)$^+$.

Example 65d 1-(2-{[3-(1-{4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}piperidin-4-yl)propanoyl](methyl)amino}ethyl)piperidin-4-yl biphenyl-2-ylcarbamate trihydrochloride The compound (161 mg, 0.175 mmol) obtained in Example 65c was used to give a Boc-deprotected compound 1-[2-(methyl{3-[1-(4-{methyl[3-(methylamino)propyl]carbamoyl}phenyl)piperidin-4-yl]propanoyl}amino)ethyl]piperidin-4-yl biphenyl-2-ylcarbamate (129 mg; yield, 92%) as a colorless oily substance according to the method described in Example 6d.

The resulting Boc-deprotected compound was used to give a free form (201 mg; yield, 79%) of the title compound as a white solid according to the method described in Example 11e.

The resulting free compound (175 mg, 0.146 mmol) was used to give the title compound (150 mg; yield, 69%) as a white solid according to the method described in Example 41c.

MS (FAB): m/z 1372 (M+H)$^+$.

IR (KBr) ν max 3424, 2928, 1737, 1639, 1450, 1282, 1225, 1181, 1139, 755 cm$^{-1}$.

Example 66

1-(2-{[4-(1-{4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}methyl)carbamoyl]phenyl}piperidin-4-yl)butanoyl](methyl)amino}ethyl)piperidin-4-yl biphenyl-2-ylcarbamate trihydrochloride

[Formula 71]

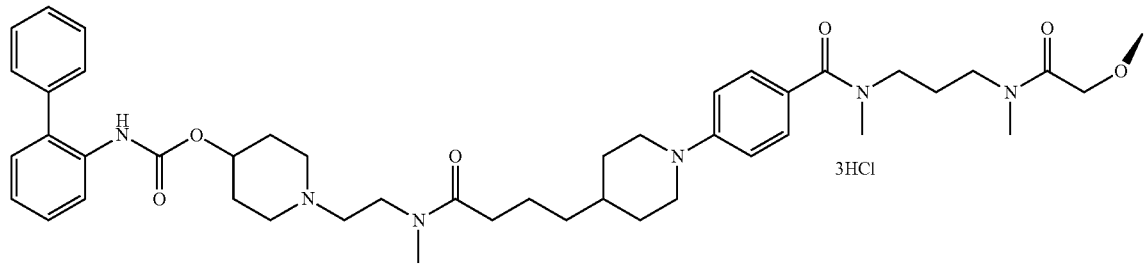

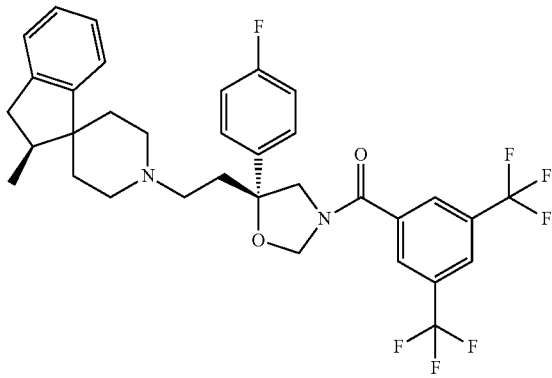

Methyl 4-(piperidin-4-yl)butanoate (200 mg, 1.11 mmol) was used to give the title compound (175 mg; yield, 13%) as a white solid according to the method described in Example 65.

MS (FAB): m/z 1387 (M+H)+ (free form).

IR (KBr) ν max 3423, 2935, 1726, 1644, 1360, 1282, 1225, 1181, 1138, 753 cm$^{-1}$.

Example 67

4-[({4-[(2-{4-[(Biphenyl-2-ylcarbamoyl)oxy]piperidin-1-yl}ethyl)(methyl)carbamoyl]benzyl}amino)methyl]phenyl 4-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]butanoate IR (KBr) ν$_{max}$ 1718, 1518, 1444, 1282, 1251, 1109, 820, 783, 759, 706 cm$^{-1}$.

Example 67b

1-{2-[(4-{([tert-Butoxycarbonyl)(4-hydroxybenzyl)amino]methyl}benzoyl)(methyl)amino]ethyl}piperidin-4-yl biphenyl-2-ylcarbamate The compound (3.0 g, 11 mmol) obtained in Example 67a was dissolved in a mixed solvent of 1,4-dioxane (60 mL) and water (11 mL), then triethylamine (1.69 mL, 12.2 mmol) and di-tert-butyl dicarbonate (2.65 g, 12.2 mmol) were added at room temperature, and the mixture was stirred at room temperature for 6 hours. After the reaction was completed, the solvent was evaporated under reduced pressure, dichloromethane was added to the resulting residue, and the residue

[Formula 72]

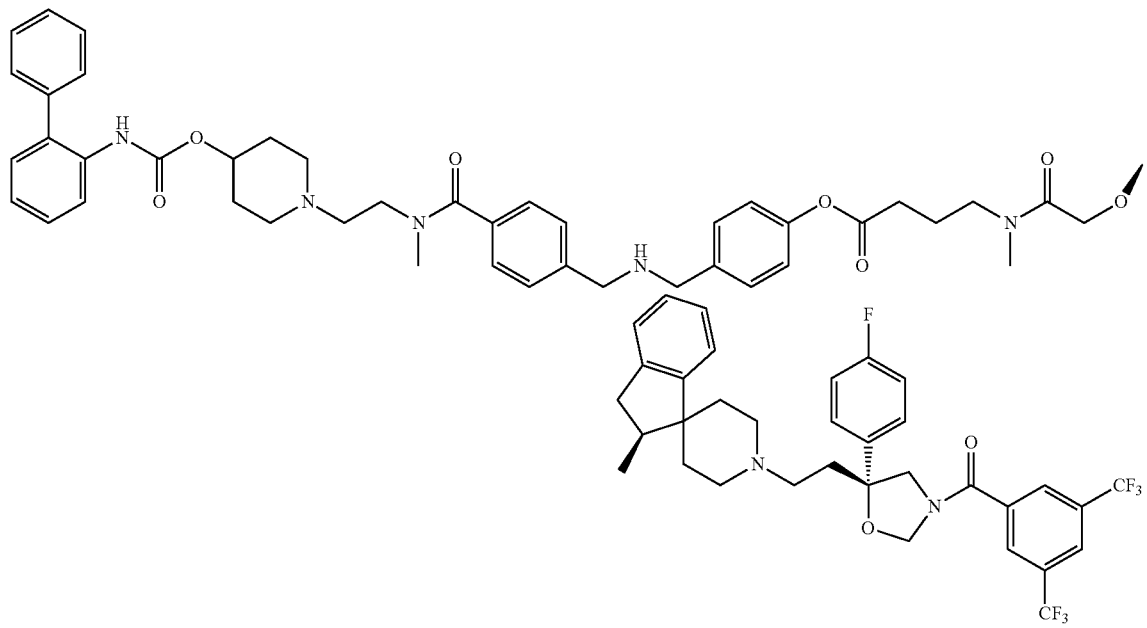

Example 67a

Methyl 4-{[(4-hydroxybenzyl)amino]methyl}benzoate

Methyl 4-(Aminomethyl)benzoate (6.88 g, 34.2 mmol) and 4-hydroxybenzaldehyde (4.60 g, 37.7 mmol) were dissolved in ethanol (300 mL), the mixture was heated to reflux for 6 hours, sodium borohydride (2.07 g, 54.7 mmol) was added at room temperature, and the mixture was stirred at room temperature for 1 hour. After the reaction was completed, a saturated aqueous sodium hydrogencarbonate solution was added, and the mixture was extracted with dichloromethane. The resulting organic layer was washed with saturated sodium chloride solution and dried with anhydrous sodium sulfate, and the solvent was evaporated under reduced pressure. The resulting residue was reprecipitated with dichloromethane-hexane to give the title compound (4.90 g; yield, 52%) as a white solid.

MS (EI) m/z: 271 (M)+.

was washed with a 1 N aqueous hydrochloric acid solution, further washed with water, and then dried with anhydrous sodium sulfate. The solvent was evaporated under reduced pressure, the resulting residue was dissolved in a mixed solvent of methanol (55 mL) and water (55 mL), a 1 N aqueous sodium hydroxide solution (16.7 mL, 16.7 mmol) was added at room temperature, and the mixture was stirred at the same temperature for 1 hour and at 50° C. for 19 hours. After the reaction was completed, 1 N hydrochloric acid was added, and the mixture was extracted with ethyl acetate. The solvent was evaporated under reduced pressure, and the resulting precipitate was washed with a mixed solvent of dichloromethane and hexane to give crude 4-{([tert-butoxycarbonyl)(4-hydroxybenzyl)amino]methyl}benzoic acid (2.75 g; yield, 69%).

The resulting crude product (498 mg, 1.39 mmol) and 1-[2-(methylamino)ethyl]piperidin-4-yl biphenyl-2-ylcarbamate (448 mg, 1.26 mmol) were used to give a crude product of the title compound according to the method described in Example 41a. The resulting crude product was purified by reverse phase liquid chromatography (XTerra Prep MS C18 OBD, 5 μm, 30×100 mm) (acetonitrile:0.1% aqueous ammonium acetate solution (w/w), 10:90→100:0, v/v) to give the title compound (318 mg; yield, 36%).

MS (FAB) m/z: 693 (M+H)⁺.

IR (KBr) ν$_{max}$ 2933, 1734, 1691, 1612, 1517, 1238, 1163, 1045, 751, 704 cm⁻¹.

Example 67c

4-{[{4-[(2-{4-[(Biphenyl-2-ylcarbamoyl)oxy]piperidin-1-yl}ethyl)(methyl)carbamoyl]benzyl}tert-butoxycarbonyl)amino]methyl}phenyl 4-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]butanoate The compound (137 mg, 0.199 mmol) obtained in Example 67b and the compound (158 mg, 0.199 mmol) obtained in Example 63e were dissolved in dichloromethane (4 mL), 1-ethyl-3-(3-dimethylaminopropyl)carbodiimide hydrochloride (56.9 mg, 0.298 mmol) was added at room temperature, and the mixture was stirred at the same temperature for 3 hours. After the reaction was completed, a saturated aqueous sodium hydrogencarbonate solution was added, and the mixture was extracted with dichloromethane. The resulting organic layer was dried with anhydrous sodium sulfate, and the solvent was evaporated under reduced pressure. The resulting residue was purified by NH silica gel column chromatography purified to give a crude product of the title compound. The crude product was purified by reverse phase liquid chromatography (XTerra Prep MS C18 OBD, 5 μm, 30×100 mm) (acetonitrile:0.1% aqueous ammonium acetate solution [w/w], 70:30→80:20, v/v) to give the title compound (269 mg; yield, 92%) as a white solid.

MS (FAB) m/z: 1468 (M+H)⁺.

IR (KBr) ν$_{max}$ 2931, 1693, 1646, 1510, 1359, 1281, 1140, 848, 756, 705 cm⁻¹.

Example 67d

4-[({4-[(2-{4-[(Biphenyl-2-ylcarbamoyl)oxy]piperidin-1-yl}ethyl)(methyl)carbamoyl]benzyl}amino)methyl]phenyl 4-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]butanoate The compound (220 mg, 0.149 mmol) obtained in Example 67c was used to give a crude product of the title compound according to the method described in Example 6d. The resulting crude product was purified by reverse phase liquid chromatography (XTerra Prep MS C18 OBD, 5 μm, 30×100 mm) (acetonitrile:0.1% aqueous ammonium acetate solution [w/w], 10:90→100:0, v/v) to give the title compound (33 mg; yield, 16%) as a light yellow solid.

MS (FAB) m/z: 1368 (M+H)⁺.

IR (KBr) ν$_{max}$ 2929, 1731, 1645, 1510, 1359, 1281, 1139, 847, 756, 704 cm⁻¹.

Example 68

4-[({4-[(2-{4-[(Biphenyl-2-ylcarbamoyl)oxy]piperidin-1-yl}ethyl)(methyl)carbamoyl]benzyl}amino)methyl]phenyl 7-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]heptanoate

[Formula 73]

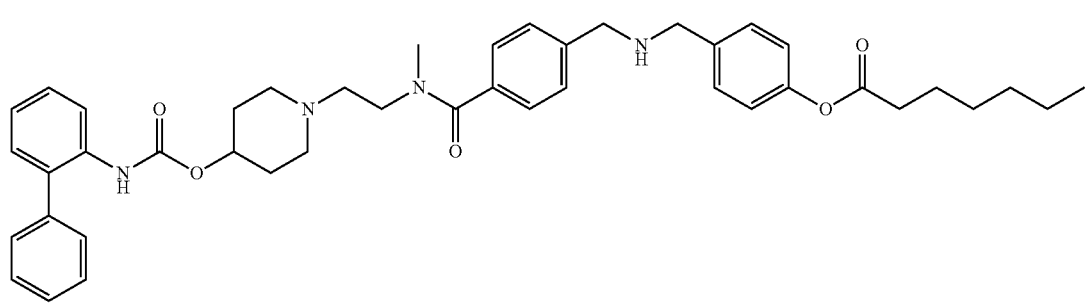

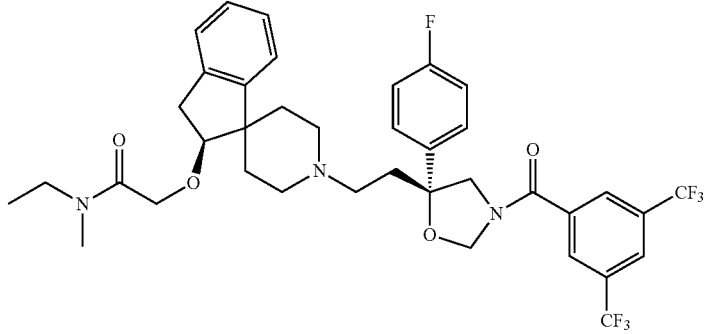

Example 68a

Ethyl 7-(methylamino)heptanoate

Ethyl 7-bromoheptanoate (6.00 g, 25.3 mmol) was dissolved in acetonitrile (30 mL), N-methyl-benzylamine (6.53 mL, 50.6 mmol) and potassium carbonate (13.99 g, 101 mmol) were added at room temperature, and the mixture was heated to reflux for 6 hours. The mixture was left to stand for cooling, and the reaction mixture was diluted with ethyl acetate and washed with water. The organic layer was dried with anhydrous magnesium sulfate, and then the solvent was evaporated under reduced pressure to give crude ethyl 7-[benzyl(methyl)amino]heptanoate (11.5 g) as a light yellow oily substance. The resulting crude product was dissolved in 60 mL of ethanol, 10% palladium-carbon (0.72 g) was added, and the mixture was stirred at 60° C. under a hydrogen atmosphere for 16 hours. The mixture was left to stand for cooling, insoluble matter was removed by filtration, and the solvent of the filtrate was evaporated under reduced pressure. The residue was purified by NH silica gel chromatography (ethyl acetate:methanol=10:0→10/1, v/v) to give the title compound (4.67 g; yield, 98%) as a colorless oily substance.

$^1$H HMR (CDCl$_3$, 400 MHz): δ 1.25 (3H, t, J=7.0 Hz), 1.30-1.70 (8H, m), 2.29 (2H, t, J=7.4 Hz), 2.43 (3H, s), 2.56 (2H, t, J=7.4 Hz), 4.12 (2H, q, J=7.4 Hz).

Example 68b

Ethyl 7-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]heptanoate The compound (625 mg, 0.901 mmol) obtained in Example 1j was dissolved in dichloromethane (9 mL), triethylamine (0.376 mL, 2.70 mmol) and isobutyl chloroformate (183 μL, 1.35 mmol) were added under ice cooling, and the mixture was stirred at the same temperature. The compound (467 mg, 2.70 mmol) obtained in Example 68a was added under ice cooling, and then the temperature was increased to room temperature. After the reaction was completed, a saturated aqueous sodium hydrogencarbonate solution was added, and the mixture was extracted with dichloromethane (×2). The resulting organic layer was dried with anhydrous sodium sulfate, and the solvent was evaporated under reduced pressure. The resulting residue was purified by NH silica gel column chromatography (a elution solvent, ethyl acetate) to give the title compound (615 mg; yield, 79%).

MS (FAB) m/z: 864 (M+H)$^+$.

IR (ATR) $v_{max}$ 2932, 1731, 1645, 1358, 1279, 1176, 1136, 906, 847, 757 cm$^{-1}$.

Example 68c

7-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]heptanoic acid The compound (595 mg, 0.901 mmol) obtained in Example 68b was dissolved in tetrahydrofuran (12 mL), a 1 N aqueous sodium hydroxide solution (1.03 mL, 1.03 mmol), water (0.3 mL) and methanol (4 drops) were added, and the mixture was stirred at room temperature. After the reaction was completed, 1 N hydrochloric acid and water were added, the mixture was extracted with methylene chloride, and the resulting organic layer was dried with anhydrous sodium sulfate. The solvent was evaporated under reduced pressure, and the resulting residue was purified by reverse phase liquid chromatography (XTerra Prep MS C18 OBD, 5 μm, 30×100 mm) (acetonitrile:0.1% aqueous ammonium acetate solution, 10:90→100:0, v/v) to give the title compound (233 mg; yield, 40%).

MS (FAB) m/z: 836 (M+H)$^+$.

IR (KBr) $v_{max}$ 2933, 1652, 1511, 1433, 1359, 1281, 1181, 1139, 758, 682 cm$^{-1}$.

Example 68d

4-[({4-[(2-{4-[(Biphenyl-2-ylcarbamoyl)oxy]piperidin-1-yl}ethyl)(methyl)carbamoyl]benzyl}amino)methyl]phenyl 7-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino] heptanoate The compound (120 mg, 0.173 mmol) obtained in Example 67b and the compound (159 mg, 0.190 mmol) obtained in Example 68c were dissolved in dichloromethane (3.4 mL), 1-ethyl-3-(3-dimethylaminopropyl)carbodiimide hydrochloride (50 mg, 0.26 mmol) was added, and the mixture was stirred overnight at room temperature. After the reaction was completed, the solvent was evaporated under reduced pressure, and the resulting residue was purified by NH silica gel column chromatography (ethyl acetate:methanol=10:0→10:1, v/v) to give crude 4-{[{4-[(2-{4-[(biphenyl-2-ylcarbamoyl)oxy]piperidin-1-yl}ethyl)(methyl)carbamoyl]benzyl}tert-butoxycarbonyl)amino]methyl}phenyl 7-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino] heptanoate (78 mg; yield, 30%).

The resulting crude product (78 mg, 0.052 mmol) was dissolved in 1,4-dioxane (4 mL), a 4 N hydrochloric acid-dioxane solution (2 mL) was added, and the mixture was stirred at room temperature for 2 hours. After the reaction was completed, toluene and acetonitrile were added to the reaction solution, and the solvent was evaporated under reduced pressure. The resulting residue was purified by NH silica gel column chromatography (elution solvents, hexane:ethyl acetate:methanol=5:5:0→0:10:0→0:8:2, v/v/v) and by reverse phase liquid chromatography (XTerra Prep MS C18 OBD, 5 μm, 30×100 mm) (acetonitrile:0.1% aqueous ammonium acetate solution, 60:40→100:0, v/v) to give the title compound (52 mg; yield, 71%) as a light yellow solid.

MS (FAB) m/z: 1410 (M+H)$^+$.

IR (KBr) $v_{max}$ 2929, 1731, 1644, 1510, 1359, 1281, 1139, 847, 755, 704 cm$^{-1}$.

Example 69

4-[({4-[(2-{4-[(Biphenyl-2-ylcarbamoyl)oxy]piperi-
din-1-yl}ethyl)(methyl)carbamoyl]benzyl}amino)
methyl]phenyl 6-[({[(2S)-1'-{2-[(5R)-3-[3,5-bis(trif-
luoromethyl)benzoyl]-5-(4-fluorophenyl)-1,3-
oxazolidin-5-yl]ethyl}-2,3-dihydrospiro[indene-1,4'-
piperidin]-2-yl]oxy}acetyl)(methyl)amino]hexanoate

[Formula 74]

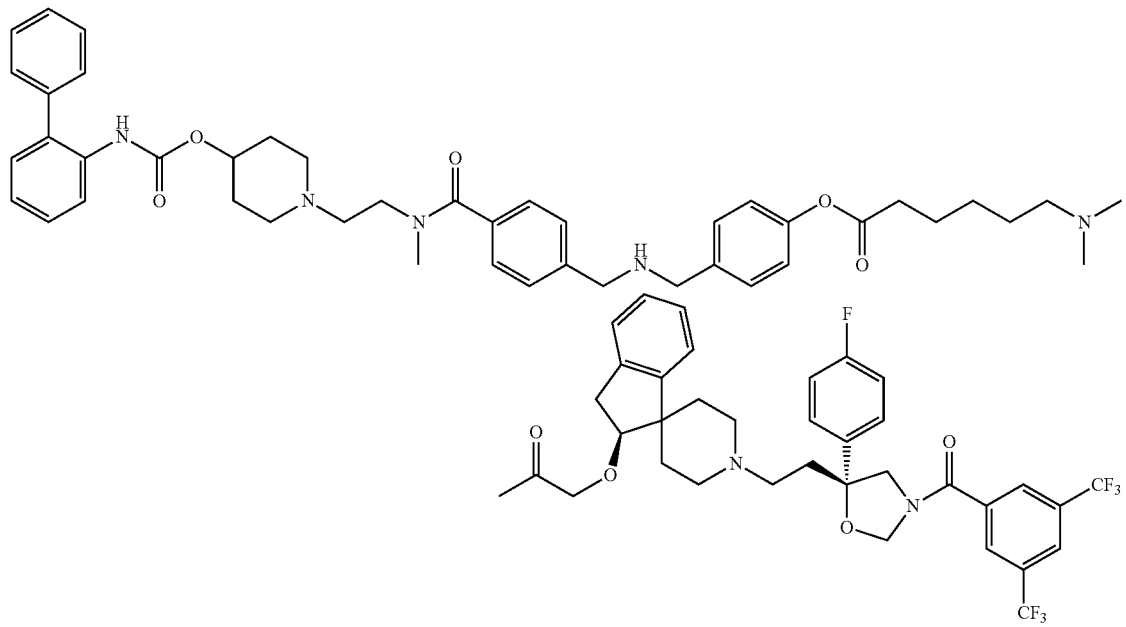

Example 69a

Ethyl 6-(methylamino)hexanoate

Ethyl 6-bromohexanoate (6.00 g, 26.9 mmol) and benzyl-methylamine (6.52 g, 53.8 mmol) were used to give the title compound (4.65 g; yield, 99%) as a colorless oily substance according to the method described in Example 68a.

$^1$H HMR (CDCl$_3$, 400 MHz): δ 1.25 (3H, t, J=7.0 Hz), 1.28-1.70 (6H, m), 2.30 (2H, t, J=7.4 Hz), 2.43 (3H, s), 2.58 (2H, t, J=7.4 Hz), 4.12 (2H, q, J=7.4 Hz).

Example 69b

Ethyl 6-[({[(2S)-1'-{2-[(5R)-3-[3,5-bis(trifluorom-
ethyl)benzoyl]-5-(4-fluorophenyl)-1,3-oxazolidin-5-
yl]ethyl}-2,3-dihydrospiro[indene-1,4'-piperidin]-2-
yl]oxy}acetyl)(methyl)amino]hexanoate The compound (272 mg, 1.56 mmol, 3.0 eq.) obtained in Example 69a was used to give the title compound (358 mg; yield, 80%) according to the method described in Example 68b.

MS (FAB) m/z: 850 (M+H)$^+$.

IR (ATR) ν$_{max}$ 2934, 1729, 1642, 1357, 1278, 1174, 1134, 906, 838, 750 cm$^{-1}$.

Example 69c

7-[({[(2S)-1-{2-[(5R)-3-[3,5-Bis(trifluoromethyl)
benzoyl]-5-(4-fluorophenyl)-1,3-oxazolidin-5-yl]
ethyl}-2,3-dihydrospiro[indene-1,4'-piperidin]-2-yl]
oxy}acetyl)(methyl)amino]heptanoic acid The compound (280 mg, 0.33 mmol) obtained in Example 69b was used to give a crude title compound according to the method described in Example 68c. The resulting crude product was purified by reverse phase liquid chromatography (XTerra Prep MS C18 OBD, 5 μm, 30×100 mm) (acetonitrile: 0.1% aqueous ammonium acetate solution, 10:90→30:70→50:50→100:0, v/v) to give the title compound (100 mg; yield, 37%) as a white solid.

MS (FAB) m/z: 822 (M+H)$^+$.

IR (KBr) ν$_{max}$ 2934, 1651, 1359, 1281, 1181, 1139, 848, 758, 682 cm$^{-1}$.

Example 69d

4-[({4-[(2-{4-[(Biphenyl-2-ylcarbamoyl)oxy]piperi-
din-1-yl}ethyl)(methyl)carbamoyl]benzyl}amino)
methyl]phenyl 6-[({[(2S)-1'-{2-[(5R)-3-[3,5-bis(trif-
luoromethyl)benzoyl]-5-(4-fluorophenyl)-1,3-
oxazolidin-5-yl]ethyl}-2,3-dihydrospiro[indene-1,4'-
piperidin]-2-yl]oxy}acetyl)(methyl)amino]hexanoate The compound (76 mg, 0.11 mmol) obtained in Example 67b and the compound (90 mg, 0.11 mmol) obtained in

195

Example 69c were used to give the title compound (27 mg; yield, 17%) as a light yellow solid according to the method described in Example 68d.

MS (FAB) m/z: 1396 (M+H)$^+$.

IR (KBr) $v_{max}$ 2929, 1731, 1644, 1510, 1359, 1281, 1139, 847, 756, 705 cm$^{-1}$.

Example 70

4-[({4-[(2-{4-[(Biphenyl-2-ylcarbamoyl)oxy]piperidin-1-yl}ethyl)(methyl)carbamoyl]benzyl}amino)methyl]phenyl N-({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)-N-methylglycinate

196

Example 70b

N-({[(2S)-1-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)-N-methylglycine The compound (400 mg, 0.513 mmol) obtained in Example 70a was used to give the title compound (353 mg; yield, 90%) as a white solid according to the method described in Example 63e.

MS (FAB) m/z: 766 (M+H)$^+$.

IR (KBr) $v_{max}$ 2934, 1738, 1657, 1360, 1282, 1182, 1139, 848, 759, 682 cm$^{-1}$.

[Formula 75]

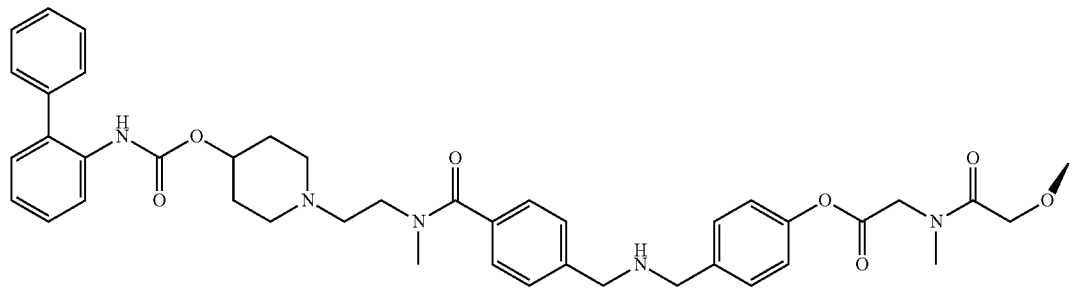

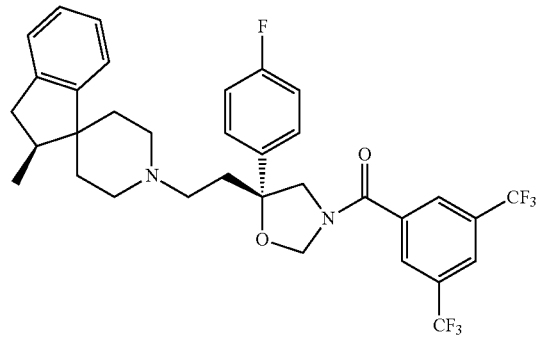

Example 70a

Methyl N-({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)-N-methylglycinate Methyl N-methylglycinate hydrochloride (178 mg, 1.28 mmol) was used to give title compound (454 mg; yield, 68%) according to the method described in Example 68b.

MS (FAB) m/z: 780 (M+H)$^+$.

IR (KBr) $v_{max}$ 2928, 1752, 1653, 1359, 1282, 1139, 907, 848, 758, 682 cm$^{-1}$.

Example 70c

4-[({4-[(2-{4-[(Biphenyl-2-ylcarbamoyl)oxy]piperidin-1-yl}ethyl)(methyl)carbamoyl]benzyl}amino)methyl]phenyl N-({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)-N-methylglycinate The compound (100 mg, 0.145 mmol) obtained in Example 67b and the compound (121 mg, 0.159 mmol) obtained in Example 70b were used to give the title compound (75 mg; yield, 32%) as a light yellow solid according to the method described in Example 68d.

MS (FAB) m/z: 1340 (M+H)$^+$.

IR (KBr) $v_{max}$ 2929, 1730, 1650, 1510, 1359, 1281, 1140, 847, 756, 705 cm$^{-1}$.

Example 71

4-[({4-[(2-{4-[(Biphenyl-2-ylcarbamoyl)oxy]piperidin-1-yl}ethyl)(methyl)carbamoyl]benzyl}amino)methyl]phenyl N-({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)-N-methyl-β-alaninate

[Formula 76]

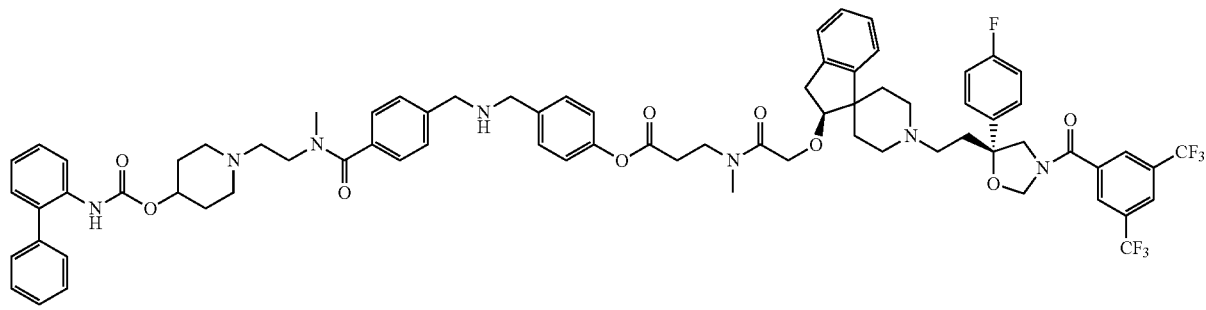

Example 71a

Methyl N-({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)-N-methyl-β-alaninic acid Methyl N-methyl-β-alaninate hydrochloride (199 mg, 1.30 mmol) was used to give the title compound (428 mg; yield, 63%) according to the method described in Example 68b.
MS (ESI) m/z: 794 (M+H)$^+$.

Example 71b

N-({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)-N-methyl-β-alanine The compound (415 mg, 0.523 mmol) obtained in Example 71a was used to give the title compound (369 mg; yield, 91%) as a white solid according to the method described in Example 63e.
MS (ESI) m/z: 780 (M+H)$^+$.
IR (KBr) $v_{max}$ 2938, 1728, 1654, 1511, 1360, 1282, 1179, 1139, 907, 848, 682 cm$^{-1}$.

Example 71c

4-[({4-[(2-{4-[(Biphenyl-2-ylcarbamoyl)oxy]piperidin-1-yl}ethyl)(methyl)carbamoyl]benzyl}amino)methyl]phenyl N-({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)-N-methyl-β-alaninate The compound (105 mg, 0.152 mmol) obtained in Example 67b and the compound (153 mg, 0.197 mmol) obtained in Example 71b were used to give the title compound (92 mg; yield, 76%) as a light yellow solid according to the method described in Example 68d.
MS (FAB) m/z: 1354 (M+H)$^+$.
IR (KBr) $v_{max}$ 2929, 1730, 1646, 1510, 1359, 1281, 1139, 847, 756, 704 cm$^{-1}$.

Example 72

1-(2-{[6-({4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}amino)hexanoyl](methyl)amino}ethyl)piperidin-4-yl biphenyl-2-ylcarbamate

[Formula 77]

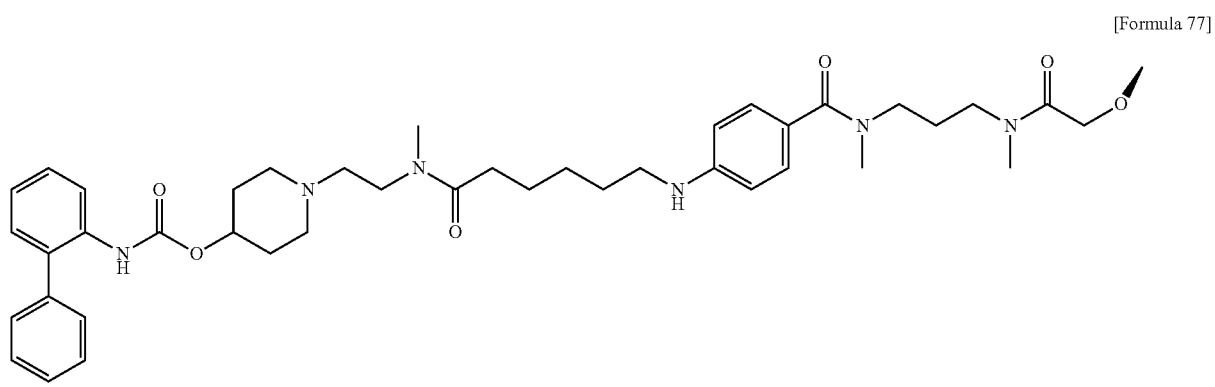

-continued

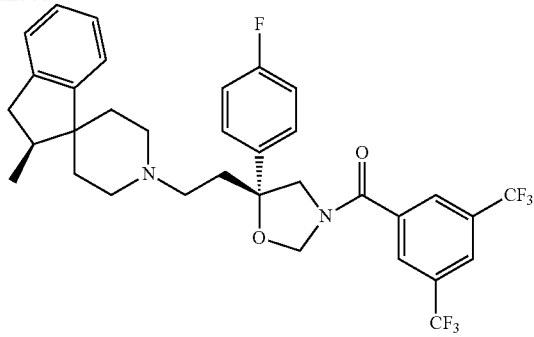

The compound (350 mg, 0.545 mmol) obtained in Example 15c was dissolved in 1,4-dioxane (10 mL), a 4 N hydrochloric acid-dioxane solution (1.36 mL, 5.44 mmol) was added, then methanol (1 mL) was added, and the mixture was stirred at room temperature for 1 hour, at 50° C. for 4 hours, and at 70° C. for 2 hours. After the reaction was completed, toluene was added, and the solvent was evaporated under reduced pressure to give a dihydrochloride of crude 4-({6-[(2-{4-[(biphenyl-2-ylcarbamoyl)oxy]piperidin-1-yl}ethyl)(methyl)amino]-6-oxohexyl}amino)benzoic acid. The resulting crude carboxylic acid compound and the compound (385 mg, 0.495 mmol) obtained in Example 1k were dissolved in dichloromethane (15 mL), triethylamine (151 μL, 1.09 mmol) and 4-(dimethylamino)pyridine (3.0 mg) were added, and the mixture was stirred at room temperature for 30 minutes. The reaction mixture was evaporated under reduced pressure, and the resulting residue was purified by NH silica gel column chromatography (n-hexane:ethyl acetate:methanol=1:1:0→0:1:0→0:9:1, v/v/v) to give a crude title compound (670 mg). The resulting crude title compound was purified by reverse phase preparative column chromatography (Waters; XTerra Prep MS C18 OBD, 5 μm, 30×100 mm) (acetonitrile:0.1% aqueous ammonium acetate solution=10:90→100:0, v/v) to give the title compound (59 mg; yield, 18%) as a light yellow solid.

MS (FAB) m/z: 1347 (M+H)$^+$.

IR (KBr) $v_{max}$ 2931, 1729, 1645, 1609, 1359, 1281, 1139, 837, 758, 705 cm$^{-1}$.

Example 73

1-{2-[(6-{[4-({3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}carbamoyl)phenyl]amino}hexanoyl)(methyl)amino]ethyl}piperidin-4-yl biphenyl-2-ylcarbamate trihydrochloride

[Formula 78]

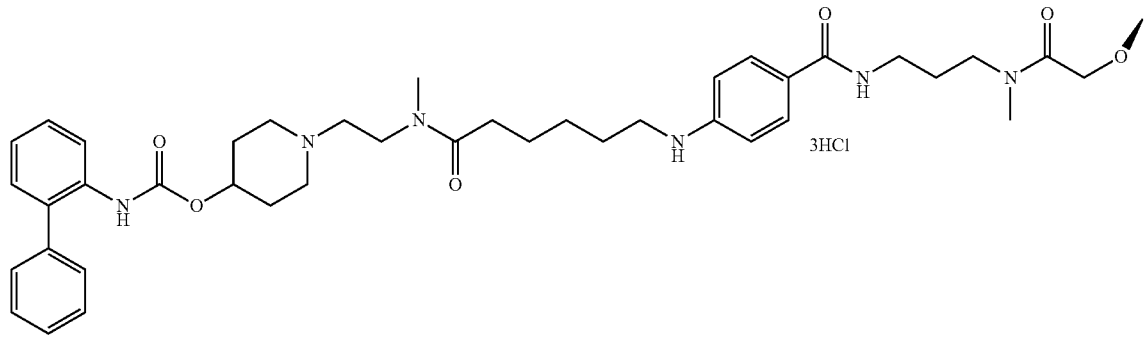

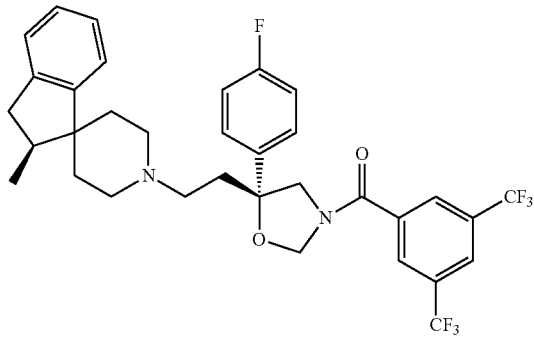

Example 73a

N-(3-Bromopropyl)-4-nitrobenzamide 30 mL of toluene was added to 3-bromopropylamine hydrobromide (1.20 g, 5.50 mmol), and triethylamine (1.53 mL, 11.0 mmol) was added dropwise with stirring under ice cooling. After the dropwise addition was completed, 4-nitrobenzoyl chloride (928 mg, 5.50 mmol) was added little by little, and the mixture was stirred at room temperature for 15 minutes. The reaction mixture was diluted with ethyl acetate, and the organic layer was washed with an aqueous saturated sodium hydrogencarbonate solution, a 0.1 N aqueous hydrochloric acid solution, and saturated sodium chloride solution. The organic layer was dried with anhydrous magnesium sulfate, and then the solvent was evaporated under reduced pressure to give the title compound (1.11 g; yield, 77%) as light yellow crystals.

MS (APCI) m/z: 287 (M+H)$^+$.

Example 73b tert-Butyl methyl{3-[(4-nitrobenzoyl)amino]propyl}carbamate 10 mL of a 9.8 M N-methylamine-methanol solution was added to the compound (1.10 g, 3.83 mmol) obtained in Example 73a, and the mixture was stirred at room temperature for 4.5 hours. The solvent of the reaction mixture was evaporated under reduced pressure, the resulting residue was redissolved in a mixed solvent of methanol and toluene, and the solvent was evaporated to dryness under reduced pressure. The resulting residue (1.29 g) was dissolved in 30 mL of dichloromethane, triethylamine (1.07 mL, 7.66 mmol), di-tert-butyl dicarbonate (1.25 g, 5.75 mmol) and 4-dimethylaminopyridine (30 mg) were added, and the mixture was stirred at room temperature for 12 hours. The solvent was evaporated under reduced pressure, then ethyl acetate was added to dilute the mixture, and the organic layer was washed successively with water, a 0.1 N aqueous hydrochloric acid solution, an aqueous saturated sodium hydrogencarbonate solution, and saturated sodium chloride solution. The organic layer was dried with anhydrous magnesium sulfate, the solvent was evaporated under reduced pressure, and the resulting yellow oily substance was purified by silica gel chromatography (n-hexane:ethyl acetate, 10:1→50:50, v/v) to give the title compound (1.31 g; yield, 100%) as a colorless oily substance.

MS (FAB+) m/z: 338 (M+H)$^+$.
IR (liquid film) $v_{max}$ 3323, 2976, 2932, 1667, 1602, 1727, 1348, 1158, 871, 720 cm$^{-1}$.

Example 73c tert-Butyl {3-[(4-aminobenzoyl)amino]propyl}methylcarbamate

The compound (1.27 g, 3.78 mmol) obtained in Example 73b was dissolved in 40 mL of methanol, 100 mg of 10% palladium-carbon was added, and the mixture was stirred at room temperature under a hydrogen atmosphere for 2 hours. The reaction mixture was filtered through celite, and then the solvent of the filtrate was evaporated under reduced pressure to give the title compound (1.14 g; yield, 98%) as a colorless oily substance.

MS (FAB+) m/z: 308 (M+H)$^+$.
IR (KBr) $v_{max}$ 3439, 3338, 3226, 1672, 1629, 1604, 1553, 1511, 1298, 1186, 1152, 876, 843, 771 cm$^{-1}$.

Example 73d

1-{2-[(6-{[4-({3-([tert-Butoxycarbonyl)(methyl)amino]propyl}carbamoyl)phenyl]amino}hexanoyl)(methyl)amino]ethyl}piperidin-4-yl biphenyl-2-yl-carbamate The compound (92 mg, 0.299 mmol) obtained in Example 73c and the compound (128 mg, 0.275 mmol) obtained in Example 4g were used to give the title compound (150 mg; yield, 66%) as a light yellow oily substance according to the method described in Example 43a.

MS (FAB+) m/z: 757 (M+H)$^+$.
IR (liquid film) $v_{max}$ 3344, 2933, 1692, 1632, 1607, 1518, 1398, 1302, 1157, 1045, 836, 750, 703, 664 cm$^{-1}$.

Example 73e

1-[2-(Methyl{6-[(4-{[3-(methylamino)propyl]carbamoyl}phenyl)amino]hexanoyl}amino)ethyl]piperidin-4-yl biphenyl-2-ylcarbamate trihydrochloride The compound (135 mg, 0.178 mmol) obtained in Example 73d was dissolved in 2.0 mL of dichloromethane, 2.0 mL of a 2 N hydrochloric acid-methanol solution was added, and the mixture was stirred at room temperature for 16 hours. 10 mL of toluene was added to the reaction mixture, and then the solvent was evaporated under reduced pressure to give a crude title compound.

MS (APCI) m/z: 657 (M+H)$^+$.

Example 73f

1-{2-[(6-{[4-({3-[({[(2S)-1'-{2-[(5R)-3-[3,5-Bis(trifluoromethyl)benzoyl]-5-(4-fluorophenyl)-1,3-oxazolidin-5-yl]ethyl}-2-dihydrospiro[indene-1,4'-piperidin]-2-yl]oxy}acetyl)(methyl)amino]propyl}carbamoyl)phenyl]amino}hexanoyl)(methyl)amino]ethyl}piperidin-4-yl biphenyl-2-ylcarbamate The crude product (140 mg, 0.178 mmol) obtained in Example 73e was used to give the title compound (49 mg; yield, 25%) as a white solid according to the method described in Example 11e.

MS (FAB) m/z: 1333 (M+H)$^+$.

Example 73g

1-{2-[(6-{[4-({3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}carbamoyl)phenyl]amino}hexanoyl)(methyl)amino]ethyl}piperidin-4-yl biphenyl-2-ylcarbamate trihydrochloride The compound (49 mg, 0.037 mmol) obtained in Example 73f was dissolved in 5 mL of dichloromethane, 56 μL of a 4 N hydrochloric acid-dioxane solution was added at room temperature, and the mixture was stirred. 5 mL of n-hexane was added to the reaction solution, the mixture was stirred at room temperature, and then the solvent was evaporated under reduced pressure. n-Hexane and diisopropyl ether were added to the resulting white solid, and the solid was collected by filtration to give the title compound (44 mg; yield, 83%) as a white solid.

MS (FAB) m/z: 1333 (M+H)$^+$. (free form)
IR (KBr) $v_{max}$ 2932, 1729, 1642, 1610, 1511, 1358, 1281, 1139, 838, 756, 704, 680 cm$^{-1}$.

Example 74

1-{2-[{6-[{4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]benzyl}(methyl)amino]hexanoyl}(methyl)amino]ethyl}piperidin-4-yl biphenyl-2-ylcarbamate

[Formula 79]

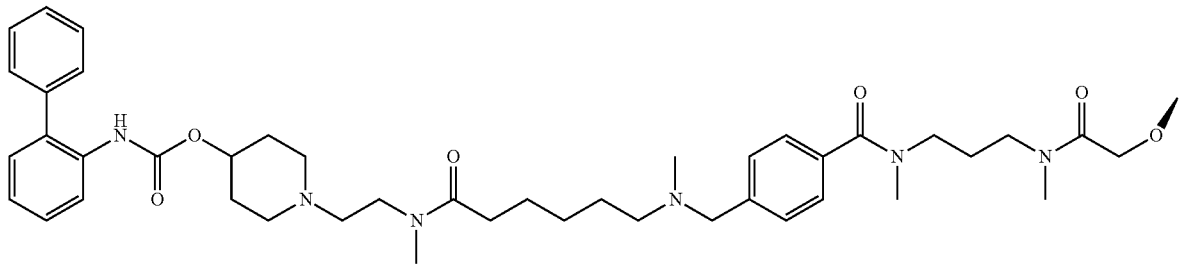

Example 74a

Methyl 4-{[{6-[(2-{4-[(biphenyl-2-ylcarbamoyl)oxy]piperidin-1-yl}ethyl)(methyl)amino]-6-oxohexyl}(methyl)amino]methyl}benzoate The compound (128 mg, 0.267 mmol) obtained in Example 2a and methyl 4-formylbenzoate (65.6 mg, 0.400 mmol) were used to give the title compound (110 mg; yield, 65%) as a colorless oily substance according to the method described in Example 18b.

MS (FAB) m/z: 629 (M+H)$^+$.

IR (Liquid film) $v_{max}$ 2945, 1722, 1644, 1521, 1449, 1437, 1280, 1111, 1045, 757 cm$^{-1}$.

Example 74b

1-{2-[{6-[{4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methy)amino]propyl}(methyl)carbamoyl]benzyl}(methyl)amino]hexanoyl}(methyl)amino]ethyl}piperidin-4-yl biphenyl-2-ylcarbamate The compound (90 mg, 0.14 mmol) obtained in Example 74a was dissolved in a mixed solvent of methanol (1.4 mL) and water (1.4 mL), a 1 N aqueous sodium hydroxide solution (0.214 mL, 0.214 mmol) was added, and the mixture was stirred at room temperature for 3 hours and then at 50° C. for 2 hours. A 1 N aqueous hydrochloric acid solution (0.300 mL) and toluene were added, and then the solvent was evaporated under reduced pressure. The resulting residue and the compound (74 mg, 0.095 mmol) obtained in Example 1k were used to give the title compound (63 mg; yield, 48%) as a white solid according to the method described in Example 11e.

MS (FAB) m/z: 1375 (M+H)$^+$.

IR (KBr) $v_{max}$ 2929, 1730, 1644, 1449, 1359, 1180, 1139, 847, 755, 703 cm$^{-1}$.

Example 75

1-(2-{[6-({4-[{3-[({[(2S)-1-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]benzyl}amino)hexanoyl](methyl)amino}ethyl)piperidin-4-yl biphenyl-2-ylcarbamate

[Formula 80]

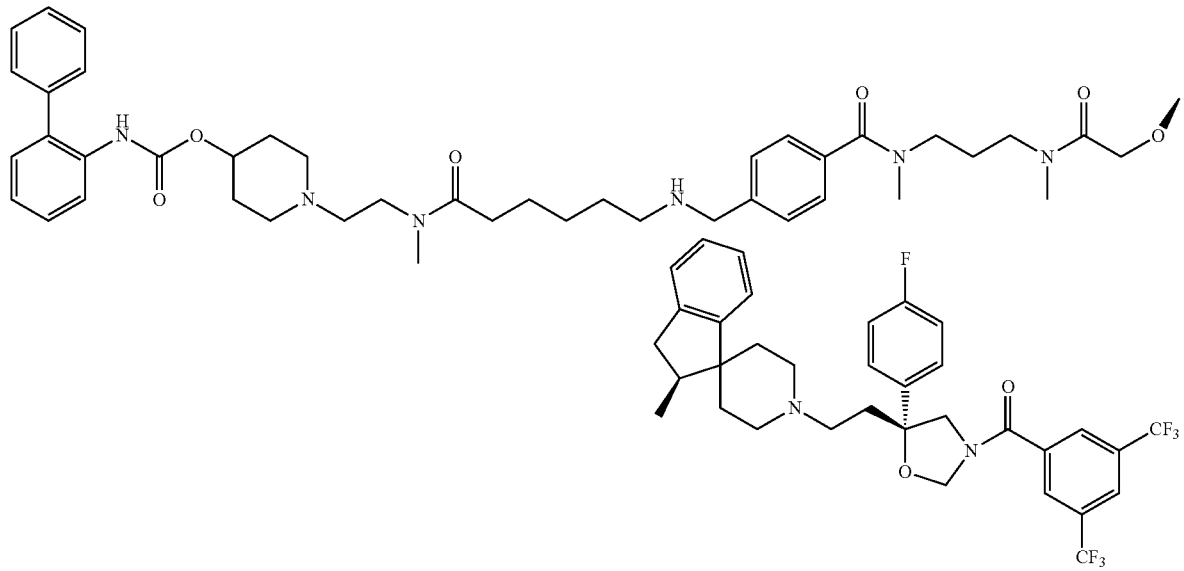

The compound (109 mg, 0.234 mmol) obtained in Example 1a and the compound (142 mg, 0.156 mmol) obtained in Example 45a were used to give the title compound (51 mg; yield, 24%) as a white solid according to the method described in Example 1m.

MS (FAB) m/z: 1361 (M+H)$^+$.

IR (KBr) $\nu_{max}$ 2928, 1728, 1644, 1449, 1281, 1180, 1139, 847, 755, 703 cm$^{-1}$.

Example 76

1-{2-[{6-[{4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}(methyl)amino]hexanoyl}(methyl)amino]ethyl}piperidin-4-yl biphenyl-2-ylcarbamate

[Formula 81]

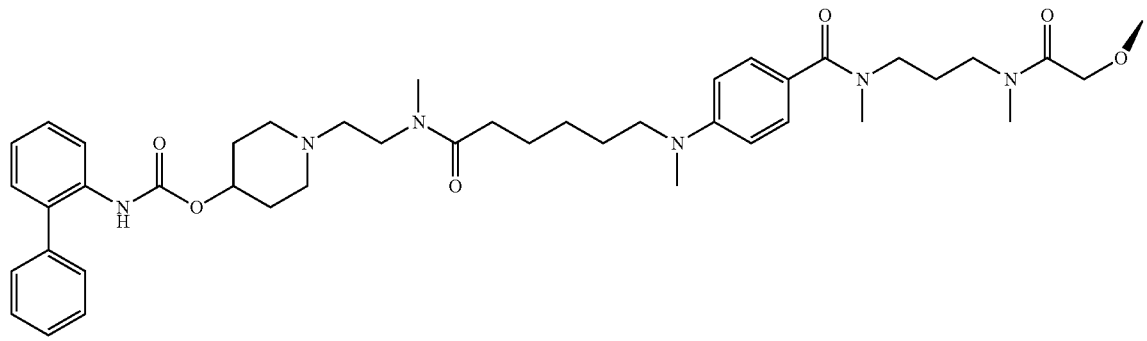

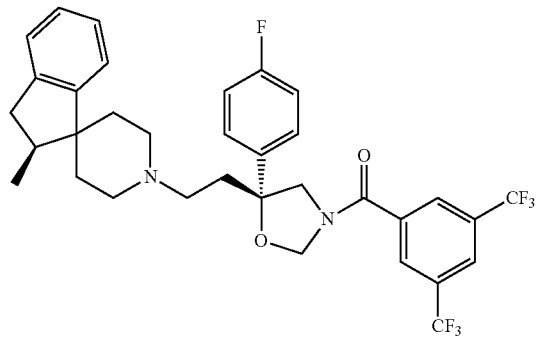

The compound (147 mg, 0.224 mmol) obtained in Example 22a was dissolved in 1,4-dioxane (6.6 mL), a 4 N hydrochloric acid-dioxane solution (2.2 mL, 8.8 mmol) was added, and the mixture was stirred at 70° C. for 6 hours. After the reaction was completed, toluene was added, and the solvent was evaporated under reduced pressure to give a crude carboxylic acid compound. The resulting crude carboxylic acid compound and the compound (116 mg, 0.149 mmol) obtained in Example 1k were used to give the title compound (57 mg; yield, 34%) as a white solid according to the method described in Example 11e.

MS (FAB) m/z: 1361 (M+H)+.

IR (KBr) $\nu_{max}$ 2927, 1730, 1646, 1608, 1449, 1359, 1182, 1139, 847, 759 cm$^{-1}$.

Example 77

1-{2-[{6-[(4-{-4-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]butanoyl}phenyl)amino]hexanoyl}(methyl)amino]ethyl}piperidin-4-yl biphenyl-2-ylcarbamate

[Formula 82]

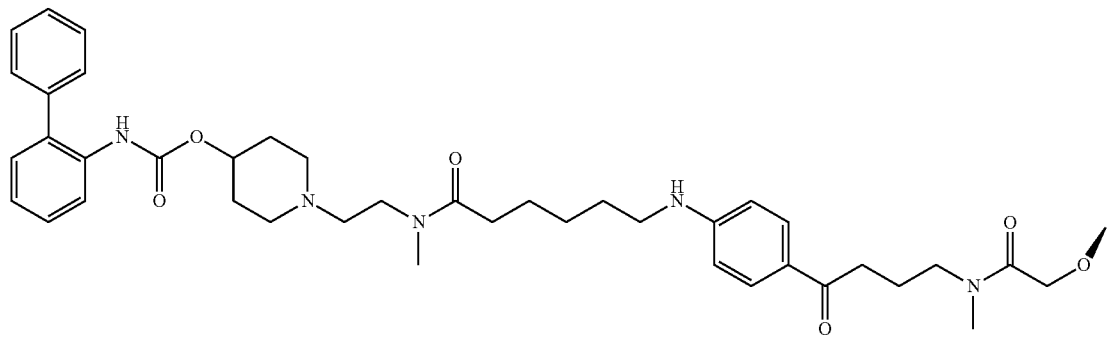

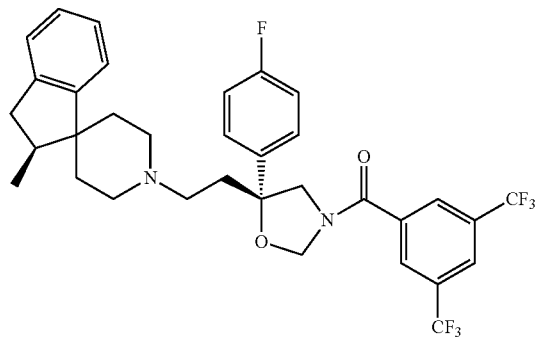

Example 77a tert-Butyl [4-(4-aminophenyl)-4-oxobutyl]methylcarbamate

4-Bromo-N,N-bis(trimethylsilyl)aniline (1.64 mL, 5.82 mmol) was dissolved in tetrahydrofuran (9 mL), and a 1.6 N n-butyllithium-hexane solution (3.23 mL, 5.33 mmol) was added at −78° C. A solution of tert-butyl {4-[methoxy(methyl)amino]-4-oxobutyl}methylcarbamate (1.26 g, 4.85 mmol) in tetrahydrofuran (9 mL) was further added at −78° C. The temperature was increased to room temperature, water (2 mL) was added, then 1 N tetrabutylammonium fluoride (10 mL, 10 mmol) was added, and the mixture was stirred at room temperature for 2 hours. A saturated aqueous sodium hydrogencarbonate solution was added, then the mixture was extracted with dichloromethane and ethyl acetate, and the organic layers were combined and dried with anhydrous sodium sulfate. The solvent was evaporated under reduced pressure, and the resulting residue was purified by silica gel column chromatography (elution solvents, hexane:ethyl acetate=4:1→2:1, v/v) to give the title compound (1.32 g; yield, 71%).

MS (FAB) m/z: 293 (M+H)$^+$.
IR (KBr) $\nu_{max}$ 3442, 3361, 1677, 1660, 1634, 1594, 1173, 984, 828, 773 cm$^{-1}$.

Example 77b

Ethyl 6-[(4-{4-([tert-butoxycarbonyl)(methyl)amino]butanoyl}phenyl)amino]hexanoate The compound (1.80 g, 6.16 mmol) obtained in Example 77a was used to give the title compound (2.00 g; yield, 75%) as a brown oily substance according to the method described in Example 15b.

MS (FAB) m/z: 435 (M+H)$^+$.
IR (ATR) $\nu_{max}$ 2932, 1690, 1594, 1392, 1364, 1247, 1160, 1032, 824, 770 cm$^{-1}$.

Example 77c

1-{2-[{6-[(4-{4-([tert-Butoxycarbonyl)(methyl)amino]butanoyl}phenyl)amino]hexanoyl}(methy)amino]ethyl}piperidin-4-yl biphenyl-2-ylcarbamate The compound (470 mg, 1.08 mmol) obtained in Example 77b was dissolved in a mixed solvent of ethanol (5 mL) and water (5 mL), a 1 N aqueous sodium hydroxide solution (1.62 mL, 1.62 mmol) was added, and the mixture was stirred at room temperature. After the reaction was completed, a 1 N aqueous hydrochloric acid solution was added, and then the mixture was extracted with dichloromethane (×3). The solvent was evaporated under reduced pressure, the resulting residue and 1-[2-(methylamino)ethyl]piperidin-4-yl biphenyl-2-ylcarbamate (346 mg, 0.981 mmol) were dissolved in dichloromethane (10 mL), 1-ethyl-3-(3-dimethylaminopropyl)carbodiimide hydrochloride (375 mg, 1.96 mmol) was added, and the mixture was stirred at room temperature for 14 hours. After the reaction was completed, a saturated aqueous sodium hydrogencarbonate solution was added, and the mixture was extracted with dichloromethane (×3). The resulting organic layer was dried with anhydrous sodium sulfate. The solvent was evaporated under reduced pressure, then the residue was purified by NH silica gel column chromatography (elution solvents, hexane:ethyl acetate=9:1→1:1→0:1, v/v) and then by silica gel column chromatography (elution solvents, ethyl acetate:methanol=10:0→9:1, v/v) to give the title compound (298 mg; yield, 41%) as a white solid.

MS (FAB) m/z: 742 (M+H)$^+$.
IR (KBr) $\nu_{max}$ 3347, 2934, 1693, 1599, 1523, 1175, 1045, 770, 749, 703 cm$^{-1}$.

Example 77d

1-{2-[{6-[(4-{-4-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]butanoyl}phenyl)amino]hexanoyl}(methyl)amino]ethyl}piperidin-4-yl biphenyl-2-ylcarbamate The compound (280 mg, 0.377 mmol) obtained in Example 77c was dissolved in 1,4-dioxane (4 mL), a 4 N hydrochloric acid-ethyl acetate solution (0.943 mL, 3.77 mmol) and methanol (2 mL) were added, and the mixture was stirred at room temperature for 2 hours. After the reaction was completed, the solvent was evaporated under reduced pressure to give crude 1-(2-{methyl[6-({-4-[4-(methylamino)butanoyl]benzyl}amino)hexanoyl]amino}ethyl)piperidin-4-yl biphenyl-2-ylcarbamate trihydrochloride. The resulting crude product was used to give the title compound (50 mg; yield, 13%) as a white solid according to the method described in Example 11e.

MS (FAB) m/z: 1318 (M+H)$^+$.
IR (KBr) $\nu_{max}$ 2929, 1729, 1647, 1599, 1359, 1281, 1177, 1139, 838, 754 cm$^{-1}$.

Example 78

1-{2-[{6-[(4-{4-[({[(2S)-1-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]butanoyl}benzyl)(methyl)amino]hexanoyl}(methyl)amino]ethyl}piperidin-4-yl biphenyl-2-ylcarbamate

[Formula 83]

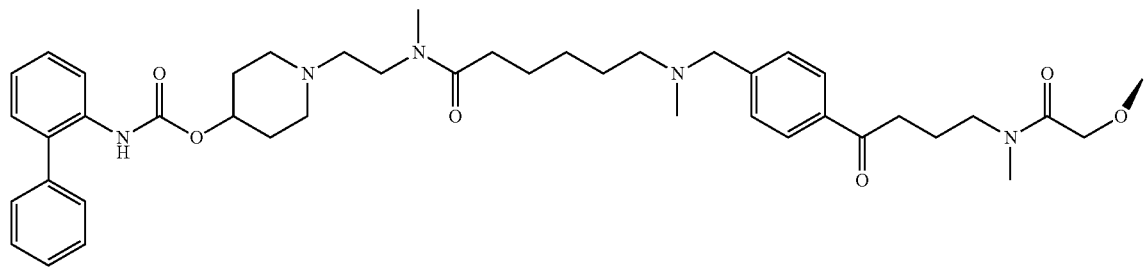

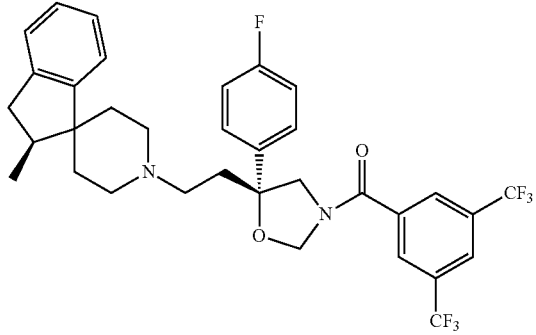

Example 78a tert-Butyl {4-[4-(hydroxymethyl)phenyl]-4-oxobutyl}methylcarbamate

[(4-Bromobenzyl)oxy](tert-butyl)dimethylsilane (2.30 g, 7.64 mmol), a compound described in the literature (Eur. J. Org. Chem.; EN, 8, 2001, 1549), was dissolved in tetrahydrofuran (7.6 mL), a 1.6 M n-butyllithium-hexane solution (4.37 mL, 7.00 mmol) was added at −78° C., and the mixture was stirred at the same temperature for 30 minutes. A solution of tert-butyl {4-[methoxy(methyl)amino]-4-oxobutyl}methylcarbamate (1.65 g, 6.36 mmol), a compound described in the literature (Bio. Org. Med. Chem. 2004, 12, 5147-5160), in tetrahydrofuran (7.6 mL) was further added at −78° C., and the temperature was increased to room temperature. After the reaction was completed, a 1 N tetrabutylammonium fluoride-tetrahydrofuran solution (12.7 mL, 12.7 mmol) was added. Subsequently, 1 N hydrochloric acid was further added. A saturated aqueous sodium hydrogencarbonate solution was further added, the mixture was extracted with ethyl acetate, and the resulting organic layer was dried with anhydrous sodium sulfate. The solvent was evaporated under reduced pressure, and the resulting residue was purified by silica gel column chromatography (elution solvents, n-hexane:ethyl acetate=1:1→1:2, v/v) to give the title compound (1.29 g; yield, 48%) as a yellow oily substance.

MS (FAB) m/z: 308 (M+H)$^+$.

IR (ATR) $\nu_{max}$ 3412, 2975, 2929, 1669, 1394, 1365, 1161, 1136, 1051, 771 cm$^{-1}$.

Example 78b

1-{2-[{6-[(4-{4-[(tert-Butoxycarbonyl)(methyl)amino]butanoyl}benzyl)(methyl)amino]hexanoyl}(methyl)amino]ethyl}piperidin-4-yl biphenyl-2-ylcarbamate The compound (651 mg, 2.12 mmol) obtained in Example 78a was dissolved in dichloromethane (20 mL), triethylamine (0.590 mL, 4.24 mmol) and methanesulfonyl chloride (0.245 mL, 3.18 mmol) were added under ice cooling, and the mixture was stirred at room temperature for 30 minutes. After the reaction was completed, a saturated aqueous sodium hydrogencarbonate solution was added, and the mixture was extracted with ethyl acetate. The resulting organic layer was dried with anhydrous sodium sulfate. The solvent was evaporated under reduced pressure to give a crude 4-{4-[(tert-butoxycarbonyl)(methyl)amino]butanoyl}benzyl methanesulfonate (851 mg) as a yellow oily substance.

The resulting crude product (543 mg) and the compound (591 mg, 1.23 mmol) obtained in Example 2a were dissolved in acetonitrile (12 mL), N,N-diisopropylethylamine (428 mL, 2.46 mmol) was added, and the mixture was stirred at room temperature for 4 hours. After the reaction was completed, a saturated aqueous sodium hydrogencarbonate solution was added, and the mixture was extracted with dichloromethane and dried with anhydrous sodium sulfate. The solvent was evaporated under reduced pressure, and the resulting residue was purified by NH silica gel column chromatography (elution solvents, n-hexane:ethyl acetate=1:1→0:1, v/v) to give the title compound (464 mg; yield, 49%) as a light yellow oily substance.

MS (FAB) m/z: 770 (M+H)$^+$.

IR (Liquid film) $\nu_{max}$ 2937, 1688, 1521, 1450, 1208, 1045, 874, 770, 749, 703 cm$^{-1}$.

Example 78c

1-{2-[{6-[(4-{-4[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]butanoyl}benzyl)(methyl)amino]hexanoyl}(methyl)amino]ethyl}piperidin-4-yl biphenyl-2-ylcarbamate The compound (460 mg, 0.598 mmol) obtained in Example 78b was dissolved in 1,4-dioxane (6 mL), a 4 N hydrochloric acid-dioxane solution (1.49 mL, 5.98 mmol) and methanol (1 mL) were added under ice cooling, and the mixture was stirred at room temperature for 5.5 hours. After the reaction was completed, the solvent was evaporated under reduced pressure to give crude 1-(2-{methyl[6-(methyl{-4-[4-(methylamino)butanoyl]benzyl}amino)hexanoyl]amino}ethyl)piperidin-4-yl biphenyl-2-ylcarbamate trihydrochloride. The resulting crude product was used to give the title compound (101 mg; yield, 26%) as a white solid according to the method described in Example 11e.

MS (FAB) m/z: 1346 (M+H)$^+$.

IR (KBr) $\nu_{max}$ 2933, 1730, 1646, 1359, 1281, 1179, 1139, 847, 754, 703 cm$^{-1}$.

Example 79

1-{2-[{6-[(4-{4-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]-1-hydroxybutyl}benzyl)(methyl)amino]hexanoyl}(methyl)amino]ethyl}piperidin-4-yl biphenyl-2-ylcarbamate

[Formula 84]

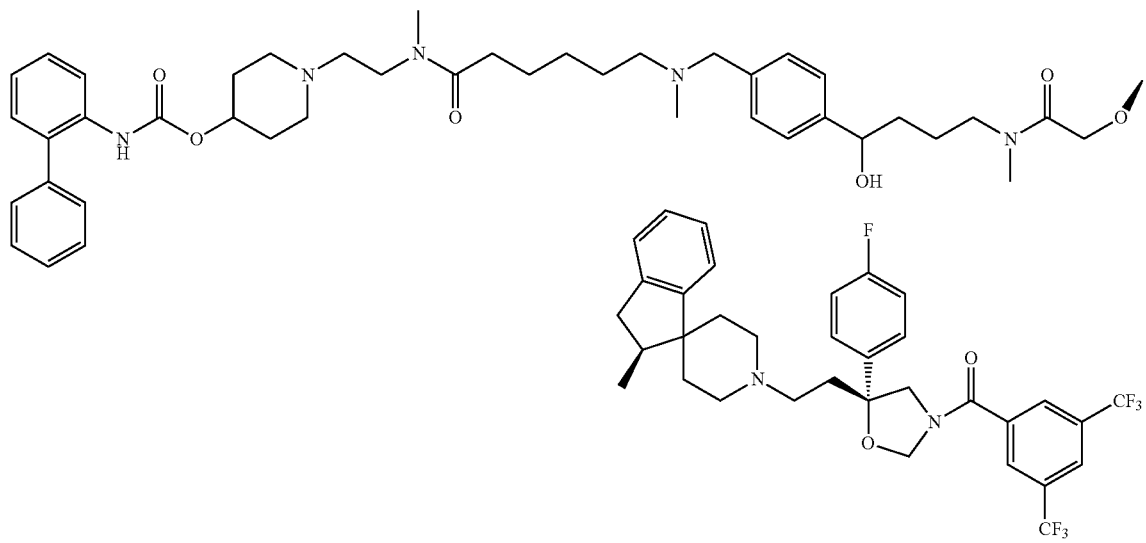

The compound (58 mg, 0.043 mmol) obtained in Example 78c was dissolved in methanol (4 mL), sodium borohydride (1.6 mg, 0.043 mmol) was added, and the mixture was stirred at room temperature for 30 minutes. After the reaction was completed, a saturated aqueous sodium hydrogencarbonate solution was added, the mixture was extracted with dichloromethane, and the resulting organic layer was dried with anhydrous sodium sulfate. The solvent was evaporated under reduced pressure, and the resulting residue was purified by NH silica gel column chromatography (elution solvents, ethyl acetate:methanol=100:0→95:5, v/v) to give a crude product of the title compound. The crude product was purified by reverse phase liquid chromatography (XTerra Prep MS C18 OBD, 5 μm, 30×100 mm) (acetonitrile:0.1% aqueous ammonium formate solution, 10:90→100:0, v/v) to give the title compound (51 mg; yield, 88%) as a white solid.

MS (FAB) m/z: 1348 (M+H)$^+$.

IR (ATR) $v_{max}$ 2941, 1729, 1645, 1358, 1280, 1180, 1139, 847, 751, 703 cm$^{-1}$.

Example 80

1-(2-{[6-({4-[{-4-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]butyl}(methyl)carbamoyl]phenyl}amino)hexanoyl](methyl)amino}ethyl)piperidin-4-yl biphenyl-2-ylcarbamate trihydrochloride

[Formula 85]

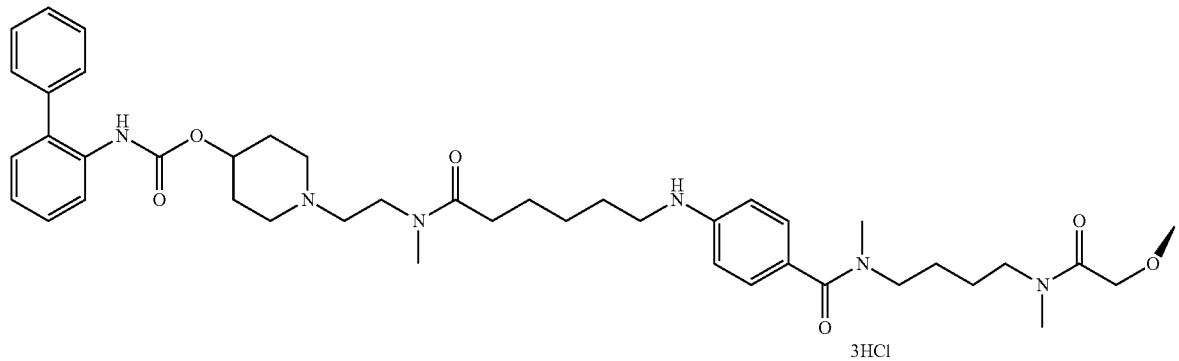

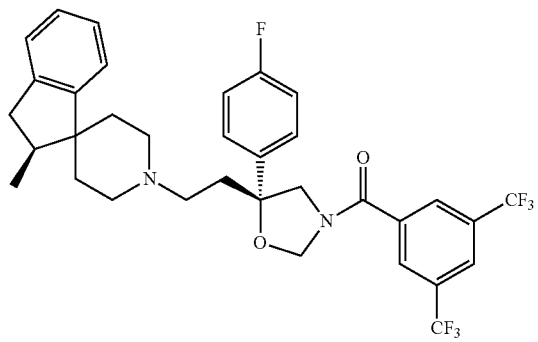

Example 80a 1-(2-{[6-({4-[(4-Hydroxybutyl)(methyl)carbamoyl]phenyl}amino)hexanoyl](methyl)amino}ethyl)piperidin-4-yl biphenyl-2-ylcarbamate The compound (1.18 g, 1.84 mmol) obtained in Example 15c was dissolved in 1,4-dioxane (27 mL), a 4 N hydrochloric acid-dioxane solution (27 mL, 110 mmol) was added, and the mixture was stirred at room temperature for 13 hours. After the reaction was completed, toluene (30 mL×2) was added, and the solvent was evaporated under reduced pressure to give crude 4-({6-[(2-{4-[(biphenyl-2-ylcarbamoyl)oxy]piperidin-1-yl}ethyl)(methyl)amino]-6-oxohexyl}amino)benzoic acid (1.483 g) as a yellow solid.

Dichloromethane (4 mL), triethylamine (0.113 mL, 0.813 mmol) and pivaloyl chloride (0.0372 mL, 0.305 mmol) were added to the resulting crude product (163 mg), and the mixture was stirred at room temperature for 40 minutes. Subsequently, a solution of 4-(methylamino)butan-1-ol (63 mg, 0.61 mmol), a compound described in the literature (J. Org. Chem., EN, 64, 20, 1999, 7515), in dichloromethane (4 mL) was added under ice cooling, and the mixture was stirred at room temperature for 90 minutes. After the reaction was completed, a saturated aqueous sodium hydrogencarbonate solution was added, the mixture was extracted with dichloromethane twice, and the resulting organic layer was dried with anhydrous sodium sulfate. The solvent was evaporated under reduced pressure, and the resulting residue was purified by NH silica gel column chromatography (elution solvents, n-hexane:ethyl acetate:methanol=1:1:0→0:1:0→0:9:1, v/v/v) to give the title compound (112 mg; yield, 82%) as a colorless oily substance.

MS (FAB) m/z: 672 (M+H)$^+$.

IR (ATR) $v_{max}$ 2933, 1717, 1607, 1521, 1206, 1060, 1044, 832, 747, 703 cm$^{-1}$.

Example 80b

1-[2-(Methyl{6-[(4-{methyl[4-(methylamino)butyl]carbamoyl}phenyl)amino]hexanoyl}amino)ethyl]piperidin-4-yl biphenyl-2-ylcarbamate The compound (107 mg, 0.159 mmol) obtained in Example 80a was dissolved in dichloromethane (6 mL), triethylamine (0.044 mL, 0.32 mmol) and methanesulfonyl chloride (0.018 mL, 0.24 mmol) were added under ice cooling, and the mixture was stirred at the same temperature for 10 minutes. Triethylamine (0.044 mL, 0.32 mmol) and methanesulfonyl chloride (0.018 mL, 0.24 mmol) were further added under ice cooling, then a 40% methyl amine-methanol solution (6 mL) was added, and the mixture was stirred at room temperature for 14 hours. After the reaction was completed, the solvent was evaporated under reduced pressure, and the resulting residue was purified by NH silica gel column chromatography (elution solvents, n-hexane:ethyl acetate:methanol=1:1:0→0:1:0→0:9:1, v/v/v) to give the title compound (84 mg; yield, 77%) as a colorless oily substance.

MS (FAB) m/z: 685 (M+H)$^+$.

IR (ATR) $v_{max}$ 2930, 1714, 1605, 1448, 1221, 1206, 1043, 831, 747, 702 cm$^{-1}$.

Example 80c 1-(2-{[6-({4-[{4-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]butyl}(methyl)carbamoyl]phenyl}amino)hexanoyl](methyl)amino}ethyl)piperidin-4-yl biphenyl-2-ylcarbamate trihydrochloride The compound (84 mg) obtained in Example 80b was used to give a free form of the title compound according to the method described in Example 11e.

The resulting free form of the title compound was used to give the title compound (53 mg; yield, 31%) as a white solid according to the method described in Example 13e.

MS (FAB) m/z: 1361 (M+H)$^+$ (free form).

IR (KCl) $v_{max}$ 3414, 2936, 1724, 1637, 1360, 1282, 1138, 848, 760, 702 cm$^{-1}$.

Example 81

1-{2-[{6-[(4-{-4-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]-1-hydroxybutyl}phenyl)amino]hexanoyl}(methyl)amino]ethyl}piperidin-4-yl biphenyl-2-ylcarbamate

[Formula 86]

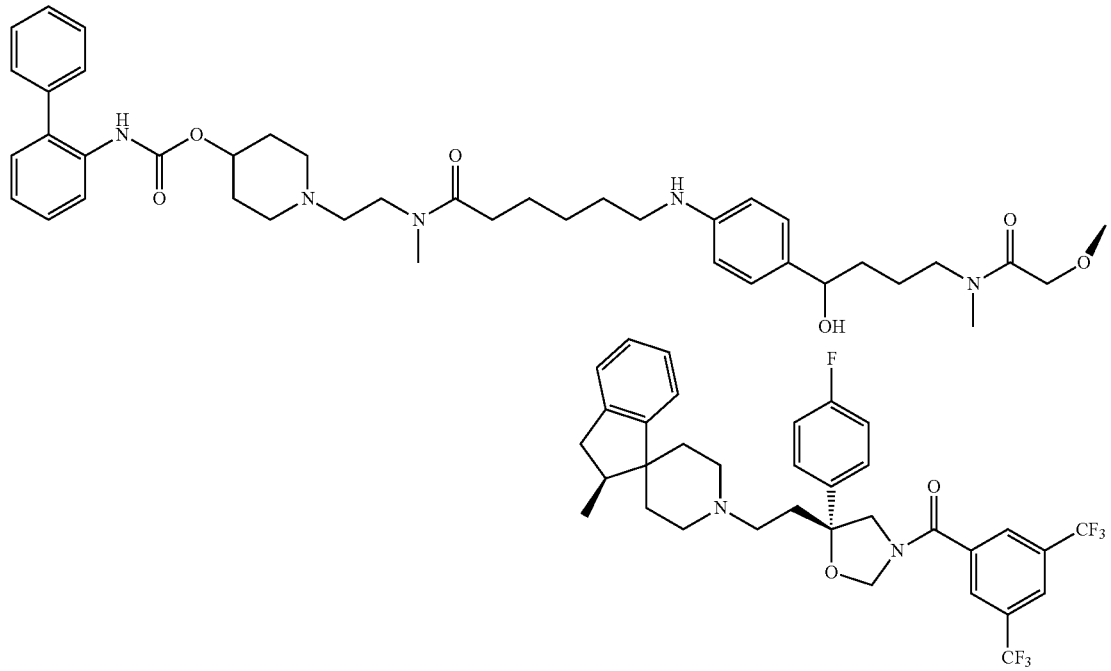

The compound (99 mg, 0.075 mmol) obtained in Example 77d was used according to the method described in the Example 79a to give the title compound (41 mg; yield, 41%) as a white solid.

MS (FAB) m/z: 1320 (M+H)$^+$.

IR (KBr) $v_{max}$ 2930, 1732, 1644, 1522, 1359, 1281, 1139, 847, 754, 703 cm$^{-1}$.

Example 82

1-{2-[(6-{[4-({4-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]butanoyl}amino)phenyl]amino}hexanoyl)(methyl)amino]ethyl}piperidin-4-yl biphenyl-2-ylcarbamate trihydrochloride

[Formula 87]

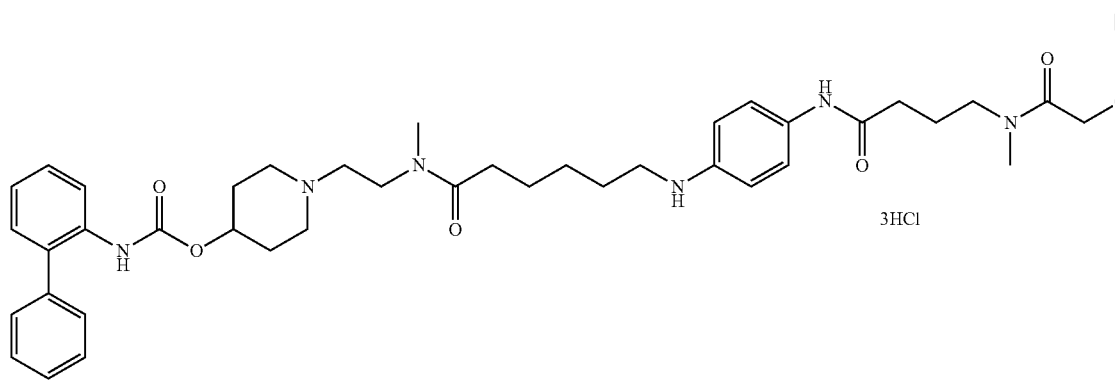

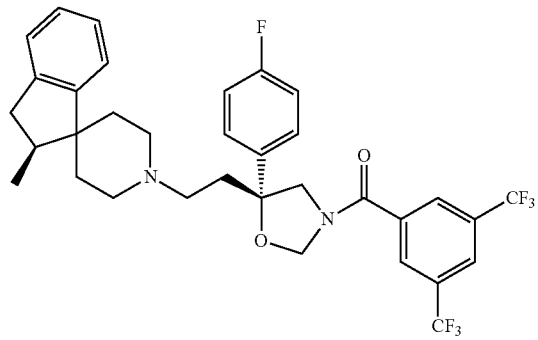

Example 82a

N-(4-Aminophenyl)-4-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]butanamide The compound (163 mg, 0.206 mmol) obtained in Example 63e and benzene-1,4-diamine (111 mg, 1.03 mmol) were suspended in a mixed solvent of dichloromethane (8 mL) and acetonitrile (8 mL), 1-ethyl-3-(3-dimethylaminopropyl)carbodiimide hydrochloride (59.0 mg, 0.309 mmol) and triethylamine (0.057 mL, 0.41 mmol) were added, and the mixture was stirred at room temperature for 3 hours. 1-Ethyl-3-(3-dimethylaminopropyl)carbodiimide hydrochloride (59.0 mg, 0.309 mmol) and 4-N,N-dimethylaminopyridine (0.5 mg, 0.004 mmol) were further added, and the mixture was stirred at room temperature for 13 hours. After the reaction was completed, a saturated aqueous sodium hydrogencarbonate solution was added to the reaction mixture, and dichloromethane was added (×2) to separate the layers. The resulting organic layer was dried with anhydrous sodium sulfate, and the solvent was evaporated under reduced pressure. The residue was purified by NH silica gel column chromatography (hexane:ethyl acetate=1:1→0:1, v/v) to give the title compound (141 mg; yield, 78%) as a light pink solid.

MS (FAB) m/z: 884 (M+H)⁺.

IR (KBr) $v_{max}$ 2932, 1649, 1515, 1359, 1281, 1181, 1138, 838, 758, 682 cm⁻¹.

Example 82b

1-{2-[(6-{[4-({4-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]butanoyl}amino)phenyl]amino}hexanoyl)(methyl)amino]ethyl}piperidin-4-yl biphenyl-2-ylcarbamate trihydrochloride The compound (142 mg, 0.161 mmol) obtained in Example 82a and the compound (79 mg, 0.17 mmol) obtained in Example 4g were used to give a free form of the title compound according to the method described in Example 1m. The resulting free form of the title compound was used to give the title compound (28 mg; yield, 12%) as a white solid according to the method described in Example 13e.

MS (FAB) m/z: 1333 (M+H)⁺.

IR (KBr) $v_{max}$ 3417, 2934, 1725, 1644, 1513, 1360, 1282, 1138, 837, 760 cm⁻¹.

Example 83

1-(2-{[6-({4-[{4-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]butanoyl}(methyl)amino]phenyl}amino)hexanoyl](methyl)amino}ethyl)piperidin-4-yl biphenyl-2-ylcarbamate

[Formula 88]

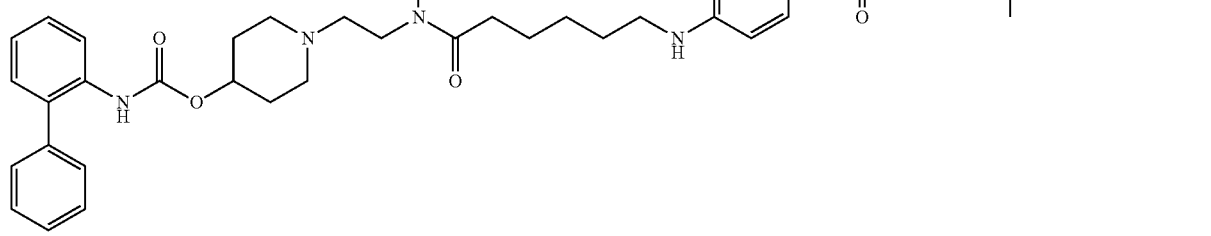

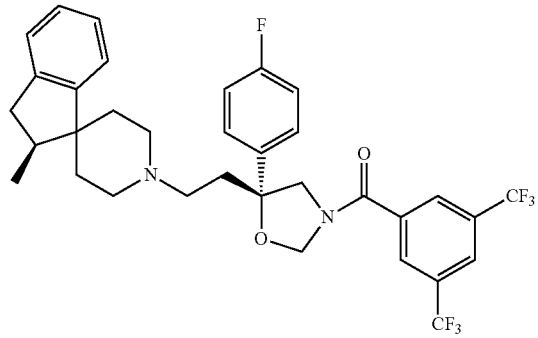

Example 83a tert-Butyl (4-aminophenyl)methylcarbamate

N-Methyl-4-nitroaniline (2.08 g, 13.7 mmol) was dissolved in tetrahydrofuran (137 mL), di-tert-butyl dicarbonate (3.58 g, 16.4 mmol) and 4-N,N-dimethylaminopyridine (33 mg, 0.27 mmol) were added, and the mixture was stirred at 50° C. for 2 hours. After the reaction was completed, ethyl acetate was added, and then the organic layer was washed with a saturated aqueous potassium carbonate solution (×2) and saturated sodium chloride solution. The solvent was evaporated under reduced pressure to give crude tert-butyl methyl(4-nitrophenyl)carbamate (3.49 g). The resulting crude product (3.30 g) was dissolved in a mixed solvent of ethyl acetate (65 mL) and methanol (65 mL), 10% palladium-carbon (330 mg) was added, and the mixture was stirred at room temperature under a hydrogen atmosphere for 13 hours. After the reaction was completed, the reaction solution was filtered through celite. The solvent of the filtrate was evaporated under reduced pressure, and the resulting residue was purified by silica gel column chromatography to give the title compound (1.90 g; yield, 66%) as a white solid.

MS (FAB) m/z: 222 (M)$^+$.

IR (KBr) $\nu_{max}$ 3443, 3354, 1678, 1519, 1366, 1148, 974, 860, 831, 571 cm$^{-1}$.

Example 83b 1-(2-{[6-({4-([tert-Butoxycarbonyl)(methyl)amino]phenyl}amino)hexanoyl](methyl)amino}ethyl)piperidin-4-yl biphenyl-2-ylcarbamate The compound (189 mg, 0.852 mmol) obtained in Example 83a and the compound (198 mg, 0.426 mmol) obtained in Example 4g were used to give the title compound (266 mg; yield, 93%) as a yellow solid according to the method described in Example 18b.

MS (FAB) m/z: 672 (M+H)$^+$.

IR (ATR) $\nu_{max}$ 2929, 1688, 1633, 1363, 1204, 1147, 1042, 824, 747, 702 cm$^{-1}$.

Example 83c

Benzyl {6-[(2-{4-[(biphenyl-2-ylcarbamoyl)oxy]piperidin-1-yl}ethyl)(methyl)amino]-6-oxohexyl}{4-[(tert-butoxycarbonyl)(methyl)amino]phenyl}carbamate The compound (257 mg, 0.383 mmol) obtained in Example 83b was dissolved in dichloromethane (4 mL), triethylamine (107 mL, 0.766 mmol) and benzyl chlorocarbonate (0.082 mL, 0.58 mmol) were added, and the mixture was stirred at 50° C. for 2 hours. A saturated aqueous sodium hydrogencarbonate solution was added, the mixture was extracted with methylene chloride (×3), and the resulting organic layer was dried with anhydrous sodium sulfate. The solvent was evaporated under reduced pressure, the resulting residue was dissolved in tetrahydrofuran (4 mL), 55% sodium hydride-paraffin (25.0 mg, 0.573 mmol) and benzyl chlorocarbonate (0.082 mL, 0.58 mmol) were added, and the mixture was stirred. After the reaction was completed, a saturated aqueous sodium hydrogencarbonate solution was added to the reaction mixture, and dichloromethane was further added to separate the layers. The resulting organic layer was separated and dried with anhydrous sodium sulfate, and the solvent was evaporated under reduced pressure. The residue was purified by NH silica gel column chromatography to give the title compound (235 mg; yield, 76%) as a brown oily substance.

MS (FAB) m/z: 806 (M+H)$^+$.

IR (ATR) $\nu_{max}$ 2934, 1697, 1515, 1365, 1301, 1206, 1149, 1044, 750, 701 cm$^{-1}$.

Example 83d

Benzyl {6-[(2-{4-[(biphenyl-2-ylcarbamoyl)oxy]piperidin-1-yl}ethyl)(methyl)amino]-6-oxohexyl}[4-(methylamino)phenyl]carbamate The compound (204 mg, 0.253 mmol) obtained in Example 83c was used to give the title compound (134 mg; yield, 75%) as a colorless oily substance according to the method described in Example 6d.

MS (FAB) m/z: 706 (M+H)$^+$.

IR (ATR) $\nu_{max}$ 2934, 1693, 1521, 1448, 1404, 1284, 1205, 1043, 748, 699 cm$^{-1}$.

Example 83e 1-(2-{[6-({4-[{-4-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]butanoyl}(methyl)amino]phenyl}amino)hexanoyl](methyl)amino}ethyl)piperidin-4-yl biphenyl-2-ylcarbamate The compound (113 mg, 0.160 mmol) obtained in Example 83d and the compound (116 mg, 0.146 mmol) obtained in Example 63e were dissolved in dichloromethane (3 mL), 1-ethyl-3-(3-dimethylaminopropyl)carbodiimide hydrochloride (56 mg, 0.292 mmol) and 4-N,N-dimethylaminopyridine (0.4 mg, 3 μmol) were added, and the mixture was stirred at room temperature for 3 hours. After the reaction was completed, a saturated aqueous sodium hydrogencarbonate solution was added to the reaction mixture, and ethyl acetate (×3) was further added to separate the layers. The resulting organic layer was dried with anhydrous sodium sulfate, and the solvent was evaporated under reduced pressure to give crude benzyl {6-[(2-{4-[(biphenyl-2-ylcarbamoyl)oxy]piperidin-1-yl}ethyl)(methyl)amino]-6-oxohexyl}{4-[{4-[({[(2S)-1-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]butanoyl}(methyl)amino]phenyl}carbamate (180 mg; yield, 76%) as a white solid.

The resulting crude product (165 mg, 0.111 mmol) was dissolved in a mixed solvent of ethyl acetate (4 mL) and methanol (4 mL), 10% palladium-carbon (165 mg) was added, and the mixture was stirred at room temperature under a hydrogen atmosphere for 2 hours. After the reaction was completed, the reaction solution was filtered through celite, the solvent of the filtrate was evaporated under reduced pressure, and the resulting residue was purified by NH silica gel column chromatography (elution solvents, hexane:ethyl acetate:methanol=1:1:0→0:10:0→0:9:1, v/v/v) and by reverse phase liquid chromatography (XTerra Prep MS C18 OBD, 5 μm, 30×100 mm) (elution solvents, acetonitrile:0.1% aqueous ammonium formate solution=10:90→100:0, v/v) to give the title compound (101 mg; yield, 68%).

MS (FAB) m/z: 1347 (M+H)$^+$.

IR (KBr) $\nu_{max}$
2933, 1732, 1647, 1522, 1359, 1281, 1139, 904, 837, 755, 702 cm$^{-1}$.

Example 84

1-(2-{[6-({4-[{-4-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]butanoyl}(methyl)amino]phenyl}amino)hexanoyl](methyl)amino}ethyl)piperidin-4-yl biphenyl-2-ylcarbamate trihydrochloride

[Formula 89]

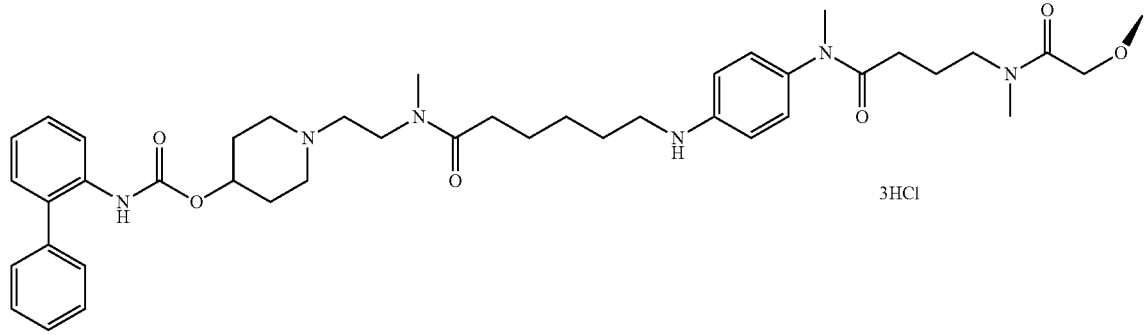

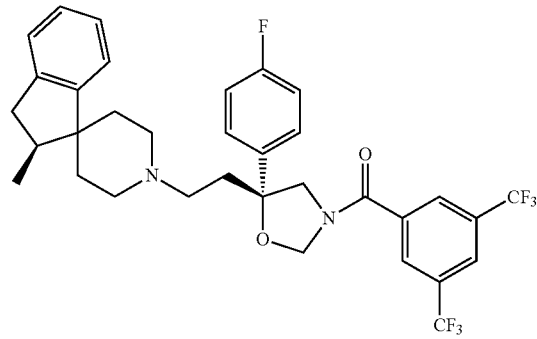

225

The compound (101 mg, 0.075 mmol) obtained in Example 83e was used to give the title compound (73 mg; yield, 69%) as a white solid according to the method described in Example 13e.

MS (FAB) m/z: 1347 (M+H)+ (free form).

IR (KBr) $v_{max}$ 3422, 2934, 1728, 1649, 1512, 1282, 1138, 848, 753, 703 cm$^{-1}$.

Example 85

1-(2-{[6-({4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-3-chlorophenyl}amino)hexanoyl](methyl)amino}ethyl)piperidin-4-yl biphenyl-2-ylcarbamate trihydrochloride

226

Example 85b 1-(2-{[6-({4-[{3-([tert-Butoxycarbonyl)(methy)amino]propyl}(methyl)carbamoyl]-3-chlorophenyl}amino)hexanoyl](methyl)amino}ethyl)piperidin-4-yl biphenyl-2-ylcarbamate The compound (149 mg, 0.420 mmol) obtained in Example 85a and the compound (163 mg, 0.351 mmol) obtained in Example 4g were used to give the title compound (166 mg; yield, 59%) as a white solid according to the method described in Example 18b.

MS (FAB) m/z: 805 (M+H)+.

IR (KBr) $v_{max}$ 3339, 2934, 1731, 1693, 1631, 1607, 1521, 1207, 1045, 749 cm$^{-1}$.

[Formula 90]

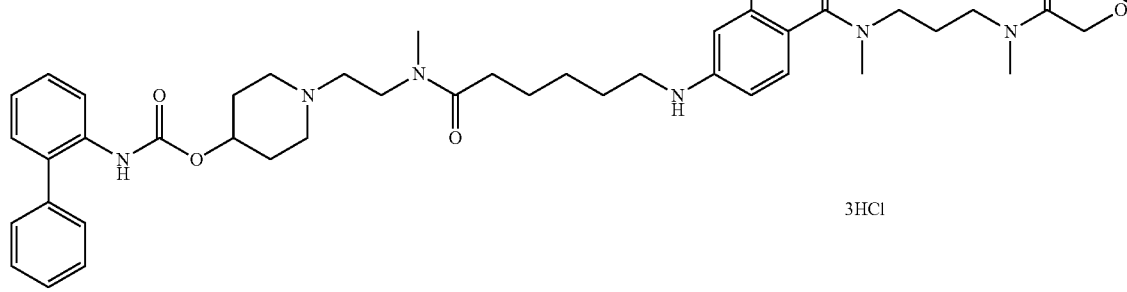

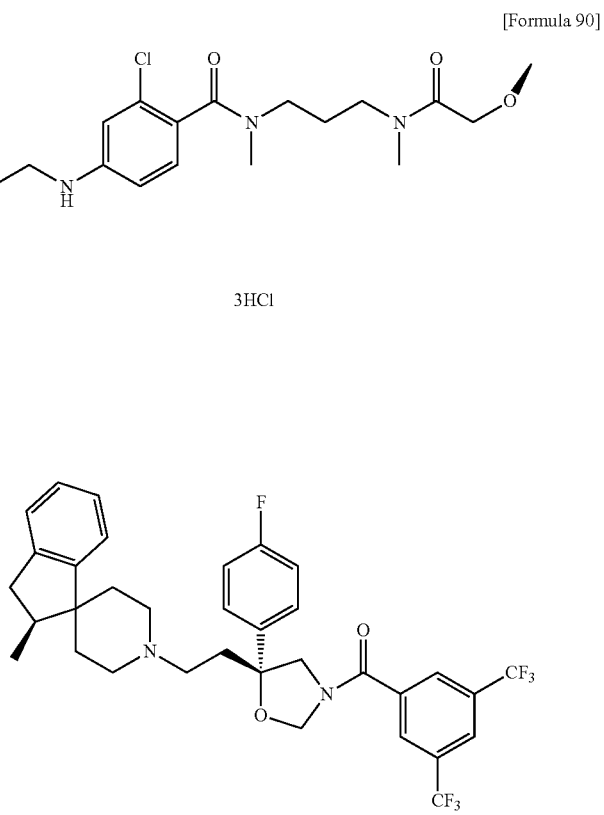

Example 85a tert-Butyl {3-[(4-amino-2-chlorobenzoyl)(methyl)amino]propyl}methylcarbamate 4-Amino-3-chlorobenzoic acid (401 mg, 2.35 mmol) and tert-butyl methyl[3-(methylamino)propyl]carbamate (473 mg, 2.35 mmol) were used to give the title compound (621 mg; yield, 75%) as a white solid according to the method described in Example 12a.

MS (FAB) m/z: 356 (M+H)+.

IR (ATR) $v_{max}$ 3349, 2975, 2931, 1677, 1602, 1396, 1161, 1136, 1087, 823 cm$^{-1}$.

Example 85c

1-{2-[{6-[(3-Chloro-4-{methyl[3-(methylamino)propyl]carbamoyl}phenyl)amino]hexanoyl}(methyl)amino]ethyl}piperidin-4-yl biphenyl-2-ylcarbamate The compound (160 mg, 0.199 mmol) obtained in Example 85b was used to give the title compound (125 mg; yield, 89%) according to the method described in Example 83d.

MS (FAB) m/z: 705 (M+H)+.

IR (ATR) $v_{max}$ 2942, 1721, 1627, 1607, 1520, 1449, 1222, 1207, 1045, 749 cm$^{-1}$.

Example 85d 1-(2-{[6-({4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-3-chlorophenyl}amino)hexanoyl](methyl)amino}ethyl)piperidin-4-yl biphenyl-2-ylcarbamate trihydrochloride The compound (92.0 mg, 0.130 mmol) obtained in Example 85c and the compound (108 mg, 0.156 mmol) obtained in Example 1j were used to give the title compound (65 mg; yield, 34%) as a white solid according to the method described in Example 80c.

MS (FAB) m/z: 1381 (M+H)$^+$ (free form).
IR (KBr) $v_{max}$ 3421, 2936, 1726, 1641, 1360, 1282, 1139, 848, 760, 702 cm$^{-1}$.

Example 86

1-(2-{[6-({4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(isopropyl)carbamoyl]phenyl}amino)hexanoyl](methyl)amino}ethyl)piperidin-4-yl biphenyl-2-ylcarbamate trihydrochloride ethylamine (0.633 mL, 4.55 mmol) and methanesulfonyl chloride (0.262 mL, 3.41 mmol) were added under ice cooling, and the mixture was stirred at the same temperature for 10 minutes. Isopropylamine (1.3 g, 23 mmol) was further added, and then the mixture was stirred overnight at room temperature. After the reaction was completed, a saturated aqueous sodium hydrogencarbonate solution was added, the mixture was extracted with methylene chloride (×3), and the resulting organic layer was dried with anhydrous sodium sulfate. The solvent was evaporated under reduced pressure, and the resulting residue was purified by NH silica gel column chromatography (elution solvents, n-hexane:ethyl acetate=9:1→1:1, v/v) to give the title compound (362 mg; yield, 73%).

MS (FAB) m/z: 231 (M+H)$^+$.
IR (ATR) $v_{max}$ 2974, 1686, 1393, 1364, 1151, 1040, 934, 771, 553, 527 cm$^{-1}$.

Example 86b 1-(2-{[6-({4-[{3-([tert-Butoxycarbonyl)(methyl)amino]propyl}(isopropyl)carbamoyl]phenyl}amino)hexanoyl](methyl)amino}ethyl)piperidin-4-yl biphenyl-2-ylcarbamate The compound (1.18 g, 1.84 mmol) obtained in Example 15c was dissolved in 1,4-dioxane (27 mL), a 4 N hydrochloric acid-dioxane solution (27 mL, 110 mmol) was added, and the mixture was stirred at room temperature for 13 hours. After the reaction was completed, toluene (30 mL×2) was added,

[Formula 91]

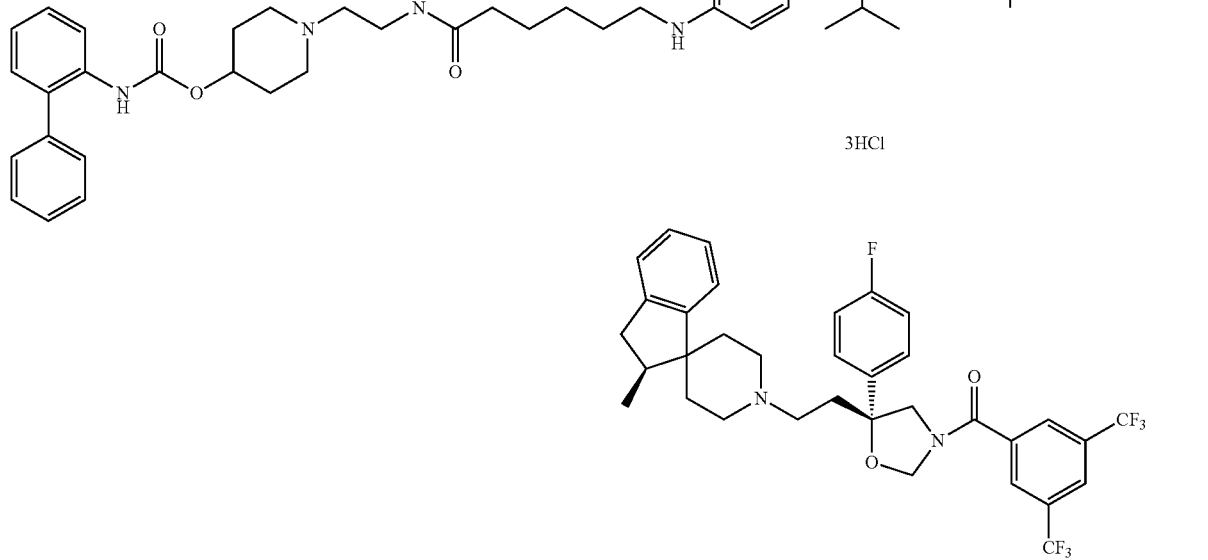

Example 86a tert-Butyl [3-(isopropylamino)propyl]methylcarbamate tert-Butyl (3-hydroxypropyl)methylcarbamate (430 mg, 2.27 mmol) was dissolved in dichloromethane (5 mL), triand then the solvent was evaporated under reduced pressure to give crude 4-({6-[(2-{4-[(biphenyl-2-ylcarbamoyl)oxy]piperidin-1-yl}ethyl)(methyl)amino]-6-oxohexyl}amino)benzoic acid (1.483 g) as a yellow solid. Dichloromethane (4 mL), triethylamine (0.548 mL, 3.94 mmol) and pivaloyl chloride (0.106 mL, 0.867 mmol) were added to the resulting crude product (345 mg), and the mixture was stirred at room temperature for 10 minutes. The compound (272 mg, 1.18 mmol) obtained in Example 86a was further added, and the mixture was stirred at 80° C. for 3 days. After the reaction was completed, a saturated aqueous sodium hydrogencarbonate solution was added to the reaction mixture, and dichloromethane was further added (×3) to separate the layers. The resulting organic layer was separated and dried with anhydrous sodium sulfate, and the solvent was evaporated under reduced pressure. The residue was purified by NH silica gel column chromatography to give the title compound (152 mg; yield, 31%).

MS (FAB) m/z: 799 (M+H)$^+$.

IR (ATR) $v_{max}$ 2933, 1686, 1607, 1438, 1206, 1152, 1043, 831, 748, 703 cm$^{-1}$.

Example 86c

1-{2-[{6-[(4-{Isopropyl[3-(methylamino)propyl]carbamoyl}phenyl)amino]hexanoyl}(methyl)amino]ethyl}piperidin-4-yl biphenyl-2-ylcarbamate The compound (140 mg, 0.175 mmol) obtained in Example 86b was used to give the title compound (73 mg; yield, 60%) according to the method described in Example 83d.

MS (FAB) m/z: 699 (M+H)$^+$.

IR (ATR) $v_{max}$ 2941, 1715, 1610, 1524, 1449, 1207, 1045, 829, 748, 702 cm$^{-1}$.

Example 86d 1-(2-{[6-({4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(isopropyl)carbamoyl]phenyl}amino)hexanoyl](methyl)amino}ethyl)piperidin-4-yl biphenyl-2-ylcarbamate trihydrochloride The compound (51 mg, 0.073 mmol) obtained in Example 86c and the compound (101 mg, 0.146 mmol) obtained in Example 1j were used to give the title compound (92 mg; yield, 85%) as a white solid according to the method described in Example 80c.

MS (FAB) m/z: 1375 (M+H)$^+$ (free form).

IR (KBr) $v_{max}$ 3422, 2936, 1726, 1645, 1359, 1282, 1138, 848, 753, 703 cm$^{-1}$.

Example 87

1-(2-{[6-({4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methoxy)carbamoyl]phenyl}amino)hexanoyl](methyl)amino}ethyl)piperidin-4-yl biphenyl-2-ylcarbamate trihydrochloride

[Formula 92]

3HCl

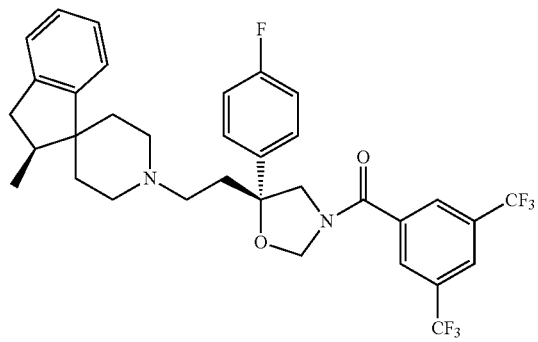

Example 87a tert-Butyl
[3-(methoxyamino)propyl]methylcarbamate tert-Butyl (3-hydroxypropyl)methylcarbamate (551 mg, 2.92 mmol) was dissolved in dichloromethane (15 mL), triethylamine (0.811 mL, 5.83 mmol) and methanesulfonyl chloride (0.337 mL, 4.38 mmol) were added under ice cooling, and the mixture was stirred at the same temperature for 30 minutes. After the reaction was completed, a saturated aqueous sodium hydrogencarbonate solution was added, the mixture was extracted with methylene chloride, and the resulting organic layer was dried with anhydrous sodium sulfate. The solvent was evaporated under reduced pressure, the resulting residue was purified by short-path silica gel column chromatography (elution solvents, n-hexane:ethyl acetate=1:1→0:1, v/v) to give crude 3-([tert-butoxycarbonyl)(methyl)amino] propyl methanesulfonate as a colorless oily substance. The resulting crude product was dissolved in ethanol (15 mL), N,N-diisopropylethylamine (5.07 mL, 29.2 mmol) and methoxyamine hydrochloride (2.43 g, 29.2 mmol) were added, and the mixture was stirred at 50° C. for 14 hours. After the reaction was completed, a saturated aqueous sodium hydrogencarbonate solution was added, the mixture was extracted with methylene chloride, and the resulting organic layer was dried with anhydrous sodium sulfate. The solvent was evaporated under reduced pressure, and the resulting residue was purified by NH silica gel column chromatography (elution solvents, n-hexane:ethyl acetate:methanol=9:1:0→0:1:0→0:9:1, v/v/v) to give the title compound (362 mg; yield, 19%).

MS (FAB) m/z: 219 (M+H)$^+$.

IR (ATR) $v_{max}$ 2975, 2934, 1685, 1392, 1365, 1150, 1048, 877, 771 cm$^{-1}$.

Example 87b 1-(2-{[6-({4-[{3-([tert-Butoxycarbonyl)(methyl)
amino]propyl}(methoxy)carbamoyl]phenyl}amino)
hexanoyl](methyl)amino}ethyl)piperidin-4-yl biphenyl-2-ylcarbamate The compound (1.18 g, 1.84 mmol) obtained in Example 15c was dissolved in 1,4-dioxane (27 mL), a 4 N hydrochloric acid-dioxane solution (27 mL, 110 mmol) was added, and the mixture was stirred at room temperature for 13 hours. After the reaction was completed, toluene (30 mL×2) was added, and then the solvent was evaporated under reduced pressure to give a crude 4-({6-[(2-{4-[(biphenyl-2-ylcarbamoyl)oxy] piperidin-1-yl}ethyl)(methyl)amino]-6-oxohexyl}amino) benzoic acid (1.483 g) as a yellow solid. Triethylamine (0.220 mL, 1.58 mmol) and 2-chloro-1-methylpyridinium bromide (202 mg, 0.791 mmol) were added to a solution of the resulting crude product (370 mg) and the compound (115 mg, 0.527 mmol) obtained in Example 87a in dichloromethane, and the mixture was stirred at 50° C. for 8 hours. After the reaction was completed, a saturated aqueous sodium hydrogencarbonate solution was added to the reaction mixture, and dichloromethane was further added (×3) to separate the layers. The resulting organic layer was separated and dried with anhydrous sodium sulfate, and the solvent was evaporated under reduced pressure. The residue was purified by NH silica gel column chromatography (elution solvents, n-hexane:ethyl acetate:methanol=1:1:0→0:1:0→0:9:1, v/v/v) to give the title compound (138 mg; yield, 33%) as a colorless oily substance.

MS (FAB) m/z: 787 (M+H)$^+$.

IR (ATR) $v_{max}$ 2932, 1690, 1603, 1521, 1393, 1205, 1155, 1044, 831, 751 cm$^{-1}$.

Example 87c

1-{2-[{6-[(4-{Methoxy[3-(methylamino)propyl]
carbamoyl}phenyl)amino]hexanoyl}(methyl)amino]
ethyl}piperidin-4-yl biphenyl-2-ylcarbamate The compound (130 mg, 0.165 mmol) obtained in Example 87b was dissolved in a mixed solvent of 1,4-dioxane (1.6 mL) and methanol (1.6 mL), a 4 N hydrochloric acid-dioxane solution (0.412 mL, 1.65 mmol) was added, and the mixture was stirred at room temperature for 4 hours. After the reaction was completed, a saturated aqueous sodium hydrogencarbonate solution was added, the mixture was extracted (×3) with methylene chloride, and the resulting organic layer was dried with anhydrous sodium sulfate. The solvent was evaporated under reduced pressure, and the resulting residue was purified by NH silica gel column chromatography to give the title compound (48 mg; yield, 42%) as a colorless oily substance.

MS (FAB) m/z: 687 (M+H)$^+$.

IR (ATR) $v_{max}$ 2935, 1716, 1605, 1523, 1225, 1061, 1045, 832, 751, 703 cm$^{-1}$.

Example 87d 1-(2-{[6-({4-[{3-[({[(2S)-1'-{2-[(5R)-3-[3,5-Bis
(trifluoromethyl)benzoyl]-5-(4-fluorophenyl)-1,3-
oxazolidin-5-yl]ethyl}-2,3-dihydrospiro[indene-1,4'-
piperidin]-2-yl]oxy}acetyl)(methyl)amino]propyl}
(methoxy)carbamoyl]phenyl}amino)hexanoyl]
(methyl)amino}ethyl)piperidin-4-yl biphenyl-2-
ylcarbamate trihydrochloride The compound (47 mg, 0.068 mmol) obtained in Example 87c and the compound (71 mg, 0.10 mmol) obtained in Example 1j were used to give the title compound (70 mg; yield, 70%) as a white solid according to the method described in Example 80c.

MS (FAB) m/z: 1363 (M+H)$^+$ (free form).

IR (KBr) $v_{max}$ 3421, 2935, 1727, 1647, 1360, 1282, 1138, 848, 753, 703 cm$^{-1}$.

Example 88

1-{2-[{6-[(4-{2-[{3-[({[(2S)-1'-{2-[(5R)-3-[3,5-Bis (trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl} (methyl)amino]-2-oxoethyl}-1,3-thiazol-2-yl)amino] hexanoyl}(methyl)amino]ethyl}piperidin-4-yl biphenyl-2-ylcarbamate trihydrochloride

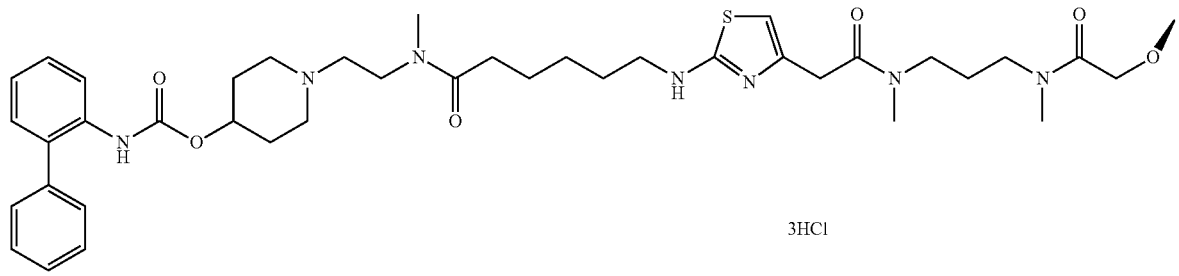

[Formula 93]

3HCl

Example 88a

1-{2-[{6-[(Aminocarbonothioyl)amino]hexanoyl} (methyl)amino]ethyl}piperidin-4-yl biphenyl-2-yl-carbamate Methyl 6-[(aminocarbonothioyl)amino]hexanoate (335 mg, 1.64 mmol) was dissolved in methanol (10 mL), a 1 N aqueous sodium hydroxide solution (2.46 mL, 2.46 mmol) was added, and the mixture was stirred at room temperature for 4 hours. After the reaction was completed, 1 N hydrochloric acid (2.46 mL, 2.46 mmol) was added, and then the solvent was evaporated under reduced pressure. The resulting residue was dissolved in dichloromethane, 1-[2-(methylamino)ethyl] piperidin-4-yl biphenyl-2-ylcarbamate (578 mg, 1.64 mmol), 1-ethyl-3-(3-dimethylaminopropyl)carbodiimide hydrochloride (469 mg, 2.46 mmol) and triethylamine (0.342 mL, 2.46 mmol) were added, and the mixture was stirred overnight at room temperature. After the reaction was completed, a saturated aqueous sodium hydrogencarbonate solution was added, the mixture was extracted 3 times with methylene chloride, and the resulting organic layer was dried with anhydrous sodium sulfate. The solvent was evaporated under reduced pressure, and the resulting residue was purified by NH silica gel column chromatography (elution solvents, n-hexane:ethyl acetate:methanol=1:1:0→0:10:0→0:9:1, v/v/v) to give the title compound (291 mg; yield, 34%).

MS (FAB) m/z: 526 (M+H)⁺.

IR (KBr) $v_{max}$ 3308, 2933, 1728, 1626, 1521, 1449, 1207, 1044, 749, 703 cm$^{-1}$.

Example 88b

Ethyl [2-({6-[(2-{4-[(biphenyl-2-ylcarbamoyl)oxy] piperidin-1-yl}ethyl)(methyl)amino]-6-oxohexyl}amino)-1,3-thiazole-4-yl]acetate The compound (503 mg, 0.958 mmol) obtained in Example 88a was dissolved in ethanol (10 mL), ethyl 4-chloro-3-oxobutanoate (0.143 mL, 1.054 mmol) was further added, and the mixture was stirred at 80° C. for 2 hours. After the reaction was completed, a saturated aqueous sodium hydrogencarbonate solution was added, the mixture was extracted (×3) with dichloromethane, and the resulting organic layer was dried with anhydrous sodium sulfate. The solvent was evaporated under reduced pressure, and the resulting residue was purified by NH silica gel column chromatography (elution solvents, n-hexane:ethyl acetate:methanol=1:1:0→0:1:0→0:9:1, v/v/v) to give the title compound (594 mg; yield, 98%) as a yellow oily substance.

MS (FAB) m/z: 636 (M+H)⁺.

IR (ATR) $v_{max}$ 2934, 1728, 1629, 1519, 1448, 1204, 1145, 1042, 747, 702 cm$^{-1}$.

Example 88c

1-{2-[{6-[(4-{2-[{3-([tert-Butoxycarbonyl)(methyl)
amino]propyl}(methyl)amino]-2-oxoethyl}-1,3-thia-
zol-2-yl)amino]hexanoyl}(methyl)amino]
ethyl}piperidin-4-yl biphenyl-2-ylcarbamate The compound (261 mg, 0.411 mmol) obtained in Example 88b and tert-butyl methyl[3-(methylamino)propyl] carbamate (124 mg, 0.616 mmol), a compound described in the literature (J. Med. Chem., EN, 1999, 33, 97), were used to give the title compound (91 mg; yield, 28%) according to the method described in Example 88a.
MS (FAB) m/z: 792 (M+H)$^+$.
IR (ATR) $v_{max}$ 2935, 1692, 1637, 1523, 1449, 1207, 1161, 1045, 749, 702 cm$^{-1}$.

Example 88d

1-{2-[{6-[(4-{2-[{3-[({[(2S)-1'-{2-[(5R)-3-[3,5-Bis
(trifluoromethyl)benzoyl]-5-(4-fluorophenyl)-1,3-
oxazolidin-5-yl]ethyl}-2,3-dihydrospiro[indene-1,4'-
piperidin]-2-yl]oxy}acetyl)(methyl)amino]propyl}
(methyl)amino]-2-oxoethyl}-1,3-thiazol-2-yl)amino]
hexanoyl}(methyl)amino]ethyl}piperidin-4-yl
biphenyl-2-ylcarbamate trihydrochloride The compound (91 mg, 0.130 mmol) obtained in Example 1j was dissolved in dichloromethane (4 mL), triethylamine (0.0303 mL, 0.218 mmol) and pivaloyl chloride (0.0146 mL, 0.120 mmol) were added, and the mixture was stirred at room temperature for 30 minutes. A solution of the compound (87 mg, 0.11 mmol) obtained in Example 88c in 1,4-dioxane (2 mL) and methanol (1 mL) and a 4 N hydrochloric acid-dioxane solution (27 µL, 1.1 mmol) were added to the reaction mixture, and the mixture was stirred overnight at room temperature. After the reaction was completed, a saturated aqueous sodium hydrogencarbonate solution was added to the reaction mixture, and the mixture was further extracted (×3) with dichloromethane. The resulting organic layer was separated and dried with anhydrous sodium sulfate, and the solvent was evaporated under reduced pressure. The residue was purified by NH silica gel column chromatography (elution solvents, hexane:ethyl acetate:methanol=1:1:0→0:1:0→0:9:1, v/v/v) to give a free crude product of the title compound. This product was purified by reverse phase liquid chromatography (XTerra Prep MS C18 OBD, 5 µm, 30×100 mm) (elution solvents, acetonitrile:0.1% aqueous ammonium formate solution=10:90→100:0, v/v) to give a free form of the title compound. A 4 N hydrochloric acid-dioxane solution was added to the resulting free form of the title compound, and then the mixture was concentrated under reduced pressure to give the title compound (25 mg; yield, 16%) as a white solid.
MS (FAB) m/z: 1368 (M+H)$^+$ (free form).
IR (KBr) $v_{max}$ 3422, 2935, 1725, 1644, 1360, 1282, 1139, 753, 704, 682 cm$^{-1}$.

Example 89

1-(2-{[6-({5-[{2-[({[(2S)-1'-{2-[(5R)-3-[3,5-Bis
(trifluoromethyl)benzoyl]-5-(4-fluorophenyl)-1,3-
oxazolidin-5-yl]ethyl}-2,3-dihydrospiro[indene-1,4'-
piperidin]-2-yl]oxy}acetyl)(methyl)amino]ethyl}
(methyl)carbamoyl]-4-methyl-2-thienyl}amino)
hexanoyl](methyl)amino}ethyl)piperidin-4-yl
biphenyl-2-ylcarbamate

[Formula 94]

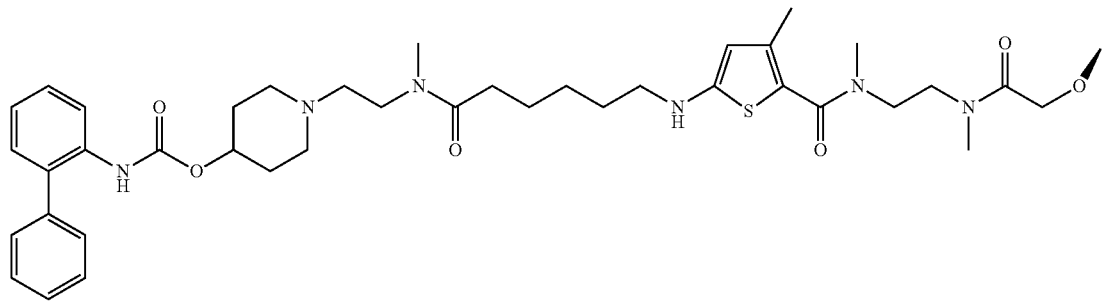

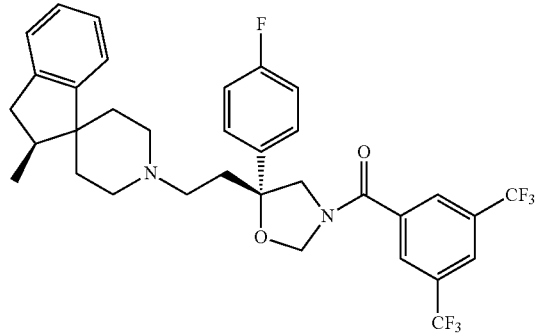

Example 89a

5-[(tert-Butoxycarbonyl)amino]-3-methylthiophene-
2-carboxylic acid

The compound (1.81 g, 6.68 mmol) obtained in Example 30b was dissolved in methanol (27 mL), a 1 N aqueous sodium hydroxide solution (26.7 mL, 26.7 mmol) was added, and the mixture was stirred at 50° C. for 19.5 hours. A 1 N aqueous sodium hydroxide solution (26.7 mL, 26.7 mmol) was added to the reaction mixture, and the mixture was stirred at 50° C. for 24 hours. Methanol was evaporated under reduced pressure, water and ethyl acetate were added to the resulting residue, and the mixture was extracted with water (×2). The resulting aqueous layer was adjusted to pH 1 with 1 N hydrochloric acid, the mixture was extracted with ethyl acetate (×2), and then the organic layer was washed with saturated sodium chloride solution. The organic layer was dried with anhydrous sodium sulfate, the solvent was evaporated under reduced pressure, and moisture was removed from the resulting residue azeotropically with toluene (×2) to give the title compound (1.23 g; yield, 62%) as a white solid.

$^1$H NMR (DMSO-$d_6$, 400 MHz): δ 1.48 (9H, s), 2.35 (3H, s), 6.38 (1H, s), 10.79 (1H, brs), 12.29 (1H, brs).

MS (APCI) m/z: 258 (M+H)$^+$.

Example 89b tert-Butyl {2-[({5-[(tert-butoxycarbonyl)amino]-3-methylthiophen-2-yl}carbonyl)(methyl)amino]ethyl}methylcarbamate The compound (600 mg, 2.33 mmol) obtained in Example 89a and tert-butyl methyl[2-(methylamino)ethyl]carbamate (439 mg, 2.33 mmol) described in the literature (J. Med. Chem. 1990, 33, 97) were dissolved in methylene chloride (23 mL), 1-ethyl-3-(3-dimethylaminopropyl)carbodiimide hydrochloride (670 mg, 3.50 mmol) and 4-dimethylaminopyridine (14 mg, 0.117 mmol) were added, and the mixture was stirred at room temperature for 1.5 hours. The solvent was evaporated under reduced pressure, 1 N hydrochloric acid was added to the resulting residue, the mixture was extracted with ethyl acetate, and then the organic layer was washed with saturated sodium chloride solution. The organic layer was dried with anhydrous sodium sulfate, then the solvent was evaporated under reduced pressure, and the resulting residue was purified by silica gel column chromatography (hexane:ethyl acetate=1:1, v/v) to give the title compound (757 mg; yield, 79%) as a light yellow solid.

$^1$H NMR (CDCl$_3$, 400 MHz): δ 1.45 (9H, s), 1.51 (9H, s), 2.18 (3H, s), 2.85 (3H, s), 3.10 (3H, s), 3.40-3.46 (2H, m), 3.59-3.64 (2H, m), 6.28 (1H, s), 6.96 (11H, brs).

MS (APCI) m/z: 428 (M+H)$^+$.

Example 89c tert-Butyl (2-{[(5-amino-3-methylthiophen-2-yl)carbonyl](methyl)amino}ethyl)methylcarbamate The compound (350 mg, 0.819 mmol) obtained in Example 89b was dissolved in methylene chloride (8 mL), trifluoroacetic acid (4 mL) was added under ice cooling, and the mixture was stirred at room temperature for 1 hour. The solvent was evaporated under reduced pressure, and moisture was removed from the resulting residue azeotropically with toluene (×2). The resulting residue was dissolved in methylene chloride (8 mL), triethylamine (0.569 mL, 4.10 mmol) and di-tert-butyl dicarbonate (215 mg, 0.983 mmol) were added, and the mixture was stirred at room temperature for 2 hours. The solvent was evaporated under reduced pressure, and the resulting residue was purified by silica gel column chromatography (hexane:ethyl acetate=1:2, v/v) to give the title compound (267 mg; yield, 100%) as a light yellow solid.

$^1$H NMR (CDCl$_3$, 400 MHz): δ 1.45 (9H, s), 2.14 (3H, s), 2.85 (3H, s), 3.09 (3H, s), 3.39-3.46 (2H, m), 3.58-3.63 (2H, m), 3.87 (2H, brs), 5.91 (1H, s).

MS (APCI) m/z: 328 (M+H)$^+$.

Example 89d 1-(2-{[6-({5-[{2-([tert-Butoxycarbonyl)(methyl)amino]ethyl}(methyl)carbamoyl]-4-methylthiophen-2-yl}amino)hexanoyl](methyl)amino}ethyl)piperidin-4-yl biphenyl-2-ylcarbamate The compound (210 mg, 0.450 mmol) obtained in Example 4g and the compound (134 mg, 0.409 mmol) obtained in Example 89c were dissolved in methylene chloride (4 mL), acetic acid (79 μL) and sodium triacetoxyborohydride (130 mg, 0.614 mmol) were added, and the mixture was stirred at room temperature for 12 hours. Sodium borohydride (16 mg, 0.409 mmol) was added to the reaction mixture, and the mixture was stirred at room temperature for 1 hour. The solvent was evaporated under reduced pressure, and the resulting residue was purified by NH silica gel column chromatography (hexane:ethyl acetate=1:1→ethyl acetate:methanol=50:1, v/v) to give the title compound (153 mg; yield, 49%) as a light yellow solid.

$^1$H NMR (CDCl$_3$, 400 MHz): δ 1.40-1.45 (2H, m), 1.45 (9H, s), 1.62-1.69 (6H, m), 1.91-1.94 (2H, m), 2.15 (3H, s), 2.24-2.36 (4H, m), 2.47 (2H, t, J=7.1 Hz), 2.68-2.74 (2H, m), 2.85 (3H, s), 2.94 (1.3H, s), 3.00 (1.7H, s), 3.08-3.12 (5H, m), 3.36-3.49 (4H, m), 3.56-3.63 (2H, m), 4.06-4.11 (1H, m), 4.72 (1H, brs), 5.71 (1H, s), 6.59 (1H, brs), 7.11-7.15 (1H, m), 7.20-7.23 (1H, m), 7.34-7.38 (3H, m), 7.42-7.43 (1H, m), 7.47-7.52 (2H, m), 8.08-8.11 (1H, m).

MS (APCI) m/z: 777 (M+H)$^+$.

Example 89e

1-[2-(Methyl{6-[(4-methyl-5-{methyl[2-(methylamino)ethyl]carbamoyl}thiophen-2-yl)amino]hexanoyl}amino)ethyl]piperidin-4-yl biphenyl-2-ylcarbamate The compound (153 mg, 0.201 mmol) obtained in Example 89d was dissolved in 2 N hydrochloric acid-methanol (2.01 mL, 4.01 mmol), and the mixture was stirred at room temperature for 2 hours. Toluene was added to the reaction mixture, the solvent was evaporated under reduced pressure, the resulting residue was dissolved in ethyl acetate, and the mixture was adjusted to pH 10 with a 1 N aqueous sodium hydroxide solution. The mixture was extracted with ethyl acetate (×2) and dried with anhydrous sodium sulfate. The solvent was evaporated under reduced pressure, and the resulting residue was purified by NH silica gel column chromatography (ethyl acetate:methanol=100:0→methylene chloride:methanol=10:1, v/v) to give the title compound (122 mg; yield, 92%) as a white solid.

$^1$H NMR (CDCl$_3$, 400 MHz): δ 1.40-1.44 (2H, m), 1.52-1.57 (2H, m), 1.63-1.68 (6H, m), 1.89-1.95 (2H, m), 2.15 (3H, s), 2.27-2.35 (4H, m), 2.43-2.49 (4H, m), 2.68-2.75 (2H, m), 2.81 (2H, t, J=6.6 Hz), 2.94 (1.1H, s), 3.00 (1.9H, s), 3.07-

3.13 (4H, m), 3.38 (1H, t, J=6.6 Hz), 3.46-3.49 (1H, m), 3.58 (2H, t, J=6.6 Hz), 4.05-4.08 (1H, m), 4.72 (1H, brs), 5.71 (1H, s), 6.60 (1H, brs), 7.11-7.16 (1H, m), 7.21-7.23 (1H, m), 7.26-7.30 (1H, m), 7.35-7.38 (3H, m), 7.42-7.43 (1H, m), 7.47-7.52 (2H, m), 8.08-8.11 (1H, m).
MS (APCI) m/z: 677 (M+H)$^+$.

Example 89f 1-(2-{[6-({5-[{2-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]ethyl}(methyl)carbamoyl]-4-methyl-2-thienyl}amino)hexanoyl](methyl)amino}ethyl)piperidin-4-yl biphenyl-2-ylcarbamate The compound (122 mg, 0.184 mmol) obtained in Example 89e was used to give the title compound (121 mg; yield, 49%) as a white solid according to the method described in Example 11e.
MS (FAB) m/z: 1353 (M+H)$^+$.
IR (KBr) $\nu_{max}$ 2930, 1731, 1646, 1512, 1449, 1359, 1281, 1181, 1139, 754 cm$^{-1}$.

Example 90

1-{2-[{6-[{5-[{2-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]ethyl}(methyl)carbamoyl]-4-methyl-2-thienyl}(methyl)amino]hexanoyl}(methyl)amino]ethyl}piperidin-4-yl biphenyl-2-ylcarbamate

Example 90a tert-Butyl {5-[{2-([tert-butoxycarbonyl)(methyl)amino]ethyl}(methyl)carbamoyl]-4-methylthiophen-2-yl}methylcarbamate Sodium hydride (50 mg, 55%, 1.14 mmol) was added to a solution of the compound (407 mg, 0.952 mmol) obtained in Example 89b in N,N-dimethylformamide (3 mL) under ice cooling, and the mixture was stirred at room temperature for 30 minutes. Methyl iodide (0.119 mL, 1.90 mmol) was added to the reaction mixture, and the mixture was stirred at room temperature for 2.5 hours. The reaction mixture was diluted with ethyl acetate, and the organic layer was washed successively with water (×3) and saturated sodium chloride solution. The organic layer was dried with anhydrous sodium sulfate, then the solvent was evaporated under reduced pressure, and the resulting residue was purified by silica gel column chromatography (hexane:ethyl acetate=1:1, v/v) to give the title compound (418 mg; yield, 99%) as a white solid.
$^1$H NMR (CDCl$_3$, 400 MHz): δ 1.45 (9H, s), 1.54 (9H, s), 2.20 (3H, s), 2.85 (3H, s), 3.10 (3H, s), 3.32 (3H, s), 3.40-3.46 (2H, m), 3.61-3.64 (2H, m), 6.24 (1H, s).
MS (APCI) m/z: 442 (M+H)$^+$.

Example 90b tert-Butyl methyl[2-(methyl{[3-methyl-5-(methylamino)thiophen-2-yl]carbonyl}amino)ethyl]carbamate The compound (418 mg, 0.947 mmol) obtained in Example 90a, triethylamine (0.658 mL, 4.74 mmol) and di-tert-butyl dicarbonate (248 mg, 1.14 mmol) were used to give

[Formula 95]

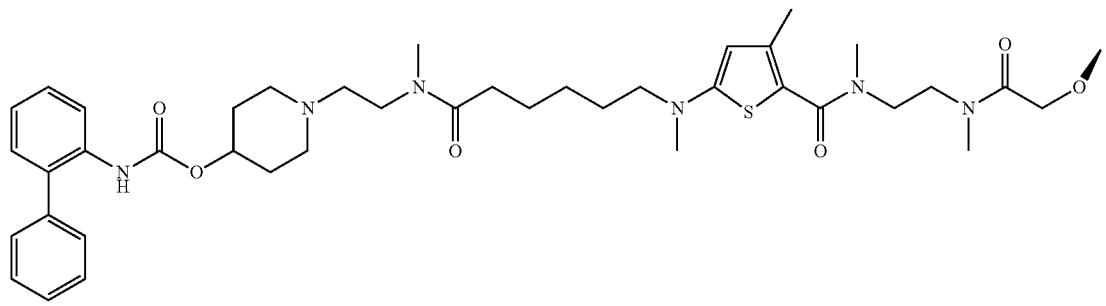

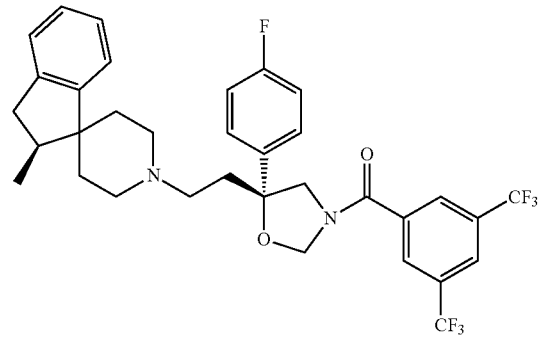

the title compound (319 mg; yield, 99%) as a yellow oily substance according to the method described in Example 89c.

$^1$H NMR (CDCl$_3$, 400 MHz): δ 1.45 (9H, s), 2.17 (3H, s), 2.85 (3H, s), 2.86 (3H, s), 3.10 (3H, s), 3.41-3.46 (2H, m), 3.59-3.63 (2H, m), 3.98 (1H, brs), 5.73 (1H, s).

MS (APCI) m/z: 342 (M+H)$^+$.

Example 90c

1-[2-(Methyl{6-[methyl(4-methyl-5-{methyl[2-(methylamino)ethyl]carbamoyl}thiophen-2-yl)amino]hexanoyl}amino)ethyl]piperidin-4-yl biphenyl-2-ylcarbamate The compound (240 mg, 0.515 mmol) obtained in Example 4g, the compound (160 mg, 0.469 mmol) obtained in Example 90b, acetic acid (91 μL), sodium triacetoxyborohydride (149 mg, 0.704 mmol) and sodium borohydride (18 mg, 0.469 mmol) were used to give a crude aminated compound (189 mg) according to the method described in Example 89d.

The resulting crude aminated compound and 2 N hydrochloric acid-methanol (2.39 mL, 4.78 mmol) were used to give the title compound (149 mg; yield, 42%) as a white solid according to the method described in Example 89e.

H NMR (CDCl$_3$, 400 MHz): δ 1.32-1.37 (3H, m), 1.59-1.69 (6H, m), 1.88-1.94 (2H, m), 2.18 (3H, m), 2.24-2.34 (4H, m), 2.43-2.48 (5H, m), 2.67-2.75 (2H, m), 2.81 (2H, t, J=6.8 Hz), 2.88 (3H, s), 2.93 (1H, s), 3.00 (2H, s), 3.08 (3H, s), 3.18-3.22 (2H, m), 3.35-3.39 (1H, m), 3.45-3.49 (1H, m), 3.57-3.60 (2H, m), 4.72 (1H, brs), 6.58-6.62 (1H, m), 7.11-7.15 (2H, m), 7.20-7.26 (1H, m), 7.34-7.38 (3H, m), 7.41-7.43 (1H, m), 7.47-7.52 (2H, m), 8.09-8.10 (1H, m).

MS (APCI) m/z: 691 (M+H)$^+$.

Example 90d

1-{2-[{6-[{5-[{2-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]ethyl}(methyl)carbamoyl)-4-methyl-2-thienyl}(methyl)amino]hexanoyl}(methyl)amino]ethyl}piperidin-4-yl biphenyl-2-ylcarbamate The compound (149 mg, 0.216 mmol) obtained in Example 90c was used to give the title compound (217 mg; yield, 73%) as a white solid according to the method described in Example 11e.

MS (FAB) m/z: 1353 (M+H)$^+$.

IR (KBr) ν$_{max}$ 2930, 1731, 1646, 1512, 1449, 1359, 1281, 1181, 1139, 754 cm$^{-1}$.

Example 91

1-(2-{[6-({4-[{3-[({[(2S)-1'-{2-[(5R)-3-[3,5-Bis(trifluoromethyl)benzoyl]-5-(3-bromo-4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}amino)hexanoyl](methyl)amino}ethyl)piperidin-4-yl biphenyl-2-ylcarbamate

[Formula 96]

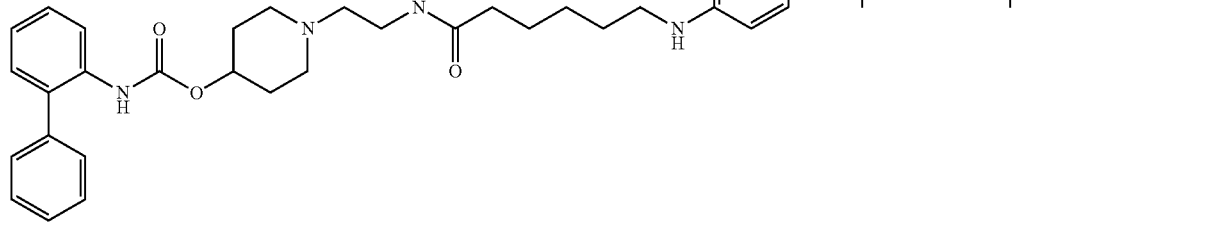

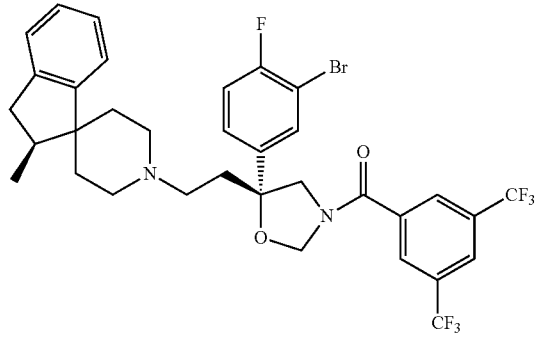

Example 91a

2-Bromo-1-fluoro-4-(prop-1-en-2-yl)benzene 1-(3-Bromo-4-fluorophenyl)ethanone (5.0 g, 23.0 mmol) was dissolved in toluene (100 mL), a 3.0 M methylmagnesium chloride-tetrahydrofuran solution (11.5 mL, 34.6 mmol) was added dropwise with stirring under ice cooling, and the mixture was stirred at room temperature under a nitrogen atmosphere for 1 hour. Subsequently, acetic acid (1 mL) was added with stirring under ice cooling, and the mixture was stirred with heating to reflux for 4 hours. After the reaction was completed, a saturated aqueous sodium hydrogencarbonate solution was added with stirring under ice cooling, and ethyl acetate was further added to separate the layers. The resulting organic layer was separated, washed with saturated sodium chloride solution, and then dried with anhydrous sodium sulfate, and the solvent was evaporated under reduced pressure. The residue was purified by silica gel column chromatography (hexane:ethyl acetate=50:1, v/v) to give the title compound (2.06 g; yield, 42%) as a colorless oily substance.

$^1$H HMR (CDCl$_3$, 500 MHz): δ 2.1 (3H, s), 5.1 (1H, s), 5.3 (1H, s), 7.0-7.1 (1H, m), 7.3-7.4 (1H, m), 7.6-7.7 (1H, m).

Example 91b 3-(3-Bromo-4-fluorophenyl)but-3-en-1-ol

A molecular sieve 4A (3.14 g) and a boron trifluoride-diethyl ether complex (2.16 mL, 17.5 mmol) were added to methylene chloride (31 mL), and the mixture was stirred at room temperature for 1 hour. Subsequently, paraformaldehyde (0.46 g, 14.6 mmol) and the compound (3.14 g, 14.6 mmol) obtained in Example 91a were added at −5° C., and the mixture was stirred at the same temperature for 18 hours. After the reaction was completed, a saturated aqueous sodium hydrogencarbonate solution was added, and ethyl acetate was further added to separate the layers. The resulting organic layer was separated, washed with saturated sodium chloride solution, and then dried with anhydrous sodium sulfate, and the solvent was evaporated under reduced pressure. The residue was purified by silica gel column chromatography (hexane:ethyl acetate=5:1→3:1, v/v) to give the title compound (1.24 g; yield, 35%) as a colorless oily substance.

$^1$H HMR (CDCl$_3$, 400 MHz): δ 1.3-1.4 (1H, m), 2.7-2.8 (2H, m), 3.7-3.8 (1H, m), 5.2 (1H, s), 5.4 (1H, s), 7.0-7.1 (1H, m), 7.3-7.4 (1H, m), 7.6-7.7 (1H, m).

Example 91c

{[3-(3-Bromo-4-fluorophenyl)but-3-en-1-yl]oxy}(tert-butyl)dimethylsilane

The compound (2.17 g, 8.85 mmol) obtained in Example 91b was dissolved in methylene chloride (33 mL), imidazole (0.90 g, 13.3 mmol) and tert-butyl(chloro)dimethylsilane (1.60 g, 10.6 mmol) were added with stirring under ice cooling, and the mixture was stirred at room temperature under a nitrogen atmosphere for 20 hours. After the reaction was completed, water was added, and ethyl acetate was further added to separate the layers. The resulting organic layer was separated, washed with saturated sodium chloride solution, and then dried with anhydrous sodium sulfate, and the solvent was evaporated under reduced pressure. The residue was purified by silica gel column chromatography (hexane:ethyl acetate=50:1, v/v) to give the title compound (3.02 g; yield, 95%) as a colorless oily substance.

$^1$H HMR (CDCl$_3$, 400 MHz): δ 0.0 (6H, s), 0.9 (9H, s), 2.6-2.7 (2H, m), 3.7-3.8 (2H, m), 5.1 (1H, s), 5.3 (1H, s), 7.0-7.1 (1H, m), 7.3-7.4 (1H, m), 7.5-7.6 (1H, m).

Example 91d (2R)-2-(3-Bromo-4-fluorophenyl)-4-{[tert-butyl(dimethyl)silyl]oxy}butane-1,2-diol The compound (2.62 g., 7.29 mmol) obtained in Example 91c was dissolved in a mixed solvent (130 mL) of tert-butanol and water (1/1), the mixture was stirred under ice cooling, AD-mix-β (14.6 g) was added, and the mixture was stirred in a water bath for 16 hours. After the reaction was completed, saturated aqueous sodium thiosulfate solution was added, and ethyl acetate was further added to separate the layers. The resulting organic layer was separated, washed with saturated sodium chloride solution, and then dried with anhydrous sodium sulfate, and the solvent was evaporated under reduced pressure. The residue was purified by silica gel column chromatography (hexane:ethyl acetate=3:1, v/v) to give the title compound (2.85 g; yield, 89%) as a yellow oily substance.

MS (FAB): m/z 393 (M+H)$^+$.

IR (ATR) ν max 1493, 1471, 1389, 1255, 1066, 1045, 891, 825, 777, 710 cm$^{-1}$.

Column for HPLC analysis, CHIRALCEL OF (0.46 cmφ× 25 cm L) produced by Daicel Chemical Industries, Ltd.; elution solvents, 97:3 n-hexane:2-propanol; flow rate, 0.5 mL/min; tR(R)=16.4 min, tR(S)=18.6 min; optical purity, 96.6% ee.

Example 91e (2R)-2-(3-Bromo-4-fluorophenyl)-4-{[tert-butyl(dimethyl)silyl]oxy}-2-hydroxybutyl methanesulfonate The compound (1.50 g, 3.80 mmol) obtained in Example 91d was dissolved in methylene chloride (60 mL), the mixture was stirred under ice cooling, methanesulfonyl chloride (0.35 mL, 4.56 mmol) and triethylamine (0.79 mL, 5.70 mmol) were added, and the mixture was stirred at the same temperature under a nitrogen atmosphere for 4 hours. After the reaction was completed, water was added to the reaction mixture under ice cooling, and ethyl acetate was further added to separate the layers. The resulting organic layer was separated, washed with saturated sodium chloride solution, and then dried with anhydrous sodium sulfate, and the solvent was evaporated under reduced pressure to give a crude title compound (1.98 g) as a colorless oily substance.

MS (FAB): m/z 471 (M+H)$^+$.

IR (ATR) ν max 1494, 1354, 1255, 1174, 1079, 962, 896, 824, 778, 527 cm$^{-1}$.

Example 91f (2R)-1-Amino-2-(3-bromo-4-fluorophenyl)-4-{[tert-butyl(dimethyl)silyl]oxy}butan-2-ol The compound (1.79 g, 3.80 mmol) obtained in Example 91e was dissolved in N,N'-dimethylformamide (60 mL), the mixture was stirred at room temperature, a potassium salt of phthalimide (1.41 g, 7.60 mmol) was added, and the mixture was stirred at 110° C. for 18 hours. After the reaction was completed, saturated aqueous ammonium chloride was added to the reaction mixture under ice cooling, and ethyl acetate was further added to separate the layers. The resulting organic layer was separated, washed with saturated sodium chloride solution, and then dried with anhydrous sodium sulfate, and then the solvent was evaporated under reduced pressure. The resulting residue (3.0 g) was dissolved in ethanol (60 mL), the mixture was stirred at room temperature, hydrazine monohydrate (0.74 mL, 15.2 mmol) was added, and the mixture was stirred at 60° C. for 3.5 hours. After the reaction was completed, the reaction mixture was filtered, and the filtrate was washed with ethyl acetate. The solvent was evaporated under reduced pressure to give the crude title compound (1.71 g) as a pale yellow oily substance.

MS (FAB): m/z 392 (M+H)$^+$.
IR (ATR) ν max 1493, 1471, 1388, 1253, 1070, 891, 828, 775, 695, 666 cm$^{-1}$.

Example 91g (5R)-3-[3,5-Bis(trifluoromethyl)benzoyl]-5-(3-bromo-4-fluorophenyl)-5-(2-{[tert-butyl(dimethyl)silyl]oxy}ethyl)-1,3-oxazolidine The compound (0.90 g, 2.15 mmol) obtained in Example 91f was used to give the title compound (669 mg, yield 48%) as a colorless oily substance according to the method described in Example 1b.

MS (FAB): m/z 644 (M+H)$^+$.
IR (ATR) ν max 1650, 1356, 1278, 1176, 1135, 1090, 905, 827, 776, 681 cm$^{-1}$.

Example 91h

2-[(5R)-3-[3,5-Bis(trifluoromethyl)benzoyl]-5-(3-bromo-4-fluorophenyl)-1,3-oxazolidin-5-yl]ethanol The compound (0.67 g, 1.04 mmol) obtained in Example 91g was used to give the title compound (438 mg; yield, 79%) as a colorless oily substance according to the method described in Example 1c.

MS (FAB): m/z 530 (M+H)$^+$.
IR (ATR) ν max 1640, 1358, 1277, 1174, 1131, 1046, 906, 756, 700, 681 cm$^{-1}$.

Example 91i

2-[(5R)-3-[3,5-Bis(trifluoromethyl)benzoyl]-5-(3-bromo-4-fluorophenyl)-1,3-oxazolidin-5-yl]ethyl methanesulfonate The compound (438 mg, 0.83 mmol) obtained in Example 91h was used to give the title compound (470 mg; yield, 94%) as a white solid according to the method described in Example 1d.

MS (FAB): m/z 608 (M+H)$^+$.
IR (ATR) ν max 1646, 1355, 1277, 1170, 1129, 1046, 957, 906, 681, 527 cm$^{-1}$.

Example 91j

Ethyl {[(2S)-1'-{2-[(5R)-3-[3,5-bis(trifluoromethyl)benzoyl]-5-(3-bromo-4-fluorophenyl)-1,3-oxazolidin-5-yl]ethyl}-2,3-dihydrospiro[indene-1,4'-piperidin]-2-yl]oxy}acetate The compound (470 mg, 0.77 mmol) obtained in Example 91i and the compound (335.4 mg, 1.16 mmol) obtained in Example 1h were used to give the title compound (415 mg; yield, 67%) as a white solid according to the method described in Example 1i.

MS (FAB): m/z 801 (M+H)$^+$.
IR (KBr) ν max 1755, 1652, 1432, 1358, 1281, 1182, 1137, 906, 757, 682 cm$^{-1}$.

Example 91k

{[(2S)-1'-{2-[(5R)-3-[3,5-Bis(trifluoromethyl)benzoyl]-5-(3-bromo-4-fluorophenyl)-1,3-oxazolidin-5-yl]ethyl}-2,3-dihydrospiro[indene-1,4'-piperidin]-2-yl]oxy}acetic acid The compound (415 mg, 0.52 mmol) obtained in Example 91j was used to give the title compound (379 mg; yield, 95%) as a white solid according to the method described in Example 1j.

MS (FAB): m/z 773 (M+H)$^+$.
IR (KBr) ν max 1651, 1431, 1359, 1281, 1179, 1138, 1109, 907, 758, 682 cm$^{-1}$.

Example 91l

1-[2-(Methyl{6-[(4-{methyl[3-(methylamino)propyl]carbamoyl}phenyl)amino]hexanoyl}amino)ethyl]piperidin-4-yl biphenyl-2-ylcarbamate The compound (1.01 mg, 1.57 mmol) obtained in Example 15c was dissolved in 1,4-dioxane (36 mL), a 4 N hydrochloric acid-dioxane solution (11.8 mL, 47.1 mmol) was added, and the mixture was stirred at room temperature for 12 hours. After the reaction was completed, toluene was added, and then the solvent was evaporated under reduced pressure to give crude 4-({6-[(2-{4-[(biphenyl-2-ylcarbamoyl)oxy]piperidin-1-yl}ethyl)(methyl)amino]-6-oxohexyl}amino)benzoic acid. The resulting crude carboxylic acid compound and N,N'-dimethylpropane-1,3-diamine (1.60 g, 15.7 mmol) were used to give the title compound (960 mg; yield, 91%) as a white solid according to the method described in Example 12a.

MS (FAB): m/z 671 (M+H)$^+$.
IR (KBr) ν max 3308, 2937, 2797, 1715, 1610, 1528, 1480, 1231, 1046, 833, 749, 702 cm$^{-1}$.

Example 91 m 1-(2-{[6-({4-[{3-[({[(2S)-1'-{2-[(5R)-3-[3,5-Bis(trifluoromethyl)benzoyl]-5-(3-bromo-4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}amino)hexanoyl](methyl)amino}ethyl)piperidin-4-yl biphenyl-2-ylcarbamate The compound (179 mg, 0.23 mmol) obtained in Example 91k and the compound (147.5 mg, 0.22 mmol) obtained in Example 91l were used to give the title compound (127 mg; yield, 39%) as a white solid according to the method described in Example 11e.

MS (FAB): m/z 1425 (M+H)$^+$.
IR (KBr) ν max 2933, 1732, 1645, 1495, 1358, 1281, 1179, 1139, 1045, 757 cm$^{-1}$.

Example 92

1-{2-[{6-[(4-{[4-({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)piperazin-1-yl]carbonyl}phenyl)amino]hexanoyl}(methyl)amino]ethyl}piperidin-4-yl biphenyl-2-ylcarbamate

[Formula 97]

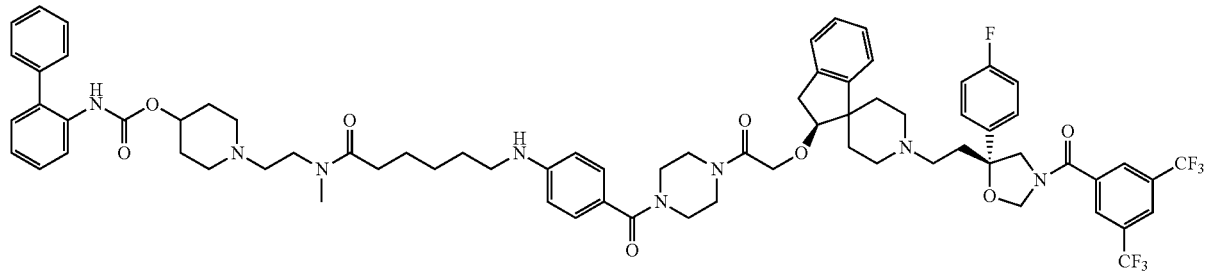

Example 92a tert-Butyl 4-{[4-({6-[(2-{4-[(biphenyl-2-ylcarbamoyl)oxy]piperidin-1-yl}ethyl)(methyl)amino]-6-oxohexyl}amino)phenyl]carbonyl}piperazine-1-carboxylate The compound (200 mg, 0.311 mmol) obtained in Example 15c was dissolved in 1,4-dioxane, a 4 N hydrochloric acid-dioxane solution (4.67 mL, 18.7 mmol) was added, and the mixture was stirred at room temperature for 12 hours. After the reaction was completed, toluene was added, and then the solvent was evaporated under reduced pressure to give crude 4-({6-[(2-{4-[(biphenyl-2-ylcarbamoyl)oxy]piperidin-1-yl}ethyl)(methyl)amino]-6-oxohexyl}amino)benzoic acid. The resulting crude carboxylic acid compound and tert-butyl piperazine-1-carboxylate (58 mg, 0.311 mmol) were dissolved in methylene chloride, triethylamine (0.259 mL, 1.87 mmol) and 1-ethyl-3-(3-dimethylaminopropyl)carbodiimide hydrochloride (90 mg, 0.467 mmol) were added, and the mixture was stirred at room temperature for 17 hours. The solvent was evaporated under reduced pressure, the resulting residue was dissolved in ethyl acetate, water and saturated aqueous sodium hydrogencarbonate were added, and the mixture was extracted with ethyl acetate. The organic layer was washed with saturated sodium chloride solution and dried with anhydrous sodium sulfate, then the solvent was evaporated under reduced pressure, and the resulting residue was purified by NH silica gel column chromatography (hexane:ethyl acetate=1:2→0:100, v/v) to give the title compound (98 mg; yield, 42%) as a white solid.

H NMR (CDCl$_3$, 400 MHz): δ 1.47 (9H, s), 1.64-1.70 (6H, m), 1.89-1.95 (2H, m), 2.05-2.11 (1H, m), 2.24-2.36 (4H, m), 2.47 (2H, t, J=7.1 Hz), 2.68-2.75 (2H, m), 2.94 (1.2H, s), 3.00 (1.8H, s), 3.12-3.17 (2H, m), 3.35-3.39 (1H, m), 3.43-3.50 (6H, m), 3.58-3.61 (4H, m), 3.98 (1H, brs), 4.70-4.75 (1H, m), 6.55 (1H, d, J=8.5 Hz), 6.56-6.59 (1H, m), 7.11-7.15 (1H, m), 7.20-7.29 (4H, m), 7.33-7.38 (3H, m), 7.42-7.44 (1H, m), 7.47-7.52 (2H, m), 8.09-8.11 (1H, m).

MS (APCI) m/z: 755 (M+H)$^+$.

Example 92b

1-{2-[Methyl(6-{[4-(piperazin-1-ylcarbonyl)phenyl]amino}hexanoyl)amino]ethyl}piperidin-4-yl biphenyl-2-ylcarbamate The compound (98 mg, 0.130 mmol) obtained in Example 92a and 2 N hydrochloric acid-methanol (1.30 mL, 2.60 mmol) were used to give the title compound (66 mg; yield, 78%) as a white solid according to the method described in Example 89e.

H NMR (CDCl$_3$, 400 MHz): δ 1.42-1.48 (2H, m), 1.62-1.72 (5H, m), 1.88-1.96 (2H, m), 2.24-2.36 (4H, m), 2.47 (2H, t, J=7.1 Hz), 2.68-2.75 (2H, m), 2.86-2.88 (2H, m), 2.94 (1.2H, s), 3.00 (1.8H, s), 3.12-3.17 (2H, m), 3.37 (1H, t, J=7.1 Hz), 3.48 (1H, t, J=7.1 Hz), 3.58-3.62 (4H, m), 3.93-3.96 (1H, m), 4.70-4.75 (1H, m), 6.55 (2H, d, J=8.7 Hz), 6.60-6.61 (1H, m), 7.11-7.16 (1H, m), 7.21-7.23 (1H, m), 7.26-7.30 (3H, m), 7.34-7.40 (2H, m), 7.42-7.44 (1H, m), 7.47-7.52 (2H, m), 8.09-8.11 (1H, m).

MS (APCI) m/z: 655 (M+H)$^+$.

Example 92c

1-{2-[{6-[(4-{[4-({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)piperazin-1-yl]carbonyl}phenyl)amino]hexanoyl}(methyl)amino]ethyl}piperidin-4-yl biphenyl-2-ylcarbamate The compound (74 mg, 0.106 mmol) obtained in Example 1j was dissolved in methylene chloride (1.5 mL), triethylamine (17 μL, 0.121 mmol) and pivaloyl chloride (13 μL, 0.105 mmol) were added under ice cooling, and the mixture was stirred at room temperature for 25 minutes. A solution of the compound (66 mg, 0.101 mmol) obtained in Example 92b in methylene chloride (1.5 mL) was added dropwise to the reaction mixture under ice cooling, and the mixture was stirred at room temperature for 2.5 days. The solvent was evaporated under reduced pressure, and the resulting residue was purified by NH silica gel column chromatography (ethyl acetate:methanol=100:0→40:1, v/v) and further by reverse phase preparative column chromatography (Waters; XTerra Prep MS C18 OBD, 5 μm, 30×100 mm) (acetonitrile:0.1% aqueous ammonium formate solution=60:40, v/v) to give the title compound (89 mg; yield, 66%) as a white solid.

MS (FAB) m/z: 1331 (M+H)$^+$.

IR (KBr) $v_{max}$ 2929, 1734, 1645, 1436, 1359, 1281, 1180, 1138, 839, 757 cm$^{-1}$.

Example 93

1-(2-{[6-({6-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methy)amino]propyl}(methyl)carbamoyl]-1,3-benzothiazol-2-yl}amino)hexanoyl](methyl)amino}ethyl)piperidin-4-yl biphenyl-2-ylcarbamate Example 93b tert-Butyl (3-{[(2-bromo-1,3-benzothiazol-6-yl)carbonyl](methyl)amino}propyl)methylcarbamate The compound (100 mg, 0.387 mmol) obtained in Example 93a, tert-butyl methyl[3-(methylamino)propyl]carbamate (78 mg, 0.387 mmol) and 1-ethyl-3-(3-dimethylaminopropyl)carbodiimide hydrochloride (89 mg, 0.464 mmol) were used to give the title compound (132 mg; yield, 77%) as a yellow oily substance according to the method described in Example 89b.

H NMR (CDCl$_3$, 400 MHz): δ 1.34-1.45 (9H, m), 1.75-1.96 (2H, m), 2.67-2.75 (1.5H, m), 2.85-2.92 (2H, m), 2.98-3.00 (1.5H, m), 3.06-3.13 (2H, m), 3.23-3.38 (2H, m), 3.54-3.59 (1H, m), 7.47-7.53 (1H, m), 7.87-7.90 (1H, m), 8.00 (1H, d, J=8.0 Hz).

MS (APCI) m/z: 342 (M+H)$^+$ (from with Boc removed).

[Formula 98]

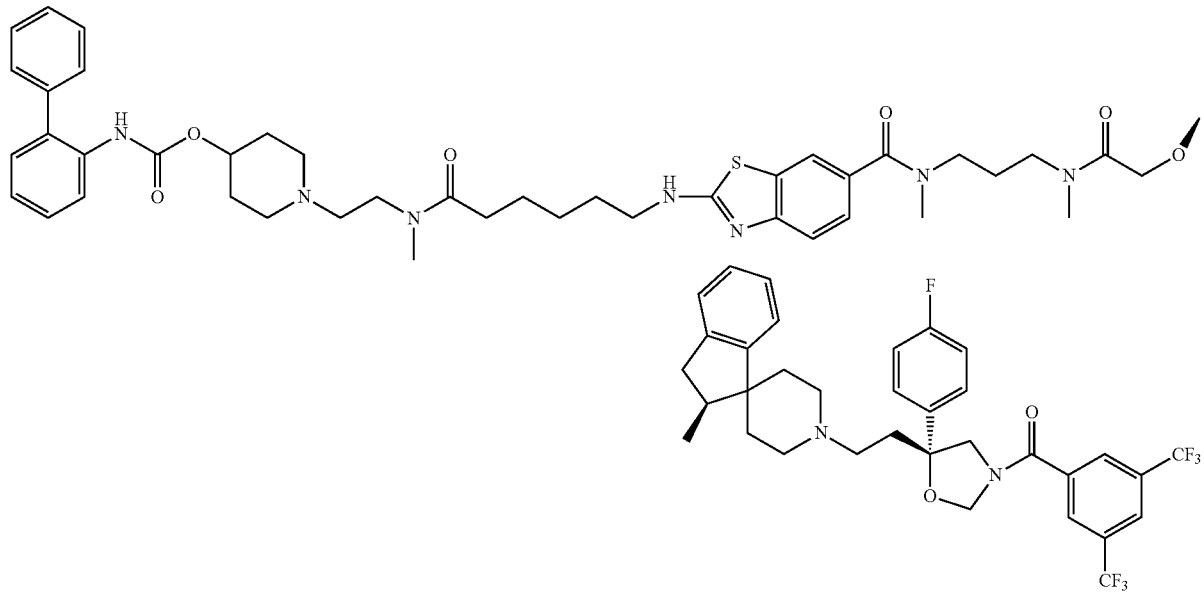

Example 93a

2-Bromo-1,3-benzothiazole-6-carboxylic acid

2-Amino-1,3-benzothiazole-6-carboxylic acid (1.58 g, 8.14 mmol) and cupric bromide (2.18 g, 9.76 mmol) were dissolved in acetonitrile (16 mL), a solution of tert-butyl nitrate (1.45 mL, 12.2 mmol) in acetonitrile (41 mL) was added slowly, and then the mixture was stirred at room temperature for 19.5 hours. 1 N Hydrochloric acid was added to the reaction mixture, and then the mixture was extracted with ethyl acetate (×2). The organic layer was washed with saturated sodium chloride solution and dried with anhydrous sodium sulfate, and then the solvent was evaporated under reduced pressure to give the title compound (2.02 g; yield, 96%) as a yellow solid.

H NMR (CDCl$_3$, 400 MHz): δ 8.07 (2H, s), 8.78 (1H, s)

MS (APCI) m/z: 258 (M+H)$^+$.

Example 93c 1-(2-{[6-({6-[{3-([tert-Butoxycarbonyl)(methyl)amino]propyl}(methyl)carbamoyl]-1,3-benzothiazol-2-yl}amino)hexanoyl](methyl)amino}ethyl)piperidin-4-yl biphenyl-2-ylcarbamate The compound (133 mg, 0.298 mmol) obtained in Example 1a and the compound (132 mg, 0.298 mmol) obtained in Example 93b were dissolved in n-butanol (3 mL), triethylamine (62 μL, 0.447 mmol) was added, and the mixture was stirred with heating to reflux for 15 hours. A solution of the compound (133 mg, 0.298 mmol) obtained in Example 1a in n-butanol (2 mL) was added to the reaction mixture, and the mixture was further stirred with heating to reflux for 24 hours. Subsequently, triethylamine (62 μL, 0.447 mmol) was added to the reaction mixture, and the mixture was further stirred with heating to reflux for 24 hours. The solvent was evaporated under reduced pressure, and the resulting residue was purified by NH silica gel column chromatography (ethyl acetate:methanol=100:0→50:1, v/v) to give the title compound (157 mg; yield, 64%) as a light yellow solid.

H NMR (CDCl₃, 400 MHz): δ 1.35-1.54 (9H, m), 1.61-1.76 (7H, m), 1.82-1.94 (4H, m), 2.24-2.39 (5H, m), 2.45-2.50 (2H, m), 2.67-2.75 (3H, m), 2.80-2.87 (2H, m), 2.93-3.00 (3H, m), 3.03-3.05 (2H, m), 3.23-3.28 (2H, m), 3.37 (2H, t, J=6.9 Hz), 3.46-3.51 (4H, m), 4.69-4.75 (2H, m), 5.66-5.70 (1H, m), 6.58-6.61 (2H, m), 6.74 (1H, brs), 7.11-7.16 (1H, m), 7.20-7.22 (1H, m), 7.30-7.32 (1H, m), 7.34-7.38 (2H, m), 7.41-7.42 (1H, m), 7.44-7.52 (2H, m), 7.66 (1H, brs), 8.08-8.10 (1H, m).

MS (APCI) m/z: 828 (M+H)⁺.

MS (FAB) m/z: 1404 (M+H)⁺.

IR (KBr) ν$_{max}$ 2930 1732, 1642, 1537, 1438, 1359, 1281, 1138, 838, 756 cm⁻¹.

Example 94

1-{2-[(N-{4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}-β-alanyl)(methyl)amino]ethyl}piperidin-4-yl biphenyl-2-ylcarbamate

[Formula 99]

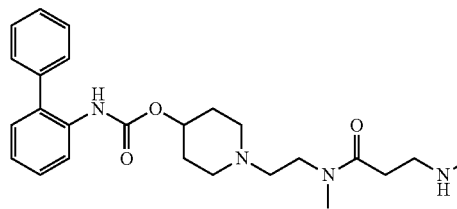

Example 93d

1-[2-(Methyl{6-[(6-{methyl[3-(methylamino)propyl]carbamoyl}-1,3-benzothiazol-2-yl)amino]hexanoyl}amino)ethyl]piperidin-4-yl biphenyl-2-ylcarbamate The compound (157 mg, 0.190 mmol) obtained in Example 93c and 2 N hydrochloric acid-methanol (1.90 mL, 3.79 mmol) were used to give the title compound (101 mg; yield, 73%) as a white solid according to the method described in Example 89e.

MS (APCI) m/z: 728 (M+H)⁺.

Example 93e 1-(2-{[6-({6-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-1,3-benzothiazol-2-yl}amino)hexanoyl](methyl)amino}ethyl)piperidin-4-yl biphenyl-2-ylcarbamate The compound (101 mg, 0.146 mmol) obtained in Example 1j, triethylamine (23 µL, 0.167 mmol), pivaloyl chloride (18 µL, 0.144 mmol) and the compound (101 mg, 0.139 mmol) obtained in Example 93d were used to give the title compound (47 mg; yield, 24%) as a white solid according to the method described in Example 92c.

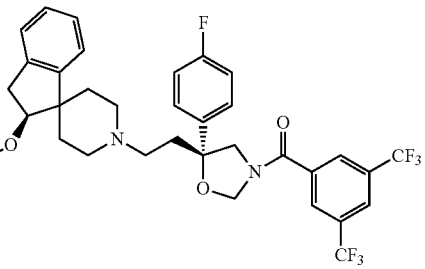

Example 94a

Ethyl N-{4-[{3-([tert-butoxycarbonyl)(methyl)amino]propyl}(methyl)carbamoyl]phenyl}-β-alaninate 4-[(3-Ethoxy-3-oxopropyl)amino]benzoic acid (200 mg, 0.84 mmol) (U.S. Pat. No. 5,977,101 A1) was dissolved in methylene chloride (6 mL), triethylamine (0.14 mL, 1.01 mmol) and pivaloyl chloride (0.10 mL, 0.84 mmol) were added under ice cooling, and the mixture was stirred at the same temperature under a nitrogen atmosphere for 15 minutes. Subsequently, a solution of tert-butyl methyl[3-(methylamino)propyl]carbamate (179 mg, 0.89 mmol) in methylene chloride (2 mL) was added under ice cooling, and the mixture was stirred at room temperature under a nitrogen atmosphere for 16 hours. After the reaction was completed, a saturated aqueous sodium hydrogencarbonate solution was added, and ethyl acetate was further added to separate the layers. The resulting organic layer was separated, washed with saturated sodium chloride solution, and then dried with anhydrous sodium sulfate, and then the solvent was evaporated under reduced pressure. The residue was purified by NH silica gel column chromatography (hexane:ethyl acetate, 1:9, v/v) to give the title compound (315 mg; yield, 89%) as a light yellow oily substance.

MS (ESI): m/z 422 (M+H)⁺ (free form).

Example 94b 1-(2-{[3-({4-[{3-([tert-Butoxycarbonyl)(methyl)amino]propyl}(methyl)carbamoyl]phenyl}amino)propanoyl](methyl)amino}ethyl)piperidin-4-yl biphenyl-2-ylcarbamate The compound (355 mg, 0.84 mmol) obtained in Example 94a was dissolved in ethanol (4 mL), a 1 N aqueous sodium hydroxide solution (1.26 mL, 1.26 mmol) was added, and the mixture was stirred at room temperature for 2.5 hours. After the reaction was completed, a 1 N aqueous hydrochloric acid solution (1.26 mL, 1.26 mmol) was added to the reaction mixture under ice cooling, and ethyl acetate was further added to separate the layers. The resulting organic layer was separated, washed with saturated sodium chloride solution, and then dried with anhydrous sodium sulfate, and the solvent was evaporated under reduced pressure to give crude N-{4-[{3-([tert-butoxycarbonyl)(methyl)amino]propyl}(methyl) carbamoyl]phenyl}-β-alanine.

The resulting crude product was dissolved in methylene chloride (6 mL), triethylamine (0.14 mL, 1.01 mmol) and pivaloyl chloride (0.10 mL, 0.84 mmol) were added under ice cooling, and the mixture was stirred at the same temperature under a nitrogen atmosphere for 15 minutes. Subsequently, a solution of 1-[2-(methylamino)ethyl]piperidin-4-yl biphenyl-2-ylcarbamate (447 mg, 1.26 mmol) in methylene chloride (2 mL) was added under ice cooling, and the mixture was stirred at room temperature under a nitrogen atmosphere for 16 hours. After the reaction was completed, a saturated aqueous sodium hydrogencarbonate solution was added, and ethyl acetate was further added to separate the layers. The resulting organic layer was separated, washed with saturated sodium chloride solution, and then dried with anhydrous sodium sulfate, and the solvent was evaporated under reduced pressure. The residue was purified by NH silica gel column chromatography (ethyl acetate) to give the title compound (379 mg; yield, 62%) as a white solid.

MS (ESI): m/z 729 (M+H)$^+$ (free form).

Example 94d

1-{2-[(N-{4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methy)amino]propyl}(methyl)carbamoyl]phenyl}-β-alanyl)(methyl)amino]ethyl}piperidin-4-yl biphenyl-2-ylcarbamate The compound (119 mg, 0.17 mmol) obtained in Example 1j and the compound (98 mg, 0.16 mmol) obtained in Example 94c were used to give the title compound (130 mg; yield, 64%) as a white solid according to the method described in Example 11e.

MS (FAB): m/z 1305 (M+H)$^+$ (free form).

IR (KBr) ν max 2928, 1734, 1644, 1610, 1359, 1281, 1179, 1138, 1045, 758 cm$^{-1}$.

Example 95

1-{2-[(N-{4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methy)amino]propyl}(methyl)carbamoyl]phenyl}-N-methyl-β-alanyl)(methyl)amino]ethyl}piperidin-4-yl biphenyl-2-ylcarbamate

[Formula 100]

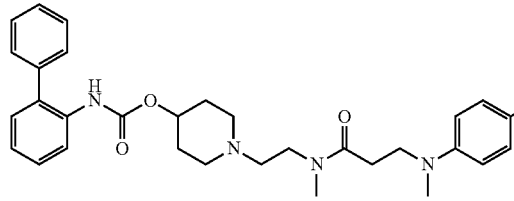

Example 94c 1-(2-{Methyl[N-(4-{methyl[3-(methylamino)propyl]carbamoyl}phenyl)-β-alanyl]amino}ethyl)piperidin-4-yl biphenyl-2-ylcarbamate The compound (150 mg, 0.21 mmol) obtained in Example 94b was dissolved in ethanol (0.5 mL), a 4 N hydrochloric acid-1,4-dioxane solution (5.1 mL, 20.6 mmol) was added, and the mixture was stirred at room temperature under a nitrogen atmosphere for 6 hours. After the reaction was completed, the solvent was evaporated under reduced pressure. Ethyl acetate was added under ice cooling, a saturated aqueous sodium hydrogencarbonate solution was further added to neutralize the mixture and separate the layers. The resulting organic layer was separated, washed with saturated sodium chloride solution, and then dried with anhydrous sodium sulfate, and the solvent was evaporated under reduced pressure. The residue was purified by NH silica gel column chromatography (ethyl acetate:methanol, 10:1, v/v) to give the title compound (98 mg; yield, 76%) as a colorless oily substance.

Example 95a

Ethyl N-{4-[{3-([tert-butoxycarbonyl)(methyl)amino]propyl}(methyl)carbamoyl]phenyl}-N-methyl-β-alaninate The compound (239 mg, 0.57 mmol) obtained in Example 94a was dissolved in methanol (15 mL), paraformaldehyde (179 mg, 5.67 mmol) and 10% palladium-carbon (48 mg, 20% by weight) were added, and the mixture was stirred at 60° C. under a hydrogen atmosphere for 18 hours. After the reaction was completed, the reaction mixture was filtered through celite, the filtrate was washed with methanol, and the solvent was evaporated under reduced pressure. The residue was purified by NH silica gel column chromatography (hexane:ethyl acetate, 10:1, v/v) to give the title compound (172 mg; yield, 70%) as a pale pink oily substance.

MS (FAB): m/z 436 (M+H)$^+$ (free form).

IR (ATR) ν max 1730, 1688, 1606, 1482, 1392, 1364, 1161, 1046, 824, 763 cm$^{-1}$.

Example 95b

1-{2-[(N-{4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}-N-methyl-β-alanyl)(methyl)amino]ethyl}piperidin-4-yl biphenyl-2-ylcarbamate The compound (172 mg, 0.39 mmol) obtained in Example 95a was used according to the methods described in Examples 94b, 94c, and 94d to give the title compound (150 mg; yield, 29%) as a white solid.

MS (FAB): m/z 1319 (M+H)⁺ (free form).

IR (KBr) ν max 2935, 1732, 1644, 1609, 1358, 1281, 1182, 1138, 1045, 758 cm⁻¹.

Example 96

1-(2-{[6-({4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-2-chloro-5-methoxyphenyl}amino]hexanoyl](methyl)amino}ethyl)piperidin-4-yl biphenyl-2-ylcarbamate compound (655 mg; yield, 68%) as a colorless oily substance according to the method described in Example 12a.

MS (FAB): m/z 386 (M+H)⁺ (free form).

Example 96b 1-(2-{[6-({4-[{3-[(tert-Butoxycarbonyl)(methyl)amino]propyl}(methyl)carbamoyl]-2-chloro-5-methoxyphenyl}amino)hexanoyl](methyl)amino}ethyl)piperidin-4-yl biphenyl-2-ylcarbamate The compound (219 mg, 0.57 mmol) obtained in Example 96a and the compound (294 mg, 0.63 mmol) obtained in Example 4g were used to give the title compound (209 mg; yield, 17%) as a white solid according to the method described in Example 18b.

MS (FAB): m/z 835 (M+H)⁺ (free form).

Example 96c 1-(2-{[6-({4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-2-chloro-5-methoxyphenyl}amino)hexanoyl](methyl)amino}ethyl)piperidin-4-yl biphenyl-2-ylcarbamate The compound (293 mg, 0.35 mmol) obtained in Example 96b was used according to the methods described in

[Formula 101]

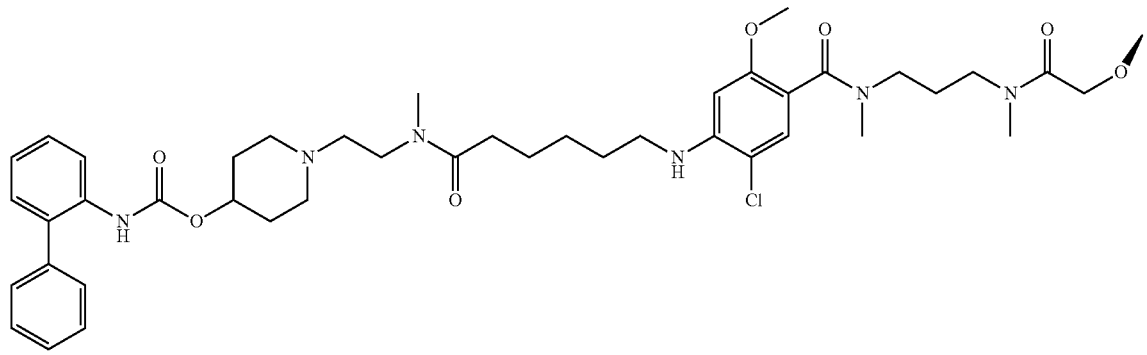

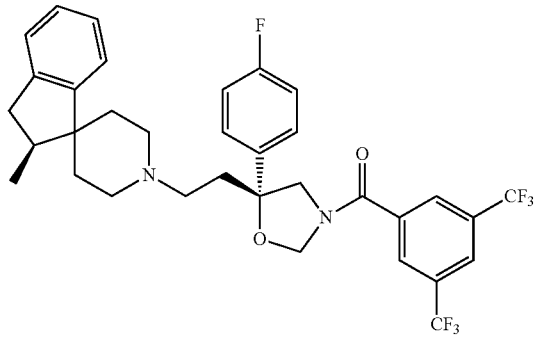

Example 96a tert-Butyl (3-{[(4-amino-5-chloro-2-methoxyphenyl)carbonyl](methyl)amino}propyl)methylcarbamate 4-Amino-5-chloro-2-methoxybenzoic acid (500 mg, 2.48 mmol) and tert-butyl methyl[3-(methylamino)propyl]carbamate (652 mg, 3.22 mmol) were used to give the title Examples 94b, 94c, and 94d to give the title compound (150 mg; yield, 60%) as a white solid.

MS (FAB): m/z 1411 (M+H)⁺ (free form).

IR (KBr) ν max 2936, 1644, 1608, 1359, 1281, 1219, 1178, 1138, 1045, 753 cm⁻¹.

Example 97

1-{2-[{6-[(4-{[N-({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)-N-methyl-β-alanyl](methyl)amino}phenyl)amino]hexanoyl}(methyl)amino]ethyl}piperidin-4-yl biphenyl-2-ylcarbamate

[Formula 102]

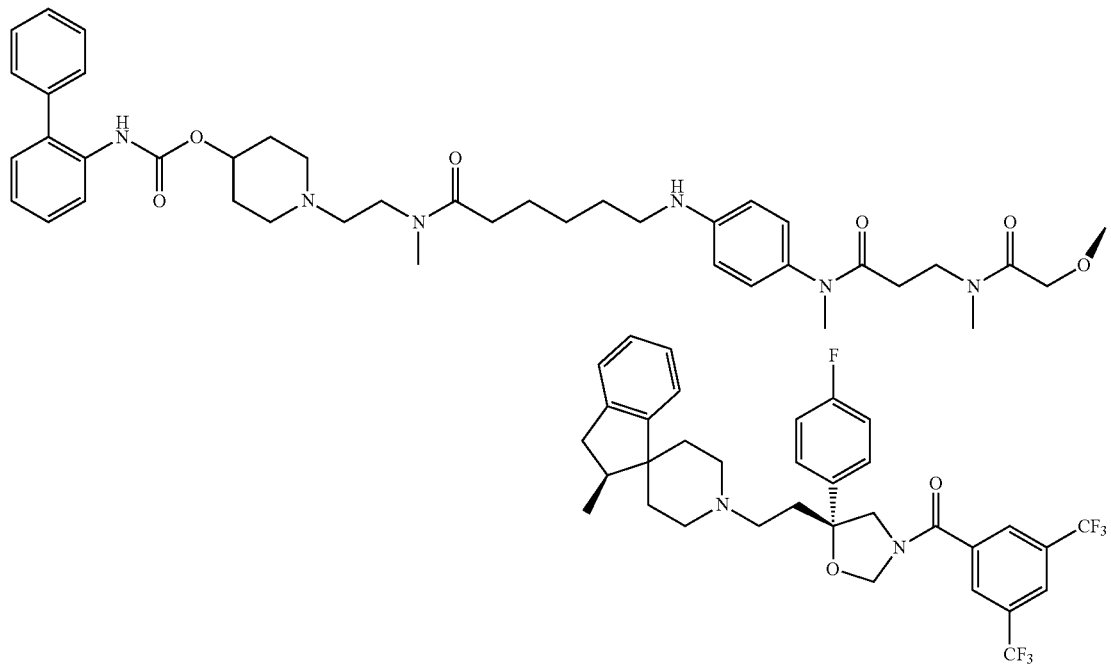

Example 97a 1-(2-{[6-({4-([tert-Butoxycarbonyl)(methyl)amino]phenyl}amino)hexanoyl](methyl)amino}ethyl)piperidin-4-yl biphenyl-2-ylcarbamate tert-Butyl (4-aminophenyl)methylcarbamate (573 mg, 2.58 mmol) and the compound (600 mg, 1.29 mmol) obtained in Example 4g were used to give the title compound (593 mg; yield, 69%) as a colorless oily substance according to the method described in Example 18b.

Example 97b

Benzyl {6-[(2-{4-[(biphenyl-2-ylcarbamoyl)oxy]piperidin-1-yl}ethyl)(methyl)amino]-6-oxohexyl}{4-([tert-butoxycarbonyl)(methyl)amino]phenyl}carbamate The compound (593 mg, 0.883 mmol) obtained in Example 97a was dissolved in tetrahydrofuran (9 mL), 55% sodium hydride (42 mg, 0.971 mmol) was added under ice cooling, and the mixture was stirred under ice cooling under a nitrogen atmosphere for 15 minutes. Subsequently, benzyl chloroformate (0.19 mL, 1.32 mmol) was added, and the mixture was stirred at room temperature for 18 hours. After the reaction was completed, water was added, and ethyl acetate was further added to separate the layers. The resulting organic layer was separated, washed with saturated sodium chloride solution, and then dried with anhydrous sodium sulfate, and the solvent was evaporated under reduced pressure. The residue was purified by NH silica gel column chromatography (hexane:ethyl acetate, 1:5→1:15, v/v) to give the title compound (660 mg; yield, 93%) as a colorless oily substance.

Example 97c

Benzyl {6-[(2-{4-[(biphenyl-2-ylcarbamoyl)oxy]piperidin-1-yl}ethyl)(methyl)amino]-6-oxohexyl}[4-(methylamino)phenyl]carbamate The compound (660 mg, 0.819 mmol) obtained in Example 97b was used to give the title compound (574 mg; yield, 99%) as a white solid according to the method described in Example 6d.

Example 97d

Benzyl {6-[(2-{4-[(biphenyl-2-ylcarbamoyl)oxy]piperidin-1-yl}ethyl)(methyl)amino]-6-oxohexyl}(4-{[N-(tert-butoxycarbonyl)-N-methyl-β-alanyl](methyl)amino}phenyl)carbamate N-(tert-Butoxycarbonyl)-N-methyl-β-alanine (41 mg, 0.19 mmol) and the compound (150 mg, 0.21 mmol) obtained in Example 97c were used to give the title compound (190 mg; yield, 100%) as a white solid according to the method described in Example 41a.

MS (ESI): m/z 791 (M+H)+ (form with Boc removed).

Example 97e

Benzyl {6-[(2-{4-[(biphenyl-2-ylcarbamoyl)oxy] piperidin-1-yl}ethyl)(methyl)amino]-6-oxohexyl} {-4-[methyl(N-methyl-β-alanyl)amino] phenyl}carbamate The compound (190 mg, 0.21 mmol) obtained in Example 97d was used to give the title compound (133 mg; yield, 79%) as a white solid according to the method described in Example 6d.

MS (FAB): m/z 791 (M+H)+ (free form).

Example 97f

Benzyl {6-[(2-{4-[(biphenyl-2-ylcarbamoyl)oxy] piperidin-1-yl}ethyl)(methyl)amino]-6-oxohexyl}(4-{[N-({[(2S)-1'-{2-[(5R)-3-[3,5-bis(trifluoromethyl) benzoyl]-5-(4-fluorophenyl)-1,3-oxazolidin-5-yl] ethyl}-2,3-dihydrospiro[indene-1,4'-piperidin]-2-yl] oxy}acetyl)-N-methyl-β-alanyl](methyl) amino}phenyl)carbamate The compound (111 mg, 0.16 mmol) obtained in Example 1j and the compound (133 mg, 0.17 mmol) obtained in Example 97e were used to give the title compound (180 mg; yield, 73%) as a white solid according to the method described in Example 11e.

MS (FAB): m/z 1467 (M+H)+ (free form).

IR (ATR) ν max 2934, 1709, 1650, 1512, 1359, 1281, 1177, 1138, 1045, 754 cm−1.

Example 97g

1-{2-[{6-[(4-{[N-({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)-N-methyl-β-alanyl](methyl) amino}phenyl)amino]hexanoyl}(methyl)amino] ethyl}piperidin-4-yl biphenyl-2-ylcarbamate The compound (180 mg, 0.12 mmol) obtained in Example 97f was dissolved in a mixed solvent of ethanol (3 mL) and ethyl acetate (3 mL), 10% palladium-carbon (36 mg, 20% by weight) was added, and the mixture was stirred at room temperature under a hydrogen atmosphere for 18 hours. After the reaction was completed, the reaction mixture was filtered through celite, the filtrate was washed with methanol, and the solvent was evaporated under reduced pressure. The residue was purified by NH silica gel column chromatography (ethyl acetate:methanol, 30:1, v/v) to give the title compound (141 mg; yield, 86%) as a white solid.

MS (FAB): m/z 1333 (M+H)+ (free form).

IR (KBr) ν max 2932, 1733, 1647, 1523, 1438, 1359, 1281, 1178, 1139, 754 cm−1.

Example 98

1-{2-[{6-[(4-{[N-({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)-N-methyl-β-alanyl](methyl) amino}phenyl)(methyl)amino]hexanoyl}(methyl) amino]ethyl}piperidin-4-yl biphenyl-2-ylcarbamate

[Formula 103]

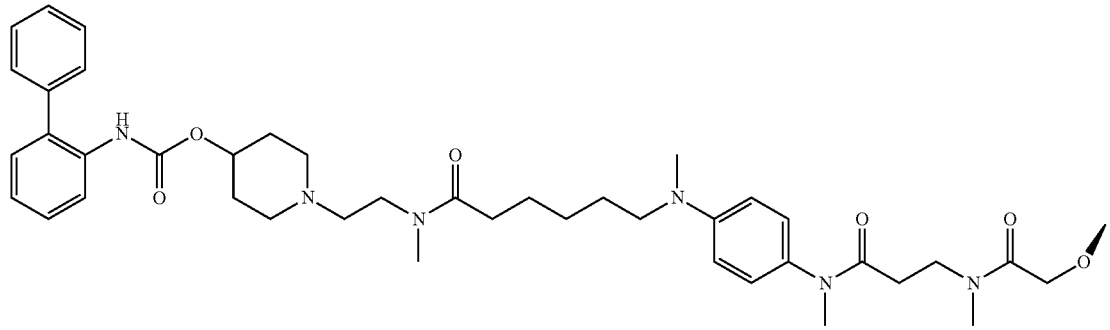

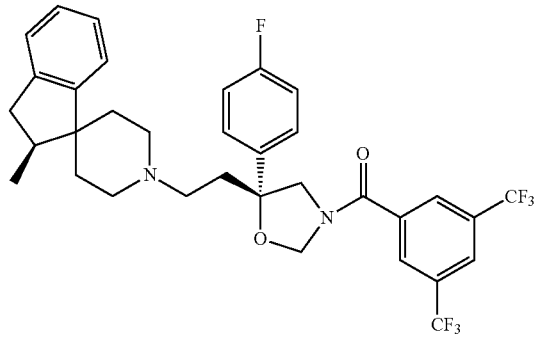

261

The compound (75 mg, 0.06 mmol) obtained in Example 97g and a 35% aqueous formaldehyde solution (46 μL, 0.56 mmol) were used to give the title compound (62 mg; yield, 82%) as a white solid according to the method described in Example 41b.

MS (FAB): m/z 1347 (M+H)$^+$ (free form).

IR (KBr) ν max 2936, 1732, 1649, 1522, 1359, 1281, 1181, 1138, 1045, 756 cm$^{-1}$.

Example 99

1-{2-[{6-[{4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-2-chloro-5-methoxyphenyl}(methyl)amino]hexanoyl}(methyl)amino]ethyl}piperidin-4-yl biphenyl-2-ylcarbamate

[Formula 104]

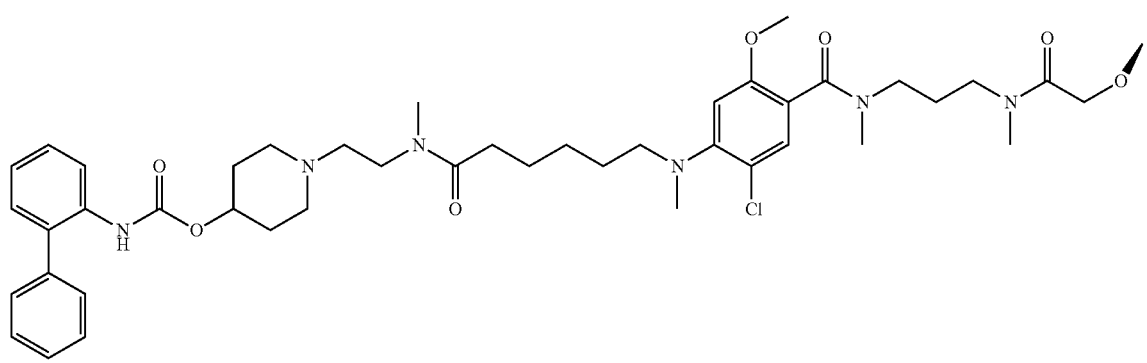

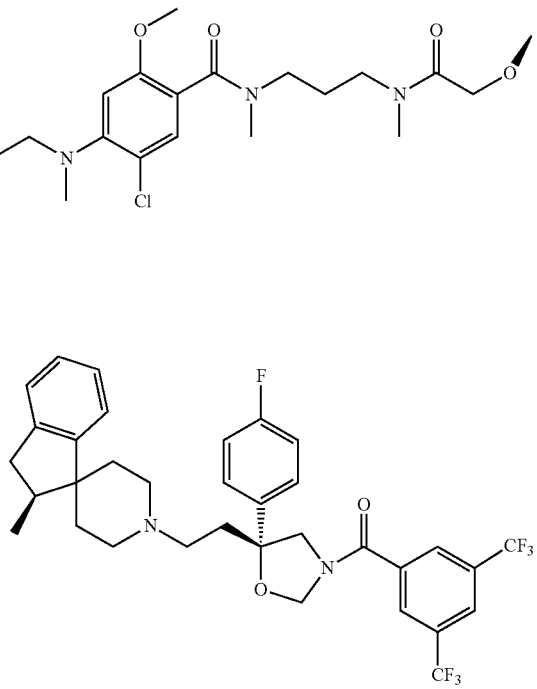

Example 99a tert-Butyl 4-amino-5-chloro-2-methoxybenzoate

4-Amino-5-chloro-2-methoxybenzoic acid (1.0 g, 4.96 mmol) was dissolved in t-butanol (20 mL), 1-ethyl-3-(3-dimethylaminopropyl)carbodiimide hydrochloride (1.05 g, 5.46 mmol) was added with stirring at room temperature, and the mixture was stirred at room temperature under a nitrogen atmosphere for 17 hours. After the reaction was completed, the reaction mixture was filtered, and the filtrate was washed with hexane. The resulting filtrate was recrystallized with ethanol to give the title compound (0.97 g; yield, 76%) as a white solid.

MS (EI+): m/z 770 (M$^+$) (free form).

262

Example 99b tert-Butyl 5-chloro-4-[(6-ethoxy-6-oxohexyl)amino]-2-methoxybenzoate The compound (480 mg, 1.86 mmol) obtained in Example 99a was dissolved in N,N-dimethylformamide (6 mL), 55% sodium hydride (89 mg, 2.79 mmol) was added under ice cooling, and the mixture was stirred at the same temperature under a nitrogen atmosphere for 20 minutes. Subsequently, ethyl 6-bromohexanoate (623 mg, 2.79 mmol) was added, and the mixture was stirred at room temperature for 1 hour. After the reaction was completed, water was added, and ethyl acetate was further added to separate the layers. The resulting organic layer was separated, washed with saturated sodium chloride solution, and then dried with anhydrous sodium sulfate, and the solvent was evaporated under reduced pressure. The residue was purified by silica gel column chromatography (hexane:ethyl acetate, 1:3, v/v) to give the title compound (338 mg; yield, 45%) as a pale orange color oily substance.

MS (FAB): m/z 399 (M$^+$) (free form).

IR (KBr) ν max 1600, 1568, 1454, 1366, 1336, 1240, 1221, 1159, 1087, 1036 cm$^{-1}$.

Example 99c tert-Butyl 5-chloro-4-[(6-ethoxy-6-oxohexyl)(methyl)amino]-2-methoxybenzoate Moisture was removed from a mixture of the compound (216 mg, 0.84 mmol) obtained in Example 99b and a 35% aqueous formaldehyde solution (0.34 mL, 4.19 mmol) azeotropically 3 times with toluene, the resulting mixture was dissolved in dichloroethane (6 mL), sodium triacetoxyborohydride (533 mg, 2.51 mmol) was added under ice cooling, and the mixture was stirred at room temperature under a nitrogen atmosphere for 16 hours. After the reaction was completed, a saturated aqueous sodium hydrogencarbonate solution was added, and ethyl acetate was further added to separate the layers. The resulting organic layer was separated, washed with saturated sodium chloride solution, and then dried with anhydrous sodium sulfate, and the solvent was evaporated under reduced pressure. The residue was purified by silica gel column chromatography (hexane:ethyl acetate, 2:1, v/v) to give the title compound (200 mg; yield, 60%) as a pale orange color oily substance.

MS (FAB): m/z 414 (M+H)$^+$ (free form).

Example 99d tert-Butyl-4-[{6-[(2-{4-[(biphenyl-2-ylcarbamoyl)oxy]piperidin-1-yl}ethyl)(methyl)amino]-6-oxo-hexyl}(methyl)amino]-5-chloro-2-methoxybenzoate The compound (200 mg, 0.48 mmol) obtained in Example 99c was dissolved in ethanol (4 mL), a 1 N aqueous sodium hydroxide solution (1.00 mL, 1.00 mmol) was added, and the mixture was stirred at room temperature for 2 hours. After the reaction was completed, a 1 N aqueous hydrochloric acid solution (1.00 mL, 1.00 mmol) was added to the reaction mixture under ice cooling, and ethyl acetate was further added to separate the layers. The resulting organic layer was separated, washed with saturated sodium chloride solution, and then dried with anhydrous sodium sulfate, and the solvent was evaporated under reduced pressure to give crude 6-{[4-(tert-butoxycarbonyl)-2-chloro-5-methoxyphenyl](methyl)amino}hexanoic acid (189 mg).

The resulting crude product (189 mg) was dissolved in methylene chloride (5 mL), triethylamine (76 µL, 0.55 mmol) and pivaloyl chloride (56 µL, 0.48 mmol) were added under ice cooling, and the mixture was stirred at the same temperature under a nitrogen atmosphere for 15 minutes. Subsequently, a solution of 1-[2-(methylamino)ethyl]piperidin-4-yl biphenyl-2-ylcarbamate (242 mg, 0.68 mmol) in methylene chloride (2 mL) was added under ice cooling, and the mixture was stirred at room temperature under a nitrogen atmosphere for 16 hours. After the reaction was completed, a saturated aqueous sodium hydrogencarbonate solution was added, and ethyl acetate was further added to separate the layers. The resulting organic layer was separated, washed with saturated sodium chloride solution, and then dried with anhydrous sodium sulfate, and the solvent was evaporated under reduced pressure. The residue was purified by NH silica gel column chromatography (hexane:ethyl acetate, 1:9, v/v) to give the title compound (305 mg; yield, 93%) as a white solid.

MS (FAB): m/z 665 (M+H)$^+$ (free form).

Example 99e

1-{2-[{6-[{4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methy)amino]propyl}(methyl)carbamoyl]-2-chloro-5-methoxyphenyl}(methyl)amino]hexanoyl}(methyl)amino]ethyl}piperidin-4-yl biphenyl-2-ylcarbamate The compound (305 mg, 0.42 mmol) obtained in Example 99d was used according to the methods described in Examples 94b, 94c, and 94d to give the title compound (102 mg; yield, 61%) as a white solid.

MS (FAB): m/z 1425 (M+H)$^+$ (free form).
IR (KBr) ν max 2933, 1733, 1643, 1359, 1281, 1224, 1180, 1138, 1045, 753 cm$^{-1}$.

Example 100

1-{2-[{-4-[({4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]benzyl}amino)methyl]benzoyl}(methyl)amino]ethyl}piperidin-4-yl biphenyl-2-ylcarbamate trihydrochloride

[Formula 105]

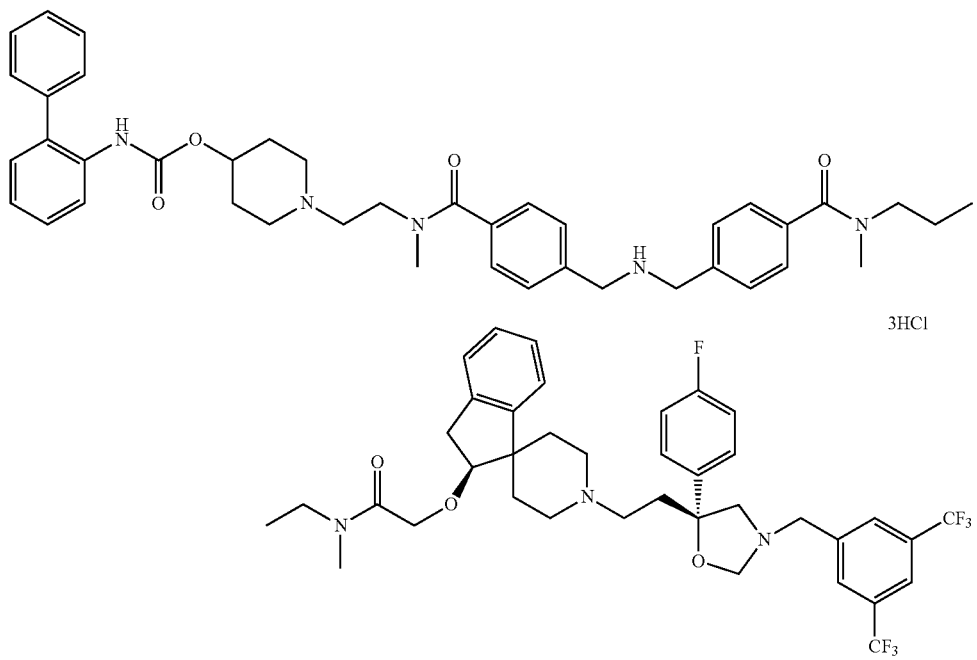

Example 100a

Benzyl methyl 4,4'-[iminobis(methylene)]dibenzoate

Benzyl 4-formylbenzoate (618 mg, 2.57 mmol) and methyl 4-(aminomethyl)benzoate hydrochloride (622 mg, 3.09 mmol) were dissolved in 20 mL of toluene and 2.0 mL of methanol, and the solvent was evaporated under reduced pressure. The resulting white solid was dissolved in 15 mL of 2-propanol, sodium triacetoxyborohydride (1.64 g, 7.72 mmol) was added, and the mixture was stirred at room temperature for 5 hours. The reaction mixture was diluted with ethyl acetate and washed with a saturated aqueous sodium hydrogencarbonate solution and saturated sodium chloride solution. The organic layer was dried with anhydrous magnesium sulfate, then the solvent was evaporated under reduced pressure, and the resulting yellow oily substance was purified by silica gel chromatography (n-hexane:ethyl acetate, 90:10→80:20, v/v) to give the title compound (0.54 g; yield, 54%) as a white solid.

$^1$H NMR (CDCl$_3$, 400 MHz): δ 3.856 (2H, s), 3.864 (2H, s), 3.91 (3H, s), 5.36 (2H, s), 7.10-7.50 (9H, m), 8.01 (2H, d, J=8.6 Hz), 8.05 (2H, d, J=8.6 Hz).

MS (ESI) m/z: 390 (M+H)$^+$.

Example 100b

Benzyl methyl 4,4'-{[(tert-butoxycarbonyl)imino]bis(methylene)}dibenzoate

The compound (0.53 g, 1.36 mmol) obtained in Example 100a was dissolved in 25 mL of dichloromethane, triethylamine (379 μL, 2.72 mmol), di-tert-butyl dicarbonate (445 mg, 2.04 mmol) and 4-dimethylaminopyridine (1.7 mg, 0.014 mmol) were added, and the mixture was stirred at room temperature for 1.5 hours. The solvent was evaporated under reduced pressure, then ethyl acetate was added to dilute the mixture, and the organic layer was washed successively with water, a 0.1 N aqueous hydrochloric acid solution, a saturated aqueous sodium hydrogencarbonate solution, and saturated sodium chloride solution. The organic layer was dried with anhydrous magnesium sulfate, then the solvent was evaporated under reduced pressure, and the resulting yellow oily substance was purified by silica gel chromatography (n-hexane:ethyl acetate, 100:0→60:40, v/v) to give the title compound (443 mg; yield, 67%) as a colorless oily substance.

$^1$H NMR (CDCl$_3$, 400 MHz): δ 1.47 (9H, s), 3.92 (3H, s), 4.38 (2H, brs), 4.49 (2H, brs), 5.37 (2H, s), 7.19-7.47 (9H, m), 7.99 (2H, d, J=8.3 Hz), 8.04 (2H, d, J=7.8 Hz).

MS (FAB+) m/z: 490 (M+H)$^+$.

IR (liquid film) ν$_{max}$ 2976, 1721, 1695, 1612, 1456, 1496, 1275, 1174, 1164, 1110, 1019, 753 cm$^{-1}$.

Example 100c

4-({(tert-Butoxycarbonyl)[4-(methoxycarbonyl)benzyl]amino}methyl)benzoic acid The compound (426 mg, 0.87 mmol) obtained in Example 100b was dissolved in 15 mL of methanol, 10% palladium-carbon (42 mg) was added, and then the mixture was stirred at room temperature at atmospheric pressure under a hydrogen atmosphere for 2 hours. 10% Palladium-carbon (120 mg) was added, then the mixture was further stirred at atmospheric pressure under a hydrogen atmosphere for 2.5 hours. The reaction mixture was filtered, and the filtrate was concentrated under reduced pressure to give a crude title compound (344 mg; yield, 99%) as a white solid.

Example 100d

Methyl 4-{[{4-[(2-{4-[(biphenyl-2-ylcarbamoyl)oxy]piperidin-1-yl}ethyl)(methyl)carbamoyl]benzyl}(tert-butoxycarbonyl)amino]methyl}benzoate The compound (233 mg, 0.58 mmol) obtained in Example 100c was dissolved in 6.0 mL of dichloromethane, and 1-[2-(methylamino)ethyl]piperidin-4-yl biphenyl-2-ylcarbamate (227 mg, 0.64 mmol) and triethylamine (163 μL, 1.17 mmol) were added. The mixture was ice cooled, 1-ethyl-3-(3-dimethylaminopropyl)carbodiimide hydrochloride (168 mg, 0.88 mmol) and 4-(dimethylamino)pyridine (10 mg, 0.082 mmol) were added, and the mixture was stirred at room temperature for 1 hour. Ethyl acetate was added to the reaction mixture to dilute the mixture, and the organic layer was washed with water and a saturated aqueous sodium hydrogencarbonate solution. The organic layer was dried with anhydrous magnesium sulfate, then the solvent was evaporated under reduced pressure, and the resulting yellow oily substance was purified by NH silica gel chromatography (n-hexane:ethyl acetate, 50:50→20:80, v/v) to give the title compound (420 mg; yield, 98%) as a white solid.

$^1$H NMR (CDCl$_3$, 400 MHz): δ 1.10-3.85 (15H, m), 4.12 and 4.13 (total 3H, each s), 4.36 (2H, brs), 4.47 (2H, brs), 4.63-4.80 (2H, m), 6.59 (1H, s), 7.04-7.51 (13H, m), 7.98-8.01 (2H, m), 8.10 (1H, brs).

MS (FAB+) m/z: 735 (M+H)$^+$.

Example 100e

4-{[{4-[(2-{4-[(Biphenyl-2-ylcarbamoyl)oxy]piperidin-1-yl}ethyl)(methyl)carbamoyl]benzyl}tert-butoxycarbonyl)amino]methyl}benzoic acid The compound (320 mg, 0.435 mmol) obtained in Example 100d was dissolved in 4 mL of tetrahydrofuran and 4 mL of methanol, a 5 N aqueous sodium hydroxide solution (100 μL) was added, and the mixture was stirred at room temperature for 5 hours. A 5 N aqueous sodium hydroxide solution (200 μL) was added, the mixture was stirred at room temperature for 15 hours, then a 5 N aqueous sodium hydroxide solution (200 μL) was further added, and the mixture was stirred at room temperature for 5 hours. A 5 N aqueous hydrochloric acid solution (500 μL) was added to the reaction mixture to neutralize the mixture, then 10 mL of methanol and 10 mL of toluene were added, and the solvent was evaporated under reduced pressure. 10 mL of methanol and 10 mL of toluene were added to the resulting residue again, and the solvent was evaporated under reduced pressure to give a crude title compound (461 mg) as a white solid.

Example 100f

1-{2-[(4-{[{4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]benzyl}tert-butoxycarbonyl)amino]methyl}benzoyl)(methyl)amino]ethyl}piperidin-4-yl biphenyl-2-ylcarbamate The crude product (461 mg) obtained in Example 100e, 1-[2-(methylamino)ethyl]piperidin-4-yl biphenyl-2-ylcarbamate (339 mg, 0.435 mmol) and triethylamine (121 μL, 0.871 mmol) were dissolved in 10 mL of dichloromethane, 1-ethyl-3-(3-dimethylaminopropyl)carbodiimide hydrochloride was added at room temperature, and the mixture was stirred at room temperature for 12 hours. The reaction mixture was diluted with ethyl acetate, and the organic layer was washed with a saturated aqueous sodium hydrogencarbonate solution. The organic layer was dried with anhydrous magnesium sulfate, then the solvent was evaporated under reduced pressure, and the resulting residue was purified by NH silica gel chromatography (n-hexane:ethyl acetate, 50:50→0:100, v/v) to give the title compound (588 mg; yield, 91%) as a white solid.

MS (FAB+) m/z: 1401 (M+H)$^+$.

IR (KBr) $v_{max}$ 2930, 1693, 1633, 1513, 1404, 1359, 1281, 1171, 1139, 1072, 848, 756, 682 cm$^{-1}$.

Example 100g

1-{2-[{-4-[({4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]benzyl}amino)methyl]benzoyl}(methyl)amino]ethyl}piperidin-4-yl biphenyl-2-ylcarbamate trihydrochloride The compound (170 mg, 0.115 mmol) obtained in Example 100f was dissolved in a mixed solvent of 6.0 mL of dichloromethane and 1.0 mL of methanol, 6.0 mL of a 4 N hydrochloric acid-dioxane solution was added, and the mixture was stirred at room temperature for 2 hours. The solvent was evaporated under reduced pressure, and the resulting residue was purified by NH silica gel chromatography (ethyl acetate:methanol, 100:0→90:10, v/v) and by reverse phase preparative chromatography (Waters Corporation; XBridge Prep C18 OBD column, 30 mm ID×150 mm, 5 μm; 0.1% [w/v] aqueous ammonium formate solution:acetonitrile, 50:50→30:70) to give a free form (126 mg; yield, 80%) of the title compound as a white solid.

The resulting free compound (126 mg) was used to give the title compound (118 mg; yield, 87%) as a white solid according to the method described in Example 73g.

MS (ESI+) m/z: 1381 (M+H)$^+$.

IR (KBr) $v_{max}$ 3422, 2932, 1726, 1640, 1513, 1449, 1438, 1360, 1282, 1139, 848, 759, 682 cm$^{-1}$.

Example 101

1-{2-[(4-{[{4-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]benzyl}(methyl)amino]methyl}benzoyl)(methyl)amino]ethyl}piperidin-4-yl biphenyl-2-ylcarbamate trihydrochloride

[Formula 106]

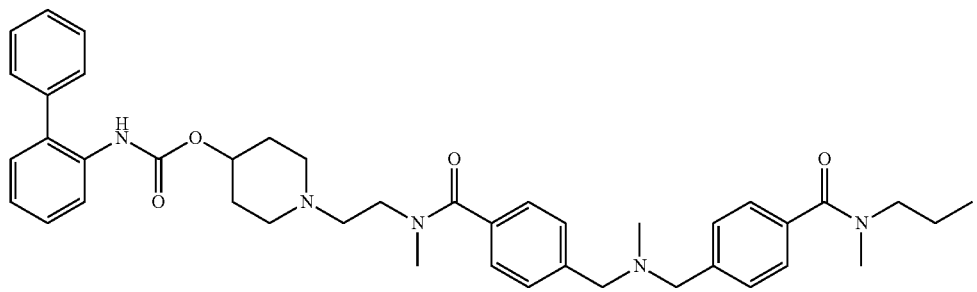

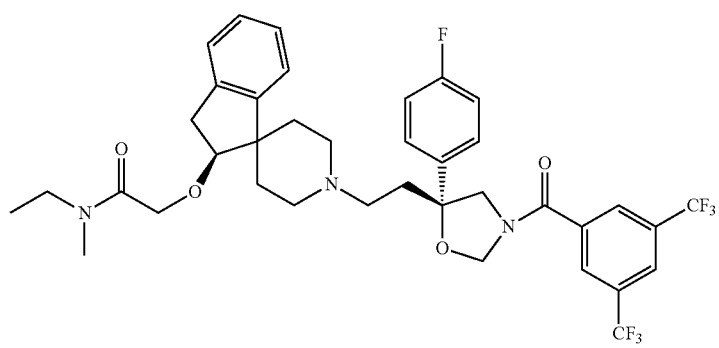

The compound (168 mg, 0.113 mmol) obtained in Example 100f was dissolved in a mixed solvent of 10 mL of dichloromethane and 2 mL of methanol, 10 mL of a 4 N hydrochloric acid-dioxane solution was added, and the mixture was stirred at room temperature for 2 hours. The solvent was evaporated under reduced pressure, the resulting residue (170 mg) was dissolved in a mixed solvent of 1.0 mL of methanol and 4.0 mL of toluene, 0.10 mL of triethylamine and 0.50 mL of an aqueous formaldehyde solution were added, and the mixture was stirred at room temperature for 20 minutes.

The reaction solution was evaporated to dryness under reduced pressure, the resulting white solid was dissolved in 6.0 mL of a mixed solvent of dichloromethane and methanol (10:1), sodium triacetoxyborohydride (136 mg, 0.641 mmol) was added under ice cooling, and the mixture was stirred at room temperature for 16 hours. The reaction mixture was diluted with ethyl acetate, and the organic layer was washed with a saturated aqueous sodium hydrogencarbonate solution and saturated sodium chloride solution. The organic layer was dried with anhydrous magnesium sulfate, then the solvent was evaporated under reduced pressure, and the resulting residue was purified by NH silica gel chromatography (ethyl acetate:methanol, 100:0→90:10, v/v) and by reverse phase preparative chromatography (Waters Corporation; XBridge Prep C18 OBD column, 30 mm ID×150 mm, 5 μm; 0.1% [w/v] aqueous ammonium formate solution:acetonitrile, 50:50→30:70) to give a free form (119 mg; yield, 75%) of the title compound as a white solid. The resulting free compound (119 mg) was used to give the title compound (108 mg; yield, 84%) as a white solid according to the method described in Example 73g.

MS (ESI+) m/z: 1395 (M+H)$^+$.

IR (KBr) $\nu_{max}$ 2931, 1725, 1639, 1513, 1480, 1360, 1282, 1223, 1180, 1138, 849, 757, 705, 682 cm$^{-1}$.

Example 102

1-(2-{[6-({4-[({4-[({[(2S)-1'-{2-[(2R)-4-[3,5-Bis(trifluoromethyl)benzoyl]-2-(3,4-dichlorophenyl)morpholin-2-yl]ethyl}-2,3-dihydrospiro[indene-1,4'-piperidin]-2-yl]oxy}acetyl)(methyl)amino]butoxy}carbonyl)amino]benzyl}amino)hexanoyl](methyl)amino}ethyl)piperidin-4-yl biphenyl-2-ylcarbamate trihydrochloride

[Formula 107]

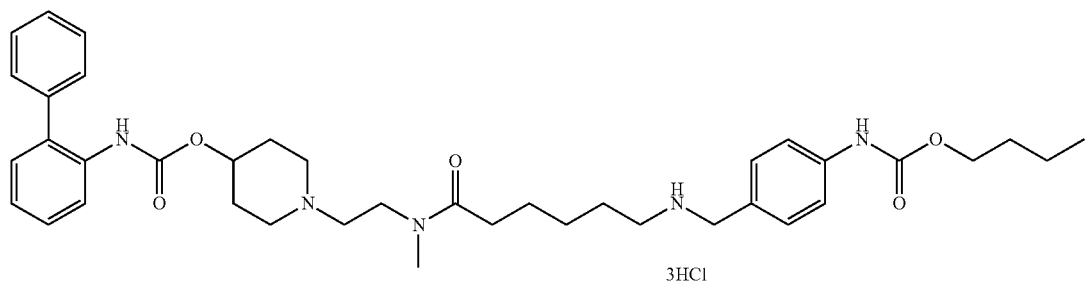

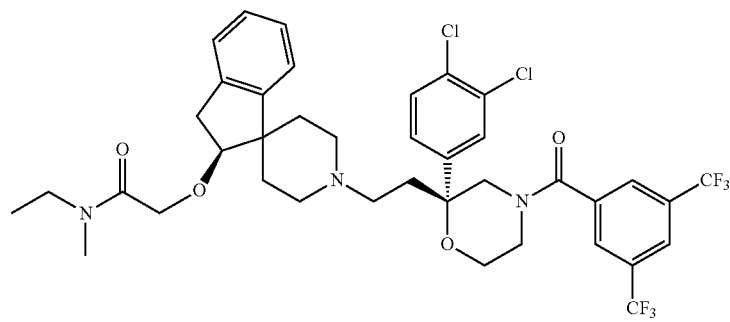

Example 102a

4-[({[(2S)-1'-{2-[(2R)-4-[3,5-Bis(trifluoromethyl)benzoyl]-2-(3,4-dichlorophenyl)morpholin-2-yl]ethyl}-2,3-dihydrospiro[indene-1,4'-piperidin]-2-yl]oxy}acetyl)(methyl)amino]butyl(4-formyl phenyl)carbamate (2-{[(2S)-1-{2-[(2R)-4-[3,5-Bis(trifluoromethyl)benzoyl]-2-(3,4-dichlorophenyl)morpholin-2-yl]ethyl}-2,3-dihydrospiro[indene-1,4'-piperidin]-2-yl]oxy}-N-(4-hydroxybutyl)-N-methylacetamide) (1.00 g, 1.18 mmol) and 4-isocyanate benzaldehyde (244 mg, 1.66 mmol) were dissolved in 5.0 mL of toluene, and the mixture was heated to reflux for 3.5 hours. The mixture was left to stand for cooling, and then the mixture was purified by silica gel column chromatography (n-hexane:ethyl acetate:methanol, 70:30:0→0:100:0->0:90:10, v/v/v) to give the title compound (1.14 g; yield, 97%) as a white solid.

MS (FAB+) m/z: 991 (M+H)$^+$.

IR (KBr) $v_{max}$ 2927, 1735, 1694, 1645, 1536, 1375, 1281, 1219, 1138, 905, 837, 756, 681 cm$^{-1}$.

Example 102b 1-(2-{[6-({4-[({4-[({[(2S)-1-{2-[(2R)-4-[3,5-Bis(trifluoromethyl)benzoyl]-2-(3,4-dichlorophenyl)morpholin-2-yl]ethyl}-2,3-dihydrospiro[indene-1,4'-piperidin]-2-yl]oxy}acetyl)(methyl)amino]butoxy}carbonyl)amino]benzyl}amino)hexanoyl](methyl)amino}ethyl)piperidin-4-yl biphenyl-2-ylcarbamate trihydrochloride The compound (111 mg, 0.206 mmol) obtained in Example 11c and the compound (212 mg, 0.214 mmol) obtained in Example 102a were dissolved in a mixed solvent of 2 mL of methanol and 10 mL of toluene, and triethylamine (75 μL, 0.534 mmol) was added. The solvent was evaporated under reduced pressure, the resulting residue was dissolved in 2 mL of methanol and 10 mL of toluene, sodium triacetoxyborohydride (136 mg, 0.641 mmol) was added, and the mixture was stirred at room temperature for 63 hours. The reaction mixture was diluted with ethyl acetate, and the organic layer was washed with a saturated aqueous sodium hydrogencarbonate solution and saturated sodium chloride solution. The organic layer was dried with anhydrous magnesium sulfate, and then the solvent was evaporated under reduced pressure. The resulting residue was purified by NH silica gel chromatography (ethyl acetate:methanol, 100:0→90:10, v/v) and by reverse phase preparative chromatography (Waters Corporation; XBridge Prep C18 OBD column, 30 mm ID×150 mm, 5 μm; 0.1% [w/v] aqueous ammonium formate solution:acetonitrile, 50:50→30:70) to give a free form (199 mg; yield, 67%) of the title compound as a white solid.

The resulting free compound (153 mg) was used to give the title compound (156 mg; yield, 95%) as a white solid according to the method described in Example 73g.

MS (FAB+) m/z: 1441 (M+H)$^+$ (free form).

IR (KBr) $v_{max}$ 3420, 2938, 1725, 1645, 1527, 1281, 1225, 1067, 905, 753, 681 cm$^{-1}$.

Example 103

1-{2-[{6-[{4-[({4-[({[(2S)-1'-{2-[(2R)-4-[3,5-Bis(trifluoromethyl)benzoyl]-2-(3,4-dichlorophenyl)morpholin-2-yl]ethyl}-2,3-dihydrospiro[indene-1,4'-piperidin]-2-yl]oxy}acetyl)(methyl)amino]butoxy}carbonyl)amino]benzyl}(methyl)amino]hexanoyl}(methyl)amino]ethyl}piperidin-4-yl biphenyl-2-ylcarbamate trihydrochloride

[Formula 108]

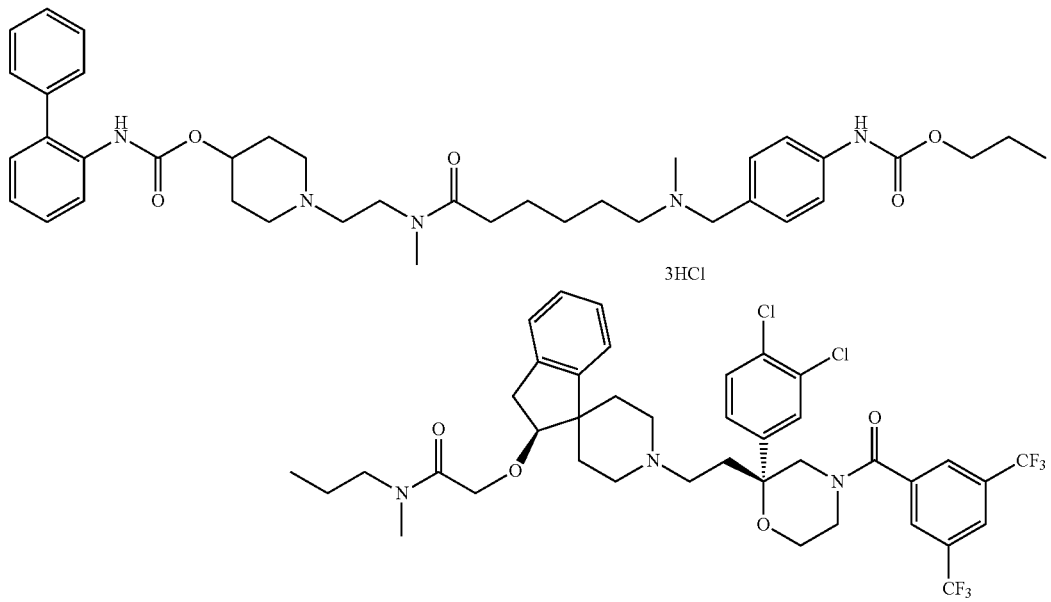

The compound (107 mg, 0.069 mmol) obtained in Example 102b was used to give the title compound (81 mg, 77%) as a white solid by a reaction in the same manner as in the method described in Example 101.

MS (FAB+) m/z: 1455 (M+H)+ (free form).

IR (KBr) $\nu_{max}$ 3421, 2938, 1725, 1645, 1529, 1474, 1450, 1281, 1225, 1138, 904, 753, 681 cm$^{-1}$.

Example 104

1-(2-{[6-({5-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-1,3-thiazol-2-yl}amino)hexanoyl](methyl)amino}ethyl)piperidin-4-yl biphenyl-2-ylcarbamate trihydrochloride ethyl acetate, 50:50→0:100, v/v) to give the title compound (186 mg; 79%) as a colorless oily substance.

MS (APCI) m/z: 622 (M+H)+.

Example 104b 1-(2-{[6-({5-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-1,3-thiazol-2-yl}amino)hexanoyl](methyl)amino}ethyl)piperidin-4-yl biphenyl-2-ylcarbamate trihydrochloride A 10 N aqueous sodium hydroxide solution (27 μL) was added to a solution of the compound obtained in Example 104a in ethanol (3.0 mL), and the mixture was stirred at room temperature for 16 hours. The mixture was ice cooled, then a

[Formula 109]

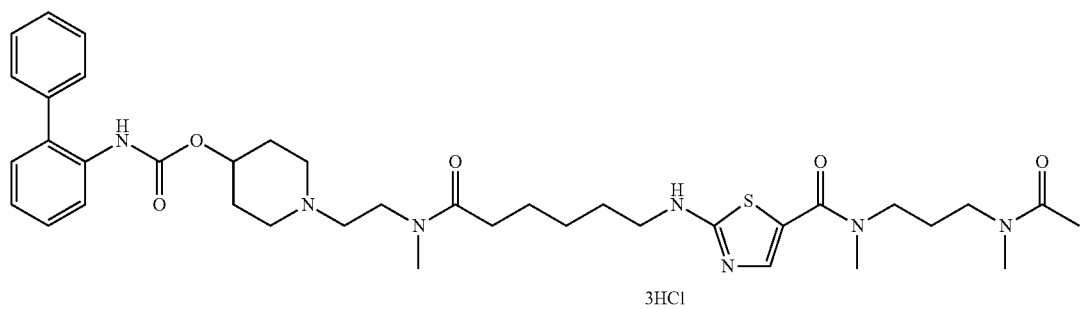

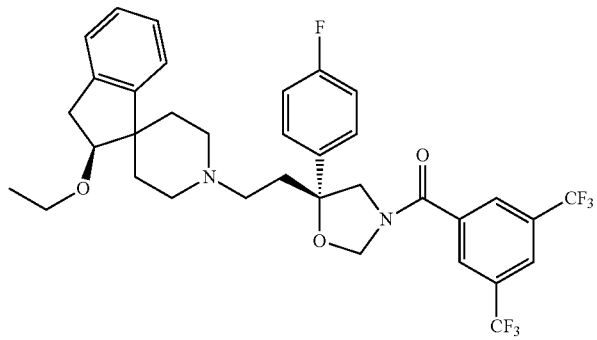

Example 104a

Ethyl 2-({6-[(2-{4-[(biphenyl-2-ylcarbamoyl)oxy]piperidin-1-yl}ethyl)(methyl)amino]-6-oxohexyl}amino)-1,3-thiazole-5-carboxylic acid 1-Butanol (3.0 mL) was added to the compound (205 mg, 0.380 mmol) obtained in Example 11c, ethyl 2-bromo-1,3-thiazole-5-carboxylate (179 mg, 0.760 mmol) and triethylamine (212 μL, 1.52 mmol), and the mixture was stirred at 160° C. for 23 hours. The mixture was left to stand for cooling, then ethyl acetate was added to dilute the mixture, and the organic layer was washed with a saturated aqueous sodium hydrogencarbonate solution. The organic layer was dried with anhydrous magnesium sulfate, and then solvent was evaporated under reduced pressure. The resulting residue was purified by NH silica gel column chromatography (n-hexane:

6 N aqueous hydrochloric acid solution (453 μL, 1) was added, and then the solvent was evaporated under reduced pressure. Methanol (2 mL) and toluene (10 mL) were added to the residue, and the solvent was evaporated under reduced pressure again to give crude 2-({6-[(2-{4-[(biphenyl-2-ylcarbamoyl)oxy]piperidin-1-yl}ethyl)(methyl)amino]-6-oxohexyl}amino)-1,3-thiazole-5-carboxylic acid (357 mg).

The resulting crude carboxylic acid compound (357 mg) and the compound (135 mg, 0.173 mmol) obtained in Example 1k were used to give a free form (24 mg; yield, 10%) of the title compound as a white solid according to the method described in Example 11e.

The resulting free compound (24 mg, 0.018 mmol) was used to give the title compound (22 mg; 85%) as a white solid according to the same procedure as in Example 73g.

MS (FAB+) m/z: 1354 (M+H)+ (free form).

IR (KBr) $\nu_{max}$ 3421, 2934, 1726, 1645, 1511, 1438, 1360, 1281, 1138, 1044, 753, 701, 681 cm$^{-1}$.

Example 105

1-(2-{[6-({5-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-4-methyl-1,3-thiazol-2-yl}amino)hexanoyl](methyl)amino}ethyl)piperidin-4-yl biphenyl-2-ylcarbamate trihydrochloride

[Formula 110]

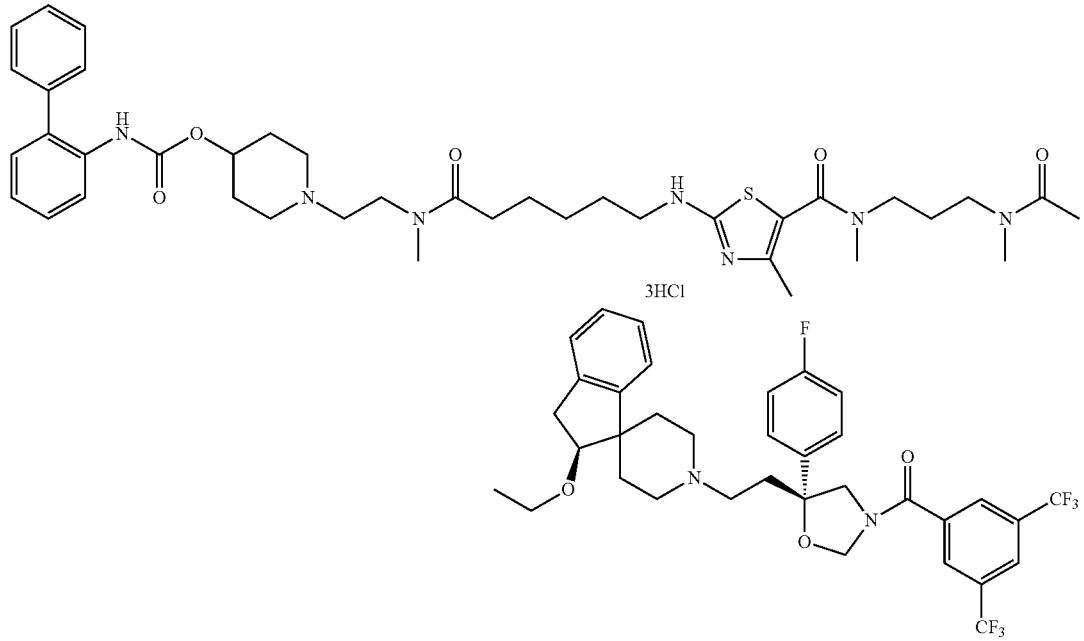

Example 105a tert-Butyl 2-({6-[(2-{4-[(biphenyl-2-ylcarbamoyl)oxy]piperidin-1-yl}ethyl)(methyl)amino]-6-oxohexyl}amino)-4-methyl-1,3-thiazole-5-carboxylate tert-Butyl 2-bromo-4-methyl-1,3-thiazole-5-carboxylate (247 mg, 0.739 mmol), the compound (199 mg, 0.369 mmol) obtained in Example 11c, triethylamine (180 μL) and 4.0 mL of n-butanol were used to give the title compound (70 mg; yield, 29%) as a colorless oily substance according to the same procedure as in Example 104b.

MS (FAB+) m/z: 664 (M+H)$^+$.

IR (Thin film) $v_{max}$ 2933, 1729, 1693, 1632, 1523, 1450, 1368, 1324, 1285, 1208, 1093, 1045, 753, 703 cm$^{-1}$.

Example 105b 1-(2-{[6-({5-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-4-methyl-1,3-thiazol-2-yl}amino)hexanoyl](methyl)amino}ethyl)piperidin-4-yl biphenyl-2-ylcarbamate trihydrochloride A 4 N hydrochloric acid-dioxane solution (10 mL) was added to the compound (66 mg, 0.099 mmol) obtained in Example 105a, and the mixture was stirred at room temperature for 18 hours. The reaction mixture was evaporated to dryness to give crude 2-({6-[(2-{4-[(biphenyl-2-ylcarbamoyl)oxy]piperidin-1-yl}ethyl)(methyl)amino]-6-oxohexyl}amino)-4-methyl-1,3-thiazole-5-carboxylic acid (70 mg). The resulting crude carboxylic acid (70 mg) and the compound (98 mg, 0.126 mmol) obtained in Example 1k were dissolved in dichloromethane (4 mL), and triethylamine (30 μL, 0.218 mmol) was added. 1-Ethyl-3-(3-dimethylaminopropyl)carbodiimide hydrochloride (38 mg, 0.198 mmol) was added under ice cooling, and the mixture was stirred at room temperature for 16 hours. The reaction mixture was diluted with ethyl acetate, and the organic layer was washed with a saturated aqueous sodium hydrogencarbonate solution and saturated sodium chloride solution. The organic layer was dried with anhydrous magnesium sulfate, then the solvent was evaporated under reduced pressure, and the resulting residue was purified by NH silica gel chromatography (ethyl acetate:methanol, 100:0→90:10, v/v) and by reverse phase preparative chromatography (Waters Corporation; XBridge Prep C18 OBD column, 30 mm ID×150 mm, 5 μm; 0.1% [w/v] aqueous ammonium formate solution:acetonitrile, 50:50->30:70) to give a free form (56 mg; yield, 41%) of the title compound as a white solid.

The resulting free compound (56 mg) was used to give the title compound (56 mg; yield, 93%) as a white solid according to the method described in Example 73g.

MS (FAB+) m/z: 1368 (M+H)$^+$ (free form).

IR (KBr) $v_{max}$ 3421, 2930, 1726, 1641, 1511, 1438, 1360, 1281, 1224, 1138, 848, 753, 702, 681 cm$^{-1}$.

Example 106

1-{2-[{6-[{5-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-4-methyl-1,3-thiazol-2-yl}(methyl)amino]hexanoyl}(methyl)amino]ethyl}piperidin-4-yl biphenyl-2-ylcarbamate trihydrochloride

[Formula 111]

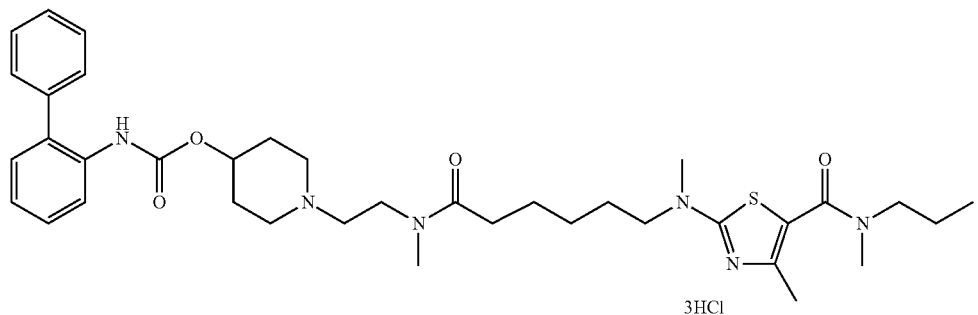

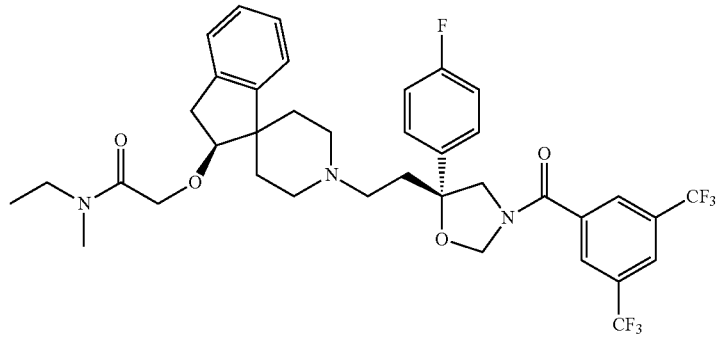

Example 106a tert-Butyl 2-[{6-[(2-{4-[(biphenyl-2-ylcarbamoyl)oxy]piperidin-1-yl}ethyl)(methyl)amino]-6-oxohexyl}(methyl)amino]-4-methyl-1,3-thiazole-5-carboxylate tert-Butyl 2-bromo-4-methyl-1,3-thiazole-5-carboxylate (134 mg, 0.482 mmol), the compound (193 mg, 0.402 mmol) obtained in Example 2a, triethylamine (84 μL), and 4.0 mL of n-butanol were used to give the title compound (242 mg; yield, 89%) as a colorless oily substance according to the same procedure as in Example 104b.

MS (FAB+) m/z: 678 (M+H)$^+$.

IR (KBr) $\nu_{max}$ 3423, 2932, 1731, 1693, 1643, 1540, 1449, 1325, 1283, 1207, 1092, 1045, 752, 704 cm$^{-1}$.

Example 106b

1-{2-[{6-[{5-[{3-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-4-methyl-1,3-thiazol-2-yl}(methyl)amino]hexanoyl}(methyl)amino]ethyl}piperidin-4-yl biphenyl-2-ylcarbamate trihydrochloride The compound (136 mg, 0.200 mmol) obtained in Example 106a was used to give the title compound (80 mg; yield, 29%) as a white solid according to the method described in Example 105b.

MS (FAB+) m/z: 1382 (M+H)$^+$ (free form).

IR (KBr) $\nu_{max}$ 3436, 2936, 1651, 1511, 1460, 1361, 1282, 1175, 1138, 908, 848, 761, 682 cm$^{-1}$.

Example 107

1-(2-{[6-({5-[{2-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]ethyl}(methyl)carbamoyl]-4-methyl-1,3-thiazol-2-yl}amino)hexanoyl](methyl)amino}ethyl)piperidin-4-yl biphenyl-2-ylcarbamate trihydrochloride

[Formula 112]

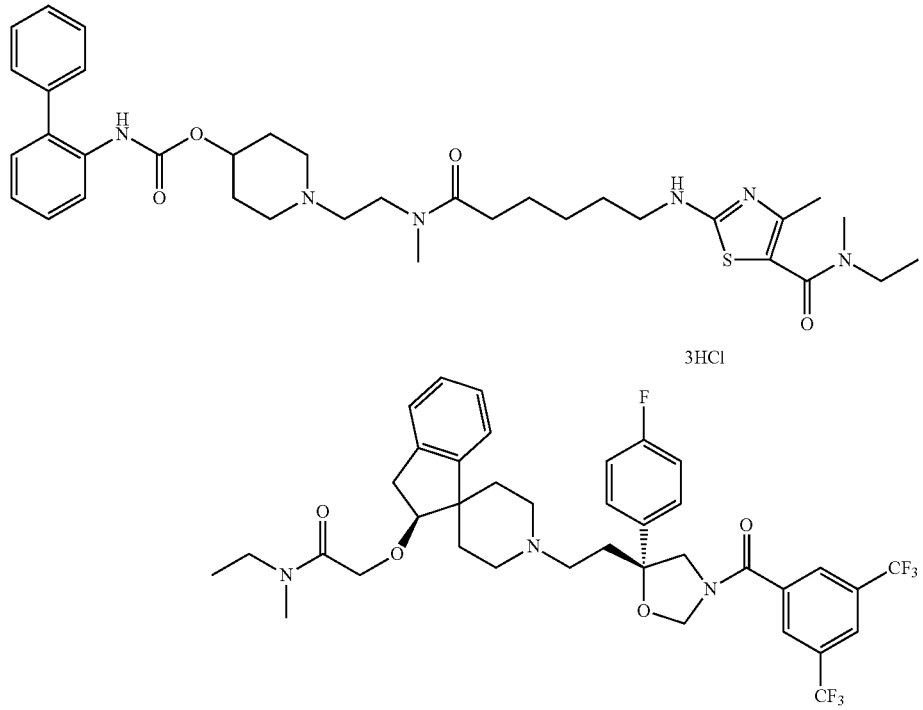

The compound (154 mg, 0.232 mmol) obtained in Example 105a and dihydrochloride of the compound (214 mg, 0.255 mmol) obtained in Example 15a were used to give the title compound (123 mg; yield, 36%) as a white solid according to the method described in Example 105b.

MS (FAB+) m/z: 1354 (M+H)$^+$ (free form).

IR (KBr) $\nu_{max}$ 3421, 2933, 1726, 1638, 1512, 1281, 1224, 1175, 1137, 1044, 907, 848, 753, 702, 681 cm$^{-1}$.

Example 108

1-{2-[{6-[{5-[{2-[({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]ethyl}(methyl)carbamoyl]-4-methyl-1,3-thiazol-2-yl}(methyl)amino]hexanoyl}(methyl)amino]ethyl}piperidin-4-yl biphenyl-2-ylcarbamate trihydrochloride

[Formula 113]

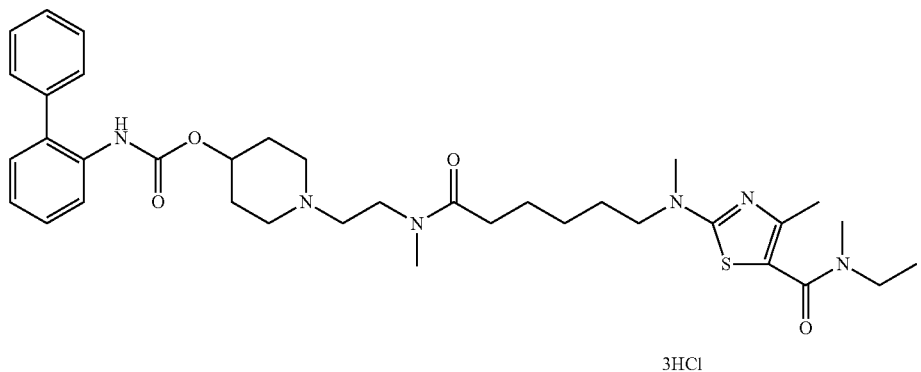

-continued

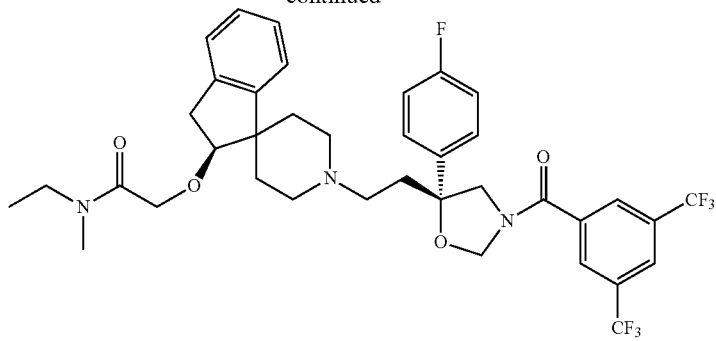

The compound (100 mg, 0.148 mmol) obtained in Example 106a and dihydrochloride of the compound (136 mg, 0.162 mmol) obtained in Example 15a were used to give the title compound (69 mg; yield, 36%) as a white solid according to the method described in Example 105b.

MS (FAB+) m/z: 1368 (M+H)$^+$ (free form).

IR (KBr) $\nu_{max}$ 3422, 2933, 1725, 1644, 1512, 1360, 1281, 1224, 1176, 1138, 904, 848, 753, 702, 681 cm$^{-1}$.

Example 109

1-{2-[{6-[(4-{[4-({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)-1,4-diazepan-1-yl]carbonyl}phenyl)amino]hexanoyl}(methyl)amino]ethyl}piperidin-4-yl biphenyl-2-ylcarbamate

[Formula 114]

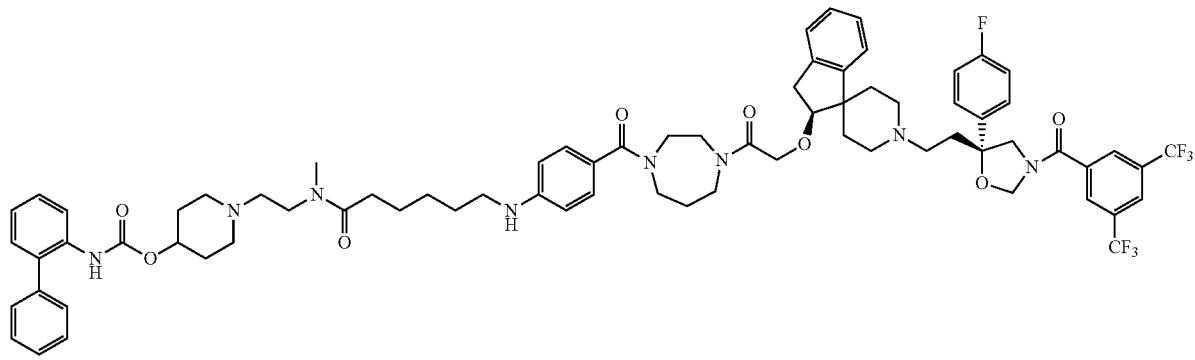

Example 109a tert-Butyl 4-[4-({6-[(2-{4-[(biphenyl-2-ylcarbamoyl)oxy]piperidin-1-yl}ethyl)(methyl)amino]-6-oxohexyl}amino)benzoyl]-1,4-diazepane-1-carboxylate 25 mL of 4 N hydrochloric acid-dioxane was added to the compound (1.01 g, 1.56 mmol) obtained in Example 15c, and the mixture was stirred at room temperature for 16 hours. The solvent of the reaction mixture was evaporated under reduced pressure to give crude 4-({6-[(2-{4-[(biphenyl-2-ylcarbamoyl)oxy]piperidin-1-yl}ethyl)(methyl)amino]-6-oxohexyl}amino)benzoate dihydrochloride as a white solid. The resulting crude carboxylic acid compound and tert-butyl 1,4-diazepane-1-carboxylate (500 mg, 2.50 mmol) were used to give the title compound (240 mg; yield, 20%) as a white solid according to the method described in Example 41a.

MS (FAB+) m/z: 769 (M+H)$^+$.

IR (Thin film) $\nu_{max}$ 2934, 1691, 1610, 1524, 1416, 1365, 1303, 1249, 1170, 1122, 1060, 1045, 831, 751, 703 cm$^{-1}$.

Example 109b

1-{2-[(6-{[4-(1,4-Diazepan-1-ylcarbonyl)phenyl]amino}hexanoyl)(methyl)amino]ethyl}piperidin-4-yl biphenyl-2-ylcarbamate trihydrochloride The compound (220 mg, 0.286 mmol) obtained in Example 109a was used to give a crude title compound (0.24 g; quantitative) as a white solid according to the method described in Example 73e.

MS (APCI) m/z: 669 (M+H)$^+$.

Example 109c

1-{2-[{6-[(4-{[4-({[(2S)-1-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)-1,4-diazepan-1-yl]carbonyl}phenyl)amino]hexanoyl}(methyl)amino]ethyl}piperidin-4-yl biphenyl-2-ylcarbamate The compound (0.24 g, 0.286 mmol) obtained in Example 109b was used to give a free form (0.104g; yield, 25%) of the title compound as a white solid according to the method described in Example 11e.
MS (APCI) m/z: 1345 (M+H)$^+$.

IR (Kbr) $v_{max}$ 2933, 1720, 1640, 1437, 1360, 1278, 1180, 1038, 848, 754, 703 cm$^{-1}$.

Example 110

1-{2-[{6-[(4-{[4-({[(2S)-1'-{2-[(5R)-3-[3,5-Bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)-1,4-diazepan-1-yl]carbonyl}phenyl)amino]hexanoyl}(methyl)amino]ethyl}piperidin-4-yl biphenyl-2-ylcarbamate trihydrochloride

[Formula 115]

The compound (0.104 g, 0.077 mmol) obtained in Example 109c was used to give the title compound (101 mg; yield, 90%) as a white solid according to the method described in Example 73g.
MS (FAB+) m/z: 1345 (M+H)$^+$.
IR (KCl) $v_{max}$ 2934, 1725, 1643, 1436, 1360, 1280, 1223, 1181, 1138, 1044, 848, 753, 681 cm$^{-1}$.
EA Anal. Calcd for $C_{74}H_{86}Cl_3F_7N_8O_8 \cdot 2H_2O$. C, 59, 62; H, 6.08; N, 7.52; Cl, 7.13. Found C, 59.92; H, 6.42; N, 7.23; Cl, 6.76.

Example 111

1-(2-{[6-({4-[{3-[({[(2S)-1'-{2-[(2R)-4-[3,5-Bis(trifluoromethyl)benzoyl]-2-(4-fluorophenyl)morpholin-2-yl]ethyl}-2,3-dihydrospiro[indene-1,4'-piperidin]-2-yl]oxy}acetyl)(methyl)amino]propyl}(methyl)carbamoyl]phenyl}amino)hexanoyl](methyl)amino}ethyl)piperidin-4-yl biphenyl-2-ylcarbamate

[Formula 116]

-continued

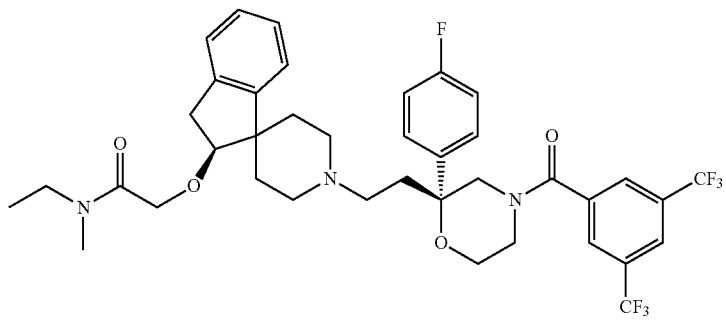

Example 111a

2-[(2R)-4-[3,5-Bis(trifluoromethyl)benzoyl]-2-(4-fluorophenyl)morpholin-2-yl]ethyl 4-chlorobenzenesulfonate 2-[(2R)-2-(4-Fluorophenyl)morpholin-2-yl]ethanol (1.76 g, 7.82 mmol) and triethylamine (1.32 mL, 9.38 mmol) were dissolved in a mixed solvent of acetonitrile (18 mL) and water (0.9 mL). A solution of 3,5-bis(trifluoromethyl)benzoyl chloride (1.48 mL, 8.21 mmol) in toluene (8.2 mL) was added dropwise with stirring under ice cooling, and then the mixture was further stirred under the same conditions for 5 minutes. The reaction mixture was diluted with ethyl acetate, and the organic layer was washed with water and saturated sodium chloride solution. The organic layer was dried with anhydrous sodium sulfate, and the solvent was evaporated under reduced pressure to give a crude 2-[(2R)-4-[3,5-bis(trifluoromethyl)benzoyl]-2-(4-fluorophenyl)morpholin-2-yl]ethanol (3.74 g) as a colorless oily substance.

The resulting crude product (3.74 g) was dissolved in acetonitrile (20 mL), and triethylamine (1.63 mL, 11.7 mmol) and 4-(dimethylamino)-pyridine (95 mg, 0.781 mmol) were added. Chlorobenzene sulfonylchloride (1.81 g, 8.60 mmol) was added little by little with stirring under ice cooling, and the mixture was stirred at room temperature for 1 hour. The reaction mixture was diluted with ethyl acetate, and the organic layer was washed with water and saturated sodium chloride solution. The organic layer was dried with anhydrous sodium sulfate, then the solvent was evaporated under reduced pressure, and the resulting residue was purified by silica gel column chromatography (n-hexane:ethyl acetate, 10:0→2:1) to give the title compound (4.08 g; yield, 82%) as a colorless oily substance.

MS (ESI+) m/z: 640 (M+H)$^+$.

Example 111b

Ethyl {[(2S)-1'-{2-[(2R)-4-[3,5-bis(trifluoromethyl)benzoyl]-2-(4-fluorophenyl)morpholin-2-yl]ethyl}-2,3-dihydrospiro[indene-1,4'-piperidin]-2-yl]oxy}acetate The compound (1.50 g, 2.34 mmol) obtained in Example 111a was used to give the title compound (1.71 g; yield, 99%) as a white solid according to the method described in Example 1i.

MS (FAB+) m/z: 737 (M+H)$^+$.

IR (KBr) $\nu_{max}$ 2926, 1751, 1645, 1511, 1477, 1441, 1376, 1280, 1136, 1030, 1006, 905, 839, 755, 682, 848 cm$^{-1}$.

Example 111c

{[(2S)-1'-{2-[(2R)-4-[3,5-Bis(trifluoromethyl)benzoyl]-2-(4-fluorophenyl)morpholin-2-yl]ethyl}-2,3-dihydrospiro[indene-1,4'-piperidin]-2-yl]oxy}acetic acid The compound (1.69 g, 2.29 mmol) obtained in Example 111b was used to give the title compound (1.71 g; yield, 99%) as a white solid according to the method described in Example 1j.

Example 111d 1-(2-{[6-({4-[{3-[({[(2S)-1'-{2-[(2R)-4-[3,5-Bis(trifluoromethyl)benzoyl]-2-(4-fluorophenyl)morpholin-2-yl]ethyl}-2,3-dihydrospiro[indene-1,4'-piperidin]-2-yl]oxy}acetyl)(methyl)amino]propyl}(methyl)carbamoyl]phenyl}amino)hexanoyl](methyl)amino}ethyl)piperidin-4-yl biphenyl-2-ylcarbamate Trihydrochloride of the compound (269 mg) obtained in Example 911 and the compound (200 mg, 0.282 mmol) obtained in Example 111c were used to give a free form (200 mg; yield, 52%) of the title compound as a white solid according to the method described in Example 11e.

MS (FAB+) m/z: 1361 (M+H)$^+$.

IR (KBr) $\nu_{max}$ 3423, 2932, 1726, 1641, 1512, 1481, 1408, 1281, 1139, 1099, 1044, 905, 848, 754, 681 cm$^{-1}$.

Example 112

1-(2-{[6-({4-[{3-[({[(2S)-1'-{2-[(2R)-4-[3,5-Bis(trifluoromethyl)benzoyl]-2-(4-fluorophenyl)morpholin-2-yl]ethyl}-2,3-dihydrospiro[indene-1,4'-piperidin]-2-yl]oxy}acetyl)(methyl)amino]propyl}(methyl)carbamoyl]phenyl}amino)hexanoyl](methyl)amino}ethyl)piperidin-4-yl biphenyl-2-ylcarbamate trihydrochloride

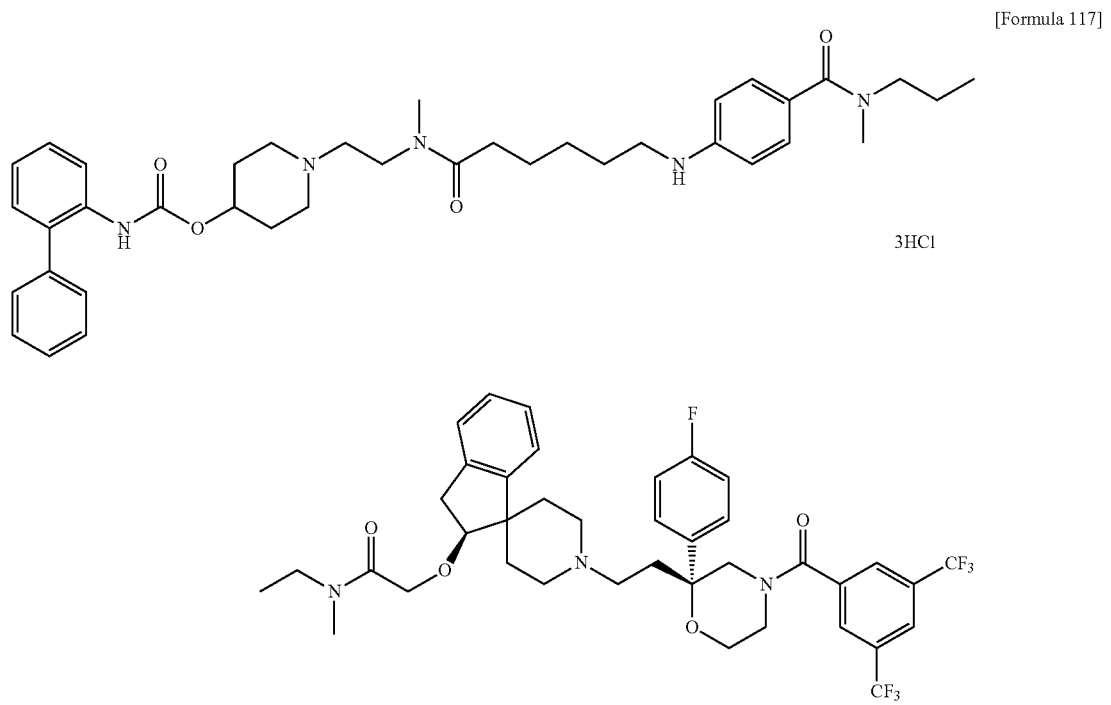

[Formula 117]

The compound (139 mg, 0.102 mmol) obtained in Example 111d was used to give the title compound (138 mg; yield, 92%) as a white solid according to the method described in Example 73g.

MS (FAB+) m/z: 1361 (M+H)$^+$ (free form).

IR (KBr) $v_{max}$ 3423, 2932, 1641, 1281, 1099, 1044, 905, 848, 754, 680 cm$^{-1}$.

EA Anal. Calcd for $C_{75}H_{87}F_7N_8O_8 \cdot 3HCl \cdot 1.5H_2O$. C, 60.14; H, 6.26; N, 7.48. Found C, 60.42; H, 6.14; N, 7.04.

Test Example 1

Test for Binding to Guinea-Pig Substance P Receptor

A preparation of a crude lung membrane sample was prepared, and a test for binding of a test substance to the sample was performed according to the method described in EP0336230A2.

The binding effect of the test substance to a substance P receptor was calculated as an affinity (Ki) of the test substance for the substance P receptor from a 50% binding concentration (IC$_{50}$) and an affinity (Kd) of [$^3$H]substance P for the substance P receptor.

The results are shown in Table 1.

TABLE 1

| Example | Ki(nM) |
|---|---|
| 1 | 1.5 |
| 4 | 1.8 |
| 5 | 1.5 |
| 7 | 0.57 |
| 8 | 2.6 |
| 9 | 2.1 |
| 13 | 2.6 |
| 14 | 1.9 |
| 15 | 1.5 |
| 16 | 2.5 |
| 18 | 1.8 |
| 25 | 1.7 |
| 27 | 1.2 |
| 29 | 1.4 |
| 30 | 1.9 |
| 32 | 1.3 |
| 34 | 1.0 |
| 36 | 1.4 |
| 38 | 1.5 |
| 39 | 1.2 |
| 40 | 1.6 |
| 41 | 0.96 |
| 43 | 1.6 |
| 66 | 2.1 |
| 72 | 1.4 |

TABLE 1-continued

| Example | Ki(nM) |
|---|---|
| 74 | 0.87 |
| 75 | 1.0 |
| 76 | 2.7 |
| 82 | 4.5 |
| 84 | 2.7 |
| 85 | 2.2 |
| 88 | 1.1 |
| 89 | 0.74 |
| 93 | 1.0 |
| 94 | 0.81 |
| 95 | 1.4 |
| 105 | 2.1 |
| 106 | 3.1 |
| 107 | 1.2 |
| 108 | 1.3 |
| 110 | 1.7 |

The above results show that the compound of the present invention has an excellent effect of binding to the substance P receptor.

Test Example 2

Test for Binding to Guinea-Pig NK$_2$ Receptor

A test for binding to the receptor can be performed using a crude guinea-pig membrane sample. Specifically, the affinity of a test substance for a guinea-pig NK$_2$ receptor can be calculated by isolating an ileum tissue, a site in which the NK$_2$ receptor is highly expressed, then preparing a crude membrane sample, reacting [$^3$H]SR 48968 or neurokinin A and the test substance together with the crude membrane sample solution, collecting the membrane components, and then measuring the radioactivity.

Test Example 3

Test for Binding to Guinea-Pig M$_3$ Receptor

A test for binding to the receptor can be performed using a crude guinea-pig membrane sample. Specifically, the affinity of a test substance for a guinea-pig M$_3$ receptor can be calculated by isolating a submandibular gland tissue, a site in which the M$_3$ receptor is highly expressed, then preparing a crude membrane sample, reacting [N-methyl-$^3$H]-(−)-Scopolamine methyl chloride and the test substance together with the crude membrane sample, collecting the membrane components, and then measuring the radioactivity.

Test Example 4

Test for Binding to Human NK$_1$ Receptor

A test for binding to the receptor can be performed using a crude membrane sample derived from human NK$_1$ receptor-expressing cells. Specifically, the affinity of a test substance for a human NK$_1$ receptor can be calculated by preparing a crude membrane sample prepared from human NK$_1$ receptor expressing COS cells, reacting [$^3$H]substance P and the test substance together with the crude membrane sample, collecting the membrane components, and then measuring the radioactivity.

Test Example 5

Test for Binding to Human NK$_2$ Receptor

Preparation of Crude Membrane Sample

A solution of cryopreserved COS cells expressing human NK$_2$ receptor was diluted with a buffer (50 mM tris-hydrochloride containing 0.04% of bovine serum albumin [BSA], pH 7.4) to obtain a concentration of $5.0 \times 10^5$ cells/mL and used as a crude membrane sample.

(b) Test for Binding to Receptor

[$^3$H]SR 48968 (GE Healthcare Japan Corporation) was diluted with a mixture of 50 mM of tris-hydrochloride (pH 7.4), 6 mM of manganese chloride tetrahydrate, 800 μg/mL of BSA, 8 μg/mL of chymostatin, 8 μg/mL of leupeptin, 80 μg/mL of bacitracin, and 20 μg/mL of phosphoramidon. A test substance and 250 μL of the crude membrane sample solution were added to 250 μL of this mixture, and the mixture was incubated at room temperature for 35 minutes ([$^3$H] SR 48968 had a final concentration of 1 nM). After the reaction, the membrane components were collected on a GF/B glass fiber filter paper (Whatman; Biomedical Research and Development Laboratories, Inc.) with an automated filtration system (Brandel; Biomedical Research and Development Laboratories, Inc.). The glass fiber filter paper was pretreated with a 0.1% polyethylenimine solution for 4 hours or longer to minimize non-specific binding. The filter collecting the membrane components was transferred to a small-size plastic vial containing 3 mL of Pico-Fluor, and the radioactivity was measured with a liquid scintillation counter (Tri-Carb 2900TR or 2300TR; Perkin Elmer).

The effect of binding to the NK$_2$ receptor was calculated as the affinity (Ki) of the test substance for the NK$_2$ receptor from a 50% binding dose (IC$_{50}$) and the affinity (Kd) of [$^3$H]SR 48968 for the NK$_2$ receptor.

The results are shown in Table 2.

TABLE 2

| Example | Ki(nM) |
|---|---|
| 1 | 0.57 |
| 4 | 0.62 |
| 5 | 0.48 |
| 7 | 0.17 |
| 8 | 0.38 |
| 9 | 0.66 |
| 13 | 0.65 |
| 14 | 0.67 |
| 15 | 0.91 |
| 16 | 0.49 |
| 18 | 0.42 |
| 25 | 0.77 |
| 27 | 0.76 |
| 29 | 0.76 |
| 30 | 0.71 |
| 32 | 0.74 |
| 34 | 0.54 |
| 36 | 0.96 |
| 38 | 0.89 |
| 39 | 0.82 |
| 40 | 0.83 |
| 41 | 0.26 |
| 43 | 1.3 |
| 66 | 0.86 |
| 72 | 0.52 |
| 74 | 0.14 |
| 75 | 0.25 |
| 76 | 1.0 |
| 82 | 0.60 |
| 84 | 0.89 |
| 85 | 1.0 |
| 88 | 0.72 |

TABLE 2-continued

| Example | Ki(nM) |
|---|---|
| 89 | 0.75 |
| 93 | 0.55 |
| 94 | 0.75 |
| 95 | 0.81 |
| 105 | 0.85 |
| 106 | 0.34 |
| 107 | 0.59 |
| 108 | 0.79 |
| 110 | 0.60 |

The above results show that the compound of the present invention has an excellent effect of binding to the neurokinin $NK_2$ receptor.

Test Example 6

Test for Binding to Human $M_3$ Receptor

Preparation of Crude Membrane Sample

A solution of cryopreserved CHO cells expressing human $M_3$ receptor was diluted with a buffer (50 mM tris-hydrochloride containing 0.5 mM of EDTA, pH 7.4) to obtain $5.0 \times 10^5$ of cells/mL and used as a crude membrane sample.

(b) Test for Binding to Receptor

[N-methyl-$^3$H]-(−)-Scopolamine methyl chloride (GE Healthcare Japan Corporation) was diluted with 50 mM of tris-hydrochloride containing 0.5 mM of EDTA (pH 7.4), a test substance and 250 μL of the crude membrane sample solution were added to 250 μL of the mixture, and the mixture was incubated at room temperature for 60 minutes. After the reaction, the membrane components were collected on a GF/B glass fiber filter paper (Whatman; Biomedical Research and Development Laboratories, Inc.) with an automated filtration system (Brandel; Biomedical Research and Development Laboratories, Inc.) ([N-methyl-$^3$H]-(−)-Scopolamine methyl chloride had a final concentration of 0.5 nM). The glass fiber filter paper was pretreated with a 0.1% polyethylenimine solution for 4 hours or longer to minimize non-specific binding. The filter collecting membrane components was transferred to a small-size plastic vial containing 3 mL of Pico-Fluor, and the radioactivity was measured with a liquid scintillation counter (Tri-Carb 2900TR or 2300TR; Perkin Elmer).

The effect of binding to the $M_3$ receptor was calculated as the affinity (Ki) of the test substance for the $M_3$ receptor from a 50% binding dose ($IC_{50}$) and the affinity (Kd) of [N-methyl-$^3$H]-(−)-Scopolamine methyl chloride for the $M_3$ receptor.

The results are shown in Table 3.

TABLE 3

| Example | Ki(nM) |
|---|---|
| 1 | 1.4 |
| 4 | 2.1 |
| 5 | 0.69 |
| 7 | 0.90 |
| 8 | 1.9 |
| 9 | 1.3 |
| 13 | 1.2 |
| 14 | 0.93 |
| 15 | 1.2 |
| 16 | 2.4 |
| 18 | 1.2 |
| 25 | 1.4 |
| 27 | 1.4 |
| 29 | 1.7 |

TABLE 3-continued

| Example | Ki(nM) |
|---|---|
| 30 | 0.62 |
| 32 | 1.1 |
| 34 | 1.5 |
| 36 | 1.8 |
| 38 | 1.8 |
| 39 | 1.4 |
| 40 | 2.0 |
| 41 | 1.4 |
| 43 | 2.6 |
| 66 | 1.5 |
| 72 | 1.6 |
| 74 | 0.32 |
| 75 | 0.52 |
| 76 | 3.4 |
| 82 | 1.6 |
| 84 | 1.2 |
| 85 | 1.9 |
| 88 | 0.31 |
| 89 | 1.2 |
| 93 | 0.60 |
| 94 | 2.0 |
| 95 | 2.1 |
| 105 | 1.4 |
| 106 | 1.3 |
| 107 | 1.4 |
| 108 | 3.0 |
| 110 | 0.93 |

The above results show that the compound of the present invention has an excellent effect of binding to the muscarine $M_3$ receptor.

Test Example 7

Effect of Suppressing Methacholine-Induced Airway Contraction (In Vivo, Intratracheal Administration)

Using healthy guinea pigs (body weight, 350 to 550 g; Hartley male guinea pigs), the effect of suppressing airway contraction induced by methacholine, which is a muscarine receptor agonist, was examined by a modified method of Konzett-Roessler (Naunyn-Schmiedebergs Arch. Exp. Pathol. Pharmakol. 195, 71 [1940]) using airway pressure as an indicator.

A tracheal cannula and a venous cannula were attached to a guinea pig anesthetized with pentobarbital (50 mg/mL of solution, 0.40 to 0.50 mL/body, subcutaneous administration). An arterial cannula filled with heparin-containing physiological saline (100 U/mL) was further attached, and blood pressure and heart rate were monitored via an amplifier and an instantaneous heart rate meter. Subsequently, gallamine (20 mg/body, intravenous administration) was administered to terminate spontaneous breathing, and then 10 mL/kg of positive pressure breathing (Ugo-Basile Biological Research Apparatus, Cat. No. 7025) was rapidly performed at 60 times/min. The airway pressure during artificial breathing was detected with a pressure transducer (TP-200T or TP-400T; Nihon Kohden Corporation) attached to a side branch of the tracheal cannula, amplified (AP-601G; Nihon Kohden Corporation), and recorded in a recorder. After the airway pressure, blood pressure, and heart rate were stabilized, 30 μg/kg of methacholine was intravenously administered from the venous cannula to induce airway contraction, and the airway pressure was measured for the following 10 minutes.

A test substance was dissolved in 5% glucose solution, and a 0.5 mL/kg solution was administered intratracheally with an intratracheal administration apparatus (model 1A-1B; Penn-Century, Inc.) 60 minutes before stimulation with methacholine.

The AUC of increase in the airway pressure over 10 minutes after administration of methacholine was measured as the intensity of methacholine-induced airway contraction and calculated as an $ID_{50}$ value from the inhibition rate based on the value of the control group (a 5% glucose solution intratracheal administration group).

The results are shown in Table 4.

TABLE 4

| Example | $ID_{50}$(ug/kg) |
|---|---|
| 1 | 17.7 |
| 4 | 25.2 |
| 9 | 16.4 |
| 14 | 12.9 |
| 15 | 37.5 |
| 16 | 19.1 |
| 18 | 38.9 |
| 25 | 45.9 |
| 27 | 21.8 |
| 29 | 26.6 |
| 30 | 8.8 |
| 32 | 35.6 |
| 34 | 25.1 |
| 36 | 14.6 |
| 38 | 25.7 |
| 39 | 55.9 |
| 40 | 75.4 |
| 43 | 75.7 |
| 72 | 63.5 |
| 74 | 43.0 |
| 76 | 29.2 |
| 84 | 14.3 |
| 85 | 32.7 |
| 88 | 6.0 |
| 93 | 37.2 |
| 94 | 39.5 |
| 95 | 46.2 |
| 105 | 40.0 |
| 110 | 31.8 |

The above results show that the compound of the present invention has an excellent antagonistic effect on the muscarine $M_3$ receptor.

Test Example 8

Effect of Suppressing Substance P-Induced Airway Contraction (In Vivo, Intratracheal Administration)

Using healthy guinea pigs (body weight, 350 to 550 g; Hartley male guinea pigs), the effect of suppressing airway contraction induced by substance P (SP), which is an $NK_1$ receptor agonist, was examined by a modified method of Konzett-Roessler (Naunyn-Schmiedebergs Arch. Exp. Pathol. Pharmakol. 195, 71 [1940]) using airway pressure as an indicator.

A tracheal cannula and a venous cannula were attached to a guinea pig anesthetized with pentobarbital (50 mg/mL solution, 0.40 to 0.50 mL/body, subcutaneous administration). An arterial cannula filled with heparin-containing physiological saline (100 U/mL) was further attached, and blood pressure and heart rate were monitored via an amplifier and an instantaneous heart rate meter. Subsequently, gallamine (20 mg/body, intravenous administration) was administered to terminate spontaneous breathing, and then 10 mL/kg of positive pressure breathing (Ugo-Basile Biological Research Apparatus, Cat. No. 7025) was rapidly performed at 60 times/min. The airway pressure during artificial breathing was detected with a pressure transducer (TP-200T or TP-400T; Nihon Kohden Corporation) attached to a side branch of the tracheal cannula, amplified (AP-601G; Nihon Kohden Corporation), and recorded in a recorder. After the airway pressure, blood pressure, and heart rate were stabilized, 20 µg/kg of SP was intravenously administered from the venous cannula to induce airway contraction, and the airway pressure was measured for the following 10 minutes.

The test substance was dissolved in a 5% glucose solution, a 0.5 mL/kg solution was intratracheally administered with an intratracheal administration apparatus (model 1A-1B; Penn-Century, Inc.) 60 minutes before stimulation with SP.

The AUC of increase in the airway pressure over 10 minutes after administration of SP was determined as the intensity of SP-induced airway contraction and calculated as an $ID_{50}$ value from the inhibition rate based on the value of the control group (5% glucose solution intratracheal administration group).

The results are shown in Table 5.

TABLE 5

| Example | $ID_{50}$(ug/kg) |
|---|---|
| 1 | 14.7 |
| 9 | 34.8 |
| 14 | 17.2 |
| 15 | 22.4 |
| 16 | 16.0 |
| 18 | 61.4 |
| 25 | 43.7 |
| 27 | 22.9 |
| 29 | 29.2 |
| 30 | 38.8 |
| 32 | 20.2 |
| 34 | 30.8 |
| 36 | 23.6 |
| 38 | 16.1 |
| 39 | 38.8 |
| 40 | 19.1 |
| 43 | 76.6 |
| 72 | 26.6 |
| 74 | 17.4 |
| 76 | 62.2 |
| 84 | 35.7 |
| 85 | 37.3 |
| 93 | 41.6 |
| 94 | 8.7 |
| 95 | 22.5 |
| 105 | 27.3 |
| 110 | 17.4 |

The above results show that the compound of the present invention has an excellent antagonistic effect on the neurokinin $NK_1$ receptor.

Test Example 9

Effect of Suppressing Neurokinin A-Induced Airway Contraction (In Vivo, Intratracheal Administration)

Using healthy guinea pigs (body weight, 350 to 550 g; Hartley male guinea pigs), the effect of suppressing airway contraction induced by neurokinin A (NKA), which is an $NK_2$ receptor agonist, was examined by a modified method of Konzett-Roessler (Naunyn-Schmiedebergs Arch. Exp. Pathol. Pharmakol. 195, 71 [1940]) using airway pressure as an indicator.

A tracheal cannula and a venous cannula were attached to a guinea pig anesthetized with pentobarbital (50 mg/mL solution, 0.40 to 0.50 mL/body, subcutaneous administration). An arterial cannula filled with heparin-containing physiological saline (100 U/mL) was further attached, and blood pressure and heart rate were monitored via an amplifier and an instantaneous heart rate meter. Subsequently, gallamine (20 mg/body, intravenous administration) was administered to terminate spontaneous breathing, and 10 mL/kg of positive pressure breathing (Ugo-Basile Biological Research Apparatus, Cat. No. 7025) was rapidly performed at 60 times/min. The airway pressure during artificial breathing was detected with a pressure transducer (TP-200T or TP-400T; Nihon Kohden Corporation) attached to a side branch of the tracheal cannula, amplified (AP-601G; Nihon Kohden Corporation), and recorded in a recorder. After the airway pressure, blood pressure, and heart rate were stabilized, 4 μg/kg of NKA was intravenously administered from the venous cannula to induce airway contraction, and the airway pressure was measured for the following 10 minutes.

The test substance was dissolved in a 5% glucose solution, and a 0.5 mL/kg solution was intratracheally administered with an intratracheal administration apparatus (model 1A-1B; Penn-Century, Inc.) 60 minutes before stimulation with NKA.

The AUC of increase in the airway pressure over 10 minutes after administration of NKA was determined as the intensity of NKA-induced airway contraction and calculated as an $ID_{50}$ value from the inhibition rate based on the value of the control group (5% glucose solution intratracheal administration group).

The results are shown in Table 6.

TABLE 6

| Example | $ID_{50}$(ug/kg) |
|---|---|
| 1 | 4.9 |
| 9 | 37.4 |
| 14 | 28.4 |
| 15 | 37.7 |
| 16 | 28.6 |
| 18 | 45.3 |
| 25 | 72.7 |
| 27 | 13.5 |
| 29 | 43.8 |
| 30 | 63.2 |
| 32 | 35.6 |
| 34 | 30.0 |
| 36 | 16.8 |
| 38 | 25.3 |
| 39 | 33.6 |
| 40 | 57.3 |
| 43 | 24.1 |
| 72 | 15.1 |
| 74 | 12.7 |
| 76 | 17.6 |
| 84 | 22.1 |
| 93 | 43.7 |
| 94 | 43.1 |
| 95 | 39.0 |
| 105 | 13.6 |
| 110 | 13.5 |

The above results show that the compound of the present invention has an excellent antagonistic effect on the neurokinin $NK_2$ receptor.

The results shown in Tables 1 to 6 show that the compound of the present invention has an excellent antagonistic effect on all of the neurokinin $NK_1$ receptor, the neurokinin $NK_2$ receptor, and the muscarine $M_3$ receptor and is useful as an agent for treating and/or preventing a disease selected from the group consisting of bronchial asthma, bronchitis, chronic obstructive pulmonary disease, coughing, sputum oversecretion, rhinitis, pain, anxiety, depression, convulsion, Parkinson's disease, incontinence of urine, irritable bowel syndrome, prostate hypertrophy, vomiting, peptic ulcer, retina testing, acute iritis, keratitis, miosis, saliva oversecretion caused by an anesthetic, airway secretion, and ulcers.

FORMULATION EXAMPLE

Formulation Example 1

Powder

A powder can be produced by mixing 5 g of the compound of Example 1, 895 g of lactose, and 100 g of maize starch with a blender.

Formulation Example 2

Granule

After 5 g of the compound of Example 1, 865 g of lactose, and 100 g of low-substituted hydroxypropylcellulose are mixed, 300 g of a 10% aqueous hydroxypropylcellulose solution is added, and the mixture is kneaded. The mixture is extruded, granulated with a granulating machine, and dried to obtain granules.

Formulation Example 3

Tablet

After 5 g of the compound of Example 74, 90 g of lactose, 34g of maize starch, 20 g of crystalline cellulose, and 1 g of magnesium stearate are mixed with a blender, the mixture is tableted with a tableting machine to obtain tablets.

Formulation Example 4

Solution for Inhalation 1

A solution is prepared to obtain a concentration of the compound of Example 9 of 10% (w/w), a concentration of benzalkonium chloride of 0.04% (w/w), a concentration of phenethyl alcohol of 0.40% (w/w), and a concentration of purified water of 89.56% (w/w).

Formulation Example 5

Solution for Inhalation 2

A solution is prepared to obtain a concentration of the compound of Example 75 of 10% (w/w), a concentration of benzalkonium chloride of 0.04% (w/w), a concentration of polyethylene glycol of 10% (w/w), a concentration of propylene glycol of 30% (w/w), and a concentration of purified water of 39.96% (w/w).

Formulation Example 6

Powder for Inhalation

A powder is prepared to obtain a concentration of the compound of Example 9 of 40% (w/w) and a concentration of lactose of 60% (w/w).

Formulation Example 7

Aerosol

An aerosol is prepared to obtain a concentration of the compound of Example 75 of 10% (w/w), a concentration of lecithin of 0.5% (w/w), a concentration of CFC-11 of 34.5% (w/w), and a concentration of CFC-12 of 55% (w/w).

INDUSTRIAL APPLICABILITY

The compound of the present invention or a pharmacologically acceptable salt thereof represented by the general formula (I) has an antagonistic effect on all of the neurokinin $NK_1$ receptor, the neurokinin $NK_2$ receptor, and the muscarine $M_3$ receptor and is useful as a medicament because of low toxicities and excellent pharmacokinetics, particularly as an agent for preventing or treating a respiratory disease, an allergic disease, and/or a neurological disease.

The invention claimed is:
1. A compound of formula (I) or a pharmacologically acceptable salt thereof:

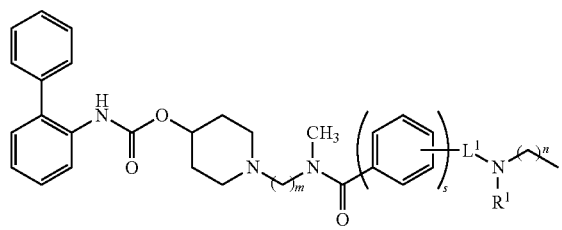
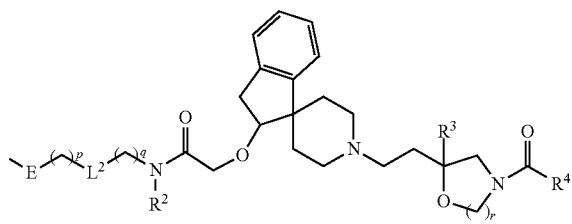

(I)

wherein
$R^1$ represents a hydrogen atom, a $C_1$-$C_6$ alkyl group, a ($C_3$-$C_6$ cycloalkyl)methyl group, a $C_2$-$C_7$ alkoxycarbonyl group or a benzyl group,
$R^2$ represents a hydrogen atom, a $C_1$-$C_6$ alkyl group or a $C_2$-$C_7$ alkoxycarbonyl group,
$R^3$ represents a phenyl group optionally substituted with 1 to 5 groups each independently selected from Substituent Group A or a heterocyclic group optionally substituted with 1 to 3 groups each independently selected from Substituent Group A,
$R^4$ represents a phenyl group optionally substituted with 1 to 5 groups each independently selected from Substituent Group A or a heterocyclic group optionally substituted with 1 to 3 groups each independently selected from Substituent Group A,
$L^1$ represents a $C_1$-$C_{10}$ alkylene group or a $C_1$-$C_{10}$ alkylene group in which one methylene group is replaced by an oxygen atom and when $R^1$ is a $C_1$-$C_6$ alkyl group, any carbon atom of $R^1$ optionally binds to any carbon atom of $L^1$,
$L^2$ represents a carbonyl group, a hydroxymethylene group, an ester group, a group represented by a formula —N($R^5$)—, a group represented by a formula —N($R^5$)—C(=O)—, a group represented by a formula —C(=O)—N($R^5$)—, a group represented by a formula —N($R^5$)—C(=O)—O— or a group represented by a formula —O—C(=O)—N($R^5$) wherein $R^5$ represents a hydrogen atom, a $C_1$-$C_6$ alkyl group, a $C_3$-$C_6$ cycloalkyl group or a $C_1$-$C_6$ alkoxy group,
E represents a phenylene group optionally substituted with 1 to 4 groups each independently selected from Substituent Group A, or a heteroarylene group optionally substituted with 1 or 2 groups each independently selected from Substituent Group A, wherein E binds to a methylene group on either side via a carbon atom thereof and when $R^1$ or $R^5$ is a $C_1$-$C_6$ alkyl group, any carbon atom of $R^1$ or $R^5$ optionally binds to any carbon atom of E,
m represents an integer of 1 to 4,
n represents an integer of 0 to 4,
p represents an integer of 0 to 2,
q represents an integer of 1 to 10,
r represents 1 or 2,
s represents 0 or 1, and
Substituent Group A represents a group consisting of a halogen atom, a $C_1$-$C_6$ alkyl group, a $C_1$-$C_6$ halogenated alkyl group, a hydroxy group, a $C_1$-$C_6$ alkoxy group, a $C_1$-$C_6$ halogenated alkoxy group, a cyano group, a carboxyl group, a $C_2$-$C_7$ alkylcarbonyloxy group, a $C_2$-$C_7$ alkoxycarbonyloxy group, a carbamoyl group, a nitro group, and an amino group.

2. The compound or pharmacologically acceptable salt thereof according to claim 1, wherein the formula (I) is a formula (II):

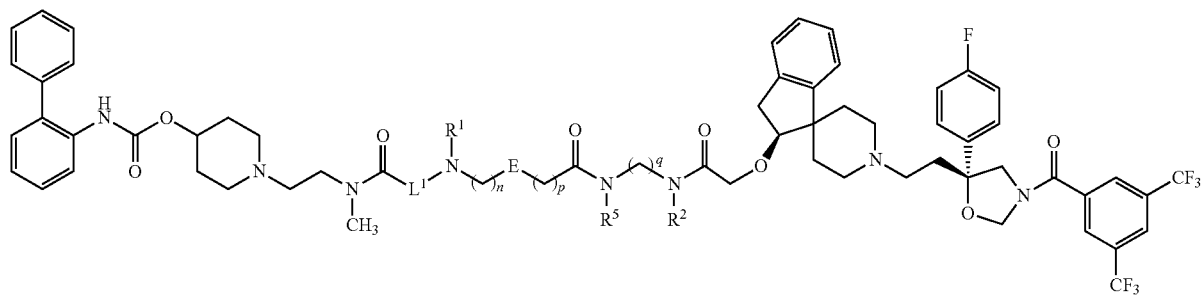

(II)

or a formula (III):

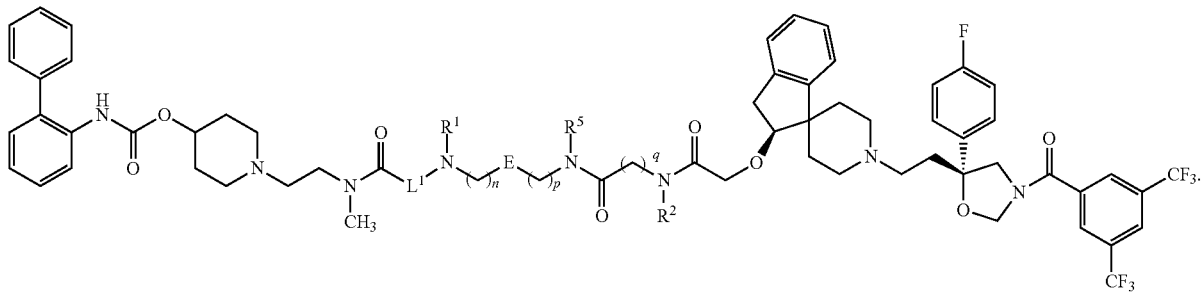

(III)

3. The compound or pharmacologically acceptable salt thereof according to claim 1, wherein the formula (I) is a formula (II):

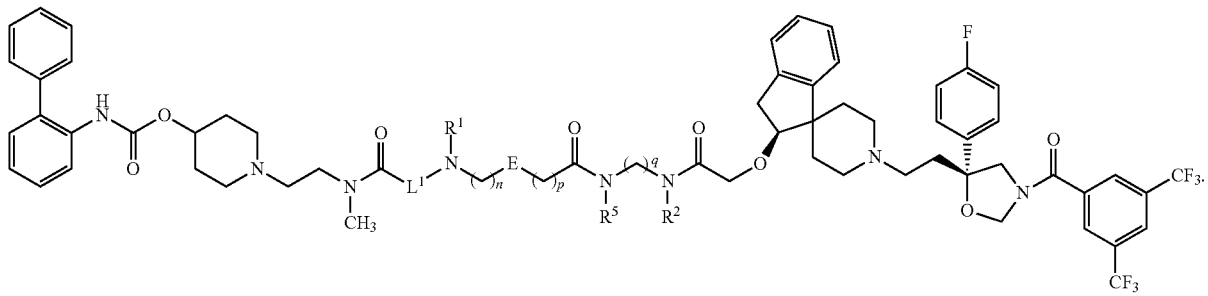

(II)

4. The compound or pharmacologically acceptable salt thereof according to claim 1, wherein $R^1$ is a hydrogen atom or a $C_1$-$C_6$ alkyl group.

5. The compound or pharmacologically acceptable salt thereof according to claim 1, wherein $R^1$ is a hydrogen atom or a methyl group.

6. The compound or pharmacologically acceptable salt thereof according to claim 1, wherein $R^2$ is a $C_1$-$C_6$ alkyl group.

7. The compound or pharmacologically acceptable salt thereof according to claim 1, wherein $R^2$ is a methyl group.

8. The compound or pharmacologically acceptable salt thereof according to claim 1, wherein $R^5$ is a hydrogen atom, a methyl group or a cyclopropyl group.

9. The compound or pharmacologically acceptable salt thereof according to claim 1, wherein $R^5$ is a methyl group.

10. The compound or pharmacologically acceptable salt thereof according to claim 1, wherein $L^1$ is a $C_1$-$C_8$ alkylene group or a $C_3$-$C_8$ alkylene group in which one methylene group is replaced by an oxygen atom.

11. The compound or pharmacologically acceptable salt thereof according to claim 1, wherein $L^1$ is an ethylene group, a trimethylene group, a tetramethylene group, a pentamethylene group, a hexamethylene group, a methyleneoxytrimethylene group, an ethyleneoxyethylene group or a trimethyleneoxymethylene group.

12. The compound or pharmacologically acceptable salt thereof according to claim 1, wherein E is a phenylene group optionally substituted with 1 or 2 groups each independently selected from a halogen atom and a $C_1$-$C_6$ alkyl group, a thienylene group, a thiazolylene group, a pyridinylene group, a pyrimidinylene group or a benzothiazolylene group optionally substituted with one group selected from a halogen atom and a $C_1$-$C_6$ alkyl group.

13. The compound or pharmacologically acceptable salt thereof according to claim 1, wherein E is a 1,3-phenylene group, a 1,4-phenylene group, a 2,5-thienylene group, a group represented by formula (IV), a group represented by formula (V), a group represented by formula (VI), a group represented by formula (VII), a group represented by formula (VIII), a group represented by formula (IX), a group represented by formula (X), a group represented by formula (XI) or a group represented by formula (XII), wherein $C_n$ and $C_p$ each represent a single bond, and $C_n$ binds to the group represented by —$(CH_2)_n$—, and $C_p$ binds to the group represented by —$(CH_2)_p$—

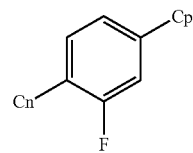

(IV)

(V) 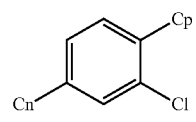

(VI) 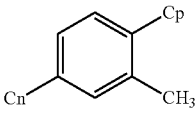

(VII) 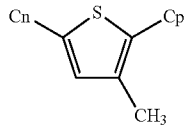

(VIII) 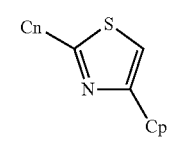

(IX) 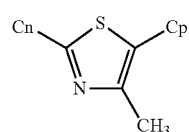

(X) 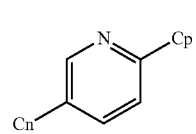

(XI) 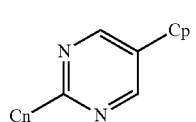

(XII) 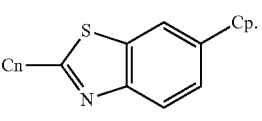

14. The compound or pharmacologically acceptable salt thereof according to claim 1, wherein E is a 1,4-phenylene group, a 2,5-thienylene group, a group represented by formula (IX), a group represented by formula (X), a group represented by formula (XI) or a group represented by formula (XII), wherein $C_n$ and $C_p$ each represent a single bond, and $C_n$ binds to the group represented by —$(CH_2)_n$—, and $C_p$ binds to the group represented by —$(CH_2)_p$—

(IX) 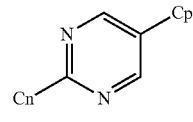

(X) 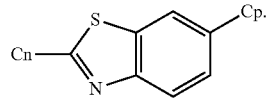

(XI) 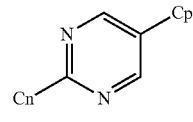

(XII) 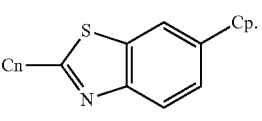

15. The compound or pharmacologically acceptable salt thereof according to claim 1, wherein n is 0 or 1.

16. The compound or pharmacologically acceptable salt thereof according to claim 1, wherein p is 0 or 1.

17. The compound or pharmacologically acceptable salt thereof according to claim 1, wherein p is 0.

18. The compound or pharmacologically acceptable salt thereof according to claim 1, wherein q is 2 or 3.

19. A compound or a pharmacologically acceptable salt thereof, selected from 1-{2-[{6-[({5-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-2-thienyl}methyl)amino]hexanoyl}(methyl)amino]ethyl}piperidin-4-yl biphenyl-2-ylcarbamate, 1-(2-{[6-(6-[{3-[([(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]pyridin-3-yl}amino)hexanoyl](methyl)amino}ethyl)piperidin-4-yl biphenyl-2-ylcarbamate, 1-(2-{[6-({5-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]pyrimidin-2-yl}amino)hexanoyl](methyl)amino}ethyl)piperidin-4-yl biphenyl-2-ylcarbamate, 1-(2-{[6-({4-[{2-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]ethyl}(methyl)carbamoyl]phenyl}amino)hexanoyl](methyl)amino}ethyl)piperidin-4-yl biphenyl-2-ylcarbamate, 1-{2-[{[3-({4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}amino)propoxy]acetyl}(methyl)amino]ethyl}piperidin-4-yl biphenyl-2-ylcarbamate, 1-{2-[{3-[2-({4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}amino)ethoxy]propanoyl}(methyl)amino]ethyl}piperidin-4-yl biphenyl-2-ylcarbamate, 1-(2-[5-({4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}amino)pentanoyl](methyl)amino}ethyl)piperidin-4-yl biphenyl-2-ylcarbamate, 1-{2-[{4-[{4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}(methyl)amino]butanoyl}(methyl)amino]ethyl}piperidin-4-yl biphenyl-2-ylcarbamate, 1-{2-[{5-[{4-[{3-[({[(2S)-1'-{2-

[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}(methyl)amino]pentanoyl}(methyl)amino]ethyl}piperidin-4-yl biphenyl-2-ylcarbamate, 1-(2-{[6-({4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}amino)hexanoyl](methyl)amino}ethyl)piperidin-4-yl biphenyl-2-ylcarbamate, 1-{2-[{6-[{4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]benzyl}(methyl)amino]hexanoyl}(methyl)amino]ethyl}piperidin-4-yl biphenyl-2-ylcarbamate, 1-(2-{[6-({4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]benzyl}amino)hexanoyl](methyl)amino}ethyl)piperidin-4-yl biphenyl-2-ylcarbamate, 1-{2-[{6-[{4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}(methyl)amino]hexanoyl}(methyl)amino]ethyl}piperidin-4-yl biphenyl-2-ylcarbamate, 1-(2-{[6-({4-[{4-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]butanoyl}(methyl)amino]phenyl}amino)hexanoyl](methyl)amino}ethyl)piperidin-4-yl biphenyl-2-ylcarbamate, 1-(2-{[6-({6-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-1,3-benzothiazol-2-yl}amino)hexanoyl](methyl)amino}ethyl)piperidin-4-yl biphenyl-2-ylcarbamate, 1-{2-[(N-{4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}-β-alanyl)(methyl)amino]ethyl}piperidin-4-yl biphenyl-2-ylcarbamate, 1-(2-{[6-({5-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-4-methyl-1,3-thiazol-2-yl}amino)hexanoyl] (methyl)amino}ethyl)piperidin-4-yl biphenyl-2-ylcarbamate and 1-{2-[{6-[(4-{[4-({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)-1,4-diazepan-1-yl]carbonyl}phenyl)amino]hexanoyl}(methyl)amino]ethyl}piperidin-4-yl biphenyl-2-ylcarbamate.

20. 1-{2-[{6-[({5-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-2-thienyl}methyl)amino]hexanoyl}(methyl)amino]ethyl}piperidin-4-yl biphenyl-2-ylcarbamate, 1-(2-{[6-({6-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]pyridin-3-yl}amino)hexanoyl](methyl)amino}ethyl)piperidin-4-yl biphenyl-2-ylcarbamate, 1-(2-{[6-({5-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]pyrimidin-2-yl}amino)hexanoyl](methyl)amino}ethyl)piperidin-4-yl biphenyl-2-ylcarbamate, 1-(2-{[6-({4-[{2-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]ethyl}(methyl)carbamoyl]phenyl}amino)hexanoyl](methyl)amino}ethyl)piperidin-4-yl biphenyl-2-ylcarbamate, 1-{2-[[3-({4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}amino)propoxy]acetyl}(methyl)amino]ethyl}piperidin-4-yl biphenyl-2-ylcarbamate, 1-{2-[{3-[2-({4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}amino)ethoxy]propanoyl}(methyl)amino]ethyl}piperidin-4-yl biphenyl-2-ylcarbamate, 1-(2-{[5-({4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}amino)pentanoyl](methyl)amino}ethyl)piperidin-4-yl biphenyl-2-ylcarbamate, 1-{2-[{4-[{4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}(methyl)amino]butanoyl}(methyl)amino]ethyl}piperidin-4-yl biphenyl-2-ylcarbamate, 1-{2-[{4-[{4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}(methyl)amino]pentanoyl}(methyl)amino]ethyl}piperidin-4-yl biphenyl-2-ylcarbamate, 1-(2-{[6-({4-[{3-[({[(2S)-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}amino)hexanoyl](methyl)amino}ethyl)piperidin-4-yl biphenyl-2-ylcarbamate, 1-{2-[{6-[{4-[{3-[({[(2S)-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]benzyl}(methyl)amino]hexanoyl}(methyl)amino]ethyl}piperidin-4-yl biphenyl-2-ylcarbamate, 1-(2-{[6-({4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]benzyl}amino)hexanoyl](methyl)amino}ethyl)piperidin-4-yl biphenyl-2-ylcarbamate, 1-{2-[{6-[{4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]butanoyl}(methyl)amino]phenyl}amino)hexanoyl](methyl)amino}ethyl)piperidin-4-yl biphenyl-2-ylcarbamate, 1-(2-

{6-({6-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-1,3-benzothiazol-2-yl}amino)hexanoyl](methyl)amino}ethyl)piperidin-4-yl biphenyl-2-ylcarbamate, 1-{2-[(N-{4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}-β-alanyl)(methyl)amino]ethyl}piperidin-4-yl biphenyl-2-ylcarbamate, 1-(2-{[6-(5-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-4-methyl-1,3-thiazol-2-yl}amino)hexanoyl](methyl)amino}ethyl)piperidin-4-yl biphenyl-2-ylcarbamate or 1-{2-[{6-[(4-{[4-({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)-1,4-diazepan-1-yl]carbonyl}phenyl)amino]hexanoyl](methyl)amino]ethyl}piperidin-4-yl biphenyl-2-ylcarbamate.

21. A pharmaceutical composition comprising a compound or a pharmacologically acceptable salt thereof according to claim 1 and a pharmaceutically acceptable carrier.

22. 1-(2-{[6-({4-[{2-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]ethyl}(methyl)carbamoyl]phenyl}amino)hexanoyl](methyl)amino}ethyl)piperidin-4-yl biphenyl-2-ylcarbamate.

23. 1-(2-{[5-({4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4]-piperidin]-2-yl]oxy}acetyl)(methyl)amino]propyl}(methyl)carbamoyl]phenyl}amino)pentanoyl](methyl)amino}ethyl)piperidin-4-yl biphenyl-2-ylcarbamate trihydrochloride.

24. 1-{2-[{4-[{4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}(methyl)amino]butanoyl}(methyl)amino]ethyl}piperidin-4-yl biphenyl-2-ylcarbamate trihydrochloride.

25. 1-{2-[{5-{4-[{3-[({[(2S)-1'-{2-[(5R)-3-[3,5-bis(trifluoromethyl)benzoyl]-5-(4-fluorophenyl)-1,3-oxazolidin-5-yl)ethyl}-2,3-dihydrospiro[indene-1,4'-piperidin]-2-yl]oxy}acetyl)(methyl)amino]propyl}(methyl)carbamoyl]phenyl}(methyl)amino]pentanoyl}(methyl)amino]ethyl}piperidin-4-yl biphenyl-2-ylcarbamate trihydrochloride.

26. 1-(2-{[6-({4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}amino)hexanoyl](methyl)amino}ethyl)piperidin-4-yl biphenyl-2-ylcarbamate.

27. 1-{2-[{6-[{4-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]phenyl}(methyl)amino]hexanoyl}(methyl)amino]ethyl}piperidin-4-yl biphenyl-2-ylcarbamate.

28. 1-(2-{[6-({5-[{3-[({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)(methyl)amino]propyl}(methyl)carbamoyl]-4-methyl-1,3-thiazol-2-yl}amino)hexanoyl](methyl)amino}ethyl)piperidin-4-yl biphenyl-2-ylcarbamate trihydrochloride.

29. 1-{2-[{6-[(4-{[4-({[(2S)-1'-{2-[(5R)-3-[3,5-bis(trifluoromethyl)benzoyl]-5-(4-fluorophenyl)-1,3-oxazolidin-5-yl]ethyl}-2,3-dihydrospiro[indene-1,4'-piperidin]-2-yl]oxy}acetyl)-1,4-diazepan-1-yl]carbonyl}phenyl)amino]hexanoyl](methyl)amino]ethyl}piperidin-4-yl biphenyl-2-ylcarbamate trihydrochloride.

* * * * *

UNITED STATES PATENT AND TRADEMARK OFFICE
CERTIFICATE OF CORRECTION

| | |
|---|---|
| PATENT NO. | : 8,476,253 B2 |
| APPLICATION NO. | : 13/234514 |
| DATED | : July 2, 2013 |
| INVENTOR(S) | : Takuya Ikeda, Takanori Yamazaki and Hiroshi Tsuchida |

It is certified that error appears in the above-identified patent and that said Letters Patent is hereby corrected as shown below:

In the Claims

In claim 13, at column 300, at lines 53-56, delete "wherein $C_n$ and $C_p$ each represent a single bond, and $C_n$ binds to the group represented by $-(CH_2)_n-$, and $C_p$ binds to the group represented by $-(CH_2)_p-$" and insert -- wherein $C_n$ and $C_p$ each represent a single bond, and $C_n$ binds to the group represented by $-(CH_2)_n-$, and $C_p$ binds to the group represented by $-(CH_2)_p-$ --.

In claim 14, at column 301, at lines 51-53, delete "wherein $C_n$ and $C_p$ each represent a single bond, and $C_n$ binds to the group represented by $-(CH_2)_n-$, and $C_p$ binds to the group represented by $-(CH_2)_p-$" and insert -- wherein $C_n$ and $C_p$ each represent a single bond, and $C_n$ binds to the group represented by $-(CH_2)_n-$, and $C_p$ binds to the group represented by $-(CH_2)_p-$ --.

In claim 19, at column 302, at line 27, delete "(methyl)amino]ethyl}piperidin-4-yl    biphenyl-2-" and insert -- (methyl)amino]ethyl}piperidin-4-yl biphenyl-2- --.

In claim 19, at column 302, at line 28, delete "ylcarbamate,  1-(2-{[6-(6-[{3-[([(2S)-1'-{2-[(5R)-3-[3,5-bis" and insert -- ylcarbamate, 1-(2-{[6-({6-[{3-[({[(2S)-1'-{2-[(5R)-3-[3,5-bis --.

In claim 19, at column 302, at line 42, delete "4'-piperidin]-2-yl]oxy}acetyl)(methyl)amino)ethyl}" and insert -- 4'-piperidin]-2-yl]oxy}acetyl)(methyl)amino]ethyl} --.

In claim 19, at column 302, at line 56, delete "biphenyl-2-ylcarbamate,    1-(2-[5-({4-[{3-[({[(2S)-1'-{2-" and insert -- biphenyl-2-ylcarbamate, 1-(2-{[5-({4-[{3-[({[(2S)-1'-{2- --.

In claim 19, at column 303, at line 5, delete "(methyl)amino}ethyl)piperidin-4-yl biphenyl-2-" and insert -- (methyl)amino}ethyl)piperidin-4-yl biphenyl-2- --.

In claim 19, at column 303, at line 49, delete "thiazol-2-yl}amino)hexanoyl](methyl)amino}ethyl)" and insert -- thiazol-2-yl}amino)hexanoyl](methyl)amino}ethyl) --.

Signed and Sealed this
Twenty-second Day of April, 2014

Michelle K. Lee
*Deputy Director of the United States Patent and Trademark Office*

CERTIFICATE OF CORRECTION (continued)
U.S. Pat. No. 8,476,253 B2

In claim 20, at column 304, at line 5, delete "(methyl)amino}ethyl)piperidin-4-yl biphenyl-2-" and insert -- (methyl)amino}ethyl)piperidin-4-yl biphenyl-2- --.

In claim 20, at column 304, at line 9, delete "piperidin]-2-yl]oxy}acetyl)(methyl)amino)ethyl}(methyl)" and insert -- piperidin]-2-yl]oxy}acetyl)(methyl)amino]ethyl}(methyl) --.

In claim 20, at column 304, at line 19, delete "rophenyl)-1,3-oxazolidin-5-yl)ethyl}-2,3-dihydrospiro[in-" and insert -- rophenyl)-1,3-oxazolidin-5-yl]ethyl}-2,3-dihydrospiro[in- --.

In claim 20, at column 304, at line 22, delete "propanoyl}(methyl)amino}ethyl]piperidin-4-yl biphenyl-2-" and insert -- propanoyl}(methyl)amino]ethyl}piperidin-4-yl biphenyl-2- --.

In claim 20, at column 304, at line 29, delete "[([(2S)-1'-{2-[(5R)-3-[3,5-bis(trifluoromethyl)benzoyl)-5-" and insert -- [({[(2S)-1'-{2-[(5R)-3-[3,5-bis(trifluoromethyl)benzoyl]-5- --.

In claim 20, at column 304, at line 34, delete "biphenyl-2-ylcarbamate,     1-{2-[{4-[{4-[{3-[({[(2S)-1'-{2-" and insert -- biphenyl-2-ylcarbamate, 1-{2-[{5-[{4-[{3-[({[(2S)-1'-{2- --.

In claim 20, at column 304, at line 39, delete "(methyl)amino]ethyl}piperidin-4-yl biphenyl-2-" and insert -- (methyl)amino]ethyl}piperidin-4-yl biphenyl-2- --.

In claim 20, at column 304, at line 40, delete "ylcarbamate,     1-(2-{[6-({4-[{3-[({[(2S)-{2-[(5R)-3-[3,5-bis" and insert -- ylcarbamate, 1-(2-{[6-({4-[{3-[({[(2S)-1'-{2-[(5R)-3-[3,5-bis --.

In claim 20, at column 304, at line 46, delete "[({[(2S)-{2-[(5R)-3-[3,5-bis(trifluoromethyl)benzoyl]-5-(4-" and insert -- [({[(2S)-1'-{2-[(5R)-3-[3,5-bis(trifluoromethyl)benzoyl]-5-(4- --.

In claim 20, at column 304, at line 50, delete "(methyl)amino]ethyl}piperidin-4-yl biphenyl-2-" and insert -- (methyl)amino]ethyl}piperidin-4-yl biphenyl-2- --.

In claim 20, at column 305, at lines 11-12, delete "ethyl}piperidin-4-yl   biphenyl-2-ylcarbamate, 1-(2-{[6-(5-[{3-[([(2S)-1'-{2-[(5R)-3-[3,5-bis(trifluoromethyl)" and insert -- ethyl}piperidin-4-yl biphenyl-2-ylcarbamate, 1-(2-{[6-({5-[{3-[({[(2S)-1'-{2-[(5R)-3-[3,5-bis(trifluoromethyl) --.

In claim 20, at column 305, at line 19, delete "(4-fluorophenyl)-1,3-oxazolidin-5-yl)ethyl}-2,3-" and insert -- (4-fluorophenyl)-1,3-oxazolidin-5-yl]ethyl}-2,3- --.

In claim 23, at column 305, at line 34, delete "yl]ethyl}-2,3-dihydrospiro[indene-1,4]-piperidin]-2-yl]" and insert -- yl]ethyl}-2,3-dihydrospiro[indene-1,4'-piperidin]-2-yl] --.

In claim 24, at column 306, at line 2, delete "phenyl}(methyl)amino]butanoyl}(methyl)amino]" and insert -- phenyl}(methyl)amino]butanoyl}(methyl)amino] --.

CERTIFICATE OF CORRECTION (continued)
U.S. Pat. No. 8,476,253 B2

In claim 24, at column 306, at line 3, delete "ethyl}piperidin-4-yl    biphenyl-2-ylcarbamate" and insert -- ethyl}piperidin-4-yl biphenyl-2-ylcarbamate --.

In claim 25, at column 306, at line 5, delete "1-{2-[{5-{4-[{3-[({[(2S)-1'-{2-[(5R)-3-[3,5-bis(trif-" and insert --1-{2-[{5-[{4-[{3-[({[(2S)-1'-{2-[(5R)-3-[3,5-bis(trif- --.

In claim 25, at column 306, at line 7, delete "yl)ethyl}-2,3-dihydrospiro[indene-1,4'-piperidin]-2-yl]" and insert -- yl]ethyl}-2,3-dihydrospiro[indene-1,4'-piperidin]-2-yl] --.

In claim 25, at column 306, at line 10, delete "ethyl}piperidin-4-yl    biphenyl-2-ylcarbamate" and insert -- ethyl}piperidin-4-yl biphenyl-2-ylcarbamate --.

In claim 26, at column 306, at line 12, delete "1-(2-{[6-({4-[{3-[([{[(2S)-1'-{2-[(5R)-3-[3,5-bis(trif-" and insert -- 1-(2-{[6-({4-[{3-[({[(2S)-1'-{2-[(5R)-3-[3,5-bis(trif- --.

In claim 28, at column 306, at line 31, delete "amino}ethyl)piperidin-4-yl    biphenyl-2-ylcarbamate" and insert -- amino}ethyl)piperidin-4-yl biphenyl-2-ylcarbamate --.